(12) United States Patent
Chen et al.

(10) Patent No.: US 8,354,443 B2
(45) Date of Patent: Jan. 15, 2013

(54) CYCLOPROPANE INDOLINONE DERIVATIVES

(75) Inventors: Li Chen, Shanghai (CN); Lichun Feng, Shanghai (CN); Yun He, Shanghai (CN); Mengwei Huang, Shanghai (CN); Hongying Yun, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 38 days.

(21) Appl. No.: 12/959,408

(22) Filed: Dec. 3, 2010

(65) Prior Publication Data

US 2011/0144106 A1   Jun. 16, 2011

(30) Foreign Application Priority Data

Dec. 11, 2009   (CN) ................. PCT/CN2009/075500

(51) Int. Cl.
*A61K 31/404* (2006.01)
*C07D 209/96* (2006.01)

(52) U.S. Cl. .................. 514/409; 548/407; 548/411

(58) Field of Classification Search .................. 548/407, 548/411; 514/409
See application file for complete search history.

(56) References Cited

U.S. PATENT DOCUMENTS

| | | | | |
|---|---|---|---|---|
| 7,205,328 B2* | 4/2007 | He et al. | .................. | 514/409 |
| 7,384,970 B2* | 6/2008 | Liu et al. | .................. | 514/415 |
| 7,495,103 B2* | 2/2009 | Hadida-Ruah et al. | ....... | 546/156 |
| 8,101,767 B2* | 1/2012 | Ruah et al. | .................. | 546/159 |
| 2004/0152755 A1 | 8/2004 | He et al. | | |
| 2004/0259890 A1 | 12/2004 | Fukami et al. | | |
| 2006/0030615 A1 | 2/2006 | Fensome et al. | | |

FOREIGN PATENT DOCUMENTS

| | | |
|---|---|---|
| CN | 1538956 | 10/2004 |
| CN | 101001625 | 7/2007 |
| JP | 57102863 | 6/1982 |
| WO | 2004/037247 | 5/2004 |
| WO | 2005/018568 | 3/2005 |
| WO | 2006/023107 | 3/2006 |
| WO | 2007/008664 | 1/2007 |

OTHER PUBLICATIONS

Liu et al (2004): STN International HCAPLUS database, (Columbus, Ohio), Accession number: 2004:817667.*
Hadida et al (2006): STN International HCAPLUS database, (Columbus, Ohio), Accession number: 2006:15782.*
Hardie, D. G., Nature Reviews of Molecular Cell Biology, vol. 8 (2007) pp. 774-785.
Woods et al., Molecular & Cellular Biology vol. 20 (2000) pp. 6704-6711.
Carling, D., Trends in Biochem. Science vol. 29 (2004) pp. 18-24.
Hardie, D. G., Annual Review of Pharmacology & Toxicology vol. 47 (2007) pp. 185-210.
Kahn et al., Cell Metabolism vol. 1 (2005) pp. 15-25.
Long et al., The Journal of Clinical Investigation vol. 116 (2006) pp. 1776-1783.
Friedman et al., Nature, vol. 395 (1998) pp. 763-770.
Muoio et al., Diabetes vol. 46 (1997) pp. 1360-1363.
Yamauchi et al., Nature Medicine vol. 7 (2001) pp. 941-946.
Minokoshi et al., Nature vol. 415 (2002) pp. 330-343.
Yamauchi et al., Nature Medicine vol. 8 (2002) pp. 1288-1295.
Semple et al., The Journal of Clinical Investigation vol. 116 (2006) pp. 581-589.
Fryer et al., The Journal of Biological Chemistry vol. 277 (2002) pp. 25226-25232.
Kadowaki et al., The Journal of Clinical Investigation vol. 116 (2006) pp. 1784-1702.
El-Mir et al., The Journal of Biological Chemistry vol. 275 (2000) pp. 223-228.
Owen et al., The Biochemical Journal vol. 348 Part 3 (2000) pp. 607-614.
Zhou et al., The Journal of Clinical Investigation vol. 108 (2001) pp. 1167-1174.
Shaw et al., Science (New York) New York vol. 310 (2005) pp. 1642-1646.
Cool et al., Cell Metabolism vol. 3 (2006) pp. 403-416.
Pang et al., The Journal of Biological Chemistry vol. 283 (2008) pp. 16051-16060.
Jiang et al., Bioorganic & Medicinal Chemistry Letters vol. 16 (2006) pp. 2109-2112.
Beckwith et al., Angewandte Chemie (2004) vol. 43 No. 1 pp. 95-98.
Moldvai et al., Arch. Pharm. Pharm. Medical Chemistry (1996) vol. 329, No. 12 pp. 541-549.
Moriconi et al., Journal of Organic Chemistry (1964) vol. 29 No. 12 pp. 3577-3584. Tully et al., Bioorganic & Medicinal Chemistry Letters (2006) vol. 16 No. 19, pp. 5107-5111.
Jiang et al., Bioorganic & Medicinal Chemistry Letters (2006) vol. 16, No. 8 pp. 2105-2108.
Forrest et al., Journal of Medicinal Chemistry (1992) vol. 35 No. 1 pp. 163-172.

* cited by examiner

*Primary Examiner* — Golam M M Shameem
(74) *Attorney, Agent, or Firm* — George W. Johnston; Patricia S. Rocha-Tramaloni; Gene J. Yao

(57) ABSTRACT

The present invention relates to a compound of formula (I)

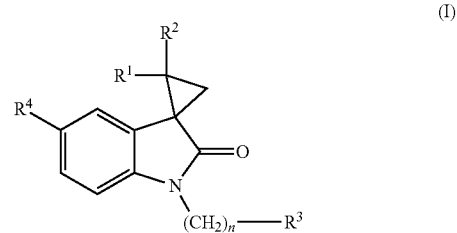

as well as pharmaceutically acceptable salt thereof, wherein $R^1$ to $R^4$ have the significance given in claim 1. The compound may be used, for example, for the treatment or prophylaxis of obesity, hyperglycemia, dyslipidemia, and type 1 or type 2 diabetes.

35 Claims, No Drawings

CYCLOPROPANE INDOLINONE DERIVATIVES

PRIORITY TO RELATED APPLICATION(S)

This application claims the benefit of International Patent Application No. PCT/CN2009/075500, filed Dec. 11, 2009, which is hereby incorporated by reference in its entirety.

FIELD OF THE INVENTION

The invention relates to compounds which are activators of AMP-activated protein kinase (AMPK) and which are useful in the treatment or prophylaxis of diseases that are related to AMPK regulation, such as obesity, dyslipidemia, hyperglycemia, type 1 or type 2 diabetes.

BACKGROUND OF THE INVENTION

Obesity and type 2 diabetes, hypertension, cancer, and cardiovascular disease, are diseases that feature serious disturbances in glucose or lipid metabolism that severely affect the health and quality of life of affected individuals. The increasing prevalence of these diseases makes finding new drug targets for treating these syndromes an urgent task.

AMP-activated protein kinase acts as a cellular energy sensor and regulator. It is activated by an increase in the cellular AMP:ATP ratio induced by metabolic stress, hormone and nutrient signals. Once activated, AMPK switches on catabolic pathways that generate ATP and switches off ATP-consuming anabolic pathways by acute regulation of the activity of key enzymes in metabolism and chronic regulation of the expression of pivotal transcription factors (Hardie, D G. *Nature reviews* 8 (2007b), 774-785; Woods, A et al. *Molecular and cellular biology* 20 (2000), 6704-6711). The growing evidence of AMPK regulatory effects on glucose and lipid metabolism makes it a potential drug target for treatment of diabetes and metabolic syndrome (Carling, D. *Trends Biochem Sci* 29 (2004), 18-24; Hardie, D G. *Annual review of pharmacology and toxicology* 47 (2007a), 185-210; Kahn, B B et al. *Cell metabolism* 1 (2005), 15-25; Long, Y C et al. *The Journal of clinical investigation* 116 (2006), 1776-1783).

At the physiological level, this concept has been supported by two adipokines, leptin and adiponectin, both of which exert excellent effects on glucose and lipid metabolism (Friedman, J M and Halaas, J L. *Nature* 395 (1998), 763-770; Muoio, D M et al. Diabetes 46 (1997), 1360-1363; Yamauchi, T et al. *Nature medicine* 7 (2001), 941-946). Recent studies suggest that leptin and adiponectin exert their antidiabetic effects by activating AMPK. Leptin stimulates muscle fatty acid oxidation by activating AMPK directly and through a hypothalamic-adrenergic pathway (Minokoshi, Y et al. *Nature* 415 (2002), 339-343). Adiponectin stimulates glucose uptake and fatty acid oxidation in vitro by activation of AMPK. Furthermore, it exerts its hypoglycemic effect by decreasing PEPCK and G6 Pase expression, whereas the administration of dominant negative al adenovirus reverses the effect in vivo (Yamauchi, T et al. *Nature medicine* 8 (2002), 1288-1295).

At the pharmacological level, the concept of AMPK as a potential target for treating metabolic syndrome has been further supported by the discovery of two major classes of existing antidiabetic drugs: thiazolidinediones (rosiglitazone, troglitazone and pioglitazone) and biguanides (metformin and phenformin) activate AMPK in cultured cells and in vivo. Rosiglitazone is traditionally considered to be a PPARγ agonist and exerts its antidiabetic effects through differentiation of adipocytes (Semple, R K et al. *The Journal of clinical investigation* 116 (2006), 581-589). Recent findings indicate that AMPK may be involved in the antidiabetic effects of rosiglitazone (Brunmair, B et al. *The Journal of biological chemistry* 277 (2002), 25226-25232; Kadowaki, T et al. *The Journal of clinical investigation* 116 (2006), 1784-1792). In the case of metformin, an existing antidiabetic agent without a defined mechanism of action, recent studies demonstrate that it could activate AMPK in vitro and in vivo by inhibiting complex I (El-Mir, M Y et al. *The Journal of biological chemistry* 275 (2000), 223-228; Owen, M R et al. *The Biochemical journal* 348 Pt 3 (2000), 607-614; Zhou, G et al. *The Journal of clinical investigation* 108 (2001), 1167-1174), and the hypoglycemic effect could be blocked completely by knockout of its upstream kinase LKB1, confirming the key role of AMPK in mediating the antidiabetic effect of metformin (Shaw, R J et al. *Science* (New York) N.Y. 310 (2005), 1642-1646).

Most recently, Cool and coworkers have identified a small direct AMPK activator, A-769662, which exerts antidiabetic effects in vivo (Cool, B et al. *Cell metabolism* 3 (2006), 403-416). Jia Li's laboratory has identified a small AMPK activator, PT1, which activates the inactive forms of AMPK $\alpha 2_{398}$ and $\alpha 1_{394}$ with micromolar activity and exerts some cellular effects (Pang, T et al. *The Journal of biological chemistry* 283 (2008), 16051-16060).

It has been found that the compounds of the present invention are potent AMPK activators. The compounds of the invention are therefore useful in the treatment or prophylaxis of diseases that are related to AMPK regulation, such as obesity, dyslipidemia, hyperglycemia, type 1 or type 2 diabetes and cancer.

SUMMARY OF THE INVENTION

The present invention relates in part to a compound of formula (I)

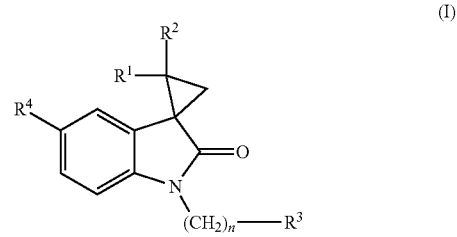

wherein
$R^1$ and $R^2$ are each independently selected from the group consisting of: hydrogen, alkyl, pyridinyl, phenyl, halophenyl, alkoxyphenyl, alkylsulfonylphenyl, cyanophenyl and trifluoromethylphenyl;
or $R^1$ and $R^2$, together with the carbon atom to which they are attached, form cycloalkyl or tetrahydropyranyl;
$R^3$ is selected from the group consisting of: hydrogen, pyridinyl, piperidinyl, carboxypyridinyl, tetrahydropyranyl, alkylamino, morpholinyl, morpholinylalkylamino, alkylmorpholinylalkylamino, alkylsulfonylpiperidinyl, alkylpiperazinyl, alkylaminoalkylpiperazinyl, pyridinylpiperazinyl, alkylaminopyrrolidinyl, 1H-imidazolyl, carboxyalkyl-1H-imidazolyl, carboxy-1H-imidazolyl, cycloalkylsulfonylaminocarbonylpyridinyl and substituted phenyl, wherein substituted phenyl is phenyl substituted with one or two substituents independently selected from the group consisting of: alkyl, halogen, hydroxyalkylamino, carboxy, alkylsulfonyl, alkylaminocarbonyl, alkylsulfonylaminocarbonyl, piperidinylcarbonyl, piperazinylcarbonyl, morpholinylcarbonyl, pyridinylpiperazinylcarbonyl, alkylpiperazinylcarbonyl, alkylsulfonylpiperazinylcarbonyl, alkylpyrrolidinylalkylaminocarbonyl, alkyl-1H-pyrazolylaminocarbonyl, oxo-oxazolidinyl, oxo-pyrrolidinyl, oxo-imidazolidinyl, morpholinylalkylaminocarbonyl, alkylaminoalkylpiperazinylcarbonyl, cycloalkyl-1H-pyrazolylaminocarbonyl and cycloalkylsulfonylaminocarbonyl;

$R^4$ is selected from the group consisting of: hydrogen, halogen, carboxy, cyano, trifluoromethyl and alkylsulfonyl; and n is 0, 1, 2 or 3;

or a pharmaceutically acceptable salt or ester thereof.

The invention also relates to a process for the manufacture of these novel compounds and medicaments containing them. The compounds of the invention have activation effect on AMP (adenosine monophosphate)-activated protein kinase, which results in lowered blood glucose. The invention thus also concerns the use of such compounds for the treatment or prophylaxis of diseases that are related to AMPK regulation, such as obesity, dyslipidemia, hyperglycemia, type 1 or type 2 diabetes.

DETAILED DESCRIPTION OF THE INVENTION

The present invention relates in part to a compound of formula (I)

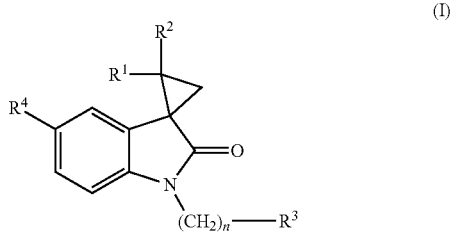

wherein $R^1$ and $R^2$ are each independently selected from the group consisting of: hydrogen, alkyl, pyridinyl, phenyl, halophenyl, alkoxyphenyl, alkylsulfonylphenyl, cyanophenyl and trifluoromethylphenyl;

or $R^1$ and $R^2$, together with the carbon atom to which they are attached, form cycloalkyl or tetrahydropyranyl;

$R^3$ is selected from the group consisting of: hydrogen, pyridinyl, piperidinyl, carboxypyridinyl, tetrahydropyranyl, alkylamino, morpholinyl, morpholinylalkylamino, alkylmorpholinylalkylamino, alkylsulfonylpiperidinyl, alkylpiperazinyl, alkylaminoalkylpiperazinyl, pyridinylpiperazinyl, alkylaminopyrrolidinyl, 1H-imidazolyl, carboxyalkyl-1H-imidazolyl, carboxy-1H-imidazolyl, cycloalkylsulfonylaminocarbonylpyridinyl and substituted phenyl, wherein substituted phenyl is phenyl substituted with one or two substituents independently selected from the group consisting of: alkyl, halogen, hydroxyalkylamino, carboxy, alkylsulfonyl, alkylaminocarbonyl, alkylsulfonylaminocarbonyl, piperidinylcarbonyl, piperazinylcarbonyl, morpholinylcarbonyl, pyridinylpiperazinylcarbonyl, alkylpiperazinylcarbonyl, alkylsulfonylpiperazinylcarbonyl, alkylpyrrolidinylalkylaminocarbonyl, alkyl-1H-pyrazolylaminocarbonyl, oxo-oxazolidinyl, oxo-pyrrolidinyl, oxo-imidazolidinyl, morpholinylalkylaminocarbonyl, alkylaminoalkylpiperazinylcarbonyl, cycloalkyl-1H-pyrazolylaminocarbonyl and cycloalkylsulfonylaminocarbonyl;

$R^4$ is selected from the group consisting of: hydrogen, halogen, carboxy, cyano, trifluoromethyl and alkylsulfonyl; and n is 0, 1, 2 or 3;

or a pharmaceutically acceptable salt or ester thereof.

As used herein, the term "alkyl", alone or in combination, signifies a saturated, linear- or branched chain alkyl group containing 1 to 8, preferably 1 to 6, more preferably 1 to 4 carbon atoms, for example methyl, ethyl, propyl, isopropyl, 1-butyl, 2-butyl, tert-butyl and the like. Preferred "alkyl" groups are methyl, ethyl, isopropyl, tert-butyl.

The term "alkoxy", alone or in combination, signifies a group alkyl-O—, wherein the "alkyl" is as defined above; for example methoxy, ethoxy, propoxy, isopropoxy, n-butoxy, i-butoxy, 2-butoxy, t-butoxy and the like. Preferred alkoxy groups are methoxy and ethoxy and more preferably methoxy.

The term "cycloalkyl", alone or in combination, refers to a saturated carbon ring containing from 3 to 7 carbon atoms, preferably from 3 to 6 carbon atoms, for example, cyclopropyl, cyclobutyl, cyclopentyl, cyclohexyl, cycloheptyl and the like. Preferred cycloalkyl groups are cyclopropyl and cyclopentyl, cyclopropyl being particularly preferred.

The term "halogen" or "halo", alone or in combination, means fluorine, chlorine, bromine or iodine. Halogen is preferably fluorine, chlorine or bromine.

The term "halophenyl" means phenyl substituted by halogen.

The term "carboxy", alone or in combination, refers to the group —COOH.

The term "carbonyl", alone or in combination, refers to the group —C(O)—.

The term "amino", alone or in combination, refers to primary (—NH$_2$—), secondary (—NH—) or tertiary amino (—N—).

The term "hydroxy", alone or in combination, refers to the group —OH.

The term "sulfonyl", alone or in combination, refers to the group —S(O)$_2$—.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula (I) and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J. et al., Organic Process Research & Development 2000, 4, 427-435; or in Ansel, H. et al., In: Pharmaceutical Dosage Forms and Drug Delivery Systems, 6th ed. (1995), pp. 196 and 1456-1457. Preferred are the sodium salts of the compounds of formula (I).

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention. Preferred are the methyl and ethyl esters of the compounds of formula (I).

Preferred is a compound according of formula (I) wherein one of $R^1$ and $R^2$ is selected from hydrogen and alkyl and the other is selected from the group consisting of: pyridinyl, halophenyl, alkylsulfonylphenyl, cyanophenyl and trifluoromethylphenyl, or $R^1$ and $R^2$, together with the carbon atom to which they are attached form cycloalkyl or tetrahydropyranyl In an embodiment, the compound of formula (I) is one wherein one of $R^1$ and $R^2$ is selected from hydrogen and alkyl and the other is selected from the group consisting of: pyridinyl, halophenyl, alkylsulfonylphenyl, cyanophenyl and trifluoromethylphenyl.

Further preferred is a compound of formula (I) wherein one of $R^1$ and $R^2$ is selected from hydrogen and isopropyl and the other is selected from the group consisting of: pyridinyl, fluorophenyl, chlorophenyl, cyanophenyl, methylsulfonylphenyl and trifluoromethylphenyl.

Preferred is a compound according of formula (I) wherein $R^3$ is the group consisting of: pyridinyl, carboxypyridinyl, tetrahydropyranyl, dialkylamino, morpholinyl, alkylsulfonylpiperidinyl, alkylpiperazinyl, dialkylaminoalkylpiperazinyl, dialkylaminopyrrolidinyl, carboxyalkyl-1H-imidazolyl, carboxy-1H-imidazolyl or substituted phenyl, wherein substituted phenyl is phenyl substituted with one or two substituents independently selected from alkyl, halogen, carboxy, alkylsulfonyl, alkylaminocarbonyl, alkylsulfonylaminocarbonyl, piperidinylcarbonyl, piperazinylcarbonyl, morpholinylcarbonyl, pyridinylpiperazinylcarbonyl, alkylpiperazinylcarbonyl, alkylsulfonylpiperazinylcarbonyl, alkylpyrrolidinylalkylaminocarbonyl, alkyl-1H-pyrazolylaminocarbonyl, oxo-oxazolidinyl, oxo-pyrrolidinyl and oxo-imidazolidinyl.

Also preferred is a compound of formula (I) wherein $R^3$ is selected from the group consisting of: carboxypyridinyl, carboxyalkyl-1H-imidazolyl, carboxyphenyl and phenyl substituted with carboxy and oxo-oxazolidinyl.

A compound of formula (I) wherein $R^4$ is selected from the group consisting of: hydrogen, halogen, cyano, trifluoromethyl and alkylsulfonyl is also preferred.

A compound of formula (I) wherein $R^4$ is selected from the group consisting of: hydrogen, halogen, carboxy, cyano, trifluoromethyl and alkylsulfonyl is also preferred.

In particular, preferred is a compound of formula (I) wherein $R^4$ is hydrogen or halogen.

In particular, preferred is a compound of formula (I) wherein $R^4$ is selected from the group consisting of: hydrogen, halogen and carboxy.

In an embodiment, $R^4$ is selected from the group consisting of: hydrogen, fluoro, chloro, and carboxy.

Furthermore, preferred is a compound of formula (I) wherein $R^4$ is selected from the group consisting of: hydrogen, fluoro and chloro.

A compound of formula (I) wherein n is 0 or 1 is preferred.

Particularly preferred is a compound of formula (I) selected from the group consisting of:

(1R,2S)-3-((2-(4-chlorophenyl)-2'-oxospiro[cyclopropane-1,3'-indoline]-1'-yl)methyl)benzoic acid;

(1S,2R)-3-((2-(4-chlorophenyl)-2'-oxospiro[cyclopropane-1,3'-indoline]-1'-yl)methyl)benzoic acid;

(1R,2R)-3-((2-(4-chlorophenyl)-2'-oxospiro[cyclopropane-1,3'-indoline]-1'-yl)methyl)benzoic acid;

(1S,2S)-3-((2-(4-chlorophenyl)-2'-oxospiro[cyclopropane-1,3'-indoline]-1'-yl)methyl)benzoic acid;

(1S,2R)-3-((2-(3-chlorophenyl)-2'-oxospiro[cyclopropane-1,3'-indoline]-1'-yl)methyl)benzoic acid;

(1R,2S)-3-((2-(3-chlorophenyl)-2'-oxospiro[cyclopropane-1,3'-indoline]-1'-yl)methyl)benzoic acid;

(1R,2R)-((2-(4-(methylsulfonyl)phenyl)-2'-oxospiro[cyclopropane-1,3'-indoline]-1'-yl)methyl)benzoic acid;

(1S,2S)-((2-(4-(methylsulfonyl)phenyl)-2'-oxospiro[cyclopropane-1,3'-indoline]-1'-yl)methyl)benzoic acid;

(1S,2R)-3-((2-(4-cyanophenyl)-2'-oxospiro[cyclopropane-1,3'-indoline]-1'-yl)methyl)benzoic acid;

(1R,2S)-3-((2-(4-cyanophenyl)-2'-oxospiro[cyclopropane-1,3'-indoline]-1'-yl)methyl)benzoic acid;

(1S,2R)-2-chloro-5-((2-(4-chlorophenyl)-2'-oxospiro[cyclopropane-1,3'-indoline]-1'-yl)methyl)benzoic acid;

(1R,2S)-2-chloro-5-((2-(4-chlorophenyl)-2'-oxospiro[cyclopropane-1,3'-indoline]-1'-yl)methyl)benzoic acid;

(1S,2R)-3-((2-(4-(methylsulfonyl)phenyl)-2'-oxospiro[cyclopropane-1,3'-indoline]-1'-yl)methyl)benzoic acid;

(1R,2S)-3-((2-(4-(methylsulfonyl)phenyl)-2'-oxospiro[cyclopropane-1,3'-indoline]-1'-yl)methyl)benzoic acid;

(1S,2R)-3-((2-(2-fluorophenyl)-2'-oxospiro[cyclopropane-1,3'-indoline]-1'-yl)methyl)benzoic acid;

(1R,2S)-3-((2-(2-fluorophenyl)-2'-oxospiro[cyclopropane-1,3'-indoline]-1'-yl)methyl)benzoic acid;

(1S,2S)-3-((2-(2-fluorophenyl)-2'-oxospiro[cyclopropane-1,3'-indoline]-1'-yl)methyl)benzoic acid;

(1R,2R)-3-((2-(2-fluorophenyl)-2'-oxospiro[cyclopropane-1,3'-indoline]-1'-yl)methyl)benzoic acid;

(1S,2R)-3-((2-(3-fluorophenyl)-2'-oxospiro[cyclopropane-1,3'-indoline]-1'-yl)methyl)benzoic acid;

(1R,2S)-3-((2-(3-fluorophenyl)-2'-oxospiro[cyclopropane-1,3'-indoline]-1'-yl)methyl)benzoic acid;

(1S,2S)-3-((2-(3-fluorophenyl)-2'-oxospiro[cyclopropane-1,3'-indoline]-1'-yl)methyl)benzoic acid;

(1R,2R)-3-((2-(3-fluorophenyl)-2'-oxospiro[cyclopropane-1,3'-indoline]-1'-yl)methyl)benzoic acid;

(1S,2S)-3-((2'-oxo-2-(2-(trifluoromethyl)phenyl)-spiro[cyclopropane-1,3'-indoline]-1'-yl)methyl)benzoic acid;

(1R,2R)-3-((2'-oxo-2-(2-(trifluoromethyl)phenyl)-spiro[cyclopropane-1,3'-indoline]-1'-yl)methyl)benzoic acid;

(1S,2R)-((5'-chloro-2-(4-chlorophenyl)-2'-oxospiro[cyclopropane-1,3'-indoline]-1'-yl)methyl)benzoic acid;

(1R,2S)-((5'-chloro-2-(4-chlorophenyl)-2'-oxospiro[cyclopropane-1,3'-indoline]-1'-yl)methyl)benzoic acid;

(1R,2R)-3-((5'-chloro-2-(4-chlorophenyl)-2'-oxospiro[cyclopropane-1,3'-indoline]-1'-yl)methyl)benzoic acid;

(1S,2S)-3-((5'-chloro-2-(4-chlorophenyl)-2'-oxospiro[cyclopropane-1,3'-indoline]-1'-yl)methyl)benzoic acid;

(1R,2R)-3-((5'-bromo-2-(4-chlorophenyl)-2'-oxospiro[cyclopropane-1,3'-indoline]-1'-yl)methyl)benzoic acid;

(1S,2S)-3-((5'-bromo-2-(4-chlorophenyl)-2'-oxospiro[cyclopropane-1,3'-indoline]-1'-yl)methyl)benzoic acid;

(1S,2R)-3-((5'-bromo-2-(4-chlorophenyl)-2'-oxospiro[cyclopropane-1,3'-indoline]-1'-yl)methyl)benzoic acid;
(1R,2S)-3-((5'-bromo-2-(4-chlorophenyl)-2'-oxospiro[cyclopropane-1,3'-indoline]-1'-yl)methyl)benzoic acid;
(1S,2S)-3-((2-(4-cyanophenyl)-2'-oxospiro[cyclopropane-1,3'-indoline]-1'-yl)methyl)benzoic acid;
(1R,2R)-3-((2-(4-cyanophenyl)-2'-oxospiro[cyclopropane-1,3'-indoline]-1'-yl)methyl)benzoic acid;
(1S,2R)-3-((2-(3-methoxyphenyl)-2'-oxospiro[cyclopropane-1,3'-indoline]-1'-yl)methyl)benzoic acid;
(1R,2S)-3-((2-(3-methoxyphenyl)-2'-oxospiro[cyclopropane-1,3'-indoline]-1'-yl)methyl)benzoic acid;
(1S,2S)-3-((2-(3-methoxyphenyl)-2'-oxospiro[cyclopropane-1,3'-indoline]-1'-yl)methyl)benzoic acid;
(1R,2R)-3-((2-(3-methoxyphenyl)-2'-oxospiro[cyclopropane-1,3'-indoline]-1'-yl)methyl)benzoic acid;
(1S,2S)-3-((2-(4-methoxyphenyl)-2'-oxospiro[cyclopropane-1,3'-indoline]-1'-yl)methyl)benzoic acid;
(1R,2R)-3-((2-(4-methoxyphenyl)-2'-oxospiro[cyclopropane-1,3'-indoline]-1'-yl)methyl)benzoic acid;
(1S,2S)-3-((2-(4-methoxyphenyl)-2'-oxospiro[cyclopropane-1,3'-indoline]-1'-yl)methyl)benzoic acid;
(1R,2S)-3-((2-(4-methoxyphenyl)-2'-oxospiro[cyclopropane-1,3'-indoline]-1'-yl)methyl)benzoic acid;
(1S,2R)-3-((2-(4-chlorophenyl)-5'-fluoro-2'-oxospiro[cyclopropane-1,3'-indoline]-1'-yl)methyl)benzoic acid;
(1R,2S)-3-((2-(4-chlorophenyl)-5'-fluoro-2'-oxospiro[cyclopropane-1,3'-indoline]-1'-yl)methyl)benzoic acid;
(1S,2S)-3-((2-(4-chlorophenyl)-5'-fluoro-2'-oxospiro[cyclopropane-1,3'-indoline]-1'-yl)methyl)benzoic acid;
(1R,2R)-3-((2-(4-chlorophenyl)-5'-fluoro-2'-oxospiro[cyclopropane-1,3'-indoline]-1'-yl)methyl)benzoic acid;
(1S,2R)-3-((-2-(4-fluorophenyl)-2'-oxospiro[cyclopropane-1,3'-indoline]-1'-yl)methyl)benzoic acid;
(1R,2S)-3-((-2-(4-fluorophenyl)-2'-oxospiro[cyclopropane-1,3'-indoline]-1'-yl)methyl)benzoic acid;
(1S,2R)-3-((2'-oxo-2-(pyridin-3-yl)spiro[cyclopropane-1,3'-indoline]-1'-yl)methyl)benzoic acid;
(1R,2S)-3-((2'-oxo-2-(pyridin-3-yl)spiro[cyclopropane-1,3'-indoline]-1'-yl)methyl)benzoic acid;
(1S,2S)-3-((-2-(4-fluorophenyl)-2'-oxospiro[cyclopropane-1,3'-indoline]-1'-yl)methyl)benzoic acid;
(1R,2R)-3-((-2-(4-fluorophenyl)-2'-oxospiro[cyclopropane-1,3'-indoline]-1'-yl)methyl)benzoic acid;
(1S,2S)-3-((2-(4-chlorophenyl)-2-isopropyl-2'-oxospiro[cyclopropane-1,3'-indoline]-1'-yl)methyl)benzoic acid;
(1R,2R)-3-((2-(4-chlorophenyl)-2-isopropyl-2'-oxospiro[cyclopropane-1,3'-indoline]-1'-yl)methyl)benzoic acid;
(1S,2S)-3-((2-(4-cyanophenyl)-2-methyl-2'-oxospiro[cyclopropane-1,3'-indoline]-1'-yl)methyl)benzoic acid;
(1R,2R)-3-((2-(4-cyanophenyl)-2-methyl-2'-oxospiro[cyclopropane-1,3'-indoline]-1'-yl)methyl)benzoic acid;
(1S,2R)-3-((2-(4-cyanophenyl)-2-methyl-2'-oxospiro[cyclopropane-1,3'-indoline]-1'-yl)methyl)benzoic acid;
(1R,2S)-3-((2-(4-cyanophenyl)-2-methyl-2'-oxospiro[cyclopropane-1,3'-indoline]-1'-yl)methyl)benzoic acid;
(+)-3-((2-(4-chlorophenyl)-2-isopropyl-2'-oxospiro[(trans)-cyclopropane-1,3'-indoline]-1'-yl)methyl)benzoic acid;
(−)-3-((2-(4-chlorophenyl)-2-isopropyl-2'-oxospiro[(trans)-cyclopropane-1,3'-indoline]-1'-yl)methyl)benzoic acid;
(1S,2S)-3-((2-(4-chlorophenyl)-2-isopropyl-2'-oxospiro[cyclopropane-1,3'-indoline]-1'-yl)methyl)benzoic acid;
(1R,2R)-3-((2-(4-chlorophenyl)-2-isopropyl-2'-oxospiro[cyclopropane-1,3'-indoline]-1'-yl)methyl)benzoic acid;
(+)-3-((2-(4-chlorophenyl)-5'-fluoro-2-isopropyl-2'-oxospiro[(trans)-cyclopropane-1,3'-indoline]-1'-yl)methyl)benzoic acid;
(−)-3-((2-(4-chlorophenyl)-5'-fluoro-2-isopropyl-2'-oxospiro[(trans)-cyclopropane-1,3'-indoline]-1'-yl)methyl)benzoic acid;
(1S,2S)-3-((2-(4-chlorophenyl)-5'-fluoro-2-isopropyl-2'-oxospiro[cyclopropane-1,3'-indoline]-1'-yl)methyl)benzoic acid;
(1R,2R)-3-((2-(4-chlorophenyl)-5'-fluoro-2-isopropyl-2'-oxospiro[cyclopropane-1,3'-indoline]-1'-yl)methyl)benzoic acid;
(1S,2S)-3-((5'-fluoro-2-(4-fluorophenyl)-2-isopropyl-2'-oxospiro[cyclopropane-1,3'-indoline]-1'-yl)methyl)benzoic acid;
(1R,2R)-3-((5'-fluoro-2-(4-fluorophenyl)-2-isopropyl-2'-oxospiro[cyclopropane-1,3'-indoline]-1'-yl)methyl)benzoic acid;
(1S,2S)-3-((2-(3-fluorophenyl)-2-isopropyl-2'-oxospiro[cyclopropane-1,3'-indoline]-1'-yl)methyl)benzoic acid;
(1R,2R)-3-((2-(3-fluorophenyl)-2-isopropyl-2'-oxospiro[cyclopropane-1,3'-indoline]-1'-yl)methyl)benzoic acid;
(1S,2S)-3-((2-(3-chlorophenyl)-2-isopropyl-2'-oxospiro[cyclopropane-1,3'-indoline]-1'-yl)methyl)benzoic acid;
(1R,2R)-3-((2-(3-chlorophenyl)-2-isopropyl-2'-oxospiro[cyclopropane-1,3'-indoline]-1'-yl)methyl)benzoic acid;
(1S,2S)-3-((2-(4-fluorophenyl)-2-isopropyl-2'-oxospiro[cyclopropane-1,3'-indoline]-1'-yl)methyl)benzoic acid;
(1R,2R)-3-((2-(4-fluorophenyl)-2-isopropyl-2'-oxospiro[cyclopropane-1,3'-indoline]-1'-yl)methyl)benzoic acid;
(+)-3-((2-(4-chlorophenyl)-2-isopropyl-2'-oxospiro[(trans)-cyclopropane-1,3'-indoline]-1'-yl)methyl)benzoic acid;
(−)-3-((2-(4-chlorophenyl)-2-isopropyl-2'-oxospiro[(trans)-cyclopropane-1,3'-indoline]-1'-yl)methyl)benzoic acid;
(1R,2S)-3-((2-(4-chlorophenyl)-2-methyl-2'-oxospiro[cyclopropane-1,3'-indoline]-1'-yl)methyl)benzoic acid;
(1S,2R)-3-((2-(4-chlorophenyl)-2-methyl-2'-oxospiro[cyclopropane-1,3'-indoline]-1'-yl)methyl)benzoic acid;
(+)-3-((2-(4-chlorophenyl)-2-methyl-2'-oxospiro[(trans)-cyclopropane-1,3'-indoline]-1'-yl)methyl)benzoic acid;
(−)-3-((2-(4-chlorophenyl)-2-methyl-2'-oxospiro[(trans)-cyclopropane-1,3'-indoline]-1'-yl)methyl)benzoic acid;
(1R,2R)-3-((2-(4-chlorophenyl)-2-methyl-2'-oxospiro[cyclopropane-1,3'-indoline]-1'-yl)methyl)benzoic acid;
(1S,2S)-3-((2-(4-chlorophenyl)-2-methyl-2'-oxospiro[cyclopropane-1,3'-indoline]-1'-yl)methyl)benzoic acid;
(+)-3-((2-(4-chlorophenyl)-2-methyl-2'-oxospiro[(cis)-cyclopropane-1,3'-indoline]-1'-yl)methyl)benzoic acid;
(−)-3-((2-(4-chlorophenyl)-2-methyl-2'-oxospiro[(cis)-cyclopropane-1,3'-indoline]-1'-yl)methyl)benzoic acid;
(1R,2S)-3-((2-(4-cyanophenyl)-5'-fluoro-2-methyl-2'-oxospiro[cyclopropane-1,3'-indoline]-1'-yl)methyl)benzoic acid;
(1S,2R)-3-((2-(4-cyanophenyl)-5'-fluoro-2-methyl-2'-oxospiro[cyclopropane-1,3'-indoline]-1'-yl)methyl)benzoic acid;
(−)-3-((2-(4-cyanophenyl)-5'-fluoro-2-methyl-2'-oxospiro[(trans)-cyclopropane-1,3'-indoline]-1-1'-yl)methyl)benzoic acid;
(+)-3-((2-(4-cyanophenyl)-5'-fluoro-2-methyl-2'-oxospiro[(trans)-cyclopropane-1,3'-indoline]-1'-yl)methyl)benzoic acid;
(1S,2S)-3-((2-(4-cyanophenyl)-2-isopropyl-2'-oxospiro[cyclopropane-1,3'-indoline]-1'-yl)methyl)benzoic acid;
(1R,2R)-3-((2-(4-cyanophenyl)-2-isopropyl-2'-oxospiro[cyclopropane-1,3'-indoline]-1'-yl)methyl)benzoic acid;
(−)-3-((2-(4-cyanophenyl)-2-isopropyl-2'-oxospiro[(trans)-cyclopropane-1,3'-indoline]-1'-yl)methyl)benzoic acid;
(+)-3-((2-(4-cyanophenyl)-2-isopropyl-2'-oxospiro[(trans)-cyclopropane-1,3'-indoline]-1'-yl)methyl)benzoic acid;

(1R,2R)-3-((2-(4-cyanophenyl)-5'-fluoro-2-methyl-2'-oxospiro[cyclopropane-1,3'-indoline]-1'-yl)methyl)benzoic acid;
(1S,2S)-3-((2-(4-cyanophenyl)-5'-fluoro-2-methyl-2'-oxospiro[cyclopropane-1,3'-indoline]-1'-yl)methyl)benzoic acid;
(−)-3-((2-(4-cyanophenyl)-5'-fluoro-2-methyl-2'-oxospiro[(cis)-cyclopropane-1,3'-indoline]-1'-yl)methyl)benzoic acid;
(+)-3-((2-(4-cyanophenyl)-5'-fluoro-2-methyl-2'-oxospiro[(cis)-cyclopropane-1,3'-indoline]-1'-yl)methyl)benzoic acid;
(1R,2S)-3-((2-(4-chlorophenyl)-5'-fluoro-2-methyl-2'-oxospiro[cyclopropane-1,3'-indoline]-1'-yl)methyl)benzoic acid;
(1S,2R)-3-((2-(4-chlorophenyl)-5'-fluoro-2-methyl-2'-oxospiro[cyclopropane-1,3'-indoline]-1'-yl)methyl)benzoic acid;
(−)-3-((2-(4-chlorophenyl)-5'-fluoro-2-methyl-2'-oxospiro[(trans)-cyclopropane-1,3'-indoline]-1'-yl)methyl)benzoic acid;
(+)-3-((2-(4-chlorophenyl)-5'-fluoro-2-methyl-2'-oxospiro[(trans)-cyclopropane-1,3'-indoline]-1'-yl)methyl)benzoic acid;
(1S,2R)-2-(4-chlorophenyl)-1'-(3-(piperidine-1-carbonyl)benzyl)spiro[cyclopropane-1,3'-indolin]-2'-one;
(1R,2S)-2-(4-chlorophenyl)-1'-(3-(piperidine-1-carbonyl)benzyl)spiro[cyclopropane-1,3'-indolin]-2'-one;
(1R,2S)-3-((2-(4-chlorophenyl)-2'-oxospiro[cyclopropane-1,3'-indoline]-1'-yl)methyl)-N-isopropylbenzamide;
(1S,2R)-3-((2-(4-chlorophenyl)-2'-oxospiro[cyclopropane-1,3'-indoline]-1'-yl)methyl)-N-isopropylbenzamide;
(1S,2R)-2-(4-chlorophenyl)-1'-(3-(piperazine-1-carbonyl)benzyl) spiro[cyclopropane-1,3'-indolin]-2'-one;
(1R,2S)-2-(4-chlorophenyl)-1'-(3-(piperazine-1-carbonyl)benzyl) spiro[cyclopropane-1,3'-indolin]-2'-one;
(1R,2S)-2-(4-chlorophenyl)-1'-(3-(morpholine-4-carbonyl)benzyl)spiro[cyclopropane-1,3'-indolin]-2'-one;
(1S,2R)-2-(4-chlorophenyl)-1'-(3-(morpholine-4-carbonyl)benzyl)spiro[cyclopropane-1,3'-indolin]-2'-one;
(1R,2S)-2-(4-chlorophenyl)-1'-(3-(4-(pyridin-4-yl)piperazine-1-carbonyl)benzyl)spiro[cyclopropane-1,3'-indolin]-2'-one;
(1S,2R)-2-(4-chlorophenyl)-1'-(3-(4-(pyridin-4-yl)piperazine-1-carbonyl)benzyl)spiro[cyclopropane-1,3'-indolin]-2'-one;
(1S,2R)-2-(4-chlorophenyl)-1'-(3-(4-isopropylpiperazine-1-carbonyl)benzyl)spiro[cyclopropane-1,3'-indolin]-2'-one;
(1R,2S)-2-(4-chlorophenyl)-1'-(3-(4-isopropylpiperazine-1-carbonyl)benzyl)spiro[cyclopropane-1,3'-indolin]-2'-one;
3-(((1S,2R)-2-(4-chlorophenyl)-2'-oxospiro[cyclopropane-1,3'-indoline]-1'-yl)methyl)-N-(2-((S)-1-methylpyrrolidin-2-yl)ethyl)benzamide
3-(((1R,2S)-2-(4-chlorophenyl)-2'-oxospiro[cyclopropane-1,3'-indoline]-1'-yl)methyl)-N-(2-((S)-1-methylpyrrolidin-2-yl)ethyl)benzamide;
(1R,2S)-3-((2-(4-chlorophenyl)-2'-oxospiro[cyclopropane-1,3'-indoline]-1'-yl)methyl)-N-(3-methyl-1H-pyrazol-5-yl)benzamide;
(1S,2R)-3-((2-(4-chlorophenyl)-2'-oxospiro[cyclopropane-1,3'-indoline]-1'-yl)methyl)-N-(3-methyl-1H-pyrazol-5-yl)benzamide;
(1S,2R)-6-((2-(4-chlorophenyl)-2'-oxospiro[cyclopropane-1,3'-indoline]-1'-yl)methyl)picolinic acid;
(1R,2S)-6-((2-(4-chlorophenyl)-2'-oxospiro[cyclopropane-1,3'-indoline]-1'-yl)methyl)picolinic acid;
(1S,2R)-6-((2-(4-fluorophenyl)-2'-oxospiro[cyclopropane-1,3'-indoline]-1'-yl)methyl)picolinic acid;
(1R,2S)-6-((2-(4-fluorophenyl)-2'-oxospiro[cyclopropane-1,3'-indoline]-1'-yl)methyl)picolinic acid;
(1S,2R)-2-(4-chlorophenyl)-1'-((tetrahydro-2H-pyran-4-yl)methyl)spiro[cyclopropane-1,3'-indolin]-2'-one;
(1R,2S)-2-(4-chlorophenyl)-1'-((tetrahydro-2H-pyran-4-yl)methyl)spiro[cyclopropane-1,3'-indolin]-2'-one;
(1S,2R)-2-(4-chlorophenyl)-1'-(2-(diethylamino)ethyl)spiro[cyclopropane-1,3'-indolin]-2'-one;
(1R,2S)-2-(4-chlorophenyl)-1'42-(diethylamino)ethyl)spiro[cyclopropane-1,3'-indolin]-2'-one;
(1S,2R)-2-(4-chlorophenyl)-1'(2-morpholinoethyl)spiro[cyclopropane-1,3'-indolin]-2'-one;
(1R,2S)-2-(4-chlorophenyl)-1'(2-morpholinoethyl)spiro[cyclopropane-1,3'-indolin]-2'-one;
(1S,2R)-2-(4-chlorophenyl)-1'-((1-(methylsulfonyl)piperidin-4-yl)methyl)spiro[cyclopropane-1,3'-indolin]-2'-one;
(1R,2S)-2-(4-chlorophenyl)-1'-((1-(methylsulfonyl)piperidin-4-yl)methyl)spiro[cyclopropane-1,3'-indolin]-2'-one;
(1S,2R)-2-(4-chlorophenyl)-1'42-(4-isopropylpiperazin-1-yl)ethyl)spiro[cyclopropane-1,3'-indolin]-2'-one;
(1R,2S)-2-(4-chlorophenyl)-1'42-(4-isopropylpiperazin-1-yl)ethyl)spiro[cyclopropane-1,3'-indolin]-2'-one;
(1S,2R)-2-(4-chlorophenyl)-1' (2-(4(2(dimethylamino)ethyl)piperazin-1-yl)ethyl)spiro[cyclopropane-1,3'-indolin]-2'-one;
(1R,2S)-2-(4-chlorophenyl)-1'-(2-(4-(2-(dimethylamino)ethyl)piperazin-1-yl)ethyl)spiro[cyclopropane-1,3'-indolin]-2'-one;
(1S,2R)-2-(4-chlorophenyl)-1'-(2-((S)-3-(dimethylamino)pyrrolidin-1-yl)ethyl)spiro[cyclopropane-1,3'-indolin]-2'-one;
(1R,2S)-2-(4-chlorophenyl)-1'-(2-((S)-3-(dimethylamino)pyrrolidin-1-yl)ethyl)spiro[cyclopropane-1,3'-indolin]-2'-one;
(1S,2R)-2-(4-chlorophenyl)-1'-(2-((R)-3-(dimethylamino)pyrrolidin-1-yl)ethyl)spiro[cyclopropane-1,3'-indolin]-2'-one;
(1R,2S)-2-(4-chlorophenyl)-1'-(2-((R)-3-(dimethylamino)pyrrolidin-1-yl)ethyl)spiro [cyclopropane-1,3'-indolin]-2'-one;
(1R,2S)-2-(4-chlorophenyl)-1'-(pyridin-4-ylmethyl)spiro[cyclopropane-1,3'-indolin]-2'-one;
(1S,2R)-2-(4-chlorophenyl)-1'-(pyridin-4-ylmethyl)spiro[cyclopropane-1,3'-indolin]-2'-one;
(1S,2R)-2-(4-chlorophenyl)-1'-(pyridin-3-ylmethyl)spiro[cyclopropane-1,3'-indolin]-2'-one;
(2R,1S)-2-(4-chlorophenyl)-1'-(pyridin-3-ylmethyl)spiro[cyclopropane-1,3'-indolin]-2'-one;
(1S,2R)-2-(4-(2-(4-chlorophenyl)-2'-oxospiro[cyclopropane-1,3'-indoline]-1'-yl)-1H-imidazol-1-yl)acetic acid;
(1R,2S)-2-(4-(2-(4-chlorophenyl)-2'-oxospiro[cyclopropane-1,3'-indoline]-1'-yl)-1H-imidazol-1-yl)acetic acid;
(1S,2R)-1-(2-(2-(4-chlorophenyl)-2'-oxospiro[cyclopropane-1,3'-indoline]-1'-yl)ethyl)-1H-imidazole-4-carboxylic acid;
(1R,2S)-1-(2-(2-(4-chlorophenyl)-2'-oxospiro[cyclopropane-1,3'-indoline]-1'-yl)ethyl)-1H-imidazole-4-carboxylic acid;
(1S,2S)-1-(2-(2-(4-chlorophenyl)-2'-oxospiro[cyclopropane-1,3'-indoline]-1'-yl)ethyl)-1H-imidazole-4-carboxylic acid;
(1R,2R)-1-(2-(2-(4-chlorophenyl)-2'-oxospiro[cyclopropane-1,3'-indoline]-1'-yl)ethyl)-1H-imidazole-4-carboxylic acid;

(1S,2R)-3-(2-(4-chlorophenyl)-2'-oxospiro[cyclopropane-1,3'-indoline]-1'-yl)benzoic acid;
(1R,2S)-3-(2-(4-chlorophenyl)-2'-oxospiro[cyclopropane-1,3'-indoline]-1'-yl)benzoic acid;
(1S,2S)-3-(-2-(4-chlorophenyl)-2'-oxospiro[cyclopropane-1,3'-indoline]-1'-yl)benzoic acid;
(1R,2R)-3-(-2-(4-chlorophenyl)-2'-oxospiro[cyclopropane-1,3'-indoline]-1'-yl)benzoic acid;
(1S,2S)-2-(4-chlorophenyl)-1'-(3-(morpholine-4-carbonyl)phenyl)spiro[cyclopropane-1,3'-indolin]-2'-one;
(1R,2R)-2-(4-chlorophenyl)-1'-(3-(morpholine-4-carbonyl)phenyl)spiro[cyclopropane-1,3'-indolin]-2'-one;
(1S,2S)-2-(4-chlorophenyl)-1'-(3-(4-methylpiperazine-1-carbonyl)phenyl)spiro[cyclopropane-1,3'-indolin]-2'-one;
(1R,2R)-2-(4-chlorophenyl)-1'-(3-(4-methylpiperazine-1-carbonyl)phenyl)spiro[cyclopropane-1,3'-indolin]-2'-one;
(1S,2S)-2-(4-chlorophenyl)-1'-(3-(4-(methylsulfonyl)piperazine-1-carbonyl)phenyl)spiro[cyclopropane-1,3'-indolin]-2'-one;
(1R,2R)-2-(4-chlorophenyl)-1'-(3-(4-(methylsulfonyl)piperazine-1-carbonyl)phenyl)spiro[cyclopropane-1,3'-indolin]-2'-one;
(1R,2S)-2-(4-chlorophenyl)-1'-(3-(morpholine-4-carbonyl)phenyl)spiro[cyclopropane-1,3'-indolin]-2'-one;
(1S,2R)-2-(4-chlorophenyl)-1'-(3-(morpholine-4-carbonyl)phenyl)spiro[cyclopropane-1,3'-indolin]-2'-one;
(1S,2R)-2-(4-chlorophenyl)-1'-(3-(4-methylpiperazine-1-carbonyl)phenyl)spiro[cyclopropane-1,3'-indolin]-2'-one;
(1R,2S)-2-(4-chlorophenyl)-1'-(3-(4-methylpiperazine-1-carbonyl)phenyl)spiro[cyclopropane-1,3'-indolin]-2'-one;
(1R,2S)-2-(4-chlorophenyl)-1'-(3-(4-(methylsulfonyl)piperazine-1-carbonyl)phenyl)spiro[cyclopropane-1,3'-indolin]-2'-one;
(1S,2R)-2-(4-chlorophenyl)-1'-(3-(4-(methylsulfonyl)piperazine-1-carbonyl)phenyl)spiro[cyclopropane-1,3'-indolin]-2'-one;
(1R,2R)-3-(2-(4-chlorophenyl)-2'-oxospiro[cyclopropane-1,3'-indoline]-1'-yl)-N-(methylsulfonyl)benzamide;
(1S,2S)-3-(2-(4-chlorophenyl)-2'-oxospiro[cyclopropane-1,3'-indoline]-1'-yl)-N-(methylsulfonyl)benzamide;
(1S,2S)-3-(2-(4-chlorophenyl)-2'-oxospiro[cyclopropane-1,3'-indoline]-1'-yl)-5-(2-oxooxazolidin-3-yl)benzoic acid;
(1R,2R)-3-(2-(4-chlorophenyl)-2'-oxospiro[cyclopropane-1,3'-indoline]-1'-yl)-5-(2-oxooxazolidin-3-yl)benzoic acid;
(1S,2S)-3-(2-(4-chlorophenyl)-2'-oxospiro[cyclopropane-1,3'-indoline]-1'-yl)-5-(methylsulfonyl)benzoic acid;
(1R,2R)-3-(2-(4-chlorophenyl)-2'-oxospiro[cyclopropane-1,3'-indoline]-1'-yl)-5-(methylsulfonyl)benzoic acid;
(1S,2S)-3-(2-(4-chlorophenyl)-2'-oxospiro[cyclopropane-1,3'-indoline]-1'-yl)-5-(2-oxopyrrolidin-1-yl)benzoic acid;
(1R,2R)-3-(2-(4-chlorophenyl)-2'-oxospiro[cyclopropane-1,3'-indoline]-1'-yl)-5-(2-oxopyrrolidin-1-yl)benzoic acid;
(1R,2R)-3-(2-(4-chlorophenyl)-5'-fluoro-2-isopropyl-2'-oxospiro[cyclopropane-1,3'-indoline]-1'-yl)-5-(2-oxooxazolidin-3-yl)benzoic acid;
(1S,2S)-3-(2-(4-chlorophenyl)-5'-fluoro-2-isopropyl-2'-oxospiro[cyclopropane-1,3'-indoline]-1'-yl)-5-(2-oxooxazolidin-3-yl)benzoic acid;
(1R,2S)-3-(2-(4-chlorophenyl)-5'-fluoro-2-isopropyl-2'-oxospiro[cyclopropane-1,3'-indoline]-1'-yl)-5-(2-oxooxazolidin-3-yl)benzoic acid;
(1S,2R)-3-(2-(4-chlorophenyl)-5'-fluoro-2-isopropyl-2'-oxospiro[cyclopropane-1,3'-indoline]-1'-yl)-5-(2-oxooxazolidin-3-yl)benzoic acid;
(1R,2R)-3-(2-(4-chlorophenyl)-2-isopropyl-2'-oxospiro[cyclopropane-1,3'-indoline]-1'-yl)-5-(2-oxooxazolidin-3-yl)benzoic acid;
(1S,2S)-3-(2-(4-chlorophenyl)-2-isopropyl-2'-oxospiro[cyclopropane-1,3'-indoline]-1'-yl)-5-(2-oxooxazolidin-3-yl)benzoic acid;
(1S,2S)-3-(2-(4-cyanophenyl)-2-isopropyl-2'-oxospiro[cyclopropane-1,3'-indoline]-1'-yl)-5-(2-oxooxazolidin-3-yl)benzoic acid;
(1R,2R)-3-(2-(4-cyanophenyl)-2-isopropyl-2'-oxospiro[cyclopropane-1,3'-indoline]-1'-yl)-5-(2-oxooxazolidin-3-yl)benzoic acid;
(1S,2S)-3-(2-(4-chlorophenyl)-2'-oxospiro[cyclopropane-1,3'-indoline]-1'-yl)-5-(2-oxoimidazolidin-1-yl)benzoic acid;
(1R,2R)-3-(2-(4-chlorophenyl)-2'-oxospiro[cyclopropane-1,3'-indoline]-1'-yl)-5-(2-oxoimidazolidin-1-yl)benzoic acid;
(R)-3-((5'-fluoro-2,2-dimethyl-2'-oxospiro[cyclopropane-1,3'-indoline]-1'-yl)methyl)benzoic acid;
(S)-3-((5'-fluoro-2,2-dimethyl-2'-oxospiro[cyclopropane-1,3'-indoline]-1'-yl)methyl)benzoic acid;
(R)-3-(5'-fluoro-2,2-dimethyl-2'-oxospiro[cyclopropane-1,3'-indoline]-1'-yl)-5-(2-oxooxazolidin-3-yl)benzoic acid;
(S)-3-(5'-fluoro-2,2-dimethyl-2'-oxospiro[cyclopropane-1,3'-indoline]-1'-yl)-5-(2-oxooxazolidin-3-yl)benzoic acid;
(R)-3-[(2-oxo-2",3",5",6"-tetrahydrodispiro[indole-3,1'-cyclopropane-2',4"-pyran]-1(2H)-yl)methyl]benzoic acid;
(S)-3-[(2-oxo-2",3",5",6"-tetrahydrodispiro[indole-3,1'-cyclopropane-2',4"-pyran]-1(2H)-yl)methyl]benzoic acid;
(R)-3-(2-oxo-1,3-oxazolidin-3-yl)-5-(2-oxo-2",3",5",6"-tetrahydrodispiro[indole-3,1'-cyclopropane-2',4"-pyran]-1(2H)-yl)benzoic acid;
(S)-3-(2-oxo-1,3-oxazolidin-3-yl)-5-(2-oxo-2",3",5",6"-tetrahydrodispiro[indole-3,1'-cyclopropane-2',4"-pyran]-1(2H)-yl)benzoic acid;
(1S,2S)-2-chloro-5-((2-(4-fluorophenyl)-2'-oxospiro[cyclopropane-1,3'-indoline]-1'-yl)methyl)benzoic acid;
(1R,2R)-2-chloro-5-((2-(4-fluorophenyl)-2'-oxospiro[cyclopropane-1,3'-indoline]-1'-yl)methyl)benzoic acid;
(1R,2S)-4-((2'-oxo-2-(pyridin-3-yl)spiro[cyclopropane-1,3'-indoline]-1'-yl)methyl)benzoic acid;
(1S,2R)-4-((2'-oxo-2-(pyridin-3-yl)spiro[cyclopropane-1,3'-indoline]-1'-yl)methyl)benzoic acid;
(1S,2R)-4-((2-(4-cyanophenyl)-2'-oxospiro[cyclopropane-1,3'-indoline]-1'-yl)methyl)benzoic acid;
(1R,2S)-4-((2-(4-cyanophenyl)-2'-oxospiro[cyclopropane-1,3'-indoline]-1'-yl)methyl)benzoic acid;
(1R,2S)-4-((2-(4-fluorophenyl)-2'-oxospiro[cyclopropane-1,3'-indoline]-1'-yl)methyl)benzoic acid;
(1R,2S)-4-((2-(4-fluorophenyl)-2'-oxospiro[cyclopropane-1,3'-indoline]-1'-yl)methyl)benzoic acid;
(1S,2R)-2-chloro-5-((2-(4-chlorophenyl)-5'-fluoro-2'-oxospiro[cyclopropane-1,3'-indoline]-1'-yl)methyl)benzoic acid;
(1R,2S)-2-chloro-5-((2-(4-chlorophenyl)-5'-fluoro-2'-oxospiro[cyclopropane-1,3'-indoline]-1'-yl)methyl)benzoic acid;
(1R,2S)-3-((2-(3-chloro-4-fluorophenyl)-2'-oxospiro[cyclopropane-1,3'-indoline]-1'-yl)methyl)benzoic acid;
(1S,2R)-3-((2-(3-chloro-4-fluorophenyl)-2'-oxospiro[cyclopropane-1,3'-indoline]-1'-yl)methyl)benzoic acid;
(1R,2S)-3-((2-(4-chlorophenyl)-2'-oxospiro[cyclopropane-1,3'-indoline]-1'-yl)methyl)-N-methylbenzamide;
(1S,2R)-3-((2-(4-chlorophenyl)-2'-oxospiro[cyclopropane-1,3'-indoline]-1'-yl)methyl)-N-methylbenzamide;
(1S,2R)-3-((2-(4-chlorophenyl)-2'-oxospiro[cyclopropane-1,3'-indoline]-1'-yl)methyl)-N,N-dimethylbenzamide;
(1R,2S)-3-((2-(4-chlorophenyl)-2'-oxospiro[cyclopropane-1,3'-indoline]-1'-yl)methyl)-N,N-dimethylbenzamide;

(1R,2S)-3-((2-(4-chlorophenyl)-2'-oxospiro[cyclopropane-1,3'-indoline]-1'-yl)methyl)-N-(3-morpholinopropyl)benzamide;
(1S,2R)-3-((2-(4-chlorophenyl)-2'-oxospiro[cyclopropane-1,3'-indoline]-1'-yl)methyl)-N-(3-morpholinopropyl)benzamide;
(1R,2S)-2-(4-chlorophenyl)-1'-(3-(4-(2-(dimethylamino) ethyl)piperazine-1-carbonyl)benzyl)spiro[cyclopropane-1,3'-indolin]-2'-one;
(1S,2R)-2-(4-chlorophenyl)-1'-(3-(4-(2-(dimethylamino) ethyl)piperazine-1-carbonyl)benzyl)spiro[cyclopropane-1,3'-indolin]-2'-one;
(1R,2S)-3-((2-(4-chlorophenyl)-2'-oxospiro[cyclopropane-1,3'-indoline]-1'-yl)methyl)-N-(2-morpholinoethyl)benzamide;
(1S,2R)-3-((2-(4-chlorophenyl)-2'-oxospiro[cyclopropane-1,3'-indoline]-1'-yl)methyl)-N-(2-morpholinoethyl)benzamide;
(1R,2S)-2-(4-chlorophenyl)-1'-(3-(4-(methylsulfonyl)piperazine-1-carbonyl)benzyl)spiro[cyclopropane-1,3'-indolin]-2'-one;
(1S,2R)-2-(4-chlorophenyl)-1'-(3-(4-(methylsulfonyl)piperazine-1-carbonyl)benzyl)spiro[cyclopropane-1,3'-indolin]-2'-one;
(1S,2R)-3-((2-(4-chlorophenyl)-2'-oxospiro[cyclopropane-1,3'-indoline]-1'-yl)methyl)-N-(3-cyclopropyl-1H-pyrazol-5-yl)benzamide;
(1R,2S)-3-((2-(4-chlorophenyl)-2'-oxospiro[cyclopropane-1,3'-indoline]-1'-yl)methyl)-N-(3-cyclopropyl-1H-pyrazol-5-yl)benzamide;
(1R,2S)-3-((2-(4-chlorophenyl)-2'-oxospiro[cyclopropane-1,3'-indoline]-1'-yl)methyl)-N-(5-cyclopropyl-1H-pyrazol-3-yl)benzamide;
(1R,2S)-3-((2-(4-chlorophenyl)-2'-oxospiro[cyclopropane-1,3'-indoline]-1'-yl)methyl)-N-(5-cyclopropyl-1H-pyrazol-3-yl)benzamide;
(1R,2S)-6-((2-(4-cyanophenyl)-2'-oxospiro[cyclopropane-1,3'-indoline]-1'-yl)methyl)-N-(cyclopropylsulfonyl)picolinamide;
(1S,2R)-6-((2-(4-cyanophenyl)-2'-oxospiro[cyclopropane-1,3'-indoline]-1'-yl)methyl)-N-(cyclopropylsulfonyl)picolinamide;
(1S,2R)-4-((2-(4-cyanophenyl)-2'-oxospiro[cyclopropane-1,3'-indoline]-1'-yl)methyl)-N-(cyclopropylsulfonyl)benzamide;
(1R,2S)-4-((2-(4-cyanophenyl)-2'-oxospiro[cyclopropane-1,3'-indoline]-1'-yl)methyl)-N-(cyclopropylsulfonyl)benzamide;
(1R,2S)-3-((2-(4-chlorophenyl)-2'-oxospiro[cyclopropane-1,3'-indoline]-1'-yl)methyl)-N-(methylsulfonyl)benzamide;
(1S,2R)-3-((2-(4-chlorophenyl)-2'-oxospiro[cyclopropane-1,3'-indoline]-1'-yl)methyl)-N-(methylsulfonyl)benzamide;
(1R,2S)-3-((2-(4-fluorophenyl)-2'-oxospiro[cyclopropane-1,3'-indoline]-1'-yl)methyl)-N-(methylsulfonyl)benzamide;
(1S,2R)-3-((2-(4-fluorophenyl)-2'-oxospiro[cyclopropane-1,3'-indoline]-1'-yl)methyl)-N-(methylsulfonyl)benzamide;
(1S,2R)-N-(cyclopropylsulfonyl)-3-((2-(4-fluorophenyl)-2'-oxospiro[cyclopropane-1,3'-indoline]-1'-yl)methyl)benzamide;
(1R,2S)-N-(cyclopropylsulfonyl)-3-((2-(4-fluorophenyl)-2'-oxospiro[cyclopropane-1,3'-indoline]-1'-yl)methyl)benzamide;
(1S,2R)-N-(cyclopropylsulfonyl)-4-((2-(4-fluorophenyl)-2'-oxospiro[cyclopropane-1,3'-indoline]-1'-yl)methyl)benzamide;
(1R,2S)-N-(cyclopropylsulfonyl)-4-((2-(4-fluorophenyl)-2'-oxospiro[cyclopropane-1,3'-indoline]-1'-yl)methyl)benzamide;
(1S,2R)-2-(4-chlorophenyl)-1'-(piperidin-4-ylmethyl) Spiro[cyclopropane-1,3'-indolin]-2'-one;
(1R,2S)-2-(4-chlorophenyl)-1'-(piperidin-4-ylmethyl) Spiro[cyclopropane-1,3'-indolin]-2'-one;
(1S,2R)-2-(4-chlorophenyl)-1'-(2-(piperidin-1-yl)ethyl) spiro[cyclopropane-1,3'-indolin]-2'-one;
(1R,2S)-2-(4-chlorophenyl)-1'-(2-(piperidin-1-yl)ethyl) spiro[cyclopropane-1,3'-indolin]-2'-one;
(1S,2R)-2-(4-chlorophenyl)-1'42-(3-morpholinopropylamino)ethyl)spiro[cyclopropane-1,3'-indolin]-2'-one;
(1R,2S)-2-(4-chlorophenyl)-1'42-(3-morpholinopropylamino)ethyl)spiro[cyclopropane-1,3'-indolin]-2'-one;
(1S,2R)-2-(4-chlorophenyl)-1'42-(3-morpholinopropylamino)ethyl)spiro[cyclopropane-1,3'-indolin]-2'-one;
(1R,2S)-2-(4-chlorophenyl)-1'42-(3-morpholinopropylamino)ethyl)spiro[cyclopropane-1,3'-indolin]-2'-one;
(1S,2R)-2-(4-chlorophenyl)-1'-(2-(2-morpholinoethylamino)ethyl)spiro[cyclopropane-1,3'-indolin]-2'-one;
(1R,2S)-2-(4-chlorophenyl)-1'-(2-(2-morpholinoethylamino)ethyl)spiro[cyclopropane-1,3'-indolin]-2'-one;
(1S,2R)-2-(4-chlorophenyl)-1'-(2-(4-(pyridin-4-yl)piperazin-1-yl)ethyl)spiro[cyclopropane-1,3'-indolin]-2'-one;
(1R,2S)-2-(4-chlorophenyl)-1'-(2-(4-(pyridin-4-yl)piperazin-1-yl)ethyl)spiro[cyclopropane-1,3'-indolin]-2'-one;
(1S,2R)-2-(4-chlorophenyl)-1'-(2-(2-(2,6-dimethylmorpholino)ethylamino)ethyl)spiro[cyclopropane-1,3'-indolin]-2'-one;
(1R,2S)-2-(4-chlorophenyl)-1'42-(2-(2,6-dimethylmorpholino)ethylamino)ethyl)spiro[cyclopropane-1,3'-indolin]-2'-one;
(1S,2R)-2-(4-chlorophenyl)-1'-(1H-imidazol-4-yl)spiro[cyclopropane-1,3'-indolin]-2'-one;
(1R,2S)-2-(4-chlorophenyl)-1'-(1H-imidazol-4-yl)spiro[cyclopropane-1,3'-indolin]-2'-one;
(1S,2R)-3-(2-(4-chlorophenyl)-2'-oxospiro[cyclopropane-1,3'-indoline]-1'-yl)-N-(methylsulfonyl)benzamide;
(1R,2S)-3-(2-(4-chlorophenyl)-2'-oxospiro[cyclopropane-1,3'-indoline]-1'-yl)-N-(methylsulfonyl)benzamide;
(1S,2S)-3-(2-(4-chlorophenyl)-2-methyl-2'-oxospiro[cyclopropane-1,3'-indoline]-1'-yl)-5-(2-oxooxazolidin-3-yl)benzoic acid;
(1R,2R)-3-(2-(4-chlorophenyl)-2-methyl-2'-oxospiro[cyclopropane-1,3'-indoline]-1'-yl)-5-(2-oxooxazolidin-3-yl)benzoic acid;
(1S,2S)-3-(2-(4-chlorophenyl)-2-isopropyl-2'-oxospiro[cyclopropane-1,3'-indoline]-1'-yl)-5-(2-oxooxazolidin-3-yl)benzoic acid;
(1R,2R)-3-(2-(4-chlorophenyl)-2-isopropyl-2'-oxospiro[cyclopropane-1,3'-indoline]-1'-yl)-5-(2-oxooxazolidin-3-yl)benzoic acid;
(1S,2S)-3-(2-(4-chlorophenyl)-2-isopropyl-2'-oxospiro[cyclopropane-1,3'-indoline]-1'-yl)-5-(2-oxooxazolidin-3-yl)benzoic acid;
(1R,2R)-3-(2-(4-chlorophenyl)-2-isopropyl-2'-oxospiro[cyclopropane-1,3'-indoline]-1'-yl)-5-(2-oxooxazolidin-3-yl)benzoic acid;
(R)-methyl-3-(2,2-dimethyl-2'-oxospiro[cyclopropane-1,3'-indoline]-1'-yl)-5-(2-oxooxazolidin-3-yl)benzoate;
(S)-methyl-3-(2,2-dimethyl-2'-oxospiro[cyclopropane-1,3'-indoline]-1'-yl)-5-(2-oxooxazolidin-3-yl)benzoate;

(R)-3-(5'-fluoro-2,2-dimethyl-2'-oxospiro[cyclopropane-1,3'-indoline]-1'-yl)-5-(2-hydroxyethylamino)benzoic acid;
(S)-3-(5'-fluoro-2,2-dimethyl-2'-oxospiro[cyclopropane-1,3'-indoline]-1'-yl)-5-(2-hydroxyethylamino)benzoic acid;
(R)-methyl-3-(2-oxo-1,3-oxazolidin-3-yl)-5-(2-oxo-2'',3'',5'',6''-tetrahydrodispiro[indole-3,1'-cyclopropane-2',4''-pyran]-1(2H)-yl)benzoate;
(S)-methyl-3-(2-oxo-1,3-oxazolidin-3-yl)-5-(2-oxo-2'',3'',5'',6''-tetrahydrodispiro[indole-3,1'-cyclopropane-2',4''-pyran]-1(2H)-yl)benzoate;
(1S,2R)-1'-(3-fluorobenzyl)-2-(4-fluorophenyl)-2'-oxospiro[cyclopropane-1,3'-indoline]-5'-carboxylic acid;
(1R,2S)-1'-(3-fluorobenzyl)-2-(4-fluorophenyl)-2'-oxospiro[cyclopropane-1,3'-indoline]-5'-carboxylic acid;
(1R,2R)-1'-(2-fluorobenzyl)-2-(4-fluorophenyl)-2'-oxospiro[cyclopropane-1,3'-indoline]-5'-carboxylic acid;
(1S,2S)-1'-(2-fluorobenzyl)-2-(4-fluorophenyl)-2'-oxospiro[cyclopropane-1,3'-indoline]-5'-carboxylic acid;
(1R,2R)-2-(4-fluorophenyl)-2'-oxospiro[cyclopropane-1,3'-indoline]-5'-carboxylic acid;
(1S,2S)-2-(4-fluorophenyl)-2'-oxospiro[cyclopropane-1,3'-indoline]-5'-carboxylic acid;
(1R,2S)-2-(4-cyanophenyl)-2'-oxospiro[cyclopropane-1,3'-indoline]-5'-carboxylic acid;
(1S,2R)-2-(4-cyanophenyl)-2'-oxospiro[cyclopropane-1,3'-indoline]-5'-carboxylic acid;
(1R,2R)-2-(4-cyanophenyl)-2'-oxospiro[cyclopropane-1,3'-indoline]-5'-carboxylic acid;
(1S,2S)-2-(4-cyanophenyl)-2'-oxospiro[cyclopropane-1,3'-indoline]-5'-carboxylic acid;
(1S,2R)-2-(4-fluorophenyl)-2'-oxospiro[cyclopropane-1,3'-indoline]-5'-carboxylic acid; and
(1R,2S)-2-(4-fluorophenyl)-2'-oxospiro[cyclopropane-1,3'-indoline]-5'-carboxylic acid.

Also particularly preferred is a compound of formula (I) selected from the group consisting of:
(2S,1R)-3-((2-(4-chlorophenyl)-2'-oxospiro[cyclopropane-1,3'-indoline]-1'-yl)methyl)benzoic acid;
(1S,2R)-3-((2-(4-chlorophenyl)-2'-oxospiro[cyclopropane-1,3'-indoline]-1'-yl)methyl)benzoic acid;
(1S,2R)-3-((2-(3-chlorophenyl)-2'-oxospiro[cyclopropane-1,3'-indoline]-1'-yl)methyl)benzoic acid;
(1R,2S)-3-((2-(3-chlorophenyl)-2'-oxospiro[cyclopropane-1,3'-indoline]-1'-yl)methyl)benzoic acid;
(1S,2R)-3-((2-(4-cyanophenyl)-2'-oxospiro[cyclopropane-1,3'-indoline]-1'-yl)methyl)benzoic acid;
(1R,2S)-3-((2-(4-cyanophenyl)-2'-oxospiro[cyclopropane-1,3'-indoline]-1'-yl)methyl)benzoic acid;
(1S,2R)-3-((2-(4-(methylsulfonyl)phenyl)-2'-oxospiro[cyclopropane-1,3'-indoline]-1'-yl)methyl)benzoic acid;
(1R,2S)-3-((2-(4-(methylsulfonyl)phenyl)-2'-oxospiro[cyclopropane-1,3'-indoline]-1'-yl)methyl)benzoic acid;
(1S,2R)-3-((2-(2-fluorophenyl)-2'-oxospiro[cyclopropane-1,3'-indoline]-1'-yl)methyl)benzoic acid;
(1R,2S)-3-((2-(2-fluorophenyl)-2'-oxospiro[cyclopropane-1,3'-indoline]-1'-yl)methyl)benzoic acid;
(1S,2S)-3-((2-(2-fluorophenyl)-2'-oxospiro[cyclopropane-1,3'-indoline]-1'-yl)methyl)benzoic acid;
(1R,2R)-3-((2-(2-fluorophenyl)-2'-oxospiro[cyclopropane-1,3'-indoline]-1'-yl)methyl)benzoic acid;
(1S,2R)-3-((2-(3-fluorophenyl)-2'-oxospiro[cyclopropane-1,3'-indoline]-1'-yl)methyl)benzoic acid;
(1R,2S)-3-((2-(3-fluorophenyl)-2'-oxospiro[cyclopropane-1,3'-indoline]-1'-yl)methyl)benzoic acid;
(1S,2S)-3-((2'-oxo-2-(2-(trifluoromethyl)phenyl)-spiro[cyclopropane-1,3'-indoline]-1'-yl)methyl)benzoic acid;
(1R,2R)-3-((2'-oxo-2-(2-(trifluoromethyl)phenyl)-spiro[cyclopropane-1,3'-indoline]-1'-yl)methyl)benzoic acid;
(1S,2R)-((5'-chloro-2-(4-chlorophenyl)-2'-oxospiro[cyclopropane-1,3'-indoline]-1'-yl)methyl)benzoic acid;
(1R,2S)-((5'-chloro-2-(4-chlorophenyl)-2'-oxospiro[cyclopropane-1,3'-indoline]-1'-yl)methyl)benzoic acid;
(1S,2S)-3-((2-(4-chlorophenyl)-5'-fluoro-2'-oxospiro[cyclopropane-1,3'-indoline]-1'-yl)methyl)benzoic acid;
(1R,2R)-3-((2-(4-chlorophenyl)-5'-fluoro-2'-oxospiro[cyclopropane-1,3'-indoline]-1'-yl)methyl)benzoic acid;
(1S,2R)-3-((2'-oxo-2-(pyridin-3-yl)spiro[cyclopropane-1,3'-indoline]-1'-yl)methyl)benzoic acid;
(1R,2S)-3-((2'-oxo-2-(pyridin-3-yl)spiro[cyclopropane-1,3'-indoline]-1'-yl)methyl)benzoic acid;
(+)-3-((2-(4-chlorophenyl)-2-isopropyl-2'-oxospiro[(trans)-cyclopropane-1,3'-indoline]-1'-yl)methyl)benzoic acid;
(−)-3-((2-(4-chlorophenyl)-2-isopropyl-2'-oxospiro[(trans)-cyclopropane-1,3'-indoline]-1'-yl)methyl)benzoic acid;
(1S,2S)-3-((2-(4-chlorophenyl)-2-isopropyl-2'-oxospiro[cyclopropane-1,3'-indoline]-1'-yl)methyl)benzoic acid;
(1R,2R)-3-((2-(4-chlorophenyl)-2-isopropyl-2'-oxospiro[cyclopropane-1,3'-indoline]-1'-yl)methyl)benzoic acid;
(1S,2R)-6-((2-(4-chlorophenyl)-2'-oxospiro[cyclopropane-1,3'-indoline]-1'-yl)methyl)picolinic acid;
(1R,2S)-6-((2-(4-chlorophenyl)-2'-oxospiro[cyclopropane-1,3'-indoline]-1'-yl)methyl)picolinic acid;
(1S,2R)-6-((2-(4-fluorophenyl)-2'-oxospiro[cyclopropane-1,3'-indoline]-1'-yl)methyl)picolinic acid;
(1R,2S)-6-((2-(4-fluorophenyl)-2'-oxospiro[cyclopropane-1,3'-indoline]-1'-yl)methyl)picolinic acid;
(1S,2R)-2-(4-(2-(4-chlorophenyl)-2'-oxospiro[cyclopropane-1,3'-indoline]-1'-yl)-1H-imidazol-1-yl)acetic acid;
(1R,2S)-2-(4-(2-(4-chlorophenyl)-2'-oxospiro[cyclopropane-1,3'-indoline]-1'-yl)-1H-imidazol-1-yl)acetic acid;
(1S,2R)-3-(2-(4-chlorophenyl)-2'-oxospiro[cyclopropane-1,3'-indoline]-1'-yl)benzoic acid;
(1R,2S)-3-(2-(4-chlorophenyl)-2'-oxospiro[cyclopropane-1,3'-indoline]-1'-yl)benzoic acid;
(1S,2S)-3-(-2-(4-chlorophenyl)-2'-oxospiro[cyclopropane-1,3'-indoline]-1'-yl)benzoic acid;
(1R,2R)-3-(-2-(4-chlorophenyl)-2'-oxospiro[cyclopropane-1,3'-indoline]-1'-yl)benzoic acid;
(1S,2S)-3-(2-(4-chlorophenyl)-2'-oxospiro[cyclopropane-1,3'-indoline]-1'-yl)-5-(2-oxooxazolidin-3-yl)benzoic acid;
(1R,2R)-3-(2-(4-chlorophenyl)-2'-oxospiro[cyclopropane-1,3'-indoline]-1'-yl)-5-(2-oxooxazolidin-3-yl)benzoic acid;
(1S,2S)-2-chloro-5-((2-(4-fluorophenyl)-2'-oxospiro[cyclopropane-1,3'-indoline]-1'-yl)methyl)benzoic acid;
(1R,2R)-2-chloro-5-((2-(4-fluorophenyl)-2'-oxospiro[cyclopropane-1,3'-indoline]-1'-yl)methyl)benzoic acid;
(1R,2S)-4-((2'-oxo-2-(pyridin-3-yl)spiro[cyclopropane-1,3'-indoline]-1'-yl)methyl)benzoic acid;
(1S,2R)-4-((2'-oxo-2-(pyridin-3-yl)spiro[cyclopropane-1,3'-indoline]-1'-yl)methyl)benzoic acid;
(1S,2R)-4-((2-(4-cyanophenyl)-2'-oxospiro[cyclopropane-1,3'-indoline]-1'-yl)methyl)benzoic acid;
(1R,2S)-4-((2-(4-cyanophenyl)-2'-oxospiro[cyclopropane-1,3'-indoline]-1'-yl)methyl)benzoic acid;
(1S,2R)-4-((2-(4-fluorophenyl)-2'-oxospiro[cyclopropane-1,3'-indoline]-1'-yl)methyl)benzoic acid;
(1R,2S)-4-((2-(4-fluorophenyl)-2'-oxospiro[cyclopropane-1,3'-indoline]-1'-yl)methyl)benzoic acid;
(1S,2R)-2-chloro-5-((2-(4-chlorophenyl)-5'-fluoro-2'-oxospiro[cyclopropane-1,3'-indoline]-1'-yl)methyl)benzoic acid;

(1R,2S)-2-chloro-5-((2-(4-chlorophenyl)-5'-fluoro-2'-oxospiro[cyclopropane-1,3'-indoline]-1'-yl)methyl)benzoic acid;
(1R,2S)-3-((2-(3-chloro-4-fluorophenyl)-2'-oxospiro[cyclopropane-1,3'-indoline]-1'-yl)methyl)benzoic acid;
(1S,2R)-3-((2-(3-chloro-4-fluorophenyl)-2'-oxospiro[cyclopropane-1,3'-indoline]-1'-yl)methyl)benzoic acid;
(1R,2S)-6-((2-(4-cyanophenyl)-2'-oxospiro[cyclopropane-1,3'-indoline]-1'-yl)methyl)-N-(cyclopropylsulfonyl)picolinamide;
(1S,2R)-6-((2-(4-cyanophenyl)-2'-oxospiro[cyclopropane-1,3'-indoline]-1'-yl)methyl)-N-(cyclopropylsulfonyl)picolinamide;
(1S,2R)-4-((2-(4-cyanophenyl)-2'-oxospiro[cyclopropane-1,3'-indoline]-1'-yl)methyl)-N-(cyclopropylsulfonyl)benzamide;
(1R,2S)-4-((2-(4-cyanophenyl)-2'-oxospiro[cyclopropane-1,3'-indoline]-1'-yl)methyl)-N-(cyclopropylsulfonyl)benzamide;
(1R,2S)-3-((2-(4-chlorophenyl)-2'-oxospiro[cyclopropane-1,3'-indoline]-1'-yl)methyl)-N-(methylsulfonyl)benzamide;
(1S,2R)-3-((2-(4-chlorophenyl)-2'-oxospiro[cyclopropane-1,3'-indoline]-1'-yl)methyl)-N-(methylsulfonyl)benzamide;
(1R,2S)-3-((2-(4-fluorophenyl)-2'-oxospiro[cyclopropane-1,3'-indoline]-1'-yl)methyl)-N-(methylsulfonyl)benzamide;
(1S,2R)-3-((2-(4-fluorophenyl)-2'-oxospiro[cyclopropane-1,3'-indoline]-1'-yl)methyl)-N-(methylsulfonyl)benzamide;
(1S,2R)-N-(cyclopropylsulfonyl)-3-((2-(4-fluorophenyl)-2'-oxospiro[cyclopropane-1,3'-indoline]-1'-yl)methyl)benzamide;
(1R,2S)-N-(cyclopropylsulfonyl)-3-((2-(4-fluorophenyl)-2'-oxospiro[cyclopropane-1,3'-indoline]-1'-yl)methyl)benzamide;
(1S,2R)-N-(cyclopropylsulfonyl)-4-((2-(4-fluorophenyl)-2'-oxospiro[cyclopropane-1,3'-indoline]-1'-yl)methyl)benzamide;
(1R,2S)-N-(cyclopropylsulfonyl)-4-((2-(4-fluorophenyl)-2'-oxospiro[cyclopropane-1,3'-indoline]-1'-yl)methyl)benzamide;
(1S,2R)-1'-(3-fluorobenzyl)-2-(4-fluorophenyl)-2'-oxospiro[cyclopropane-1,3'-indoline]-5'-carboxylic acid;
(1R,2S)-1'-(3-fluorobenzyl)-2-(4-fluorophenyl)-2'-oxospiro[cyclopropane-1,3'-indoline]-5'-carboxylic acid;
(1R,2R)-1'-(2-fluorobenzyl)-2-(4-fluorophenyl)-2'-oxospiro[cyclopropane-1,3'-indoline]-5'-carboxylic acid;
(1S,2S)-1'-(2-fluorobenzyl)-2-(4-fluorophenyl)-2'-oxospiro[cyclopropane-1,3'-indoline]-5'-carboxylic acid;
(1R,2R)-2-(4-fluorophenyl)-2'-oxospiro[cyclopropane-1,3'-indoline]-5'-carboxylic acid;
(1S,2S)-2-(4-fluorophenyl)-2'-oxospiro[cyclopropane-1,3'-indoline]-5'-carboxylic acid;
(1R,2S)-2-(4-cyanophenyl)-2'-oxospiro[cyclopropane-1,3'-indoline]-5'-carboxylic acid;
(1S,2R)-2-(4-cyanophenyl)-2'-oxospiro[cyclopropane-1,3'-indoline]-5'-carboxylic acid; and
(1R,2R) and (1S,2S)-2-(4-cyanophenyl)-2'-oxospiro[cyclopropane-1,3'-indoline]-5'-carboxylic acid.

The compounds of the present invention can be prepared by any conventional means. Suitable processes for synthesizing these compounds are provided in the schemes below. In the following schemes, $R^5$ is hydrogen, halogen, oxo-oxazolidinyl, oxo-imidazolidinyl. $R^6$ and $R^7$ are independently selected from hydrogen, alkyl, cycloalkyl, alkylsulfonyl, cycloalkylsulfonyl, aminoalkyl and aminocycloalkyl. $R^1$, $R^2$, $R^3$, $R^4$ and n are as defined above unless otherwise indicated.

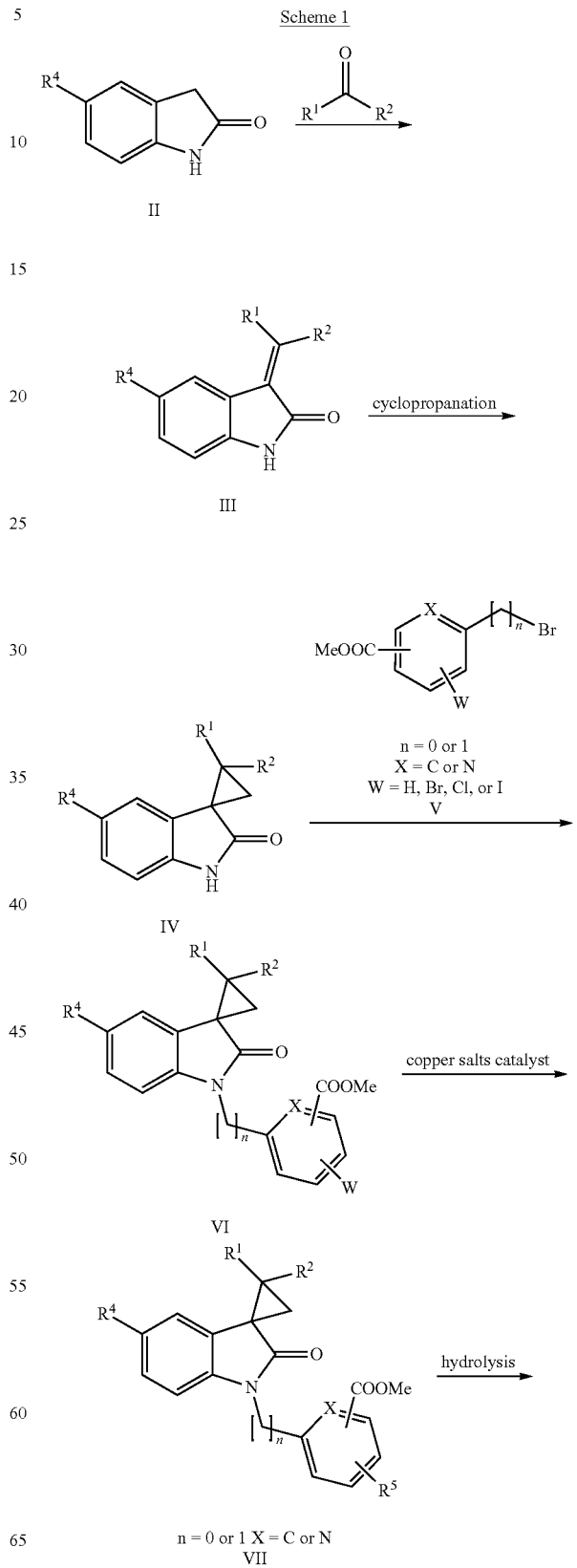

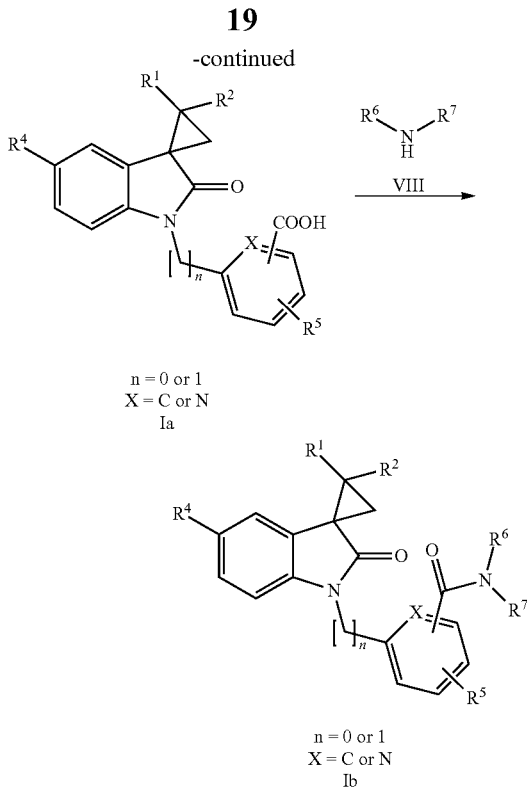

n = 0 or 1
X = C or N
Ia n = 0 or 1
X = C or N
Ib

The compounds of formula Ia and Ib can be prepared according to Scheme 1. Intermediate III is prepared as by the condensation reaction between II and different aldehydes or ketones. Cyclopropanation of III affords the intermediate IV. Alkylation between IV and bromide V affords the ester VI. Ester VII can be obtained by introducing $R^5$ to the intermediate VI under copper salts catalysts. Hydrolysis of the methyl ester VII gives the corresponding acid Ia. Amide Ib can be prepared by the coupling reaction between the acid Ia and amine VIII.

The condensation reaction between II and different aldehydes is carried out in refluxing toluene or refluxing alcohol overnight when using base such as piperidine or pyrrolidine as catalyst.

Cyclopropanation of III is carried out in organic solvents such as DMSO at 50° C. for several hours by treating trimethylsulfoxoniumiodide with sodium hydride to generate sulfurylide in situation.

In the third step outlined in Scheme 1, when n=1, alkylation of IV and the bromide V affords the methyl ester VI by using bases such as NaH, $K_2CO_3$ or $Cs_2CO_3$ in organic solvents such as THF, DMF at room temperature for several hours; when n=0, coupling of IV with arylbromide V can be carried out in the presence of a copper source such as copper(I) iodide (CuI), in combination with a ligand such as 2,2'-bipyridine, proline, N,N'-dimethyl glycine or ethylene glycol, in the presence of a suitable base such as triethylamine, sodium carbonate, potassium carbonate, cesium carbonate, sodium methoxide, sodium tert-butoxide, potassium tert-butoxide, sodium hydride or 1,8-diazabicyclo[5.4.0]undec-7-ene (DBU). The reaction can be carried out in a suitable solvent like acetonitrile, dichloromethane, tetrahydrofuran, toluene, benzene, 1,4-dioxane, N,N-dimethylformamide, dimethyl sulfoxide or N-methylpyrrolidinone at a temperature between 100° C. and 180° C. for 15 to 60 minutes under microwave irradiation. Alternatively, the reactions can be carried out at a heated temperature such as 80° C. for a longer reaction time without microwave irradiation. (Ley, S. V. et al., Angew. Chem. Int. Ed. 42 (2003) 5400).

In the fourth step, introduction of $R^5$ to the methyl ester VI can be carried out in the presence of a copper source such as copper(I) iodide (CuI), in combination with a ligand such as 2,2'-bipyridine, proline, N,N'-dimethyl glycine or ethylene glycol, in the presence of a suitable base such as triethylamine, sodium carbonate, potassium carbonate, cesium carbonate, sodium methoxide, sodium tert-butoxide, potassium tert-butoxide, sodium hydride or 1,8-diazabicyclo[5.4.0]undec-7-ene (DBU). The reaction can be carried out in a suitable solvent like acetonitrile, dichloromethane, tetrahydrofuran, toluene, benzene, 1,4-dioxane, N,N-dimethylformamide, dimethyl sulfoxide or N-methylpyrrolidinone at a temperature between 100° C. and 180° C. for 15 to 60 minutes under microwave irradiation. Alternatively, the reactions can be carried out at a heated temperature such as 80° C. for a longer reaction time without microwave irradiation. (Ley, S. V. et al., Angew. Chem. Int. Ed. 42 (2003) 5400).

Hydrolysis of the methyl esters VII can be carried out in the presence of an aqueous inorganic base such as lithium hydroxide, sodium hydroxide, or potassium hydroxide in a solvent such as methanol, 1,4-dioxane or tetrahydrofuran at room temperature for several hours to give the stereoisomers of Ia.

Conversion of the acids Ia to the corresponding amides Ib with suitable amines VIII can be easily accomplished using well known methods. The reaction is typically carried out in the presence of a coupling reagent such as dicyclohexyl carbodiimide (DCC), benzotriazol-1-yl-oxy-tris-pyrrolidino-phosphonium hexafluorophosphate (PyBop), o-(7-azabenzotriazol-1-yl-N,N,N', N'-tetramethyluronium hexafluorophosphate (HATU), o-(1H-benzotriazol-1-yl-N, N,N', N'-tetramethyluronium hexafluorophosphate (HBTU) or 1-ethyl-3-(3'-dimethylamino)carbodiimide hydrochloride salt (EDCI), in the presence or absence of hydroxybenzotriazole (HOBt) or N,N-dimethylaminopyridine (DMAP), in the presence of a base such as triethylamine or N,N-diisopropyl ethylamine. The reaction can be carried out in a solvent such as dichloromethane or N,N-dimethylformamide at room temperature for several hours (Montalbetti, C. A. G. N. et al., Tetrahedron 61 (2005) 10827).

Scheme 2

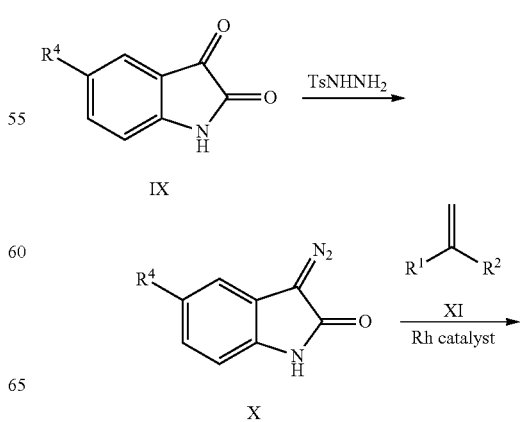

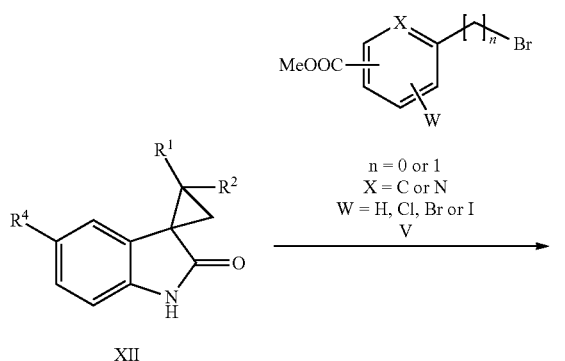

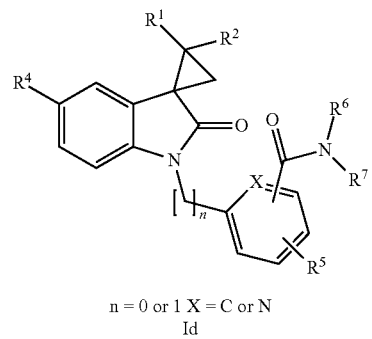

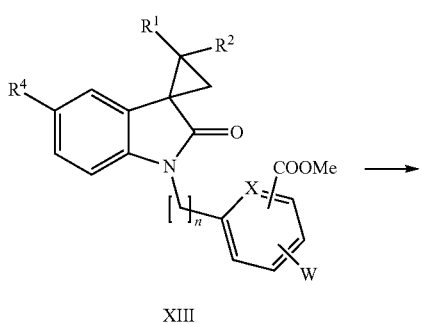

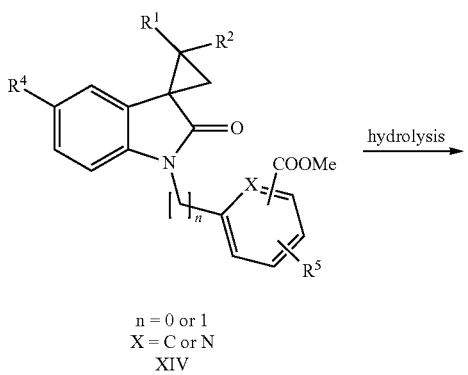

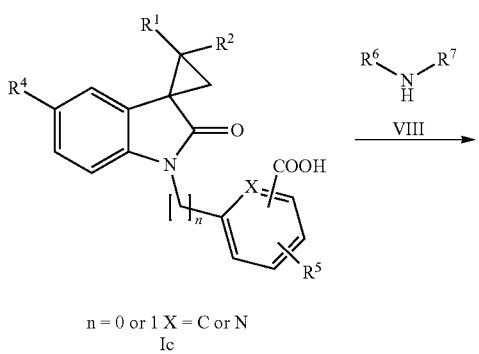

The compounds of formula Ic and Id can be prepared according to Scheme 2. The diazo compound X can be obtained by treating the isatin IX with p-toluenesulfonyl hydrazide under basic conditions. Cyclopropanation of alkene XI with diazo compound X by Rh catalyst affords the intermediate XII. Alkylation or arylation of XII with the bromide V afforded the methyl ester XIII. Introduction of $R^5$ to XIII by using copper salts as catalyst gave intermediate XIV.

Hydrolysis of the methyl ester gives the corresponding acids Ic. The hydrolysis can be carried out in the presence of an aqueous inorganic base such as lithium hydroxide, sodium hydroxide, or potassium hydroxide in a solvent such as methanol, 1,4-dioxane or tetrahydrofuran at room temperature for several hours.

Conversion of the acids Ic to the corresponding amides Id with suitable amines VIII can be easily accomplished using methods well known to someone skilled in the art. The reaction is typically carried out in the presence of a coupling reagent such as dicyclohexyl carbodiimide (DCC), benzotriazol-1-yl-oxy-tris-pyrrolidinophosphonium hexafluorophosphate (PyBop), o-(7-azabenzotriazol-1-yl)-N,N,N',N'-tetramethyluronium hexafluorophosphate (HATU), o-(1H-benzotriazol-1-yl)-N,N,N',N'-tetramethyluronium hexafluorophosphate (HBTU) or 1-ethyl-3-(3'-dimethylamino)carbodiimide hydrochloride salt (EDCI), in the presence or absence of hydroxybenzotriazole (HOBt) or N,N-dimethylaminopyridine (DMAP), in the presence of a base such as triethylamine or N,N-diisopropyl ethylamine. The reaction can be carried out in a solvent such as dichloromethane or N,N-dimethylformamide at room temperature for several hours (Montalbetti, C. A. G. N. et al., *Tetrahedron* 61 (2005) 10827).

Scheme 3

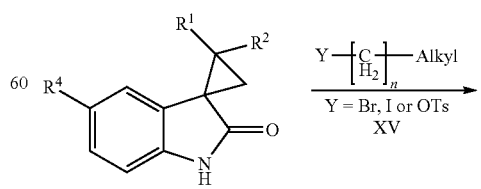

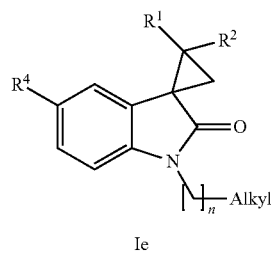

Ie

The compounds of formula Ie can be prepared according to Scheme 3. Alkylation of IV with the alkyl halide XV by using a base such as NaH, $K_2CO_3$ or $Cs_2CO_3$ in organic solvent such as THF or DMF at room temperature for several hours affords the formula of Ie.

Scheme 4

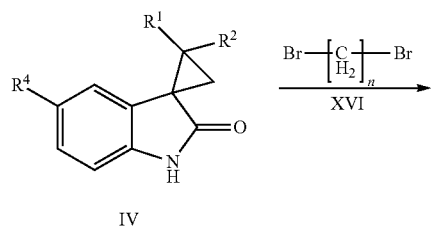

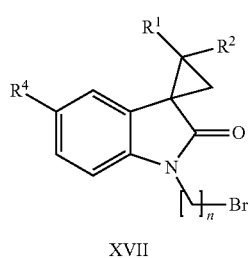

XVII

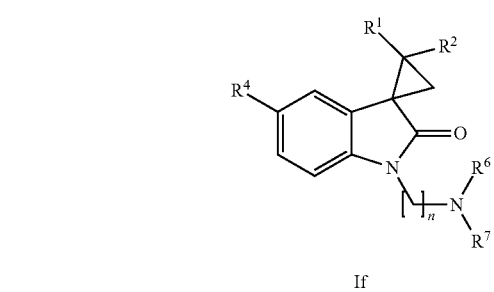

If

The compounds of formula If can be prepared according to Scheme 4. Alkylation of IV with the bromide XVI by using a base such as NaH, $K_2CO_3$ or $Cs_2CO_3$ in organic solvent such as THF or DMF at room temperature for several hours affords the bromide XVII. If can be obtained by treating XVII with amine VIII under basic condition such as NaH, $K_2CO_3$ or $Cs_2CO_3$ in organic solvent such as THF or DMF at room temperature.

Scheme 5

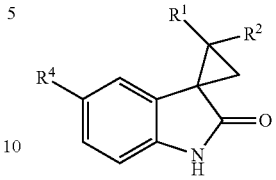 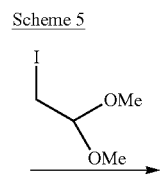

IV

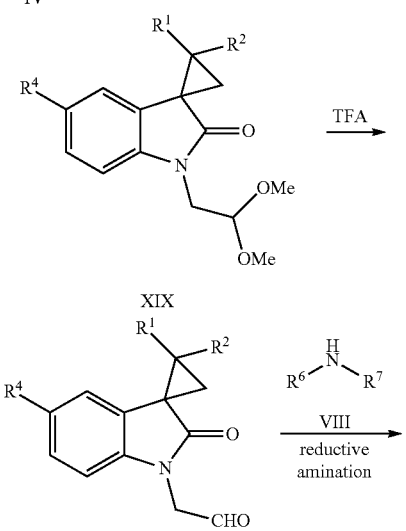

Ig

The compounds of formula Ig can be prepared according to Scheme 5.

The alkylation between IV and the XVIII affords the intermediate XIX, which can be treated with TFA to give aldehyde XX. Amines Ig can be prepared by reductive amination between XX and different amines VIII.

In the first step outlined in Scheme 5, alkylation between IV and the iodide XVIII can be carried out by using bases such as NaH, $K_2CO_3$ or $Cs_2CO_3$ in organic solvents such as THF, DMF at room temperature for several hours.

In the second step outlined in Scheme 5, deprotection of XIX with TFA can be carried out in solvent such as DCM or THF at room temperature for several hours.

Reductive amination of XX with different amines VIII can be carried out in organic solvents such as DCM, THF by using reducing reagents such as $NaBH_4$ or $NaHB(OAc)_3$ at room temperature to afford formula Ig.

Scheme 6

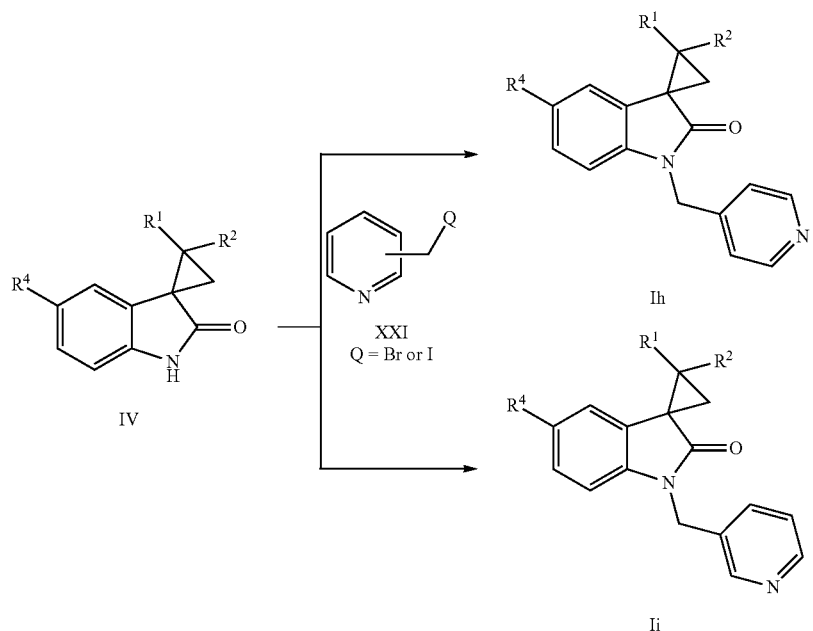

The compounds of formula Ih and Ii can be prepared according to Scheme 6. Ih and Ii can be obtained by alkylation of IV with XXI by using bases such as NaH, $K_2CO_3$ or $Cs_2CO_3$ in organic solvents such as THF or DMF at room temperature for several hours.

Scheme 7

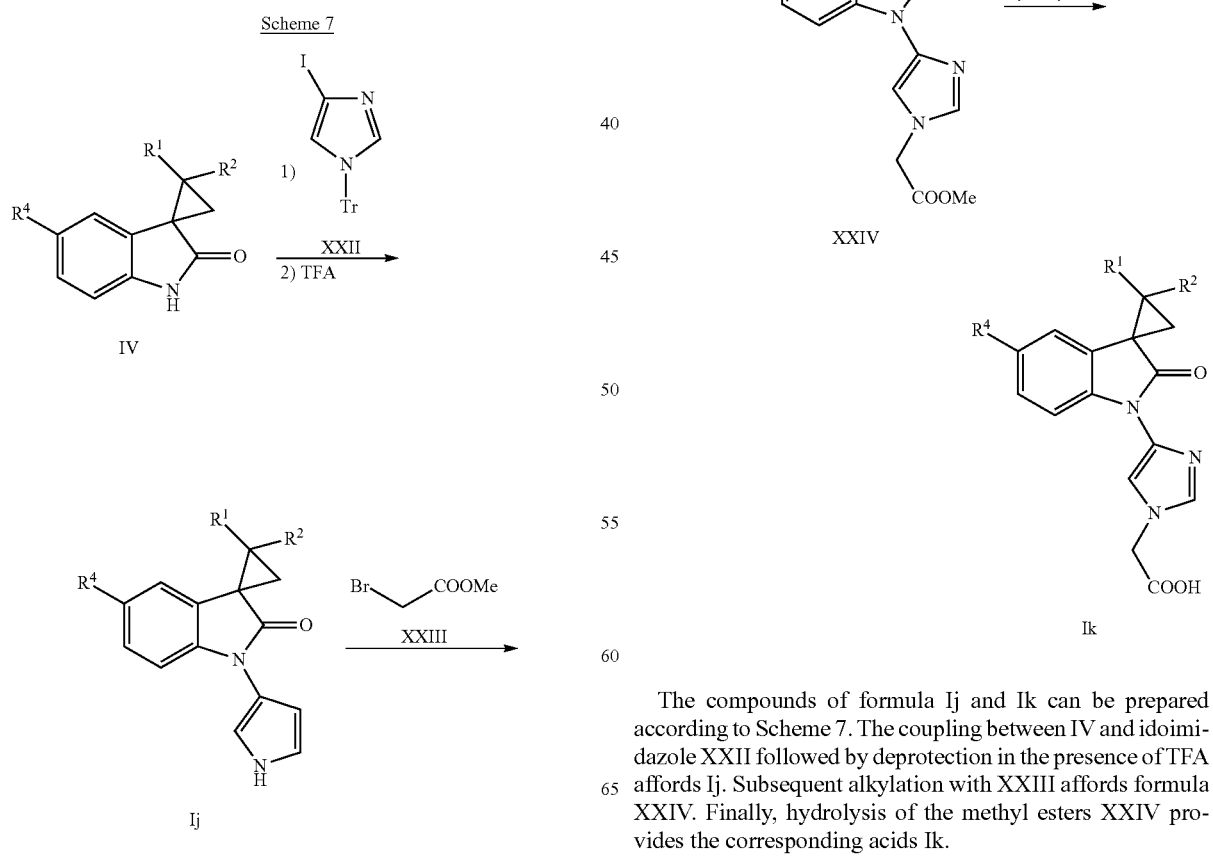

The compounds of formula Ij and Ik can be prepared according to Scheme 7. The coupling between IV and idoimidazole XXII followed by deprotection in the presence of TFA affords Ij. Subsequent alkylation with XXIII affords formula XXIV. Finally, hydrolysis of the methyl esters XXIV provides the corresponding acids Ik.

In the first step outlined in Scheme 7, the coupling reaction can be carried out in the presence of a copper source such as copper(I) iodide (CuI), in combination with a ligand such as 2,2'-bipyridine, proline, N,N'-dimethyl glycine or ethylene glycol, in the presence of a suitable base such as triethylamine, sodium carbonate, potassium carbonate, cesium carbonate, sodium methoxide, sodium tert-butoxide, potassium tert-butoxide, sodium hydride or 1,8-diazabicyclo[5.4.0]undec-7-ene (DBU). The reaction can be carried out in a suitable solvent like acetonitrile, dichloromethane, tetrahydrofuran, toluene, benzene, 1,4-dioxane, N,N-dimethylformamide, dimethyl sulfoxide or N-methylpyrrolidinone at a temperature between 100° C. and 180° C. for 15 to 60 minutes under microwave irradiation. Alternatively, the reactions can be carried out without the use of a microwave at a raised temperature such as 80° C. for a longer reaction time (Ley, S. V. et al., *Angew. Chem. Int. Ed.* 42 (2003) 5400). Deprotection can be carried out in organic solvent such as DCM or THF with TFA at room temperature to afford stereoisomers Ij.

The alkylation of 1j with bromide XXIII is carried out by using bases such as NaH, K$_2$CO$_3$ or Cs$_2$CO$_3$ in organic solvents such as THF or DMF at room temperature for several hours.

Finally, hydrolysis of the methyl ester gives the compounds Ik. The hydrolysis can be carried out in the presence of an aqueous inorganic base such as lithium hydroxide, sodium hydroxide, or potassium hydroxide in a solvent such as methanol, 1,4-dioxane or tetrahydrofuran at room temperature for several hours.

Scheme 8

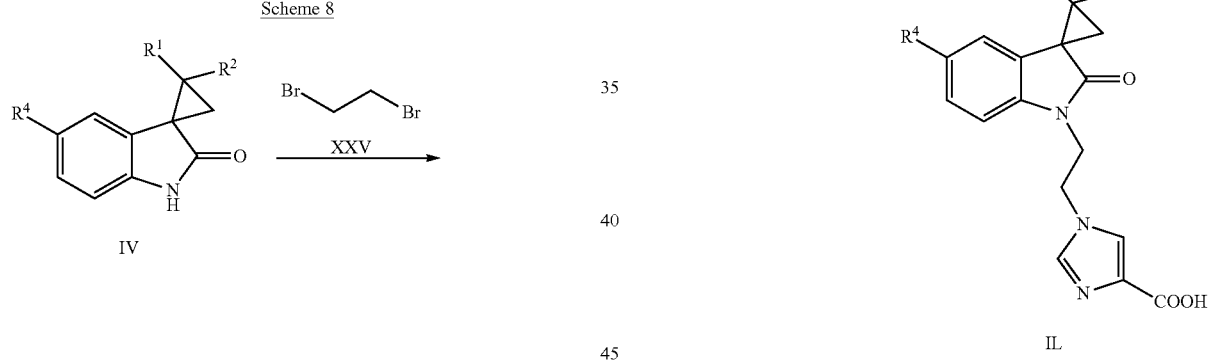

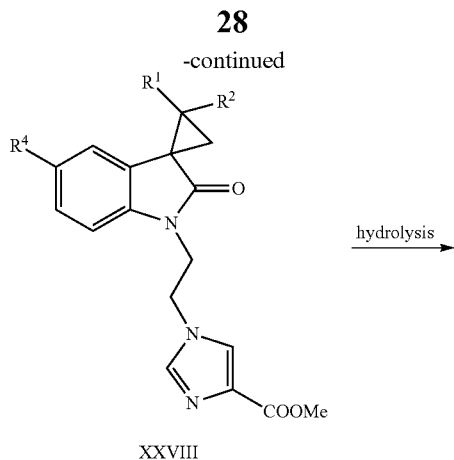

The compounds of formula IL can be prepared according to Scheme 8. The alkylation between IV and ethylene dibromide XXV affords the bromides XXVI. Nucleophilic substitution reaction between the ester XXVII and the bromide XXVI gives the methyl esters XXVIII. Hydrolysis of the methyl esters furnishes the corresponding acids IL.

In the first step outlined in Scheme 8, the condensation between IV and ethylene dibromide can be carried out in organic solvents (THF or DMF) by using bases such as NaH, K$_2$CO$_3$ or Cs$_2$CO$_3$ at room temperature for several hours.

In the second step outlined in Scheme 8, the substitution reaction between the imidazole XXVII and XXVI can be carried out in organic solvents such as THF or DMF by using bases such as NaH, K$_2$CO$_3$ or Cs$_2$CO$_3$ at room temperature for several hours.

Finally, hydrolysis of the methyl ester XXVII can afford the compounds IL. The reaction can be carried out in the presence of an aqueous inorganic bases such as lithium hydroxide, sodium hydroxide, or potassium hydroxide in a solvent such as methanol, 1,4-dioxane or tetrahydrofuran at room temperature for several hours.

The invention also relates to a process for the preparation of a compound of formula (I) comprising one of the following steps:

a) the reaction of a compound of formula (A)

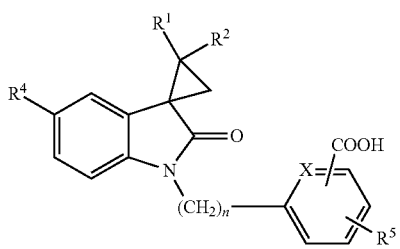
(A)

in the presence of $R^6R^7NH$ and a coupling agent;

b) the reaction of a compound of formula (B)

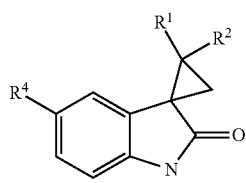
(B)

in the presence of Y—$CH_2$—R and a base;

c) the reaction of a compound of formula (C)

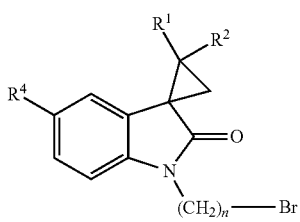
(C)

in the presence of $R^6R^7NH$ and a base;

d) the reaction of a compound of formula (D)

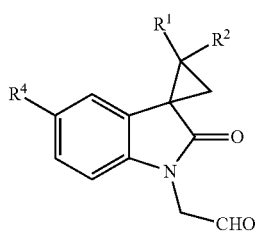
(D)

in the presence of $R^6R^7NH$ and a reducing agent;

e) the reaction of a compound of formula (E)

(E)

in the presence of a compound of formula (E1)

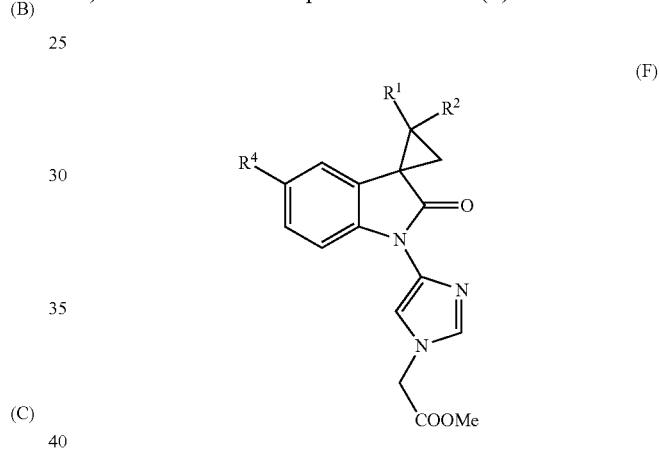
(E1)

and in the presence of a base;

f) the reaction of a compound of formula (F)

(F)

in the presence of a base;

g) the reaction of a compound of formula (G)

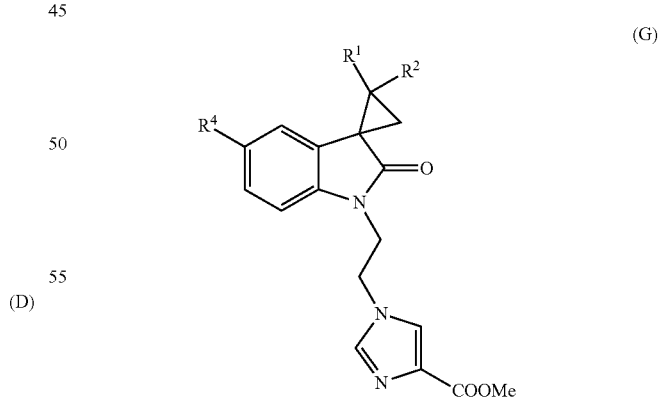
(G)

in the presence of a base;

wherein $R^1$, $R^2$, $R^3$, $R^4$ and n are defined as in any one of claims 1 to 8; wherein $R^5$ is hydrogen, halogen, oxo-oxazolidinyl or oxo-imidazolidinyl; wherein $R^6$ and $R^7$ are independently selected from hydrogen, alkyl, cycloalkyl, alkylsulfonyl, cycloalkylsulfonyl, aminoalkyl and aminocycloalkyl; wherein X is carbon or nitrogen; wherein Y is Br, I, or OTs; wherein Q is Br or I; and wherein R is alkyl.

In step (a), the coupling reagent is for example dicyclohexyl carbodiimide (DCC), benzotriazol-1-yl-oxy-tris-pyrrolidinophosphonium hexafluorophosphate (PyBop), o-(7-azabenzotriazol-1-yl)-N,N,N',N'-tetramethyluronium hexafluorophosphate (HATU), o-(1H-benzotriazol-1-yl)-N, N,N',N'-tetramethyluronium hexafluorophosphate (HBTU) or 1-ethyl-3-(3'-dimethylamino)carbodiimide hydrochloride salt (EDCI). Step (a) can be carried out in the presence or absence of hydroxybenzotriazole (HOBt) or N,N-dimethylaminopyridine (DMAP), in the presence of a base such as triethylamine or N,N-diisopropyl ethylamine. The reaction of step (a) can be carried out in a solvent such as dichloromethane or N,N-dimethylformamide. The reaction can be carried out at room temperature for several hours.

In step (b), the base can be for example NaH, $K_2CO_3$ or $Cs_2CO_3$. Step (b) can be carried out in an organic solvent such as THF or DMF. This reaction can proceed at room temperature for several hours.

In step (c), the base can be for example NaH, $K_2CO_3$ or $Cs_2CO_3$. Step (c) can be done in an organic solvent such as THF or DMF. The reaction can proceed at room temperature.

The reaction of step (d) can be carried out in an organic solvent such as DCM or THF. The reducing agent of step (d) can be for example $NaBH_4$ or $NaHB(OAc)_3$. The reaction can proceed at room temperature.

In step (e), the base can be for example NaH, $K_2CO_3$ or $Cs_2CO_3$. The solvent can be an organic solvent such as THF or DMF. The reaction can be carried out at room temperature for several hours.

In step (f), the base can be an inorganic base such as lithium hydroxide, sodium hydroxide or potassium hydroxide. The solvent of step (f) can be for example methanol, 1,4-dioxane or tetrahydrofuran. The reaction can proceed at room temperature for several hours.

In step (g), the base can be an inorganic base such as lithium hydroxide, sodium hydroxide or potassium hydroxide. The solvent of step (g) can be for example methanol, 1,4-dioxane or tetrahydrofuran. The reaction can proceed at room temperature for several hours.

The invention also relates to a compound of formula (I) for use as therapeutically active substance.

The invention also relates to a pharmaceutical composition comprising a compound of formula (I) and a therapeutically inert carrier.

The use of a compound of formula (I) for the preparation of medicaments useful in the treatment or prophylaxis diseases that are related to AMPK regulation is an object of the invention.

The invention relates in particular to the use of a compound of formula (I) for the preparation of a medicament for the treatment or prophylaxis of obesity, hyperglycemia, dyslipidemia, type 1 or type 2 diabetes, in particular type 2 diabetes.

Said medicaments, e.g. in the form of pharmaceutical preparations, can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions with an effective amount of a compound as defined above.

The above-mentioned pharmaceutical composition can be obtained by processing the compounds according to this invention with pharmaceutically inert inorganic or organic carriers. Lactose, corn starch or derivatives thereof, talc, stearic acids or its salts can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical composition can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage depends on various factors such as manner of administration, species, age and/or individual state of health. The doses to be administered daily are about 5-400 mg/kg, preferably about 10-100 mg/kg, and can be taken singly or distributed over several administrations.

A compound of formula (I) when manufactured according to the above process is also an object of the invention.

Furthermore, the invention also relates to a method for the treatment or prophylaxis of diseases that are related to AMPK regulation, which method comprises administering an effective amount of a compound of formula (I).

The invention further relates to a method for the treatment or prophylaxis of obesity, hyperglycemia, dyslipidemia, type 1 or type 2 diabetes, in particular type 2 diabetes, which method comprises administering an effective amount of a compound of formula (I).

Furthermore, the invention also relates to a compound of formula (I) for the preparation of medicaments useful in the treatment of cancer that are related to AMPK regulation and provides a method for the treatment of cancer that are related to AMPK regulation.

The invention will be illustrated by the following examples which have no limiting character. Unless explicitly otherwise stated, all reactions, reaction conditions, abbreviations and symbols have the meanings well known to a person of ordinary skill in organic chemistry.

EXAMPLES

Material and Instrumentation

Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 μm, OBD™ 30×100 mm) column or SunFire™ Perp $C_{18}$ (5 m, OBD™ 30×100 mm) column.

LC/MS spectra were obtained using a MicroMass Plateform LC (Waters™ alliance 2795-ZQ2000). Standard LC/MS conditions were as follows (running time 6 min):
Acidic condition: A: 0.1% formic acid in $H_2O$; B: 0.1% formic acid in acetonitrile;
Basic condition: A: 0.01% $NH_3.H_2O$ in $H_2O$; B: acetonitrile;
Neutral condition: A: $H_2O$; B: acetonitrile.

Example 1

(1R,2S) and (1S,2R)-3-((2-(4-chlorophenyl)-2'-oxospiro[cyclopropane-1,3'-indoline]-1'-yl)methyl)benzoic acid

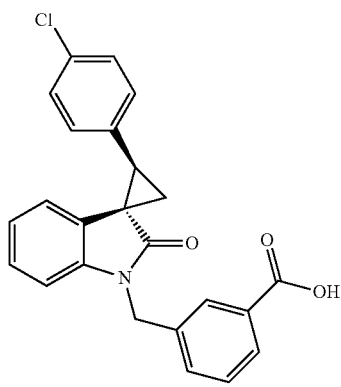

Synthesis of (Z)-3-(4-chloro-benzylidene)-1,3-dihydro-indol-2-one

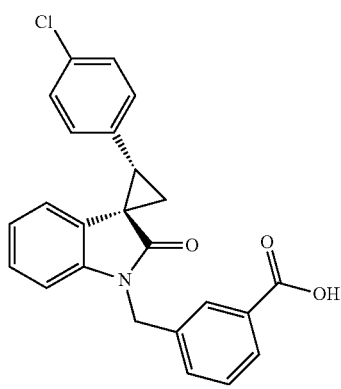

Oxindole (0.13 g, 1 mmol), 4-chlorobenzaldehyde (0.17 g, 1.2 mmol) were mixed in alcohol; then pyrrolidine (0.17 ml, 2 mmol) was added. The mixture was refluxed for 3 hours. The formed precipitates was collected by filtration and washed with alcohol twice to give the title compound as yellow powder (0.24 g, 92%). LC/MS m/e calcd. for $C_{15}H_{10}ClNO$ 255, observed (M+H)$^+$: 256.1.

Synthesis of (1R,2S) and (1S,2R)-2-(4-chlorophenyl)spiro[cyclopropane-1,3'-indolin]-2'-one

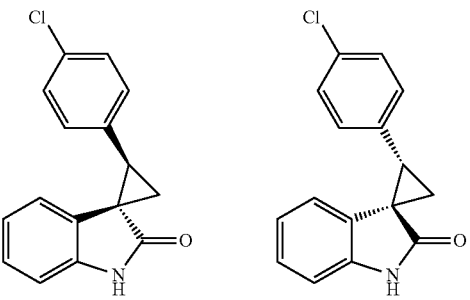 [SMILES: O=C1Nc2ccccc2[C@@]12C[C@@H]2c1ccc(Cl)cc1 ; O=C1Nc2ccccc2[C@]12C[C@H]2c1ccc(Cl)cc1]

A solution of dimethylsulfoxoniummethylide was prepared as under argon from a 60% NaH mineral oil dispersion (88 mg, 2.2 mmol), trimethylsulfoxoniumiodide (484 mg, 2.2 mmol), and DMSO (10 mL). After 20 min, a solution of (Z)-3-(4-chloro-benzylidene)-1,3-dihydro-indol-2-one (510 mg, 2 mmol) in THF (5 mL) was added dropwise over 20 min. After stirring for 1 hour at room temperature and another 1 hour at 50° C., the solution was poured into ice-cold water (20 mL) and extracted with ether (3×20 mL). The combined ethereal extracts were washed with brine, dried and evaporated to an oil, which was purified by flash column chromatography (gradient elution, 15-25% ethyl acetate in petroleum ether to give the title compound as white solid (333 mg, 62%). LC/MS m/e calcd. for $C_{16}H_{12}ClNO$ 269, observed (M+H)$^+$:270.5. $^1$H NMR (400 MHz, DMSO-d$_6$) δppm 1.95 (dd, J=8.97, 4.67 Hz, 1 H) 2.21 (dd, J=7.83, 4.80 Hz, 1 H) 3.04 (t, J=8.46 Hz, 1 H) 6.08 (d, J=7.58 Hz, 1 H) 6.59-6.71 (m, 1 H) 6.87 (d, J=7.58 Hz, 1 H) 7.01-7.10 (m, 1 H) 7.27-7.33 (m, 2 H) 7.33-7.40 (m, 2 H) 10.59 (s, 1 H).

Synthesis of racemic (1R,2S) and (1S,2R)-methyl-3-(((2-(4-chlorophenyl)-2'-oxospiro[cyclo-propane-1,3'-indoline]-1'-yl)methyl)benzoate

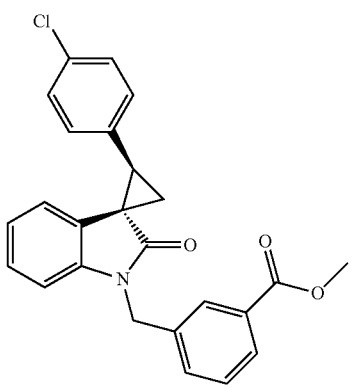

-continued

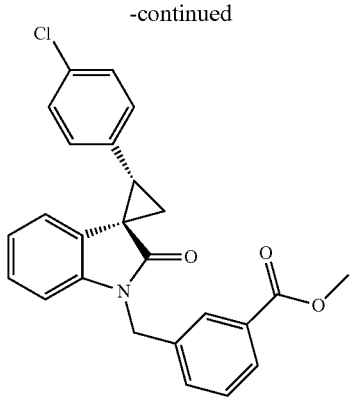

(1R,2S) and (1S,2R)-2-(4-chlorophenyl)spiro[cyclopropane-1,3'-indolin]-2'-one (2.1 mmol), methyl-(3-bromomethyl)-benzoate (725 mg, 3.15 mmol) and Cs$_2$CO$_3$ (1.369 g, 4.2 mmol) were mixed in anhydrous DMF and stirred at room temperature for 14 h. HPLC monitored the reaction finished. The solvent was removed under reduced pressure. The residue was purified by flash column chromatography (gradient elution, 15-25% ethyl acetate in petroleum ether) to give the title compound as white powder (586 mg, 67%). LC/MS m/e calcd. for C$_{25}$H$_{20}$ClNO$_3$: 417, observed (M+H)$^+$: 418.1 $^1$H NMR (400 MHz, DMSO-d$_6$) δppm 2.12 (dd, J=9.09, 4.80 Hz, 1H) 2.38 (dd, J=8.08, 5.05 Hz, 1H) 3.22 (t, J=8.59 Hz, 1H) 3.85 (s, 3H) 5.11 (s, 2H) 6.16 (d, J=7.33 Hz, 1 H) 6.72 (t, J=7.58 Hz, 1H) 6.94 (d, J=7.83 Hz, 1H) 7.07 (t, J=7.71 Hz, 1H) 7.30-7.41 (m, 4H) 7.52 (t, J=7.71 Hz, 1 H) 7.59-7.66 (m, 1 H) 7.88 (d, J=7.58 Hz, 1 H) 7.92 (s, 1H).

Synthesis of (1R,2S) and (1S,2R)-3-((2-(4-chlorophenyl)-2'-oxospiro[cyclopropane-1,3'-indoline]-1'-yl)methyl)benzoic acid

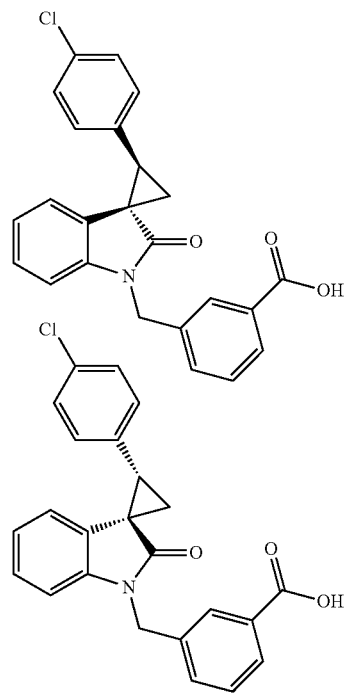

(1R,2S) and (1S,2R)-methyl-3-(((2-(4-chlorophenyl)-2'-oxospiro[cyclo-propane-1,3'-indoline]-1'-yl)methyl)benzoate (48 mg) was dissolved in 1 mL of methanol; then 0.1 mL of water was added followed by lithium hydroxide (10 mg). The mixture was stirred for 14 hours at room temperature. The solvent was removed under reduced pressure. The residue was dissolved in 2 mL of DMF and purified by preparative HPLC to give the title compound as white powder (10 mg). LC/MS m/e calcd. for C$_{24}$H$_{18}$ClNO$_3$: 403, observed (M+H)$^+$: 404.1 $^1$H NMR (400 MHz, DMSO-d$_6$) δppm 2.12 (dd, J=9.09, 4.80 Hz, 1H) 2.40 (dd, J=7.96, 4.93 Hz, 1H) 3.19-3.24 (m, 1 H) 5.10 (s, 2H) 6.17 (d, J=7.33 Hz, 1H) 6.72 (t, J=7.58 Hz, 1H) 6.95 (d, J=7.83 Hz, 1H) 7.08 (t, J=7.83 Hz, 1H) 7.30-7.41 (m, 4H) 7.50 (t, J=7.71 Hz, 1H) 7.60 (d, J=7.58 Hz, 1H) 7.82-7.89 (m, 2 H) 13.04 (s, 1H).

Example 2

(1R,2R) and (1S,2S)-3-((2-(4-chlorophenyl)-2'-oxospiro[cyclopropane-1,3'-indoline]-1'-yl)methyl)benzoic acid

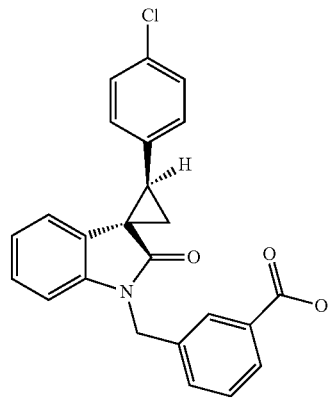

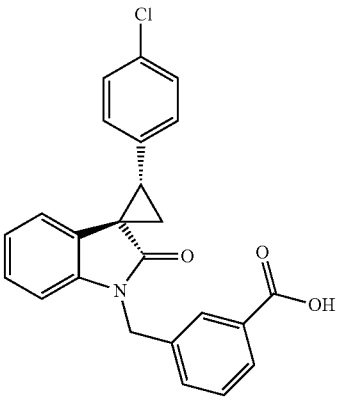

The title compound was prepared in analogy to Example 1 starting from methyl-(3-bromomethyl)-benzoate (commercially available), (1R,2S) and (1S,2R)-2-(4-chlorophenyl)spiro[cyclopropane-1,3'-indolin]-2'-one prepared as in Scheme 1. LC/MS m/e calcd. for C$_{24}$H$_{18}$ClNO$_3$: 403.1, observed (M+H)$^+$: 404.2. $^1$H NMR (400 MHz, DMSO-d$_6$) δ ppm 2.26 (dd, J=8.97, 4.67 Hz, 1 H) 2.34 (dd, J=8.34, 4.80 Hz, 1 H) 3.34 (t, J=8.72 Hz, 1 H) 4.84-5.01 (m, 2 H) 6.95 (d, J=7.58 Hz, 1 H) 7.04 (t, J=7.45 Hz, 1 H) 7.14-7.23 (m, 2 H) 7.29-7.37 (m, 4 H) 7.41-7.52 (m, 2 H) 7.76 (s, 1 H) 7.83 (d, J=7.58 Hz, 1 H) 13.05 (br. s., 1 H).

Example 3

(1S,2R) and (1R,2S)-3-((2-(3-chlorophenyl)-2'-oxospiro[cyclopropane-1,3'-indoline]-1'-yl)methyl)benzoic acid

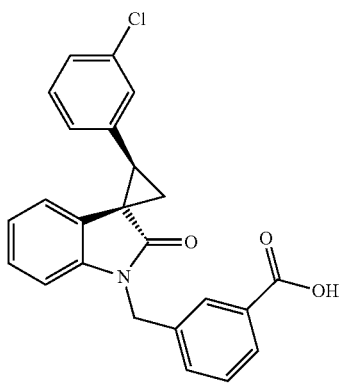

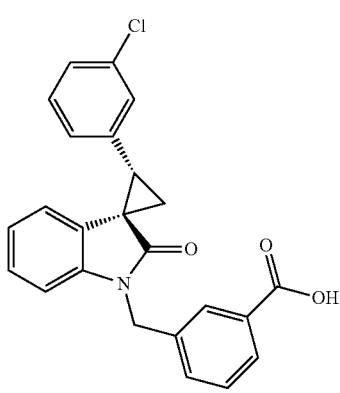

The title compound was prepared in analogy to Example 1 starting from methyl-(3-bromomethyl)-benzoate (commercially available), (1R,2S) and (1S,2R)-2-(4-chlorophenyl)spiro[cyclopropane-1,3'-indolin]-2'-one prepared as in Scheme 1. LC/MS m/e calcd. for $C_{24}H_{18}ClNO_3$: 403.1, observed (M+H)$^+$: 404.1. $^1$H NMR (400 MHz, DMSO-d$_6$) δ ppm 2.10 (dd, J=9.22, 4.93 Hz, 1 H) 2.45 (dd, J=7.96, 4.93 Hz, 1 H) 3.19-3.25 (m, 1 H) 5.10 (s, 2 H) 6.17 (d, J=7.33 Hz, 1 H) 6.71 (t, J=7.58 Hz, 1 H) 6.95 (d, J=7.83 Hz, 1 H) 7.08 (t, J=7.71 Hz, 1 H) 7.27 (s, 1 H) 7.30-7.37 (m, 2 H) 7.42 (s, 1 H) 7.50 (t, J=7.58 Hz, 1 H) 7.60 (d, J=7.83 Hz, 1H) 7.80-7.99 (m, 2 H).

Example 4

(1R,2R) and (1S,2S)-((2-(4-(methylsulfonyl)phenyl)-2'-oxospiro[cyclopropane-1,3'-indoline]-1'-yl)methyl)benzoic acid

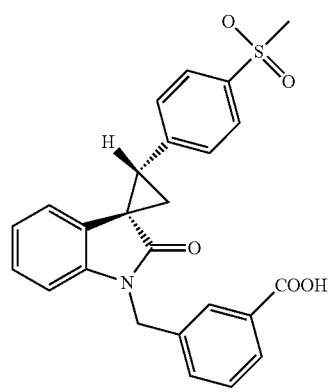

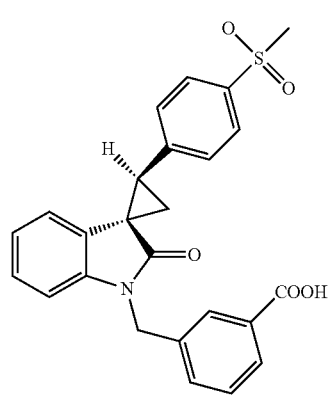

The title compound was prepared in analogy to Example 1 starting from methyl-(3-bromomethyl)-benzoate (commercially available), (1R,2R) and (1S,2S)-2-(4-(methylsulfonyl)phenyl)spiro[cyclopropane-1,3'-indolin]-2'-one prepared as in Scheme 1. LC/MS m/e calcd. for $C_{25}H_{21}NO_5S$: 447, observed (M+H)$^+$: 448.2. $^1$H NMR (400 MHz, DMSO-d$_6$) δ ppm 2.34 (dd, J=8.84, 4.80 Hz, 1 H) 2.42 (dd, J=8.34, 4.80 Hz, 1 H) 3.47 (t, J=8.72 Hz, 1 H) 4.86-5.02 (m, 2 H) 6.97 (d, J=7.83 Hz, 1 H) 7.06 (t, J=7.58 Hz, 1 H) 7.17-7.27 (m, 2H) 7.43-7.52 (m, 2 H) 7.60 (d, J=8.34 Hz, 2 H) 7.75 (s, 1 H) 7.80-7.88 (m, 3 H).

Example 5

(1S,2R) and (1R,2S)-3-((2-(4-cyanophenyl)-2'-oxospiro[cyclopropane-1,3'-indoline]-1'-yl)methyl)benzoic acid

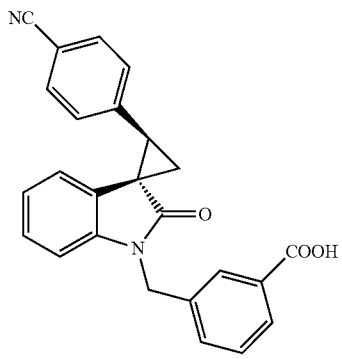

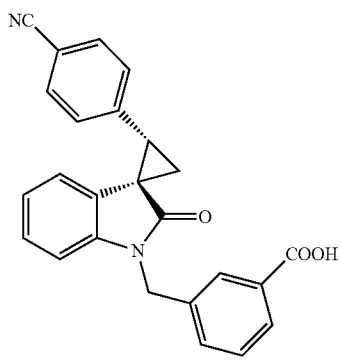

The title compound was prepared in analogy to Example 1 starting from methyl-(3-bromomethyl)-benzoate (commercially available), (1S,2R) and (1R,2S)-2-(4-cyanophenyl) spiro[cyclopropane-1,3'-indolin]-2'-one prepared as in Scheme 1. LC/MS m/e calcd. for $C_{25}H_{18}N_2O_3$: 394, observed (M+H)$^+$: 395.1. $^1$H NMR (400 MHz, DMSO-d$_6$) δppm 2.16 (dd, J=8.84, 5.05 Hz, 1 H) 2.45-2.50 (m, 1 H) 3.26-3.33 (m, 1H) 5.10 (s, 1 H) 6.18 (d, J=7.58 Hz, 1 H) 6.71 (t, J=7.58 Hz, 1 H) 6.95 (d, J=7.83 Hz, 1 H) 7.08 (t, J=7.83 Hz, 1 H) 7.47-7.57 (m, 3 H) 7.60 (d, J=7.83 Hz, 1 H) 7.79 (d, J=8.08 Hz, 2 H) 7.83-7.89 (m, 2 H) 13.04 (br. s., 1H).

Example 6

(1S,2R) and (1R,2S)-2-chloro-5-((2-(4-chlorophenyl)-2'-oxospiro[cyclopropane-1,3'-indoline]-1'-yl)methyl)benzoic acid

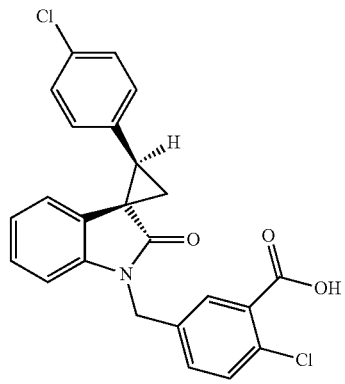

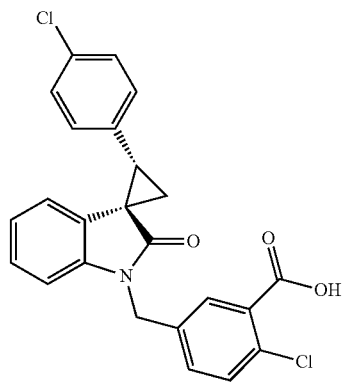

The title compound was prepared in analogy to Example 1 starting from 5-Bromomethyl-2-chloro-benzoic acid methyl ester (commercially available), (1S,2R) and (1R,2S)-2-(4-chlorophenyl)spiro[cyclopropane-1,3'-indolin]-2'-one prepared as in Scheme 1. LC/MS m/e calcd. for $C_{24}H_{17}Cl_2NO_3$: 437, observed (M+H)$^+$: 438.3. $^1$H NMR (400 MHz, DMSO-d$_6$) δppm 2.07-2.15 (m, 1 H) 2.39 (dd, J=7.83, 5.05 Hz, 1H) 3.20 (t, J=8.72 Hz, 1H) 5.06 (s, 2 H) 6.16 (d, J=7.58 Hz, 1 H)

6.73 (t, J=7.58 Hz, 1 H) 6.97 (d, J=7.83 Hz, 1 H) 7.09 (t, J=7.83 Hz, 1 H) 7.28-7.40 (m, 4 H) 7.43-7.57 (m, 2 H) 7.73 (s, 1 H).

Example 7

(1S,2R) and (1R,2S)-3-((2-(4-(methylsulfonyl)phenyl)-2'-oxospiro[cyclopropane-1,3'-indoline]-1'-yl)methyl)benzoic acid

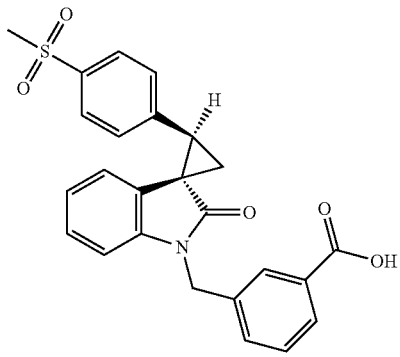

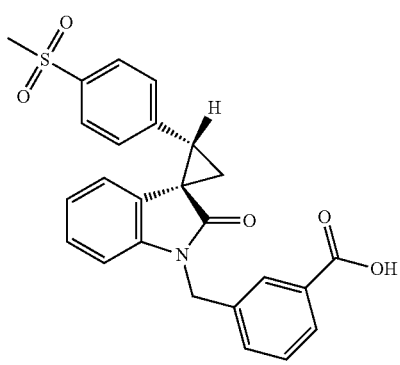

The title compound was prepared in analogy to Example 1 starting from methyl-(3-bromomethyl)-benzoate (commercially available), (1R,2S) and (1S,2R)-2-(4-(methylsulfonyl)phenyl)spiro[cyclopropane-1,3'-indolin]-2'-one prepared as in Scheme 1. LC/MS m/e calcd. for $C_{25}H_{21}NO_5S$: 447, observed (M+H)$^+$: 448.2. $^1$H NMR (400 MHz, DMSO-d$_6$) δ ppm 2.18 (dd, J=9.09, 5.05 Hz, 1 H) 2.51-2.55 (m, 1 H) 3.20 (s, 3H) 3.32 (t, J=8.59 Hz, 1 H) 5.06-5.17 (m, 2 H) 6.22 (d, J=7.33 Hz, 1 H) 6.71 (t, J=7.45 Hz, 1 H) 6.95 (d, J=7.58 Hz, 1H) 7.08 (t, J=7.83 Hz, 1 H) 7.51 (t, J=7.83 Hz, 1 H) 7.62 (d, J=8.59 Hz, 3 H) 7.84-7.90 (m, 4H) 13.06 (br.s., 1 H).

Example 8

(1S,2R) and (1R,2S)-3-((2-(2-fluorophenyl)-2'-oxospiro[cyclopropane-1,3'-indoline]-1'-yl)methyl)benzoic acid

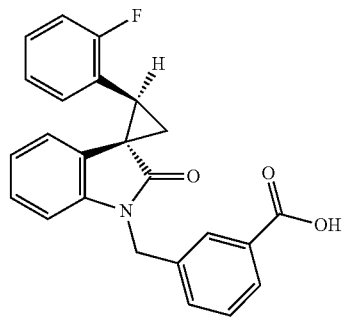

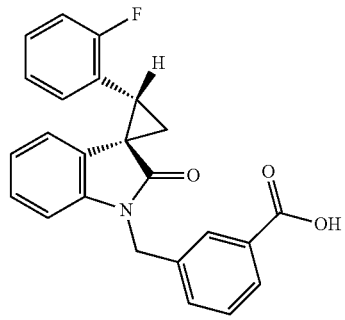

The title compound was prepared in analogy to Example 1 starting from methyl-(3-bromomethyl)-benzoate (commercially available), (1R,2S) and (1S,2R)-2-(2-fluorophenyl)spiro[cyclopropane-1,3'-indolin]-2'-one prepared as in Scheme 1. LC/MS m/e calcd. for $C_{24}H_{18}FNO_3$: 387, observed (M+H)$^+$: 388.2. $^1$H NMR (400 MHz, MeOD-d$_4$) δ ppm 2.22-2.34 (m, 2 H) 3.21 (t, J=8.59 Hz, 1 H) 5.06-5.28 (m, 2 H) 6.02 (d, J=7.58 Hz, 1 H) 6.62-6.71 (m, 1 H) 6.88 (d, J=7.83 Hz, 1 H) 6.91-6.99 (m, 1 H) 7.01-7.16 (m, 1H) 7.25 (t, J=7.07 Hz, 1 H) 7.29-7.37 (m, 1 H) 7.46 (t, J=7.71 Hz, 1 H) 7.50-7.57 (m, 2 H) 7.96 (d, J=7.83 Hz, 1H) 8.05 (s, 1 H).

Example 9

(1S,2S) and (1R,2R)-3-((2-(2-fluorophenyl)-2'-oxospiro[cyclopropane-1,3'-indoline]-1'-yl)methyl)benzoic acid

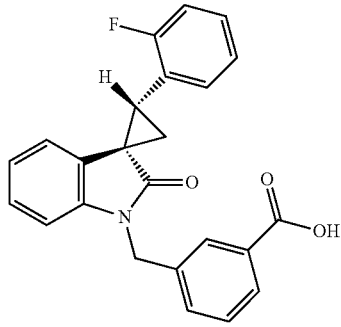

J=7.83 Hz, 1 H) 6.99-7.25 (m, 5 H) 7.23-7.34 (m, 1H) 7.38-7.51 (m, 3 H) 7.88-8.02 (m, 2 H).

Example 10

(1S,2R) and (1R,2S)-3-((2-(3-fluorophenyl)-2'-oxospiro[cyclopropane-1,3'-indoline]-1'-yl)methyl)benzoic acid

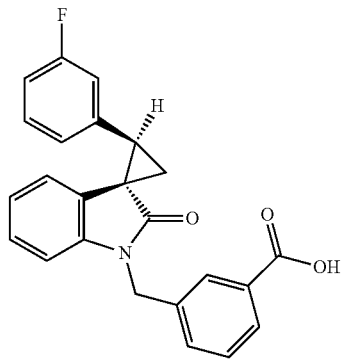

The title compound was prepared in analogy to Example 1 starting from methyl-(3-bromomethyl)-benzoate (commercially available), (1R,2R) and (1S,2S)-2-(2-fluorophenyl) spiro[cyclopropane-1,3'-indolin]-2'-one prepared as in Scheme 1. LC/MS m/e calcd. for $C_{24}H_{18}FNO_3$: 387, observed (M+H)$^+$: 388.1. $^1$H NMR (400 MHz, MeOD-d$_4$) δ ppm 2.29 (dd, J=8.97, 4.67 Hz, 1 H) 2.35 (dd, J=8.34, 4.80 Hz, 1 H) 3.22 (t, J=8.72 Hz, 1 H) 4.89-5.12 (m, 2 H) 6.92 (d, The title compound was prepared in analogy to Example 1 starting from methyl-(3-bromomethyl)-benzoate (commercially available), (1R,2S) and (1S,2R)-2-(3-fluorophenyl) spiro[cyclopropane-1,3'-indolin]-2'-one prepared as in Scheme 1. LC/MS m/e calcd. for $C_{24}H_{18}FNO_3$: 387, observed (M+H)$^+$: 388.1. $^1$H NMR (400 MHz, DMSO-d$_6$) δ ppm 2.07-2.15 (m, 1 H) 2.45 (dd, J=8.08, 5.05 Hz, 1 H) 3.24 (t, J=8.46 Hz, 1 H) 5.10 (s, 2 H) 6.20 (d, J=7.58 Hz, 1 H) 6.95 (d, J=7.83 Hz, 1 H) 7.04-7.18 (m, 3 H) 7.22 (d, J=10.11 Hz, 1

H) 7.31-7.40 (m, 1 H) 7.50 (t, J=7.71 Hz, 1 H) 7.60 (d, J=7.83 Hz, 1 H) 7.81-7.91 (m, 2H) 13.05 (s, 1H).

Example 11

(1S,2S) and (1R,2R)-3-((2-(3-fluorophenyl)-2'-oxospiro[cyclopropane-1,3'-indoline]-1'-yl)methyl)benzoic acid

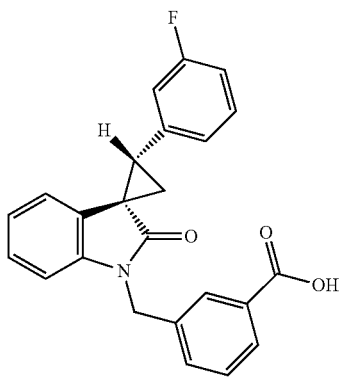

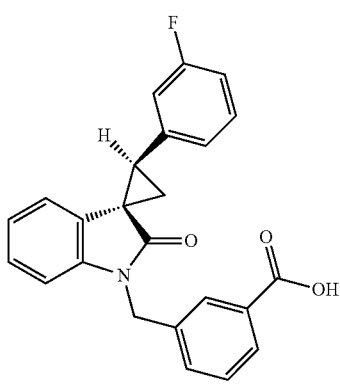

The title compound was prepared in analogy to Example 1 starting from methyl-(3-bromomethyl)-benzoate (commercially available), (1R,2R) and (1S,2S)-2-(3-fluorophenyl)spiro[cyclopropane-1,3'-indolin]-2'-one prepared as in Scheme 1. LC/MS m/e calcd. for $C_{24}H_{15}FNO_3$: 387, observed (M+H)$^+$: 388.2. $^1$H NMR (400 MHz, DMSO-d$_6$) δ ppm 2.27 (dd, J=8.84, 4.80 Hz, 1 H) 2.38 (dd, J=8.34, 4.80 Hz, 1 H) 3.36-3.41 (m, 1 H) 4.88-4.99 (m, 2 H) 6.96 (d, J=7.83 Hz, 1 H) 7.04 (t, J=7.83 Hz, 2 H) 7.12-7.24 (m, 4H) 7.27 7.34 (m, 1 H) 7.41-7.48 (m, 2 H) 7.78 (s, 1 H) 7.82 (d, J=6.57 Hz, 1 H).

Example 12

(1S,2S) and (1R,2R)-3-((2'-oxo-2-(2-(trifluoromethyl)phenyl)-spiro[cyclopropane-1,3'-indoline]-1'-yl)methyl)benzoic acid

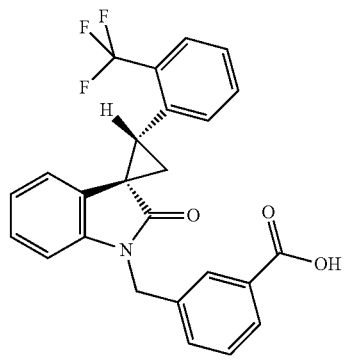

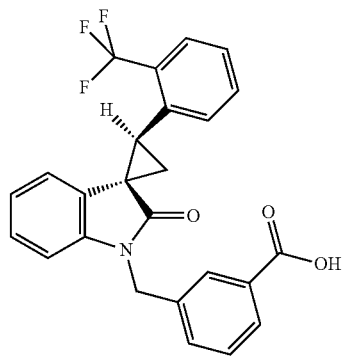

The title compound was prepared in analogy to Example 1 starting from methyl-(2-(trifluoromethyl)phenyl)-benzoate (commercially available), (1R,2R) and (1S,2S)-2-(3-fluorophenyl)spiro[cyclopropane-1,3'-indolin]-2'-one prepared as in Scheme 1. LC/MS m/e calcd. for $C_{25}H_{18}F_3NO_3$: 437, observed (M+H)$^+$: 438.1. $^1$H NMR (400 MHz, DMSO-d$_6$) δ ppm 2.16 (dd, J=9.09, 5.05 Hz, 1 H) 2.57 (dd, J=7.58, 5.56 Hz, 1 H) 3.27 (t, J=8.21 Hz, 1 H) 4.91-5.26 (m, 2 H) 6.07 (d, J=7.33 Hz, 1 H) 6.63 (t, J=7.20 Hz, 1 H) 6.93 (d, J=7.83 Hz, 1H) 7.05 (t, J=7.33 Hz, 1 H) 7.44-7.55 (m, 2 H) 7.60 (t, J=7.96 Hz, 2 H) 7.76 (t, J=7.58 Hz, 1 H) 7.87 (t, J=8.84 Hz, 2 H) 7.96 (s, 1 H) 12.99 (br. s., 1 H).

Example 13

(1S,2R) and (1R,2S)-((5'-chloro-2-(4-chlorophenyl)-2'-oxospiro[cyclopropane-1,3'-indoline]-1'-yl)methyl)benzoic acid

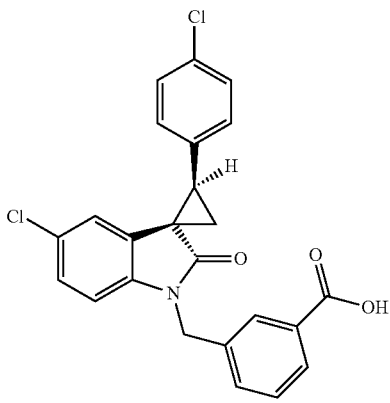

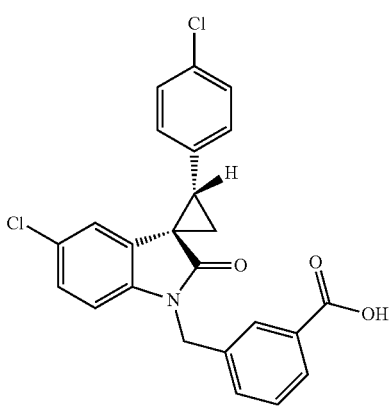

The title compound was prepared in analogy to Example 1 starting from methyl-(3-bromomethyl)-benzoate (commercially available), (1R,2S) and (1S,2R)-5'-chloro-2-(4-chlorophenyl)spiro[cyclopropane-1,3'-indolin]-2'-one prepared as in Scheme 1. LC/MS m/e calcd. for $C_{24}H_{17}Cl_2NO_3$: 437, observed (M+H)$^+$: 438.2. $^1$H NMR (400 MHz, DMSO-d$_6$) δ ppm 2.16 (dd, J=9.09, 5.05 Hz, 1 H) 2.56 (dd, J=8.08, 5.05 Hz, 1 H) 3.26 (t, J=8.59 Hz, 1 H) 5.10 (s, 2 H) 6.19 (d, J=2.02 Hz, 1 H) 6.96 (d, J=8.34 Hz, 1 H) 7.14 (dd, J=8.34, 2.02 Hz, 1H) 7.39 (q, J=8.42 Hz, 4 H) 7.50 (t, J=7.58 Hz, 1 H) 7.54-7.61 (m, 1 H) 7.81-7.89 (m, 2 H) 13.07 (s, 1 H).

Example 14

(1R,2R) and (1S,2S)-3-((5'-chloro-2-(4-chlorophenyl)-2'-oxospiro[cyclopropane-1,3'-indoline]-1'-yl)methyl)benzoic acid

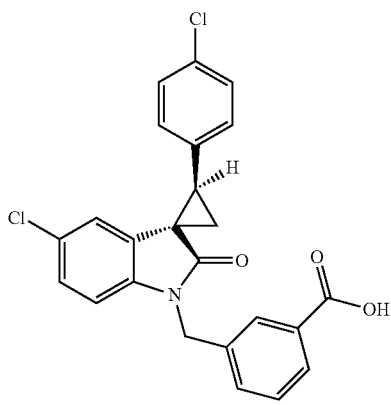

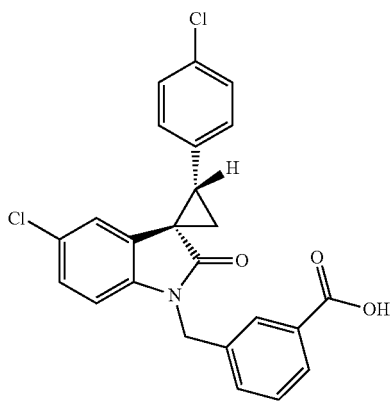

The title compound was prepared in analogy to Example 1 starting from methyl-(3-bromomethyl)-benzoate (commercially available), (1R,2R) and (1S,2S)-5'-chloro-2-(4-chlorophenyl)spiro[cyclopropane-1,3'-indolin]-2'-one prepared as in Scheme 1. LC/MS m/e calcd. for $C_{24}H_{17}Cl_2NO_3$: 437, observed (M+H)$^+$: 438.1. $^1$H NMR (400 MHz, MeOD-d$_4$) δ ppm 2.32 (dd, J=9.09, 5.05 Hz, 1 H) 2.44 (dd, J=8.59, 5.05 Hz, 1 H) 3.37 (t, J=8.97 Hz, 1 H) 4.82-5.10 (m, 4 H) 6.87 (d, J=8.08 Hz, 1 H) 7.19 (d, J=2.02 Hz, 1 H) 7.21 (s, 1 H) 7.31 (s, 4H) 7.39-7.49 (m, 2 H) 7.85 (s, 1 H) 7.93 (d, J=7.07 Hz, 1 H).

Example 15

(1R,2R) and (1S,2S)-3-((5'-bromo-2-(4-chlorophenyl)-2'-oxospiro[cyclopropane-1,3'-indoline]-1'-yl)methyl)benzoic acid

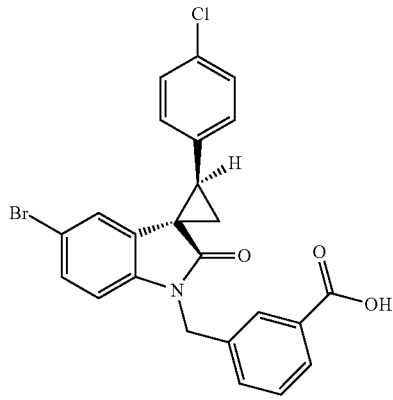

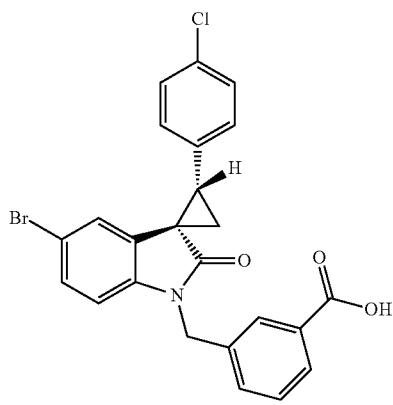

The title compound was prepared in analogy to Example 1 starting from methyl-(3-bromomethyl)-benzoate (commercially available), (1R,2R) and (1S,2S)-5'-bromo-2-(4-chlorophenyl)spiro[cyclopropane-1,3'-indolin]-2'-one prepared as in Scheme 1. LC/MS m/e calcd. for $C_{24}H_{17}BrClNO_3$: 481, observed (M+H)$^+$: 482.1. $^1$H NMR (400 MHz, MeOD-d$_4$) δ ppm 2.25-2.37 (m, 2 H) 3.34-3.40 (m, 1 H) 5.05-5.21 (m, 2 H) 6.19 (d, J=1.77 Hz, 1 H) 6.83 (d, J=8.34 Hz, 1 H) 7.20-7.30 (m, 3 H) 7.32-7.40 (m, 2 H) 7.50 (t, J=7.71 Hz, 1 H) 7.60 (d, J=7.83 Hz, 1 H) 7.90-8.01 (m, 2 H).

Example 16

(1S,2R) and (1R,2S)-3-((5'-bromo-2-(4-chlorophenyl)-2'-oxospiro[cyclopropane-1,3'-indoline]-1'-yl)methyl)benzoic acid

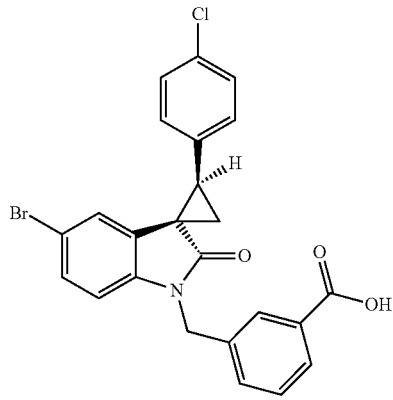

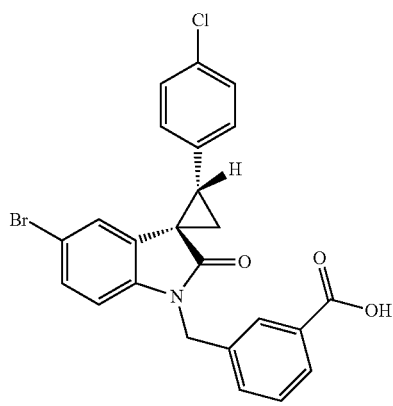

The title compound was prepared in analogy to Example 1 starting from methyl-(3-bromomethyl)-benzoate (commercially available) and racemic (1S,2R) and (1R,2S)-5'-bromo-2-(4-chlorophenyl)spiro[cyclopropane-1,3'-indolin]-2'-one prepared as in Scheme 1. LC/MS m/e calcd. for $C_{24}H_{17}BrClNO_3$: 481, observed (M+H)$^+$: 482.1. $^1$H NMR (400 MHz, MeOD-d$_4$) δppm 2.33 (dd, J=8.97, 4.93 Hz, 1 H) 2.44 (dd, J=8.84, 5.05 Hz, 1 H) 3.38 (t, J=8.84 Hz, 1 H) 4.85

(s, 1 H) 5.05 (d, J=16.17 Hz, 1 H) 6.81-6.86 (m, 1 H) 7.31 (s, 4 H) 7.33-7.38 (m, 2 H) 7.41-7.49 (m, 2 H) 7.85 (s, 1 H) 7.94 (d, J=7.07 Hz, 1 H).

Example 17

(1S,2S) and (1R,2R)-3-((2-(4-cyanophenyl)-2'-oxospiro[cyclopropane-1,3'-indoline]-1'-yl)methyl)benzoic acid

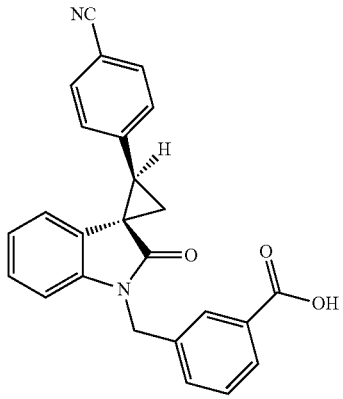

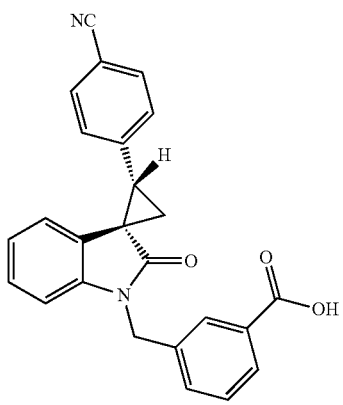

The title compound was prepared in analogy to Example 1 starting from methyl-(3-bromomethyl)-benzoate (commercially available), (1S,2S) and (1R,2R)-2-(4-cyanophenyl)spiro[cyclopropane-1,3'-indolin]-2'-one prepared as in Scheme 1. LC/MS m/e calcd. for $C_{25}H_{18}N_2O_3$: 394, observed (M+H)⁺: 394.2. ¹H NMR (400 MHz, CDCl₃) δppm 2.23 (dd, J=8.84, 5.05 Hz, 1 H) 2.52 (dd, J=8.59, 5.31 Hz, 1 H) 3.23 (t, J=8.72 Hz, 1 H) 4.95 (d, J=61.89 Hz, 2 H) 6.82 (d, J=7.83 Hz, 1 H) 7.00-7.05 (m, 1 H) 7.10 (t, J=7.45 Hz, 1 H) 7.19-7.26 (m, 1 H) 7.43 (s, 2 H) 7.49 (d, J=8.08 Hz, 2 H) 7.65 (d, J=8.08 Hz, 2 H) 7.96 (s, 1H) 8.02 (d, J=7.33 Hz, 1 H).

Example 18

(1S,2R) and (1R,2S)-3-((2-(3-methoxyphenyl)-2'-oxospiro[cyclopropane-1,3'-indoline]-1'-yl)methyl)benzoic acid

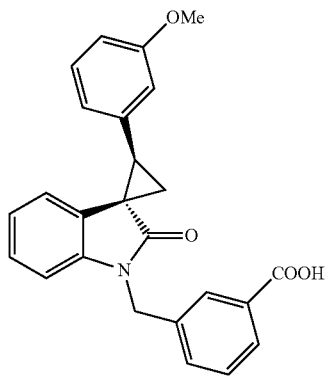

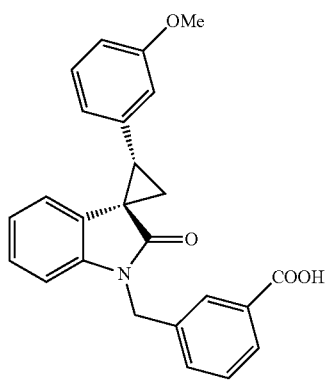

The title compound was prepared in analogy to Example 1 starting from methyl-(3-bromomethyl)-benzoate (commercially available), (1R,2S) and (1S,2R)-2-(3-methoxyphenyl)spiro[cyclopropane-1,3'-indolin]-2'-one prepared as in Scheme 1. LC/MS m/e calcd. for $C_{25}H_{21}NO_4$: 399, observed (M+H)⁺: 400.1. ¹H NMR (400 MHz, DMSO-d₆) δppm 2.09 (q, J=4.46 Hz, 1 H) 2.41 (dd, J=8.08, 4.80 Hz, 1 H) 3.20 (t, J=8.84 Hz, 1 H) 3.72 (s, 3 H) 5.10 (s, 2 H) 6.22 (d, J=7.33 Hz, 1 H) 6.70 (t, J=7.58 Hz, 1 H) 6.81-6.89 (m, 3H) 6.94 (d, J=7.83 Hz, 1 H) 7.06 (t, J=7.71 Hz, 1 H) 7.22 (t, J=8.08 Hz, 1

H) 7.50 (t, J=7.58 Hz, 1 H) 7.60 (d, J=7.58 Hz, 1 H) 7.85 (d, J=7.83 Hz, 1 H) 7.89 (s, 1 H) 13.04 (br. s., 1 H).

Example 19

(1S,2S) and (1R,2R)-3-((2-(3-methoxyphenyl)-2'-oxospiro[cyclopropane-1,3'-indoline]-1'-yl)methyl)benzoic acid

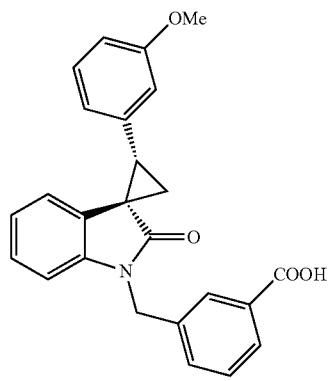

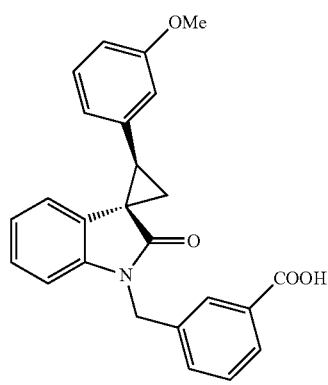

The title compound was prepared in analogy to Example 1 starting from methyl-(3-bromomethyl)-benzoate (commercially available), (1R,2R) and (1S,2S)-2-(3-methoxyphenyl) spiro[cyclopropane-1,3'-indolin]-2'-one prepared as in Scheme 1. LC/MS m/e calcd. for $C_{25}H_{21}NO_4$: 399, observed (M+H)$^+$: 400.2. $^1$H NMR (400 MHz, DMSO-d$_6$) δppm 2.24 (dd, J=9.09, 4.55 Hz, 1 H) 2.34 (dd, J=8.59, 4.55 Hz, 1 H) 3.31 (t, J=8.72 Hz, 1 H) 3.72 (s, 3 H) 4.88-5.02 (m, 2 H) 6.76-6.82 (m, 1 H) 6.85-6.90 (m, 2 H) 6.95 (d, J=7.58 Hz, 1 H) 7.04 (t, J=7.45 Hz, 1 H) 7.19 (t, J=7.96 Hz, 3 H) 7.39-7.49 (m, 2 H) 7.77-7.88 (m, 2 H) 13.02 (br.s., 1 H).

Example 20

(1S,2S) and (1R,2R)-3-((2-(4-methoxyphenyl)-2'-oxospiro[cyclopropane-1,3'-indoline]-1'-yl)methyl)benzoic acid

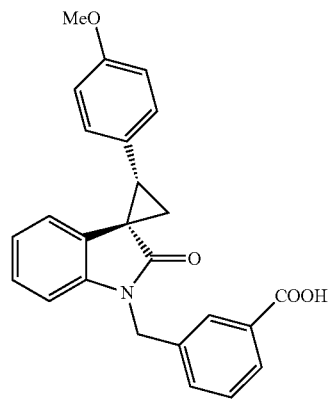

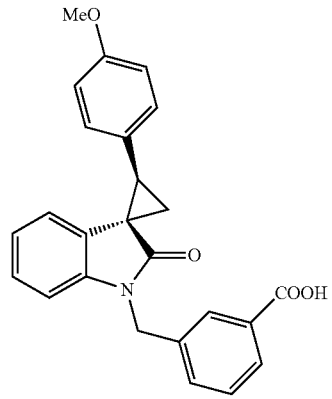

The title compound was prepared in analogy to Example 1 starting from methyl-(3-bromomethyl)-benzoate (commercially available), (1R,2R) and (1S,2S)-2-(4-methoxyphenyl) spiro[cyclopropane-1,3'-indolin]-2'-one prepared as in Scheme 1. LC/MS m/e calcd. for $C_{25}H_{21}NO_4$: 399, observed (M+H)$^+$: 400.1. $^1$H NMR (400 MHz, DMSO-d$_6$) δppm 2.23 (dd, J=8.84, 4.55 Hz, 1 H) 2.30 (dd, J=8.46, 4.67 Hz, 1 H) 3.26 (t, J=8.72 Hz, 1 H) 3.73 (s, 3 H) 4.85-5.02 (m, 2 H) 6.84 (d, J=8.59 Hz, 1 H) 6.93 (d, J=7.58 Hz, 1 H) 7.03 (t, J=7.58 Hz, 1 H) 7.14-7.27 (m, 4 H) 7.42-7.52 (m, 2 H) 7.77 (s, 1 H) 7.82 (d, J=7.07 Hz, 1 H) 13.02 (br. s., 1H).

Example 21

(1S,2R) and (1R,2S)-3-((2-(4-methoxyphenyl)-2'-oxospiro[cyclopropane-1,3'-indoline]-1'-yl)methyl)benzoic acid

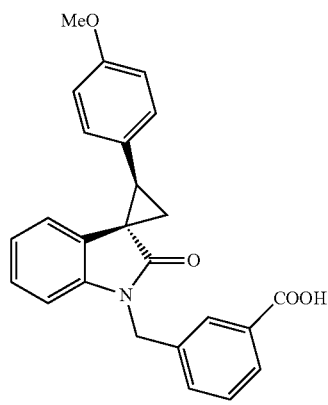

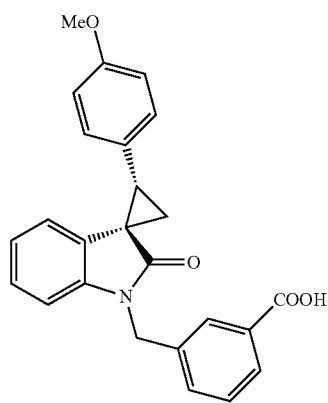

The title compound was prepared in analogy to Example 1 starting from methyl-(3-bromomethyl)-benzoate (commercially available), (1R,2S) and (1S,2R)-2-(4-methoxyphenyl) spiro[cyclopropane-1,3'-indolin]-2'-one prepared as in Scheme 1. LC/MS m/e calcd. for $C_{25}H_{21}NO_4$: 399, observed (M+H)$^+$: 400.1. $^1$H NMR (400 MHz, DMSO-d$_6$) δppm 2.05-2.14 (m, 1 H) 2.33 (dd, J=7.96, 4.67 Hz, 1 H) 3.17 (t, J=8.46 Hz, 1 H) 3.73 (s, 3 H) 5.10 (d, J=2.27 Hz, 2 H) 6.15 (d, J=7.33 Hz, 1 H) 6.69 (t, J=7.20 Hz, 1 H) 6.87 (d, J=8.59 Hz, 1 H) 6.93 (d, J=7.58 Hz, 1 H) 7.05 (t, J=7.33 Hz, 1 H) 7.22 (d, J=8.59 Hz, 2 H) 7.50 (t, J=7.58 Hz, 1 H) 7.60 (d, J=7.83 Hz, 1 H) 7.84-7.90 (m, 2 H) 13.05 (br. s., 1 H).

Example 22

(1S,2R) and (1R,2S)-3-((2-(4-chlorophenyl)-5'-fluoro-2'-oxospiro[cyclopropane-1,3'-indoline]-1'-yl)methyl)benzoic acid

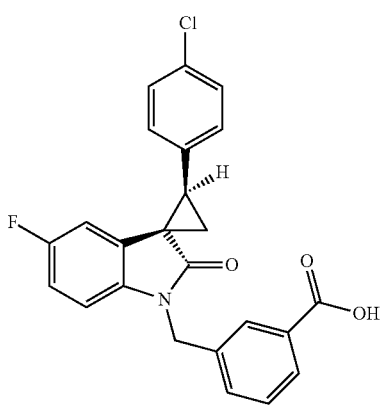

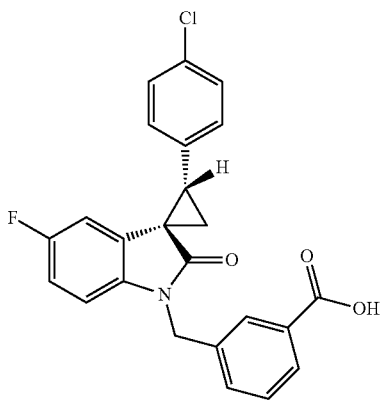

The title compound was prepared in analogy to Example 1 starting from methyl-(3-bromomethyl)-benzoate (commercially available), (1S,2R) and (1R,2S)-2-(4-chlorophenyl)-5'-fluorospiro[cyclopropane-1,3'-indolin]-2'-one prepared as in Scheme 1. LC/MS m/e calcd. for $C_{24}H_{17}ClFNO_3$: 421, observed (M+H)$^+$: 422.1. $^1$H NMR (400 MHz, DMSO-d$_6$) δ ppm 2.17 (dd, J=9.09, 4.80 Hz, 1 H) 2.45-2.50 (m, 1 H) 3.26 (t, J=8.59 Hz, 1 H) 5.03-5.17 (m, 2 H) 5.98-6.05 (m, 1 H)

6.88-6.97 (m, 2 H) 7.38 (q, J=8.59 Hz, 4H) 7.47-7.54 (m, 1 H) 7.55-7.63 (m, 1 H) 7.81-7.91 (m, 2 H) 13.05 (s, 1 H).

Example 23

(1S,2S) and (1R,2R)-3-((2-(4-chlorophenyl)-5'-fluoro-2'-oxospiro[cyclopropane-1,3'-indoline]-1'-yl)methyl)benzoic acid

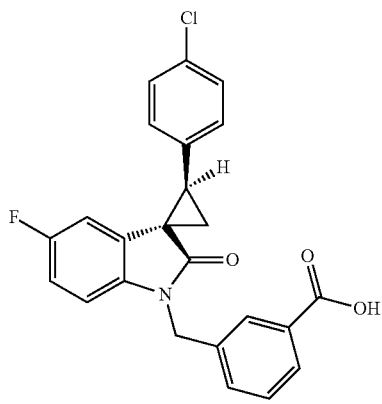

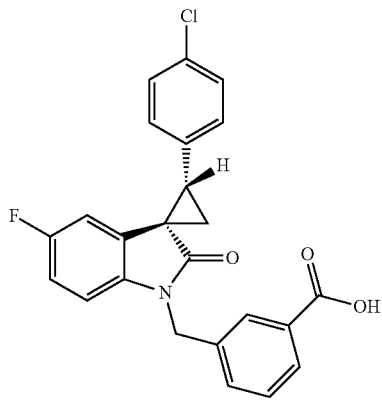

The title compound was prepared in analogy to Example 1 starting from methyl-(3-bromomethyl)-benzoate (commercially available), (1S,2S) and (1R,2R)-2-(4-chlorophenyl)-5'-fluorospiro[cyclopropane-1,3'-indolin]-2'-one prepared as in Scheme 1. LC/MS m/e calcd. for $C_{24}H_{17}ClFNO_3$: 421, observed (M+H)$^+$: 422.1. $^1$H NMR (400 MHz, DMSO-d$_6$) δ ppm 2.28-2.42 (m, 2 H) 3.41 (t, J=8.84 Hz, 1 H) 4.82-5.02 (m, 2 H) 6.86-6.96 (m, 1 H) 6.98-7.07 (m, 1 H) 7.19 (dd, J=8.59, 2.53 Hz, 1 H) 7.34 (s, 4H) 7.41-7.53 (m, 2 H) 7.74 (s, 1 H) 7.83 (d, J=6.82 Hz, 1 H) 13.04 (br. s., 1 H).

Example 24

(1S,2R) and (1R,2S)-3-((-2-(4-fluorophenyl)-2'-oxospiro[cyclopropane-1,3'-indoline]-1'-yl)methyl)benzoic acid

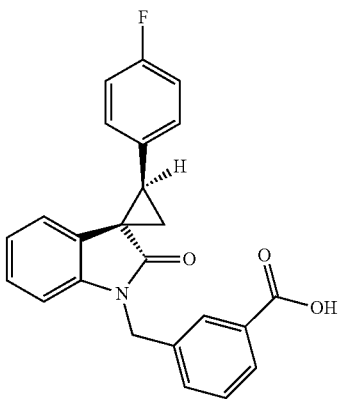

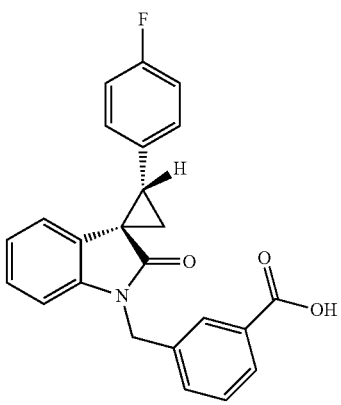

The title compound was prepared in analogy to Example 1 starting from methyl-(3-bromomethyl)-benzoate (commercially available) and racemic (1S,2R)-2-(4-fluorophenyl)spiro[cyclopropane-1,3'-indolin]-2'-one prepared as in Scheme 1. LC/MS m/e calcd. for $C_{24}H_{18}FNO_3$: 421, observed (M+H)$^+$: 422.1. $^1$H NMR (400 MHz, DMSO-d$_6$) δ ppm 2.12 (dd, J=9.09, 4.80 Hz, 1 H) 2.38 (dd, J=7.83, 5.05 Hz, 1 H) 3.21 (t, J=8.59 Hz, 1 H) 5.10 (s, 2 H) 6.12 (d, J=7.58 Hz, 1 H) 6.70 (t, J=7.58 Hz, 1 H) 6.94 (d, J=7.83 Hz, 1 H) 7.07 (t, J=7.71 Hz, 1 H) 7.14 (t, J=8.72 Hz, 2 H) 7.35 (dd, J=8.34, 5.56 Hz, 2 H) 7.50 (t, J=7.58 Hz, 1 H) 7.60 (d, J=7.58 Hz, 1 H) 7.81-7.90 (m, 2 H) 13.03 (br. s., 1 H).

Example 25

(1S,2R) and (1R,2S)-3-((2'-oxo-2-(pyridin-3-yl)spiro[cyclopropane-1,3'-indoline]-1'-yl)methyl)benzoic acid

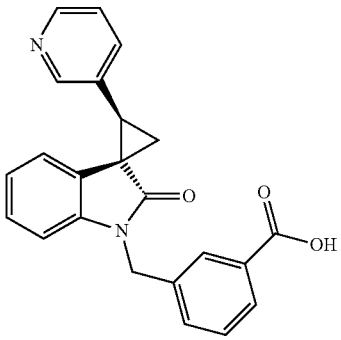

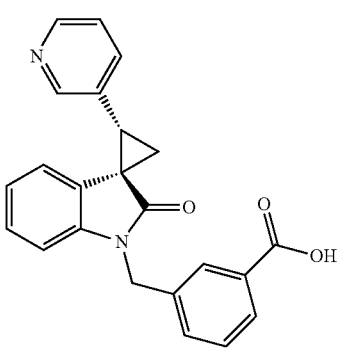

The title compound was prepared in analogy to Example 1 starting from methyl-(3-bromomethyl)-benzoate (commercially available), (1S,2R) and (1R,2S)-2-(pyridin-3-yl)spiro[cyclopropane-1,3'-indolin]-2'-one prepared as were in Scheme 1. LC/MS m/e calcd. for $C_{23}H_{18}N_2O_3$: 370, observed (M+H)$^+$: 371.1. $^1$H NMR (400 MHz, DMSO-d$_6$) δppm 2.18 (dd, J=8.59, 5.05 Hz, 1 H) 3.27 (t, J=8.59 Hz, 2 H) 5.11 (s, 2 H) 6.14 (d, J=7.33 Hz, 1 H) 6.71 (t, J=7.45 Hz, 1 H) 6.97 (d, J=7.58 Hz, 1 H) 7.05-7.15 (m, 1 H) 7.46-7.57 (m, 2 H) 7.61 (d, J=7.33 Hz, 1 H) 7.90 (br. s., 1 H) 7.86 (d, J=7.33 Hz, 2 H) 8.57 (br. s., 1 H) 8.66 (br.s., 1 H).

Example 26

(1S,2S) and (1R,2R)-3-((-2-(4-fluorophenyl)-2'-oxospiro[cyclopropane-1,3'-indoline]-1'-yl)methyl)benzoic acid

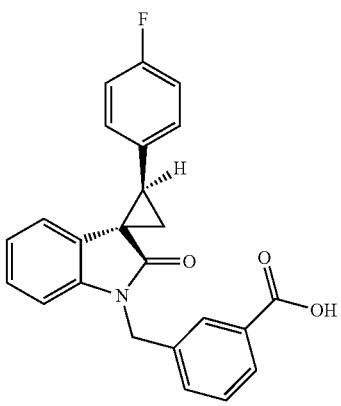

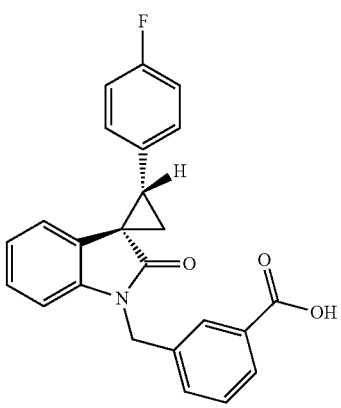

The title compound was prepared in analogy to Example 1 starting from methyl-(3-bromomethyl)-benzoate (commercially available), (1S,2S) and (1R,2R)-2-(4-fluorophenyl)spiro[cyclopropane-1,3'-indolin]-2'-one prepared as in Scheme 1. LC/MS m/e calcd. for $C_{24}H_{18}FNO_3$: 421, observed (M+H)$^+$: 422.1. $^1$H NMR (400 MHz, DMSO-d$_6$) δ ppm 2.26 (dd, J=8.97, 4.67 Hz, 1 H) 2.33 (dd, J=8.34, 4.80 Hz, 1 H) 3.14-3.29 (m, 1 H) 4.83-5.02 (m, 2 H) 6.95 (d, J=7.58 Hz, 1 H) 7.04 (t, J=7.33 Hz, 1 H) 7.10 (t, J=8.72 Hz, 2 H)

7.15-7.23 (m, 2 H) 7.35 (dd, J=8.21, 5.68 Hz, 2 H) 7.40-7.53 (m, 2 H) 7.76 (s, 1H) 7.82 (d, J=7.33 Hz, 1H).

Example 27

(1S,2S) and (1R,2R)-3-((2-(4-chlorophenyl)-2-isopropyl-2'-oxospiro[cyclopropane-1,3'-indoline]-1'-yl)methyl)benzoic acid

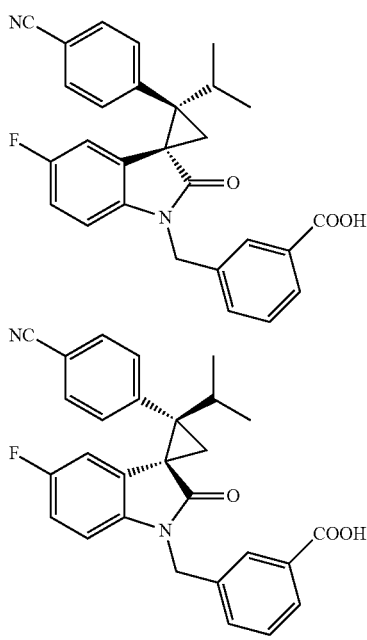

Synthesis of 1-(4-iodo-phenyl)-2-methyl-propan-1-one

A 2.0 M solution of Isopropylmagnesium chloride (10 ml, 20 mmol) was added dropwise (30 min), under nitrogen, to a stirred solution of freshly distilled 4-iodobenzoyl chloride (5.32 g, 20 mmol) and Fe(acac)$_3$ (0.35 g, 1 mmol) in 150 ml of dry THF at room temperature. After addition, the stirring was continued for 10 min at the same temperature. The reaction was quenched by pouring the mixture into dilute hydrochloric acid and extracted with several portions of ether. The combined ether extracts were washed with aq. NaHCO$_3$, water, and dried over Na$_2$SO$_4$. Removal of the organic solvents under vacuum gave the product as colorless oil. And the crude product was used for the next step without further purification.

Synthesis of 1-iodo-4-(2-methyl-1-methylene-propyl)-benzene

To a solution of 7.07 g (20 mmol) of methyltriphenylphosphonium bromide in 50 mL of dry THF at 0° C. were added t-BuLi of (14.7 ml, 1.5 M in hexane) and the solution turned brown. After 1 hour of stirring at 0° C., the crude 1-(4-Iodophenyl)-2-methyl-propan-1-one from the last step in 20 mL of THF were added dropwise and the solution was stirred for 14 hours at room temperature. After cooling to ca. 20° C., 52 mL of water were added and the solution was extracted with dichloromethane (3×50 mL). The organic layer was dried over MgSO$_4$ and the solvent was removed to give the crude title compound as white solid. The product was used for the next step without further purification.

Synthesis of 3-diazo-5-fluoroindolin-2-one

5-Fluoroisatin (64.3 mmol) was suspended in MeOH (300 mL). The suspension was heated to reflux where upon a deep-red solution was obtained. To this hot solution was added tosylhydrazine (64.8 mmol) in one portion. A yellow product started precipitating from the hot mixture. The reaction was allowed to cool to room temperature and the pale tosylhydrazone was filtered off. The product was used for the next step without further purification.

The tosylhydrazone (38.1 mmol) was treated with a solution of NaOH (76.1 mmol) in water 375 mL. The reaction mixture was stirred for 15 hours in a water bath at 50° C. and then allowed to cool to room temperature. The reaction mixture was neutralized by addition of dry ice whereupon diazo compound was precipitated. (5.94 g, 88%).

Synthesis of (1S,2S) and (1R,2R)-5'-fluoro-2-(4-iodophenyl)-2-isopropylspiro[cyclopropane-1,3'-indolin]-2'-one

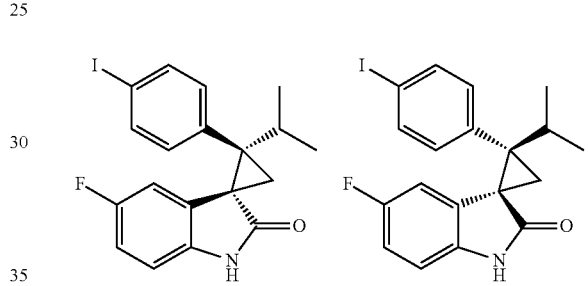

The 3-diazo-5-fluoroindolin-2-one (0.177 g, 1 mmol) and Rh(OAc)$_2$ dimer (2.2 mg) were placed into a Schlenk tube under Argon atmosphere, then dissolved in dry benzene (3 mL). The mixture was heated to 80° C. for 10 minutes. The 1-iodo-4-(3-methylbut-1-en-2-yl)benzene (0.544 g) was dissolved in dry THF (2 mL) and added into the mixture in one portion. The mixture was concentrated in vacuo, the residue was purified by flash column chromatography (Petroleum ether: AcOEt=5:1) to give the title compound as white powder (0.446 g, 53%). LC/MS m/e calcd. for C$_{19}$H$_{17}$FINO: 421, observed (M+H)$^+$: 422.1.

Synthesis of (1S,2S) and (1R,2R)-methyl-3-((-5'-fluoro-2-(4-iodophenyl)-2-isopropyl-2'-oxospiro[cyclopropane-1,3'-indoline]-1'-yl)methyl)benzoate

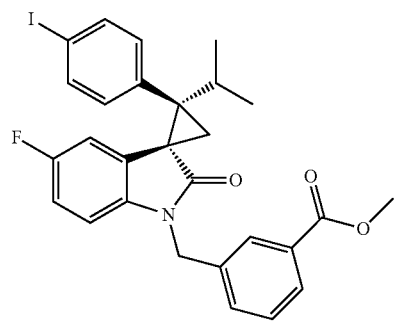

-continued

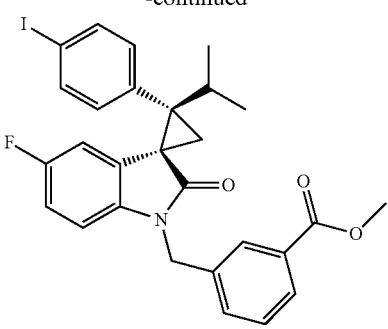

(1S,2S) and (1R,2R)-5'-fluoro-2-(4-iodophenyl)-2-isopropylspiro[cyclopropane-1,3'-indolin]-2'-one (0.88 g, 2.1 mmol), methyl-(3-bromomethyl)-benzoate (725 mg, 3.15 mmol) and $Cs_2CO_3$ (1.37 g, 4.2 mmol) were mixed in anhydrous DMF and stirred at room temperature for 14 hours. The solvent was removed under reduced pressure. The residue was purified by flash column chromatography (gradient elution, 15-25% ethyl acetate in petroleum ether) to give the title product as white solid (1.10 g, 92%). LC/MS m/e calcd. for $C_{28}H_{25}FINO$: 569, observed $(M+H)^+$: 570.1

Synthesis of (1S,2S) and (1R,2R)-methyl-3-((2-(4-cyanophenyl)-5'-fluoro-2-isopropyl-2'-oxospiro[cyclopropane-1,3'-indoline]-1'-yl)methyl)benzoate

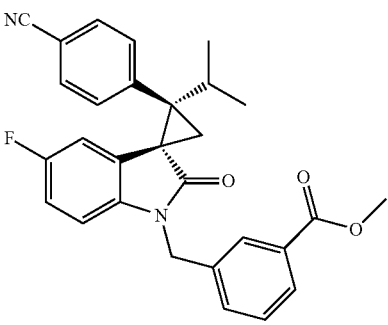

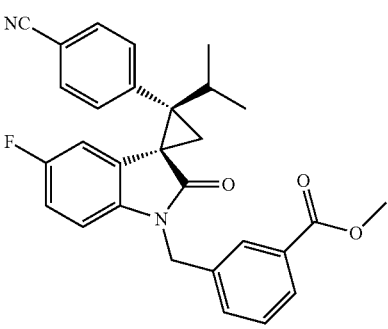

A solution of (1S,2S) and (1R,2R)-methyl-3-((-5'-fluoro-2-(4-iodophenyl)-2-isopropyl-2'-oxospiro[cyclopropane-1,3'-indoline]-1'-yl)methyl)benzoate (1.35 g, 2.4 mmol), NaCN (240 mg, 4.9 mmol), CuI (50 mg, 0.3 mmol) and $Pd(PPh_3)_4$ (140 mg, 0.12 mmol) in tetrahydrofuran (9.0 mL) was stirred at 65° C. for 2 hours. The mixture was cooled to room temperature and extracted with ethyl acetate and washed with brine, dried over anhydrous sodium sulfate, concentrated in vacuo. Purification by flash column chromatography eluting with Hexane/ethyl acetate (8:1 to 4:1) to afford light yellow oil (500 mg, yield 45.5%) LC/MS m/e calcd. for $C_{29}H_{25}FN_2O_3$: 469, observed $(M+H)^+$: 469.2

Synthesis of (1S,2S) and (1R,2R)-3-((2-(4-cyanophenyl)-5'-fluoro-2-isopropyl-2'-oxospiro[cyclopropane-1,3'-indoline]-1'-yl)methyl)benzoic acid

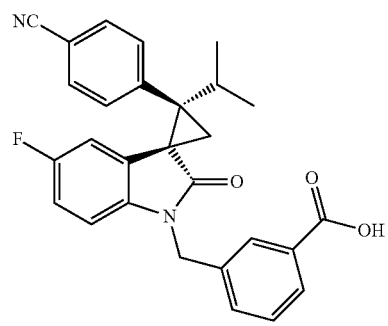

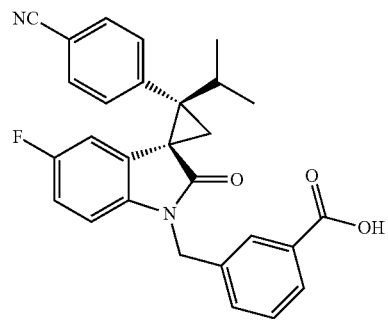

To a solution of (1S,2S) and (1R,2R)-methyl-3-((2-(4-cyanophenyl)-5'-fluoro-2-isopropyl-2'-oxospiro[cyclopropane-1,3'-indoline]-1'-yl)methyl)benzoate (500 mg, 1.1 mmol) in tetrahydrofuran (10 mL) was added 30% sodium hydroxide in water (3 mL) at room temperature and the mixture was stirred at that temperature for 16 hours. The mixture was neutralized with 2 N aqueous hydrochloric acid solution, diluted with ethyl acetate (50 mL), washed with water, dried over anhydrous sodium sulfate and then concentrated in vacuo. Purification by waters automated flash system (column: Xterra 30 mm×100 mm, sample manager 2767, pump 2525, detector: ZQ mass and UV 2487, solvent system: acetonitrile and 0.1% trifluoro-acetic acid in water) afforded the title compound (270 mg, 59.5%) as a white solid: LC/MS m/e calcd. for $C_{28}H_{23}FN_2O_3$: 454, observed $(M+H)^+$: 455.2 $^1H$ NMR (400 MHz, MeOD-$d_4$) δppm 7.97 (s, 1 H), 7.94 (d, J=7.83 Hz, 1 H), 7.85 (dd, J=7.96, 1.64 Hz, 1 H), 7.67 (dd, J=7.96, 1.39 Hz, 1 H), 7.61 (d, J=7.58 Hz, 1 H), 7.48 (q, I=7.83 Hz, 2 H), 6.74-6.86 (m, 3 H), 5.28 (d, I=15.92 Hz, 1 H), 5.17 (dd, J=8.72, 2.40 Hz, 1 H), 4.97 (d, J=16.17 Hz, 1 H), 3.04 (dt, J=13.64, 6.82 Hz, 1 H), 2.23-2.28 (m, 1 H), 2.20-2.23 (m, 1 H), 0.92 (d, J=7.07 Hz, 3 H), 0.81 (d, J=6.82 Hz, 3 H).

Example 28

(1S,2S) and (1R,2R)-3-((2-(4-cyanophenyl)-2-methyl-2'-oxospiro[cyclopropane-1,3'-indoline]-1'-yl)methyl)benzoic acid

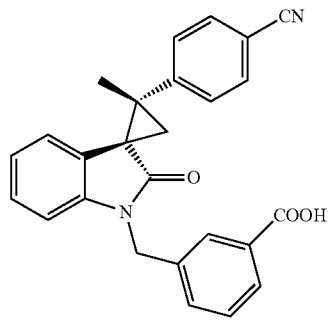

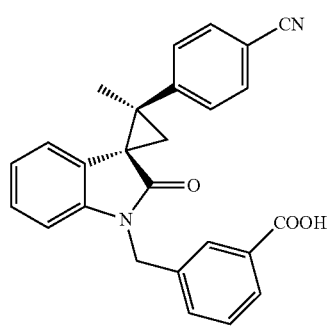

The title compound was prepared in analogy to Example 27 starting from methyl-(3-bromomethyl)-benzoate (commercially available), (1S,2S) and (1R,2R)-4-(2-methyl-2'-oxospiro[cyclopropane-1,3'-indoline]-2-yl)benzonitrile prepared as in Scheme 2. LC/MS m/e calcd. for $C_{26}H_{20}FN_2O_3$: 408, observed (M+H)$^+$: 409.1 $^1$H NMR (400 MHz, MeOD-$d_4$) δppm 7.96 (d, J=7.58 Hz, 1 H) 7.87 (s, 1 H) 7.67 (d, J=8.08 Hz, 2 H) 7.53-7.57 (m, 1 H) 7.48 (t, J=7.71 Hz, 3 H) 7.32 (d, J=7.58 Hz, 1 H) 7.26 (t, J=7.71 Hz, 1 H) 7.11 (t, J=7.58 Hz, 1 H) 6.97 (d, J=7.83 Hz, 1 H) 5.12 (d, J=15.92 Hz, 1 H) 4.75 (d, J=15.92 Hz, 1 H) 2.49 (d, J=5.05 Hz, 1H) 2.10 (d, J=5.05 Hz, 1 H) 1.72 (s, 3 H).

Example 29

(1S,2R) and (1R,2S)-3-((2-(4-cyanophenyl)-2-methyl-2'-oxospiro[cyclopropane-1,3'-indoline]-1'-yl)methyl)benzoic acid

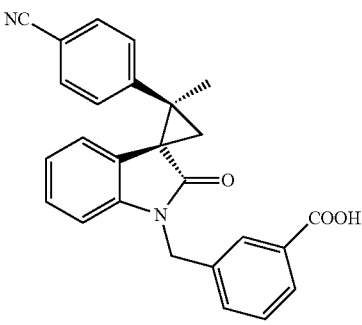

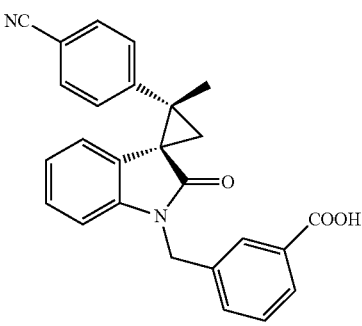

The title compound was prepared in analogy to Example 27 starting from methyl-(3-bromomethyl)-benzoate (commercially available) and racemic (1S,2R) and (1R,2S)-4-(2-methyl-2'-oxospiro[cyclopropane-1,3'-indoline]-2-yl)benzonitrile prepared as in Scheme 2. LC/MS m/e calcd. for $C_{26}H_{20}FN_2O_3$: 408, observed (M+H)$^+$: 409.1 $^1$H NMR (400 MHz, MeOD-$d_4$) δppm 7.91-7.97 (m, 2 H) 7.57 (br. s., 4 H) 7.47 (t, J=7.33 Hz, 2 H) 7.04 (d, J=7.83 Hz, 1 H) 6.86 (d, J=8.08 Hz, 1 H) 6.61 (t, J=7.71 Hz, 1 H) 5.61 (d, J=7.58 Hz, 1 H) 5.18-5.26 (m, 1 H) 5.01-5.10 (m, 1 H) 2.37 (d, J=5.05 Hz, 1 H) 2.19 (d, J=5.05 Hz, 1 H) 1.88 (s, 3 H).

Example 30 and Example 31

(−)-3-((2-(4-chlorophenyl)-2-isopropyl-2'-oxospiro[(trans)-cyclopropane-1,3'-indoline]-1'-yl)methyl)benzoic acid and (+)-3-((2-(4-chlorophenyl)-2-isopropyl-2'-oxospiro[(trans)-cyclopropane-1,3'-indoline]-1'-yl)methyl)benzoic acid

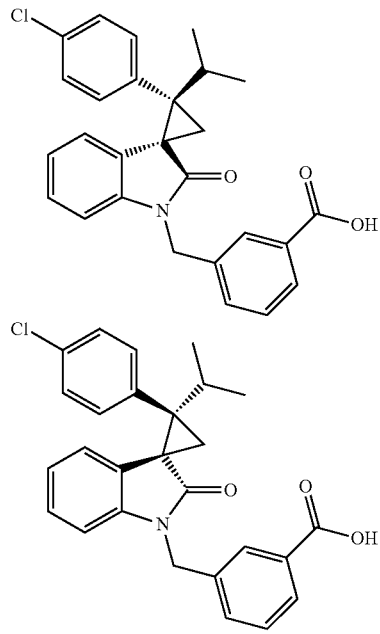

The tile compounds were obtained by separation of the stereoisomers of (1S,2S) and (1R,2R)-3-((2-(4-chlorophenyl)-2-isopropyl-2'-oxospiro[cyclopropane-1,3'-indoline]-1'-yl)methyl)benzoic acid (Example 32) by chiral preparative HPLC (Chiralpak AD) eluting with a mixture of n-heptane/5% isopropanol.

(+)-3-((2-(4-chlorophenyl)-2-isopropyl-2'-oxospiro[(trans)-cyclopropane-1,3'-indoline]-1'-yl)methyl)benzoic acid LC/MS m/e calcd. for $C_{27}H_{24}ClNO_3$: 445, observed (M+H)$^+$: 446.7. $^1$H NMR (400 MHz, MeOD) δ ppm 8.01 (s, 1 H) 7.96 (d, J=7.58 Hz, 1 H) 7.64 (d, J=7.83 Hz, 1 H) 7.46-7.52 (m, 3 H) 7.05-7.12 (m, 1 H) 7.10 (d, J=8.08 Hz, 1 H) 6.89 (d, J=7.83 Hz, 1 H) 6.64 (t, J=7.58 Hz, 1 H) 6.53 (d, J=8.34 Hz, 1 H) 5.50-5.53 (m, 2 H) 5.31 (d, J=15.92 Hz, 1 H) 5.00 (d, J=16.17 Hz, 1 H) 3.01 (dt, J=13.83, 6.85 Hz, 1 H) 2.20 (d, J=4.80 Hz, 1 H) 2.15 (d, J=4.80 Hz, 1 H) 0.94 (d, J=7.07 Hz, 3 H) 0.82 (d, J=6.82 Hz, 3 H). [α]$_D^{25}$=+114 (c=5 mg/mL, CH$_2$Cl$_2$).

(−)-3-((2-(4-chlorophenyl)-2-isopropyl-2'-oxospiro[(trans)-cyclopropane-1,3'-indoline]-1'-yl)methyl)benzoic acid LC/MS m/e calcd. for $C_{27}H_{24}ClNO_3$: 445, observed (M+H)$^+$: 446.5. $^1$H NMR (400 MHz, MeOD) δ ppm 8.01 (s, 1 H) 7.96 (d, J=7.58 Hz, 1 H) 7.64 (d, J=7.83 Hz, 1 H) 7.46-7.52 (m, 3 H) 7.05-7.12 (m, 1 H) 7.10 (d, J=8.08 Hz, 1 H) 6.89 (d, J=7.83 Hz, 1 H) 6.64 (t, J=7.58 Hz, 1 H) 6.53 (d, J=8.34 Hz, 1 H) 5.50-5.53 (m, 2 H) 5.31 (d, J=15.92 Hz, 1 H) 5.00 (d, J=16.17 Hz, 1 H) 3.01 (dt, J=13.83, 6.85 Hz, 1 H) 2.20 (d, J=4.80 Hz, 1 H) 2.15 (d, J=4.80 Hz, 1 H) 0.94 (d, J=7.07 Hz, 3 H) 0.82 (d, J=6.82 Hz, 3 H). [α]$_D^{25}$=−126.00 (c=5.2 mg/mL, CH$_2$Cl$_2$).

Example 32

(1S,2S) and (1R,2R)-3-((2-(4-chlorophenyl)-2-isopropyl-2'-oxospiro[cyclopropane-1,3'-indoline]-1'-yl)methyl)benzoic acid

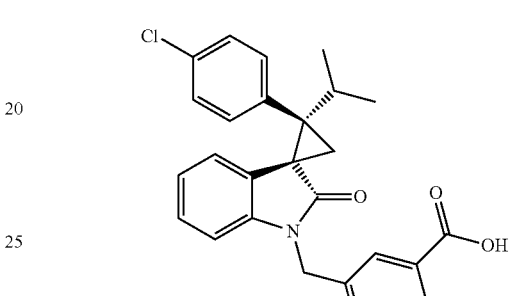

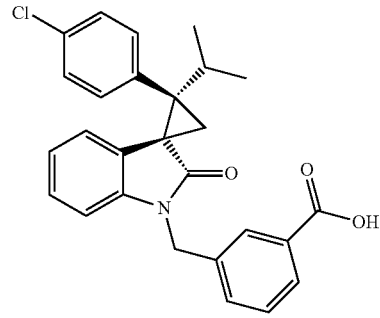

The title compound was prepared in analogy to Example 27 starting from methyl-(3-bromomethyl)-benzoate (commercially available), (1R,2R) and (1S,2S)-2-(4-chlorophenyl)-2-isopropylspiro[cyclopropane-1,3'-indolin]-2'-one prepared as in Scheme 2. LC/MS m/e calcd. for $C_{27}H_{24}ClNO_3$: 445, observed (M+H)$^+$: 446.5. $^1$H NMR (400 MHz, MeOD-d$_4$) δ ppm 8.01 (s, 1 H) 7.96 (d, J=7.58 Hz, 1 H) 7.64 (d, J=7.83 Hz, 1 H) 7.46-7.52 (m, 3 H) 7.05-7.12 (m, 1 H) 7.10 (d, J=8.08 Hz, 1 H) 6.89 (d, J=7.83 Hz, 1 H) 6.64 (t, J=7.58 Hz, 1 H) 6.53 (d, J=8.34 Hz, 1 H) 5.50-5.53 (m, 2 H) 5.31 (d, J=15.92 Hz, 1 H) 5.00 (d, J=16.17 Hz, 1 H) 3.01 (dt, J=13.83, 6.85 Hz, 1 H) 2.20

(d, J=4.80 Hz, 1 H) 2.15 (d, J=4.80 Hz, 1 H) 0.94 (d, J=7.07 Hz, 3 H) 0.82 (d, J=6.82 Hz, 3 H).

Example 33 and Example 34

(+)-3-((2-(4-chlorophenyl)-5'-fluoro-2-isopropyl-2'-oxospiro[(trans)-cyclopropane-1,3'-indoline]-1'-yl)methyl)benzoic acid and (−)-3-((2-(4-chlorophenyl)-5'-fluoro-2-isopropyl-2'-oxospiro[(trans)-cyclopropane-1,3'-indoline]-1'-yl)methyl)benzoic acid

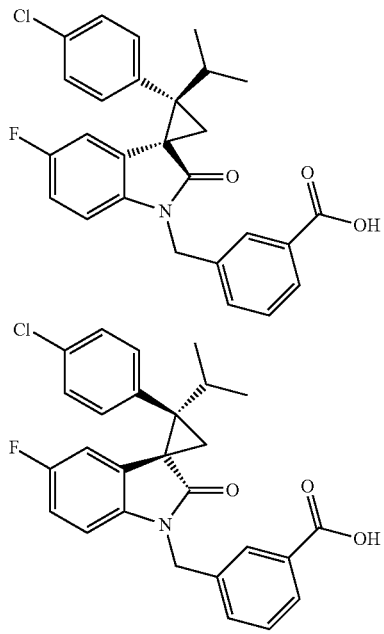

The tile compounds were obtained by separation of the stereoisomers of (1S,2S) and (1R,2R)-3-((2-(4-chlorophenyl)-5'-fluoro-2-isopropyl-2'-oxospiro[cyclopropane-1,3'-indoline]-1'-yl)methyl)benzoic acid (Example 35) by chiral preparative HPLC (Chiralpak AD) eluting with a mixture of n-heptane/5% isopropanol.

(+)-3-((2-(4-chlorophenyl)-5'-fluoro-2-isopropyl-2'-oxospiro[(trans)-cyclopropane-1,3'-indoline]-1'-yl)methyl)benzoic acid LC/MS m/e calcd. for $C_{27}H_{23}ClFNO_3$: 463, observed (M+H)$^+$: 464.2. $^1$H NMR (400 MHz, MeOD) δppm 8.01 (s, 1 H) 7.98 (d, J=7.83 Hz, 1 H) 7.64 (d, J=7.58 Hz, 1 H) 7.47-7.54 (m, 1 H) 7.51 (t, J=7.07 Hz, 2 H) 7.18 (dd, J=8.34, 1.52 Hz, 1 H) 6.85 (d, J=4.55 Hz, 1 H) 6.79-6.88 (m, 1 H) 6.59 (d, J=8.08 Hz, 1 H) 5.31 (d, J=16.17 Hz, 1 H) 5.25 (dd, J=8.97, 2.15 Hz, 1 H) 5.00 (d, J=16.17 Hz, 1 H) 3.02 (dt, J=13.64, 6.82 Hz, 1 H) 2.25 (d, J=4.80 Hz, 1 H) 2.18-2.23 (m, 1 H) 0.95 (d, J=6.82 Hz, 3 H) 0.85 (d, J=6.57 Hz, 3 H). White powder MS (ESI) (M+H)$^+$ 463.5; $[\alpha]_D^{25}$=109.52 (c=5 mg/mL, CH$_2$Cl$_2$).

(−)-3-((2-(4-chlorophenyl)-5'-fluoro-2-isopropyl-2'-oxospiro[(trans)-cyclopropane-1,3'-indoline]-1'-yl)methyl)benzoic acid LC/MS m/e calcd. for $C_{27}H_{23}ClFNO_3$: 463, observed (M+H)$^+$: 464.1. $^1$H NMR (400 MHz, MeOD) δppm 8.01 (s, 1 H) 7.98 (d, J=7.83 Hz, 1 H) 7.64 (d, J=7.58 Hz, 1 H) 7.47-7.54 (m, 1 H) 7.51 (t, J=7.07 Hz, 2 H) 7.18 (dd, J=8.34, 1.52 Hz, 1 H) 6.85 (d, J=4.55 Hz, 1 H) 6.79-6.88 (m, 1 H) 6.59 (d, J=8.08 Hz, 1 H) 5.31 (d, J=16.17 Hz, 1 H) 5.25 (dd, J=8.97, 2.15 Hz, 1 H) 5.00 (d, J=16.17 Hz, 1 H) 3.02 (dt, J=13.64, 6.82 Hz, 1 H) 2.25 (d, J=4.80 Hz, 1 H) 2.18-2.23 (m, 1 H) 0.95 (d, J=6.82 Hz, 3 H) 0.85 (d, J=6.57 Hz, 3 H). White powder MS (ESI) (M+H)+ 463.8; [ ]D25=−133.26 (c=5 mg/mL, CH2Cl2).

Example 35

(1S,2S) and (1R,2R)-3-((2-(4-chlorophenyl)-5'-fluoro-2-isopropyl-2'-oxospiro [cyclopropane-1,3'-indoline]-1'-yl)methyl)benzoic acid

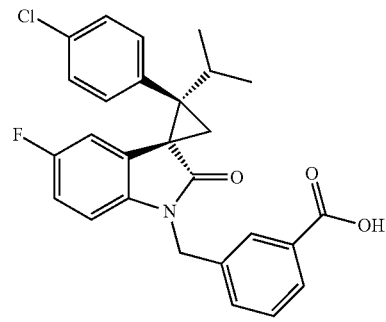

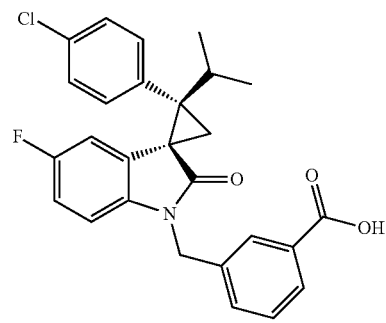

The title compound was prepared in analogy to Example 27 starting from methyl-(3-bromomethyl)-benzoate (commercially available), (1R,2R) and (1S,2S)-2-(4-chlorophenyl)-5'-fluoro-2-isopropylspiro[cyclopropane-1,3'-indolin]-2'-one prepared as in Scheme 2. LC/MS m/e calcd. for $C_{27}H_{23}ClFNO_3$: 463, observed (M+H)$^+$: 464.2. $^1$H NMR (400 MHz, MeOD-d$_4$) δppm 8.01 (s, 1 H) 7.98 (d, J=7.83 Hz, 1 H) 7.64 (d, J=7.58 Hz, 1 H) 7.47-7.54 (m, 1 H) 7.51 (t, J=7.07 Hz, 2 H) 7.18 (dd, J=8.34, 1.52 Hz, 1 H) 6.85 (d, J=4.55 Hz, 1 H) 6.79-6.88 (m, 1 H) 6.59 (d, J=8.08 Hz, 1 H) 5.31 (d, J=16.17 Hz, 1 H) 5.25 (dd, J=8.97, 2.15 Hz, 1 H) 5.00

(d, J=16.17 Hz, 1 H) 3.02 (dt, J=13.64, 6.82 Hz, 1 H) 2.25 (d, J=4.80 Hz, 1 H) 2.18-2.23 (m, 1 H) 0.95 (d, J=6.82 Hz, 3 H) 0.85 (d, J=6.57 Hz, 3 H).

Example 36

(1S,2S) and (1R,2R)-3-((5'-fluoro-2-(4-fluorophenyl)-2-isopropyl-2'-oxospiro[cyclopropane-1,3'-indoline]-1'-yl)methyl)benzoic acid

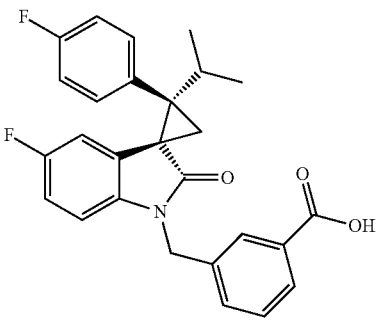

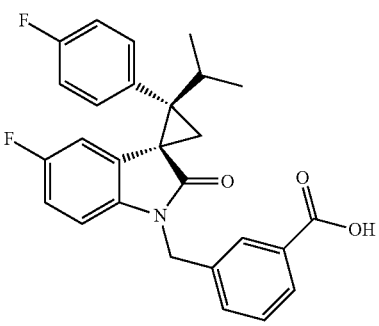

The title compound was prepared in analogy to Example 27 starting from methyl-(3-bromomethyl)-benzoate (commercially available), (1S,2S) and (1R,2R)-2-(4fluoro phenyl)-5'-fluoro-2-isopropylspiro[cyclopropane-1,3'-indolin]-2'-one racemic prepared as in Scheme 2. LC/MS m/e calcd. for $C_{27}H_{23}F_2NO_3$: 447, observed (M+H)$^+$: 448.1. $^1$H NMR (400 MHz, MeOD-d$_4$) δppm 7.99 (s, 1 H) 7.95 (d, J=7.83 Hz, 1 H) 7.61 (d, J=7.83 Hz, 1 H) 7.49 (d, J=7.58 Hz, 1 H) 7.46-7.54 (m, 1 H) 7.22 (td, J=8.65, 2.65 Hz, 1 H) 6.77-6.92 (m, 3 H) 6.60 (ddd, J=8.27, 5.62, 2.27 Hz, 1 H) 5.29 (d, J=15.92 Hz, 1 H) 5.20 (dd, J=8.84, 2.27 Hz, 1 H) 4.98 (d, J=15.92 Hz, 1 H)

2.99 (dt, J=13.64, 6.82 Hz, 1 H) 2.23 (d, J=4.80 Hz, 1 H) 2.16-2.21 (m, 1 H) 0.93 (d, J=6.82 Hz, 3 H) 0.83 (d, J=6.82 Hz, 3 H).

Example 37

(1S,2S) and (1R,2R)-3-((2-(3-fluorophenyl)-2-isopropyl-2'-oxospiro[cyclopropane-1,3'-indoline]-1'-yl)methyl)benzoic acid

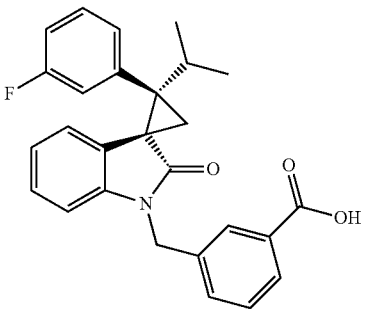

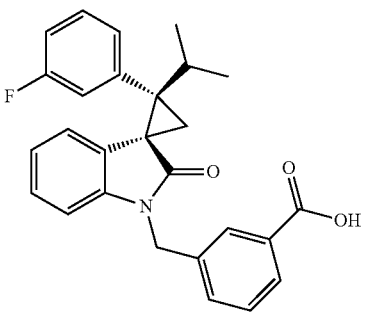

The title compound was prepared in analogy to Example 27 starting from methyl-(3-bromomethyl)-benzoate (commercially available), (1R,2R) and (1S,2S)-2-(3-fluorophenyl)-2-isopropylspiro[cyclopropane-1,3'-indolin]-2'-one prepared as in Scheme 2. LC/MS m/e calcd. for $C_{27}H_{24}FNO_3$: 429, observed (M+H)$^+$: 430.1. $^1$H NMR (400 MHz, MeOD-d$_4$) δ ppm 8.02 (s, 1 H) 7.95 (d, J=7.33 Hz, 1 H) 7.61 (d, J=7.58 Hz, 1 H) 7.48 (t, J=7.58 Hz, 1 H) 7.31 (d, J=7.83 Hz, 1 H) 7.06 (dd, J=10.86, 7.58 Hz, 2 H) 7.11 (d, J=6.32 Hz, 1 H) 6.89 (t, J=8.08 Hz, 1 H) 6.56-6.68 (m, 1 H) 6.38 (d, J=7.58 Hz, 1 H) 5.50 (t, J=8.21 Hz, 1 H) 5.28 (dd, J=15.92, 10.36 Hz, 1 H) 5.01 (d, J=16.42 Hz, 2 H) 5.07 (s, 1 H) 3.01 (d, J=6.82 Hz, 1 H) 2.19

(d, J=5.56 Hz, 1 H) 2.12-2.26 (m, 1 H) 0.95 (dd, J=6.82, 3.28 Hz, 3 H) 0.85 (dd, J=6.82, 3.79 Hz, 3H).

Example 38

(1S,2S) and (1R,2R)-3-((2-(3-chlorophenyl)-2-isopropyl-2'-oxospiro[cyclopropane-1,3'-indoline]-1'-yl)methyl)benzoic acid

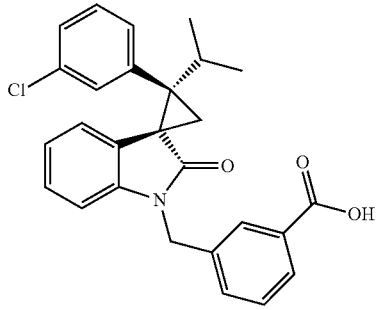

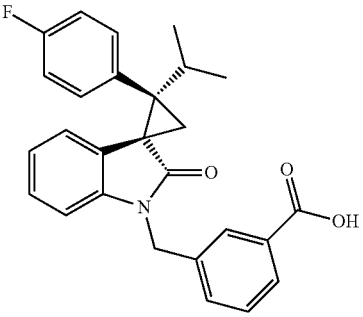

The title compound was prepared in analogy to Example 27 starting from methyl-(3-bromomethyl)-benzoate (commercially available) (1R,2R) and (1S,2S)-2-(3-chlorophenyl)-2-isopropylspiro[cyclopropane-1,3'-indolin]-2'-one prepared as in Scheme 2. LC/MS m/e calcd. for $C_{27}H_{24}ClNO_3$: 445, observed (M+H)$^+$: 446.1. $^1$H NMR (400 MHz, MeOD-d$_4$) δ ppm 8.02 (d, J=9.85 Hz, 1 H) 7.96 (d, J=7.58 Hz, 1 H) 7.62 (d, J=7.58 Hz, 1 H) 7.40-7.52 (m, 3 H) 7.32 (d, J=7.58 Hz, 1 H) 7.03-7.12 (m, J=7.01, 7.01, 7.01, 7.01 Hz, 2 H) 6.89 (dd, J=11.75, 7.96 Hz, 1 H) 6.62 (dt, J=10.61, 7.71 Hz, 1 H) 6.46-6.51 (m, 1 H) 5.48 (dd, J=16.67, 7.58 Hz, 1 H) 5.27 (t, J=16.42 Hz, 1 H) 4.95-5.08 (m, 1 H) 3.01 (dt, J=13.64, 6.82 Hz, 1 H) 2.19 (d, J=4.55 Hz, 1 H) 2.15 (t, J=5.18 Hz, 1 H) 0.94 (d, J=6.82 Hz, 3 H) 0.83 (dd, J=6.69, 2.91 Hz, 3 H).

Example 39

(1S,2S) and (1R,2R)-3-((2-(4-fluorophenyl)-2-isopropyl-2'-oxospiro[cyclopropane-1,3'-indoline]-1'-yl)methyl)benzoic acid The title compound was prepared in analogy to Example 27 starting from methyl-(3-bromomethyl)-benzoate (commercially available), (1R,2R) and (1S,2S)-2-(4-fluorophenyl)-2-isopropylspiro[cyclopropane-1,3'-indolin]-2'-one prepared as in Scheme 2. LC/MS m/e calcd. for $C_{27}H_{24}FNO_3$: 429, observed (M+H)$^+$: 430.1. $^1$H NMR (400 MHz, MeOD-d$_4$) δ ppm 8.02 (s, 1 H) 7.96 (d, J=7.83 Hz, 1 H) 7.62 (d, J=7.83 Hz, 1 H) 7.49 (q, J=7.49 Hz, 2 H) 7.19 (td, J=8.72, 2.53 Hz, 1 H) 7.07 (t, J=7.71 Hz, 1 H) 6.89 (d, J=7.83 Hz, 1 H) 6.83 (td, J=8.72, 2.78 Hz, 1 H) 6.63 (t, J=7.58 Hz, 1 H) 6.57 (ddd, J=8.21, 5.68, 2.02 Hz, 1 H) 5.49 (d, J=7.58 Hz, 1 H) 5.30 (d, J=16.17 Hz, 1 H) 5.01 (d, J=16.17 Hz, 1 H) 3.00 (dt, J=13.64, 6.82 Hz, 1 H) 2.20 (d, J=4.55 Hz, 1 H) 2.15 (d, J=4.55 Hz, 1 H) 0.94 (d, J=7.07 Hz, 3 H) 0.83 (d, J=6.82 Hz, 3 H).

Example 40 and Example 41

(−)-3-((2-(4-chlorophenyl)-2-isopropyl-2'-oxospiro[(trans)-cyclopropane-1,3'-indoline]-1'-yl)methyl)benzoic acid and (+)-3-((2-(4-chlorophenyl)-2-isopropyl-2'-oxospiro[(trans)-cyclopropane-1,3'-indoline]-1'-yl)methyl)benzoic acid

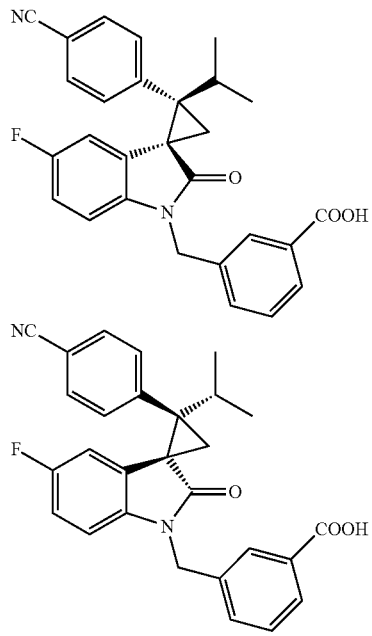

The title compounds were obtained by separation of the stereoisomers of (1S,2S) and (1R,2R)-3-((2-(4-chlorophenyl)-2-isopropyl-2'-oxospiro[cyclopropane-1,3'-indoline]-1'-yl)methyl)benzoic acid (Example 27) by chiral preparative HPLC (Chiralpak AD) eluting with a mixture of n-heptane/5% isopropanol.

(+)-3-((2-(4-chlorophenyl)-2-isopropyl-2'-oxospiro[(trans)-cyclopropane-1,3'-indoline]-1'-yl)methyl)benzoic acid LC/MS m/e calcd. for $C_{28}H_{23}FN_2O_3$: 454, observed (M+H)$^+$: 455.6. $^1$H NMR (400 MHz, MeOD) δppm 7.97 (s, 1 H) 7.94 (d, J=7.83 Hz, 1 H) 7.85 (dd, J=7.96, 1.64 Hz, 1 H) 7.67 (dd, J=7.96, 1.39 Hz, 1 H) 7.61 (d, J=7.58 Hz, 1 H) 7.48 (q, J=7.83 Hz, 2 H) 6.74-6.86 (m, 3 H) 5.28 (d, J=15.92 Hz, 1 H) 5.17 (dd, J=8.72, 2.40 Hz, 1 H) 4.97 (d, J=16.17 Hz, 1 H) 3.04 (dt, J=13.64, 6.82 Hz, 1 H) 2.23-2.28 (m, 1 H) 2.20-2.23 (m, 1 H) 0.92 (d, J=7.07 Hz, 3 H) 0.81 (d, J=6.82 Hz, 3 H). White powder. MS (ESI) (M+H)$^+$; $[\alpha]_D^{25}$=166.88 (c=5 mg/mL, CH$_2$Cl$_2$).

(−)-3-((2-(4-chlorophenyl)-2-isopropyl-2'-oxospiro[(trans)-cyclopropane-1,3'-indoline]-1'-yl)methyl)benzoic acid LC/MS m/e calcd. for $C_{28}H_{23}FN_2O_3$: 454, observed (M+H)$^+$: 455.5. $^1$H NMR (400 MHz, MeOD) δppm 7.97 (s, 1 H) 7.94 (d, J=7.83 Hz, 1 H) 7.85 (dd, J=7.96, 1.64 Hz, 1 H) 7.67 (dd, J=7.96, 1.39 Hz, 1 H) 7.61 (d, J=7.58 Hz, 1 H) 7.48 (q, J=7.83 Hz, 2 H) 6.74-6.86 (m, 3 H) 5.28 (d, J=15.92 Hz, 1 H) 5.17 (dd, J=8.72, 2.40 Hz, 1 H) 4.97 (d, J=16.17 Hz, 1 H) 3.04 (dt, J=13.64, 6.82 Hz, 1 H) 2.23-2.28 (m, 1 H) 2.20-2.23 (m, 1 H) 0.92 (d, J=7.07 Hz, 3 H) 0.81 (d, J=6.82 Hz, 3 H). $[\alpha]_D^{25}$=−151.37 (c=5 mg/mL, CH$_2$Cl$_2$).

Example 42

(1R,2S) and (1S,2R)-3-((2-(4-chlorophenyl)-2-methyl-2'-oxospiro[cyclopropane-1,3'-indoline]-1'-yl)methyl)benzoic acid

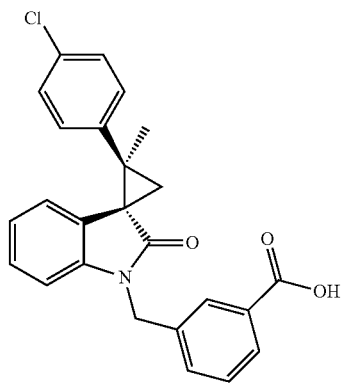

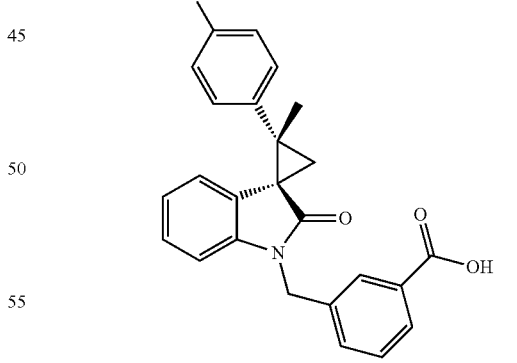

The title compound was prepared in analogy to Example 27 starting from methyl-(3-bromomethyl)-benzoate (commercially available), (1R,2S) and (1S,2R)-2-(4-chlorophenyl)-2-methylspiro[cyclopropane-1,3'-indolin]-2'-one prepared as in Scheme 2. LC/MS m/e calcd. for $C_{25}H_{20}ClNO_3$: 417, observed (M+H)$^+$: 418.1 $^1$H NMR (400 MHz, MeOD-d$_4$) δ ppm: 1.86 (s, 3 H) 2.15 (d, J=5.05 Hz, 1 H) 2.31 (d, J=5.05 Hz, 1 H) 5.07 (d, 1 H) 5.22 (d, 1 H) 5.67 (d, J=7.58 Hz, 1 H) 6.62

(t, J=7.58 Hz, 1 H) 6.85 (d, J=7.83 Hz, 1 H) 7.04 (t, J=7.83 Hz, 1 H) 7.29 (s, 2 H) 7.48 (t, J=7.96 Hz, 1 H) 7.60 (d, J=7.83 Hz, 1 H) 7.93-7.98 (m, 2 H).

Example 43 and Example 44

(+)-3-((2-(4-chlorophenyl)-2-methyl-2'-oxospiro[(trans)-cyclopropane-1,3'-indoline]-1'-yl)methyl)benzoic acid and (−)-3-((2-(4-chlorophenyl)-2-methyl-2'-oxospiro[(trans)-cyclopropane-1,3'-indoline]-1'-yl)methyl)benzoic acid

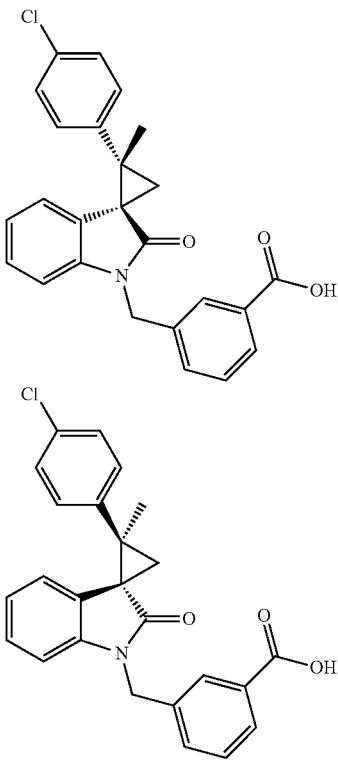

The tile compounds were obtained by separation of the stereoisomers of (1R,2S) and (1S, 2R)-3-((2-(4-chlorophenyl)-2-methyl-2'-oxospiro[cyclopropane-1,3'-indoline]-1'-yl)methyl)benzoic acid (Example 42) by chiral preparative HPLC (Chiralpak AD) eluting with a mixture of n-heptane/5% isopropanol.

(+)-3-((2-(4-chlorophenyl)-2-methyl-2'-oxospiro[(trans)-cyclopropane-1,3'-indoline]-1'-yl)methyl)benzoic acid LC/MS m/e calcd. for $C_{25}H_{20}ClNO_3$: 417, observed (M+H)+: 418.6. $^1$HNMR (400 MHz, MeOD) δppm 1.86 (s, 3 H) 2.15 (d, J=4.80 Hz, 1 H) 2.31 (d, J=5.05 Hz, 1 H) 5.07 (d, 1 H) 5.23 (d, 1 H) 5.67 (d, J=7.33 Hz, 1 H) 6.62 (t, J=7.58 Hz, 1 H) 6.85 (d, J=7.83 Hz, 1 H) 7.04 (t, J=7.71 Hz, 1 H) 7.30 (br. s., 3 H) 7.48 (t, J=7.83 Hz, 1 H) 7.60 (d, J=7.58 Hz, 1 H) 7.90-8.01 (m, 2 H). $[α]_D^{25}$=168.00 (c=4 mg/mL, MeOH).

(−)-3-((2-(4-chlorophenyl)-2-methyl-2'-oxospiro[(trans)-cyclopropane-1,3'-indoline]-1'-yl)methyl)benzoic acid LC/MS m/e calcd. for $C_{25}H_{20}ClNO_3$: 417, observed (M+H)+: 418.5. $^1$HNMR (400 MHz, MeOD) δppm 1.83 (s, 3 H) 2.12 (d, J=4.80 Hz, 1 H) 2.28 (d, J=4.80 Hz, 1 H) 5.04 (d, 1 H) 5.19 (d, 1 H) 5.64 (d, J=7.58 Hz, 1 H) 6.59 (t, J=7.71 Hz, 1 H) 6.82 (d, J=7.83 Hz, 1 H) 7.01 (t, J=7.71 Hz, 1 H) 7.27 (br. s., 2 H) 7.45 (t, J=7.96 Hz, 1 H) 7.57 (d, J=7.58 Hz, 1 H) 7.89-7.96 (m, 2 H). $[α]_D^{25}$=−158.42 (c=4 mg/mL, MeOH).

Example 45

(1R,2R) and (1S,2S)-3-((2-(4-chlorophenyl)-2-methyl-2'-oxospiro[cyclopropane-1,3'-indoline]-1'-yl)methyl)benzoic acid

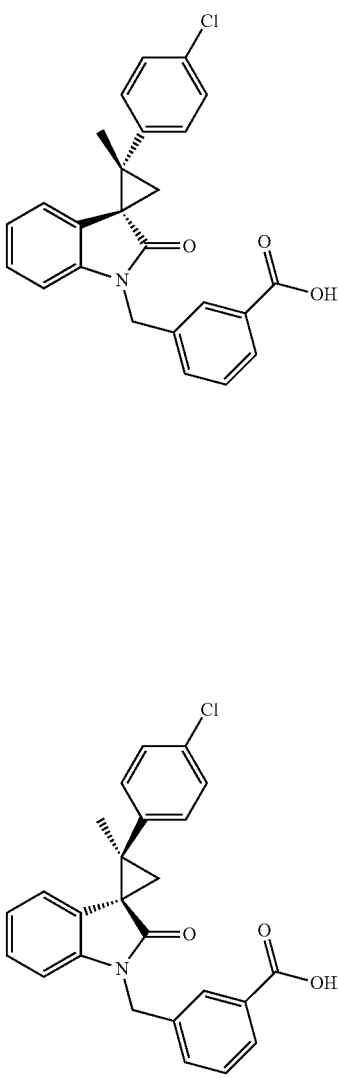

The title compound was prepared in analogy to Example 27 starting from methyl-(3-bromomethyl)-benzoate (commercially available), (1R,2R) and (1S,2S)-2-(4-chlorophenyl)-2-methylspiro[cyclopropane-1,3'-indolin]-2'-one prepared as in Scheme 2. LC/MS m/e calcd. for $C_{25}H_{20}ClNO_3$: 417, observed (M+H)+: 418.1 $^1$H NMR (400 MHz, MeOD-$d_4$) δ ppm 1.69 (s, 3 H) 2.05 (d, J=4.80 Hz, 1 H) 2.45 (d, J=4.80 Hz, 1 H) 4.75 (d, J=15.92 Hz, 1 H) 5.12 (d, J=16.17 Hz, 1 H) 6.94 (d, J=7.83 Hz, 1 H) 7.09 (t, J=7.58 Hz, 1 H) 7.24 (d, J=7.58

Hz, 2 H) 7.21 (s, 1 H) 7.27-7.31 (m, 3 H) 7.46 (t, J=7.58 Hz, 1 H) 7.51-7.56 (m, 1 H) 7.89 (s, 1H) 7.95 (d, J=7.58 Hz, 1 H).

Example 46 and Example 47

(+)-3-((2-(4-chlorophenyl)-2-methyl-2'-oxospiro[(cis)-cyclopropane-1,3'-indoline]-1'-yl)methyl)benzoic acid and (−)-3-((2-(4-chlorophenyl)-2-methyl-2'-oxospiro[(cis)-cyclopropane-1,3'-indoline]-1'-yl)methyl)benzoic acid

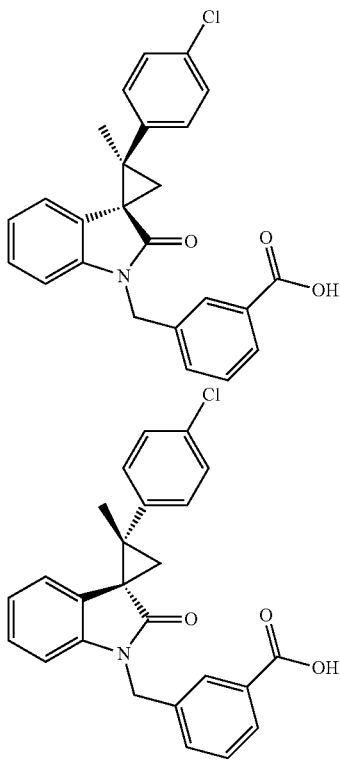

The tile compounds were obtained by separation of the stereoisomers of (1R,2R) and (1S,2S)-3-((2-(4-chlorophenyl)-2-methyl-2'-oxospiro[cyclopropane-1,3'-indoline]-1'-yl)methyl)benzoic acid (Example 45) by chiral preparative HPLC (Chiralpak AD) eluting with a mixture of n-heptane/5% isopropanol.

(+)-3-((2-(4-chlorophenyl)-2-methyl-2'-oxospiro[(cis)-cyclopropane-1,3'-indoline]-1'-yl)methyl)benzoic acid LC/MS m/e calcd. for $C_{25}H_{20}ClNO_3$: 417, observed (M+H)$^+$: 418.5. $^1$H NMR (400 MHz, MeOD) δppm 1.70 (s, 3 H) 2.06 (d, J=5.05 Hz, 1 H) 2.46 (d, J=5.05 Hz, 1 H) 4.77 (d, J=15.92 Hz, 1 H) 5.13 (d, J=16.17 Hz, 1 H) 6.96 (d, J=7.83 Hz, 1 H) 7.10 (t, J=7.58 Hz, 1 H) 7.25 (t, J=7.58 Hz, 3 H) 7.28-7.33 (m, 3 H) 7.48 (t, J=7.58 Hz, 1 H) 7.56 (d, 1 H) 7.90 (s, 1 H) 7.96 (d, J=7.58 Hz, 1 H). [α]$_D^{25}$=257.43 (c=4 mg/mL, MeOH).

(−)-3-((2-(4-chlorophenyl)-2-methyl-2'-oxospiro[(cis)-cyclopropane-1,3'-indoline]-1'-yl)methyl)benzoic acid LC/MS m/e calcd. for $C_{25}H_{20}ClNO_3$: 417, observed (M+H)$^+$: 418.4. $^1$H NMR (400 MHz, MeOD) δppm 1.70 (s, 3 H) 2.06 (d, J=5.05 Hz, 1 H) 2.46 (d, J=5.05 Hz, 1 H) 4.77 (d, J=16.17 Hz, 1 H) 5.13 (d, J=15.92 Hz, 1 H) 6.95 (d, J=7.83 Hz, 1 H) 7.10 (t, J=7.58 Hz, 1 H) 7.24 (t, J=7.45 Hz, 3 H) 7.28-7.32 (m, 3 H) 7.48 (t, J=7.71 Hz, 1 H) 7.55 (d, 1 H) 7.90 (s, 1 H) 7.96 (d, J=7.58 Hz, 1 H). [α]$_D^{25}$=−260.784 (c=4 mg/mL, MeOH).

Example 48

(1R,2S) and (1S,2R)-3-((2-(4-cyanophenyl)-5'-fluoro-2-methyl-2'-oxospiro[cyclopropane-1,3'-indoline]-1'-yl)methyl)benzoic acid

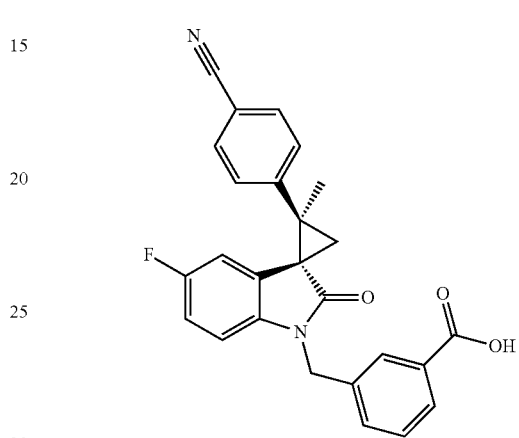

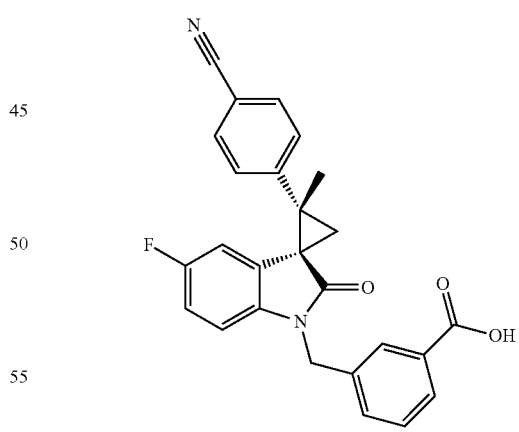

The title compound was prepared in analogy to Example 27 starting from methyl-(3-bromomethyl)-benzoate (commercially available), (1R,2S) and (1S,2R)-4-(5'-fluoro-2-methyl-2'-oxospiro[cyclopropane-1,3'-indoline]-2-yl)benzonitrile prepared as in Scheme 2. LC/MS m/e calcd. for $C_{26}H_{19}FN_2O_3$: 426, observed (M+H)$^+$: 427.1 $^1$H NMR (400 MHz, MeOD-d$_4$) δppm 1.87 (s, 3 H) 2.21 (d, J=5.31 Hz, 1 H) 2.40 (d, J=5.31 Hz, 1 H) 5.04 (d, 1 H) 5.21 (d, 1 H) 5.36 (dd, J=8.84, 2.27 Hz, 1 H) 6.73-6.87 (m, 1 H) 6.80 (d, J=4.55 Hz, 1 H) 7.48 (t, J=7.71 Hz, 1 H) 7.59 (s, 2 H) 7.69 (br. s., 2 H) 7.94 (d, J=7.58 Hz, 1 H) 7.91 (s, 1 H).

Example 49 and Example 50

(+)-3-((2-(4-cyanophenyl)-5'-fluoro-2-methyl-2'-oxospiro[(trans)-cyclopropane-1,3'-indoline]-1'-yl)methyl)benzoic acid and (−)-3-((2-(4-cyanophenyl)-5'-fluoro-2-methyl-2'-oxospiro[(trans)-cyclopropane-1,3'-indoline]-1'-yl)methyl)benzoic acid

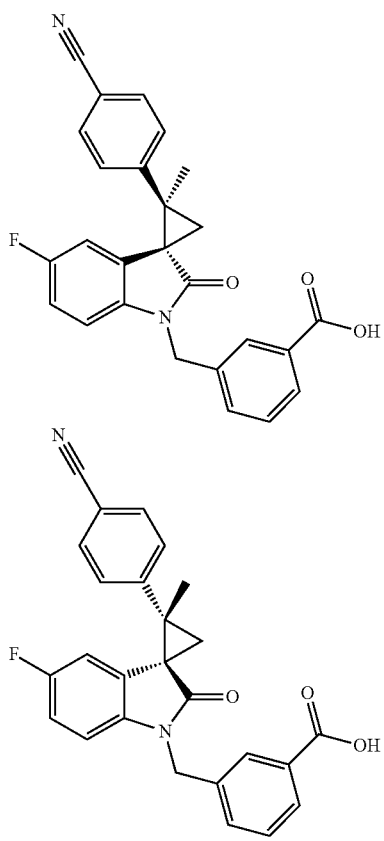

The tile compounds were obtained by separation of the stereoisomers of (1R,2S) and (1S, 2R)-3-((2-(4-cyanophenyl)-5'-fluoro-2-methyl-2'-oxospiro[cyclopropane-1,3'-indoline]-1'-yl)methyl)benzoic acid (Example 48) by chiral preparative HPLC (Chiralpak AD) eluting with a mixture of n-heptane/5% isopropanol.

(+)-3-((2-(4-cyanophenyl)-5'-fluoro-2-methyl-2'-oxospiro[(trans)-cyclopropane-1,3'-indoline]-1'-yl)methyl)benzoic acid LC/MS m/e calcd. for $C_{26}H_{19}FN_2O_3$: 426, observed (M+H)$^+$: 427.5. $^1$H NMR (400 MHz, MeOD) δppm 1.87 (s, 3 H) 2.21 (d, J=5.31 Hz, 1 H) 2.41 (d, J=5.31 Hz, 1 H) 5.04 (d, 1 H) 5.21 (d, 1 H) 5.36 (dd, J=8.84, 2.27 Hz, 1 H) 6.73-6.87 (m, 1 H) 6.80 (d, J=4.80 Hz, 1 H) 7.48 (t, J=7.71 Hz, 2 H) 7.60 (d, J=7.83 Hz, 2 H) 7.69 (br. s., 2 H) 7.94 (d, J=7.58 Hz, 1 H) 7.92 (s, 1 H). $[\alpha]_D^{25}$=203.431 (c=4 mg/mL, MeOH).

(−)-3-((2-(4-cyanophenyl)-5'-fluoro-2-methyl-2'-oxospiro[(trans)-cyclopropane-1,3'-indoline]-1'-yl)methyl)benzoic acid LC/MS m/e calcd. for $C_{26}H_{19}FN_2O_3$: 426, observed (M+H)$^+$: 427.6. $^1$H NMR (400 MHz, MeOD) δppm 1.88 (s, 3 H) 2.22 (d, J=5.31 Hz, 1 H) 2.41 (d, J=5.31 Hz, 1 H) 5.05 (d, 1 H) 5.21 (d, 1 H) 5.36 (dd, J=8.84, 2.27 Hz, 1 H) 6.80 (d, J=4.55 Hz, 1 H) 6.74-6.85 (m, 1 H) 7.48 (t, J=7.71 Hz, 1 H) 7.60 (d, J=7.58 Hz, 2 H) 7.71 (br. s., 2 H) 7.95 (d, J=7.58 Hz, 1 H) 7.92 (s, 1 H). White powder MS (ESI) (M+H)$^+$ 427.6; $[\alpha]_D^{25}$=−209.00 (c=4 mg/mL, MeOH).

Example 51

(1S,2S) and (1R,2R)-3-((2-(4-cyanophenyl)-2-isopropyl-2'-oxospiro[cyclopropane-1,3'-indoline]-1'-yl)methyl)benzoic acid

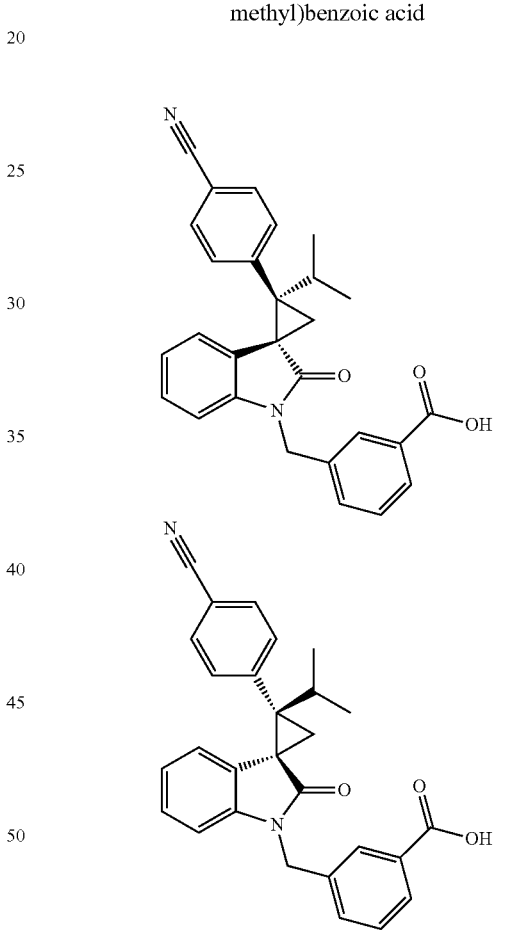

The title compound was prepared in analogy to Example 27 starting from methyl-(3-bromomethyl)-benzoate (commercially available), (1R,2R) and (1S,2S)-4-(2-isopropyl-2'-oxospiro[cyclopropane-1,3'-indoline]-2-yl)benzonitrile prepared as in Scheme 2. LC/MS m/e calcd. for $C_{28}H_{24}N_2O_3$: 436, observed (M+H)$^+$: 437.1 $^1$H NMR (400 MHz, MeOD-$d_4$) δppm 0.81 (d, J=6.82 Hz, 3 H) 0.92 (d, J=6.82 Hz, 3 H) 2.18 (d, 1 H) 2.22 (d, 1 H) 2.98-3.09 (m, 1 H) 4.98 (d, J=16.17 Hz, 1 H) 5.30 (d, J=15.92 Hz, 1 H) 5.43 (d, J=7.58 Hz, 1 H) 6.61 (t, J=7.58 Hz, 1 H) 6.71 (dd, J=8.08, 1.52 Hz, 1 H) 6.88 (d, J=7.83 Hz, 1 H) 7.06 (t, J=7.71 Hz, 1 H) 7.48 (t, J=7.71 Hz, 1 H) 7.44 (dd, J=8.08, 1.77 Hz, 1 H) 7.68 (dd, J=7.83, 1.52 Hz, 1 H) 7.63 (d, J=7.83 Hz, 1 H) 7.83 (dd, J=7.96, 1.64 Hz, 1 H) 7.94 (d, J=7.83 Hz, 1 H) 7.99 (s, 1 H).

Example 52 and Example 53

(+)-3-((2-(4-cyanophenyl)-2-isopropyl-2'-oxospiro[(trans)-cyclopropane-1,3'-indoline]-1'-yl)methyl)benzoic acid and (−)-3-((2-(4-cyanophenyl)-2-isopropyl-2'-oxospiro[(trans)-cyclopropane-1,3'-indoline]-1'-yl)methyl)benzoic acid

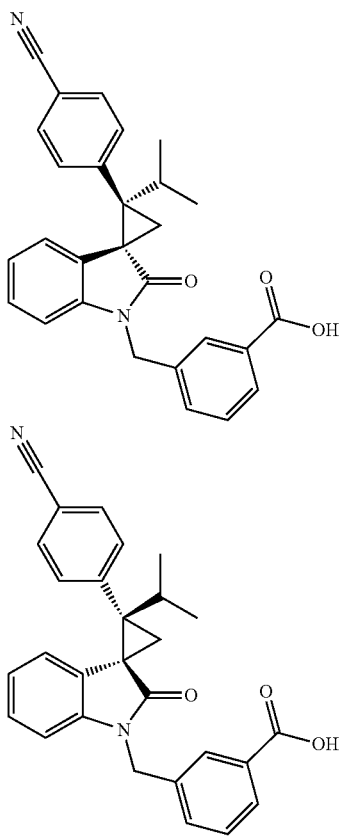

The title compounds were obtained by separation of the stereoisomers of (1S,2S) and (1R,2R)-3-((2-(4-cyanophenyl)-5'-fluoro-2-methyl-2'-oxospiro[cyclopropane-1,3'-indoline]-1'-yl)methyl)benzoic acid (Example 51) by chiral preparative HPLC (Chiralpak AD) eluting with a mixture of n-heptane/5% isopropanol.

(+)-3-((2-(4-cyanophenyl)-2-isopropyl-2'-oxospiro[(trans)-cyclopropane-1,3'-indoline]-1'-yl)methyl)benzoic acid LC/MS m/e calcd. for $C_{28}H_{24}N_2O_3$: 436, observed (M+H)$^+$: 437.7. $^1$H NMR (400 MHz, MeOD) δppm 0.80 (d, J=6.82 Hz, 3 H) 0.92 (d, J=6.82 Hz, 3 H) 2.17 (d, 1 H) 2.22 (d, 1 H) 2.97-3.10 (m, J=6.88, 6.88, 6.88, 6.88 Hz, 1 H) 4.98 (d, J=16.17 Hz, 1 H) 5.30 (d, J=15.92 Hz, 1 H) 5.43 (d, J=7.58 Hz, 1 H) 6.61 (t, J=7.58 Hz, 1 H) 6.71 (dd, J=8.08, 1.52 Hz, 1 H) 6.88 (d, J=7.83 Hz, 1 H) 7.06 (t, J=7.71 Hz, 1 H) 7.48 (t, J=7.71 Hz, 1 H) 7.44 (dd, J=8.08, 1.77 Hz, 1 H) 7.67 (dd, J=7.96, 1.64 Hz, 1 H) 7.63 (d, J=7.83 Hz, 1 H) 7.83 (dd, J=7.96, 1.64 Hz, 1 H) 7.94 (d, J=7.83 Hz, 1 H) 7.99 (s, 1 H). $[α]_D^{25}$=180.88 (c=4 mg/mL, MeOH).

(−)-3-((2-(4-cyanophenyl)-2-isopropyl-2'-oxospiro[(trans)-cyclopropane-1,3'-indoline]-1'-yl)methyl)benzoic acid LC/MS m/e calcd. for $C_{28}H_{24}N_2O_3$: 436, observed (M+H)$^+$: 437.5. $^1$H NMR (400 MHz, MeOD) δppm 0.81 (d, J=6.82 Hz, 3 H) 0.93 (d, J=6.82 Hz, 3 H) 2.18 (dd, 1 H) 2.21-2.25 (m, 1 H) 3.03 (d, J=6.82 Hz, 1 H) 4.98 (d, J=15.92 Hz, 1 H) 5.30 (d, J=16.17 Hz, 1 H) 5.44 (d, J=7.58 Hz, 1 H) 6.62 (t, J=7.58 Hz, 1 H) 6.72 (dd, J=8.08, 1.52 Hz, 1 H) 6.89 (d, J=7.83 Hz, 1 H) 7.07 (t, J=7.71 Hz, 1 H) 7.48 (t, J=7.71 Hz, 1 H) 7.45 (dd, J=8.08, 1.52 Hz, 1 H) 7.68 (d, J=7.83 Hz, 1 H) 7.65 (dd, J=18.57, 7.71 Hz, 1 H) 7.84 (dd, J=7.96, 1.64 Hz, 1 H) 7.95 (d, J=7.83 Hz, 1 H) 7.99 (s, 1 H). $[α]_D^{25}$=−182.52 (c=4 mg/mL, MeOH).

Example 54

(1R,2R) and (1S,2S)-3-((2-(4-cyanophenyl)-5'-fluoro-2-methyl-2'-oxospiro[cyclopropane-1,3'-indoline]-1'-yl)methyl)benzoic acid

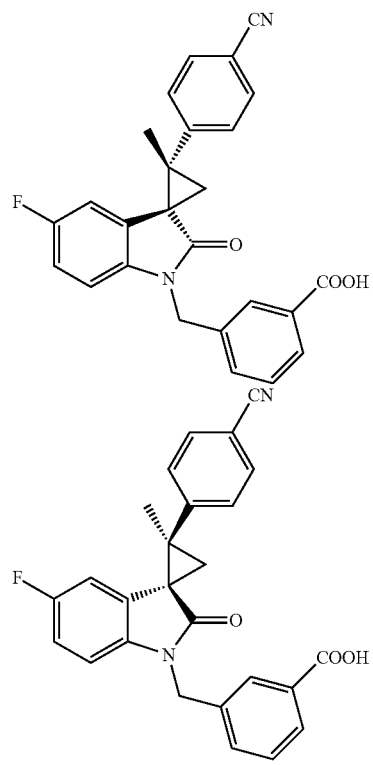

The title compound was prepared in analogy to Example 27 starting from methyl-(3-bromomethyl)-benzoate (commercially available), (1R,2R) and (1S,2S)-4-(5'-fluoro-2-methyl-2'-oxospiro[cyclopropane-1,3'-indoline]-2-yl)benzonitrile prepared as in Scheme 2. LC/MS m/e calcd. for $C_{26}H_{19}FN_2O_3$: 426, observed (M+H)$^+$: 427.1 $^1$H NMR (400 MHz, MeOD-d$_4$) δppm 1.71 (s, 3 H) 2.14 (d, J=5.05 Hz, 1 H) 2.50 (d, J=5.31 Hz, 1 H) 4.73 (d, J=15.92 Hz, 1 H) 5.10 (d, J=15.92 Hz, 1 H) 6.92 (d, J=4.29 Hz, 1 H) 6.98 (dd, J=9.09, 2.53 Hz, 1 H) 7.16 (dd, J=8.84, 2.53 Hz, 1 H) 7.47 (t, J=7.71

Hz, 2 H) 7.46 (br. s., 1 H) 7.51-7.56 (m, 1 H) 7.67 (d, J=8.59 Hz, 2 H) 7.85 (s, 1 H) 7.95 (d, J=7.83 Hz, 1 H).

Example 55 and Example 56

(+)-3-((2-(4-cyanophenyl)-5'-fluoro-2-methyl-2'-oxospiro[(cis)-cyclopropane-1,3'-indoline]-1'-yl)methyl)benzoic acid and (−)-3-((2-(4-cyanophenyl)-5'-fluoro-2-methyl-2'-oxospiro[(cis)-cyclopropane-1, 3'-indoline]-1'-yl)methyl)benzoic acid

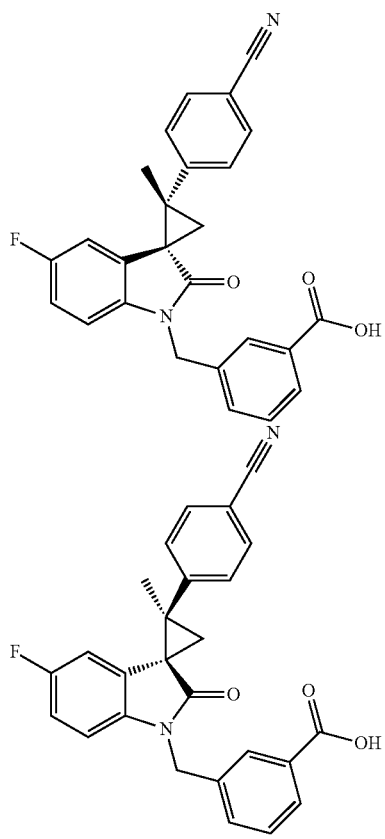

The title compounds were obtained by separation of the stereoisomers of (1R,2R) and (1S,2S)-3-((2-(4-cyanophenyl)-5'-fluoro-2-methyl-2'-oxospiro[cyclopropane-1,3'-indoline]-1'-yl)methyl)benzoic acid (Example 54) by chiral preparative HPLC (Chiralpak AD) eluting with a mixture of n-heptane/5% isopropanol.

(+)-3-((2-(4-cyanophenyl)-5'-fluoro-2-methyl-2'-oxospiro[(cis)-cyclopropane-1,3'-indoline]-1'-yl)methyl)benzoic acid LC/MS m/e calcd. for $C_{26}H_{19}FN_2O_3$: 426, observed (M+H)$^+$: 426.8. $^1$H NMR (400 MHz, MeOD) δppm 1.71 (s, 3 H) 2.14 (d, J=5.05 Hz, 1 H) 2.50 (d, J=5.05 Hz, 1 H) 4.73 (d, J=15.92 Hz, 1 H) 5.10 (d, J=15.66 Hz, 1 H) 6.93 (d, J=4.29 Hz, 1 H) 6.98 (dd, J=9.09, 2.53 Hz, 1 H) 7.16 (dd, J=8.72, 2.40 Hz, 1 H) 7.47 (t, J=7.71 Hz, 3 H) 7.53 (br. s., 1 H) 7.67 (d, J=8.59 Hz, 2 H) 7.85 (s, 1 H) 7.95 (d, J=7.58 Hz, 1 H). $[α]_D^{25}$=313.53 (c=4 mg/mL, MeOH).

(−)-3-((2-(4-cyanophenyl)-5'-fluoro-2-methyl-2'-oxospiro[(cis)-cyclopropane-1,3'-indoline]-1'-yl)methyl)benzoic acid LC/MS m/e calcd. for $C_{26}H_{19}FN_2O_3$: 426, observed (M+H)$^+$: 426.5. $^1$H NMR (400 MHz, MeOD) δppm 1.71 (s, 3 H) 2.14 (d, J=5.31 Hz, 1 H) 2.50 (d, J=5.05 Hz, 1 H) 4.73 (d, J=15.92 Hz, 1 H) 5.10 (d, J=15.92 Hz, 1 H) 6.92 (d, J=4.55 Hz, 1 H) 6.98 (dd, J=9.09, 2.53 Hz, 1 H) 7.16 (dd, J=8.72, 2.40 Hz, 1 H) 7.47 (t, J=7.58 Hz, 3 H) 7.52-7.59 (m, 1 H) 7.67 (d, J=8.59 Hz, 2 H) 7.84 (s, 1 H) 7.95 (d, J=7.83 Hz, 1H) $[α]_D^{25}$=−286.00 (c=4 mg/mL 00, MeOH).

Example 57

(1R,2S) and (1R,2S)-3-((2-(4-chlorophenyl)-5'-fluoro-2-methyl-2'-oxospiro[cyclopropane-1,3'-indoline]-1'-yl)methyl)benzoic acid

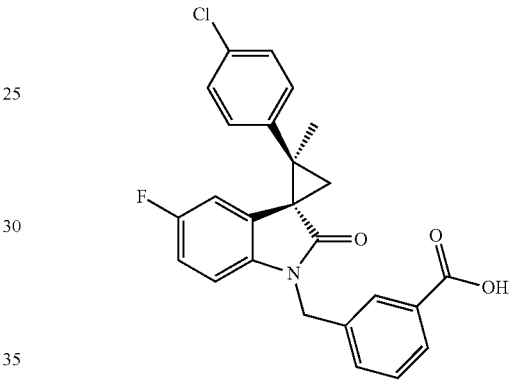

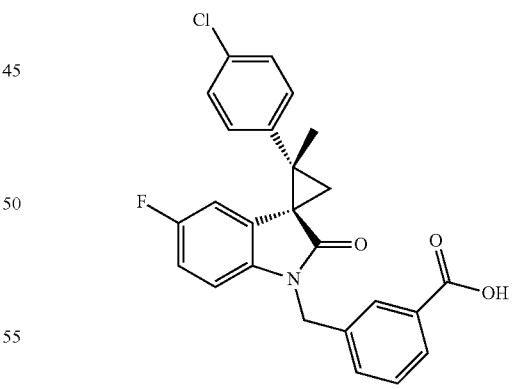

The title compound was prepared in analogy to Example 27 starting from methyl-(3-bromomethyl)-benzoate (commercially available), (1R,2S) and (1S,2R)-2-(4-chlorophenyl)-5'-fluoro-2-methylspiro[cyclopropane-1,3'-indolin]-2'-one prepared as in Scheme 2. LC/MS m/e calcd. for $C_{25}H_{19}ClFNO_3$: 435, observed (M+H)$^+$: 436.5. $^1$H NMR (400 MHz, MeOD) δ ppm 1.88 (s, 3 H) 2.20 (d, J=5.05 Hz, 1 H) 2.37 (d, J=5.05 Hz, 1 H) 5.02-5.10 (m, 1 H) 5.18-5.25 (m, 1 H) 5.41 (dd, J=8.84, 2.27 Hz, 1 H) 6.72-6.86 (m, 1 H) 6.80 (d, J=5.05 Hz, 1 H) 7.30 (br. s., 2 H) 7.50 (t, J=7.71 Hz, 1 H) 7.61 (d, J=7.58 Hz, 1 H) 7.96 (d, J=8.08 Hz, 1 H) 7.94 (br. s., 1 H).

Example 58 and Example 59

(+)-3-((2-(4-chlorophenyl)-5'-fluoro-2-methyl-2'-oxospiro[(trans)-cyclopropane-1,3'-indoline]-1'-yl)methyl)benzoic acid and (−)-3-((2-(4-chlorophenyl)-5'-fluoro-2-methyl-2'-oxospiro[(trans)-cyclopropane-1,3'-indoline]-1'-yl)methyl)benzoic acid

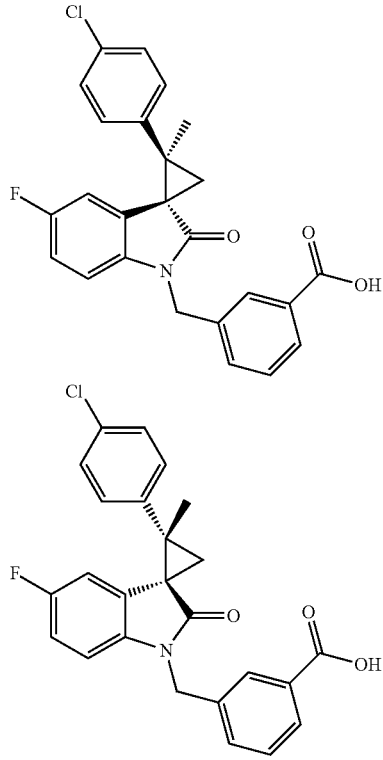

The title compounds were obtained by separation of the stereoisomers of (1R,2S) and (1R,2S)-3-((2-(4-chlorophenyl)-5'-fluoro-2-methyl-2'-oxospiro[cyclopropane-1,3'-indoline]-1'-yl)methyl)benzoic acid (Example 57) by chiral preparative HPLC (Chiralpak AD) eluting with a mixture of n-heptane/5% isopropanol.

(+)-3-((2-(4-chlorophenyl)-5'-fluoro-2-methyl-2'-oxospiro[(trans)-cyclopropane-1,3'-indoline]-1'-yl)methyl)benzoic acid LC/MS m/e calcd. for $C_{25}H_{19}ClFNO_3$: 435, observed (M+H)$^+$: 436.5. $^1$H NMR (400 MHz, MeOD) δppm 1.87 (s, 3 H) 2.19 (d, J=5.05 Hz, 1 H) 2.36 (d, J=5.05 Hz, 1 H) 5.01-5.10 (m, 1 H) 5.17-5.26 (m, 1 H) 5.41 (dd, J=8.97, 2.15 Hz, 1 H) 6.67-6.86 (m, 3 H) 7.34 (br. s., 2 H) 7.49 (t, J=7.58 Hz, 2 H) 7.60 (d, J=7.83 Hz, 1 H) 7.89-7.99 (m, 2 H). $[\alpha]_D^{25}$=191.09 (c=4 mg/mL, MeOH).

(−)-3-((2-(4-chlorophenyl)-5'-fluoro-2-methyl-2'-oxospiro[[(trans)-cyclopropane-1,3'-indoline]-1'-yl)methyl)benzoic acid LC/MS m/e calcd. for $C_{25}H_{19}ClFNO_3$: 435, observed (M+H)$^+$: 436.7. $^1$H NMR (400 MHz, MeOD) δppm 1.88 (s, 3 H) 2.20 (d, J=5.05 Hz, 1 H) 2.37 (d, J=5.05 Hz, 1 H) 5.06 (d, 1 H) 5.22 (d, 1 H) 5.41 (dd, J=8.84, 2.27 Hz, 1 H) 6.75-6.85 (m, 1 H) 6.81 (d, J=4.80 Hz, 1 H) 7.32 (br. s., 2 H) 7.50 (t, J=7.71 Hz, 2 H) 7.61 (d, J=7.83 Hz, 1 H) 7.93-7.99 (m, 2 H). $[\alpha]_D^{25}$=−186.14 (c=4 mg/mL, MeOH).

Example 60

(1S,2R) and (1R,2S)-2-(4-chlorophenyl)-1'-(3-(piperidine-1-carbonyl)benzyl)

Spiro[cyclopropane-1,3'-indolin]-2'-one

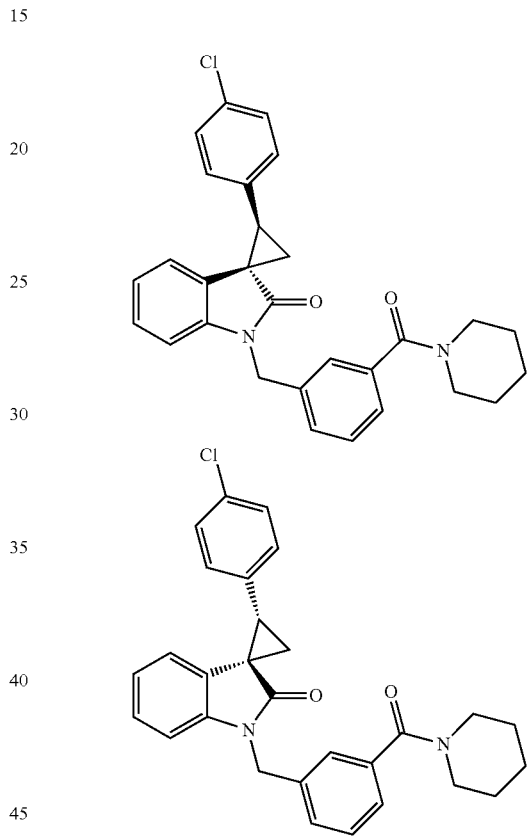

3-(((1S,2R)-2-(4-chlorophenyl)-2'-oxospiro[cyclopropane-1,3'-indoline]-1'-yl)methyl)benzoic acid and 3-(((1R,2S)-2-(4-chlorophenyl)-2'-oxospiro[cyclopropane-1,3'-indoline]-1'-yl)methyl)benzoic acid (prepared according to Scheme 1) (60 mg, 0.15 mmol), 1-(3-Dimethylaminopropyl)-3-ethylcarbodiimide hydrochloride (EDC.HCl) (44 mg, 0.225 mmol 1.5 mmol), anhydrous 1-Hydroxybenzotriazole (HOBt) (31 mg, 0.225 mmol) and piperidine (15 mg, 0.18 mmol) were dissolved in DMF. The mixture was stirred at room temperature for 14 hours. (1R,2S) and (1S,2R)-2-(4-chlorophenyl)-1'-(3-(piperidine-1-carbonyebenzyl)spiro[cyclopropane-1,3'-indolin]-2'-one were purified by preparative HPLC as a white solid (42 mg, 60%). LC/MS m/e calcd. for $C_{29}H_{27}ClN_2O_2$: 470, observed (M+H)$^+$: 471.2 $^1$H NMR (400 MHz, MeOD-d$_4$) δppm 1.41 (br. s., 2 H) 1.67 (br. s., 4 H) 2.19-2.30 (m, 2 H) 3.28 (br.s., 2 H) 3.30 (s, 1 H) 3.69 (br. s., 2 H) 5.14 (s, 2 H) 6.11 (d, J=7.33 Hz, 1 H) 6.74 (t, J=7.20 Hz, 1 H) 6.91 (d, J=7.83 Hz, 1 H) 7.03-7.15 (m, 1 H) 7.20-7.28 (m, 2 H) 7.28-7.38 (m, 4 H) 7.43-7.57 (m, 2 H).

Example 61

(1R,2S) and (1S,2R)-3-((2-(4-chlorophenyl)-2'-oxospiro[cyclopropane-1,3'-indoline]-1'-yl)methyl)-N-isopropylbenzamide

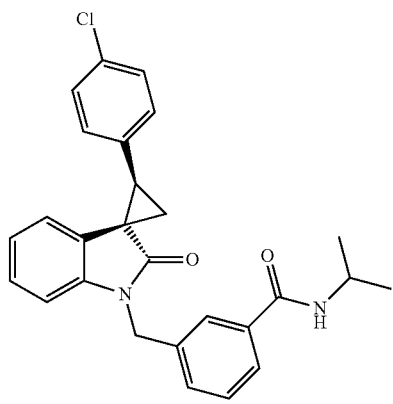

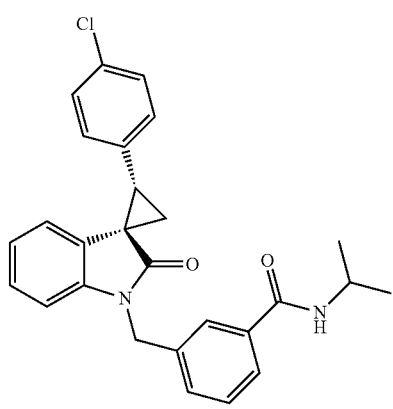

The title compound was prepared in analogy to Example 60 starting from isopropyl amine, (3-bromomethyl)-benzoate (commercially available), (1R,2S) and (1S,2R)-3-((2-(4-chlorophenyl)-2'-oxospiro[cyclopropane-1,3'-indoline]-1'-yl)methyl)benzoic acid prepared as in Scheme 1. LC/MS m/e calcd. for $C_{27}H_{25}ClN_2O_2$: 444, observed (M+H)$^+$: 445.2 $^1$H NMR (400 MHz, MeOD-$d_4$) δppm 1.23 (d, J=6.82 Hz, 6 H) 2.21 (d, J=8.59 Hz, 2 H) 3.21-3.28 (m, 1 H) 4.07-4.25 (m, 1 H) 5.10 (s, 2 H) 6.05 (d, J=7.58 Hz, 1 H) 6.69 (t, J=7.58 Hz, 1 H)

6.88 (d, J=7.83 Hz, 1 H) 7.05 (t, J=7.83 Hz, 1 H) 7.16-7.25 (m, 2 H) 7.25-7.34 (m, 2 H) 7.37-7.52 (m, 2 H) 7.69 (d, J=7.58 Hz, 1 H) 7.78 (s, 1 H).

Example 62

(1S,2R) and (1R,2S)-2-(4-chlorophenyl)-1'-(3-(piperazine-1-carbonyl)benzyl)spiro[cyclopropane-1,3'-indolin]-2'-one

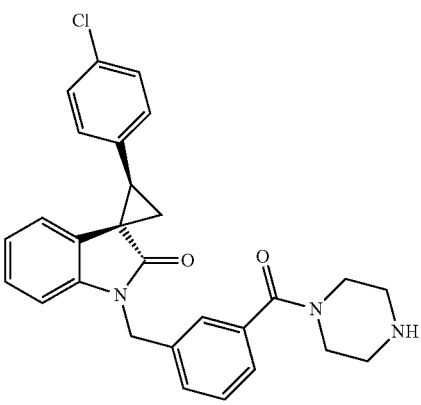

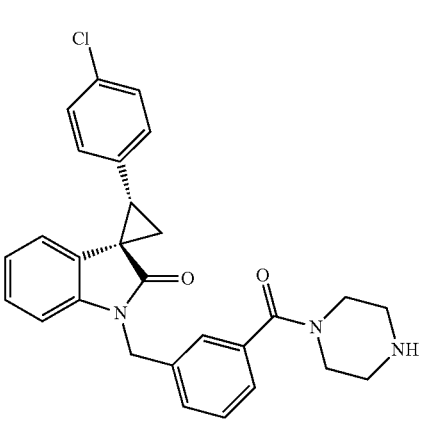

The title compound was prepared in analogy to Example 60 starting from piperazine, (3-bromomethyl)-benzoate (commercially available), (1S,2R) and (1R,2S)-3-((2-(4-chlorophenyl)-2'-oxospiro[cyclopropane-1,3'-indoline]-1'-yl) methyl)benzoic acid prepared as in Scheme 1. LC/MS m/e calcd. for $C_{28}H_{26}ClN_3O_2$: 471, observed (M+H)$^+$: 472.2 $^1$H NMR (400 MHz, MeOD-$d_4$) δppm 2.17-2.30 (m, 2 H) 3.51 (br. s., 8 H) 3.21-3.35 (m, 1 H) 5.04-5.23 (m, 2 H) 6.10 (d, J=7.58 Hz, 1 H) 6.74 (t, J=7.45 Hz, 1 H) 6.95 (d, J=7.83 Hz, 1 H) 7.05-7.16 (m, 1 H) 7.23 (d, J=8.34 Hz, 2 H) 7.29-7.38 (m, 2 H) 7.40-7.49 (m, 2 H) 7.49-7.58 (m, 2 H).

Example 63

(1R,2S) and (1S,2R)-2-(4-chlorophenyl)-1'-(3-(morpholine-4-carbonyl)benzyl)spiro[cyclopropane-1,3'-indolin]-2'-one

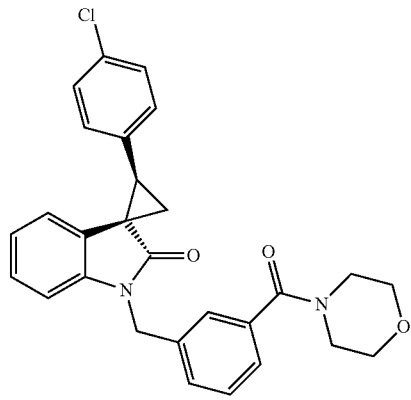

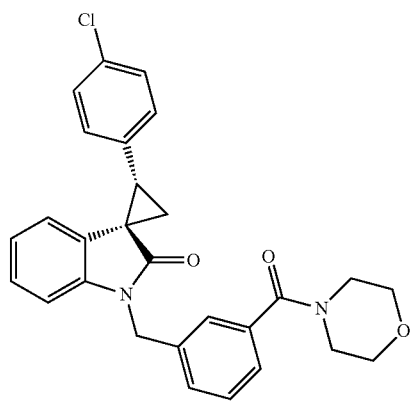

The title compound was prepared in analogy to Example 60 starting from morpholine, (3-bromomethyl)-benzoate (commercially available) and (1R,2S) and (1S,2R)-3-((2-(4-chlorophenyl)-2'-oxospiro[cyclopropane-1,3'-indoline]-1'-yl) methyl)benzoic acid prepared as in Scheme 1. LC/MS m/e calcd. for $C_{28}H_{25}ClN_2O_3$: 472, observed (M+H)$^+$: 473.2 $^1$H NMR (400 MHz, MeOD-$d_4$) δppm 2.15-2.27 (m, 2 H) 3.18-3.36 (m, 1 H) 3.47 (br. s., 4 H) 3.70 (br. s., 4 H) 5.11 (s, 2 H) 6.08 (d, J=7.58 Hz, 1 H) 6.71 (t, J=7.58 Hz, 1 H) 6.88 (d, J=8.08 Hz, 1 H) 7.01-7.12 (m, 1 H) 7.17-7.26 (m, 2 H) 7.25-7.40 (m, 4 H) 7.43-7.56 (m, 2 H).

Example 64

(1R,2S) and (1S,2R)-2-(4-chlorophenyl)-1'-(3-(4-(pyridin-4-yl)piperazine-1-carbonyl)benzyl)spiro[cyclopropane-1,3'-indolin]-2'-one

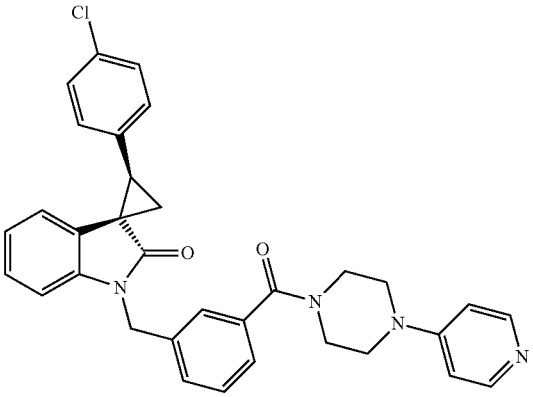

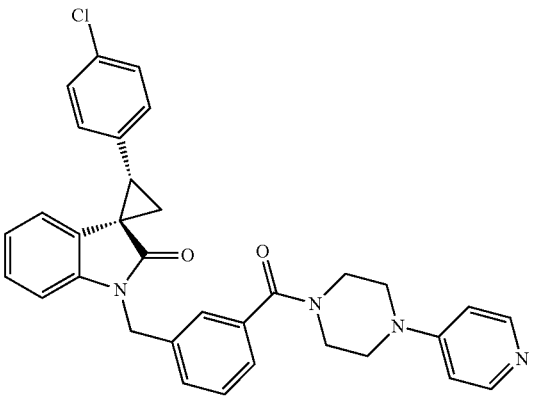

The title compound was prepared in analogy to Example 60 starting from 1-(pyridin-4-yl)piperazine, (3-bromomethyl)-benzoate (commercially available), (1R,2S) and (1S,2R)-3-((2-(4-chlorophenyl)-2'-oxospiro[cyclopropane-1,3'-indoline]-1'-yl)methyl)benzoic acid prepared as in Scheme 1. LC/MS m/e calcd. for $C_{33}H_{29}ClN_4O_2$: 548, observed (M+H)$^+$: 549.1 $^1$H NMR (400 MHz, MeOD-$d_4$) δppm 2.20-2.29 (m, 2 H) 3.26-3.31 (m, 1 H) 3.58 (br. s., 4 H) 3.88 (br. s., 4 H) 5.08-5.25 (m, 2 H) 6.14 (d, J=7.58 Hz, 1 H) 6.77 (t, J=7.58 Hz, 1 H) 6.92 (d, J=7.83 Hz, 1 H) 7.12 (t, J=7.20 Hz, 3 H) 7.21-7.32 (m, 4 H) 7.41 (s, 1 H) 7.45 (d, J=7.33 Hz, 1 H) 7.50-7.61 (m, 2 H) 8.19 (d, J=7.58 Hz, 2 H).

Example 65

(1S,2R) and (1R,2S)-2-(4-chlorophenyl)-1'-(3-(4-isopropylpiperazine-1-carbonyl)benzyl)spiro[cyclopropane-1,3'-indolin]-2'-one

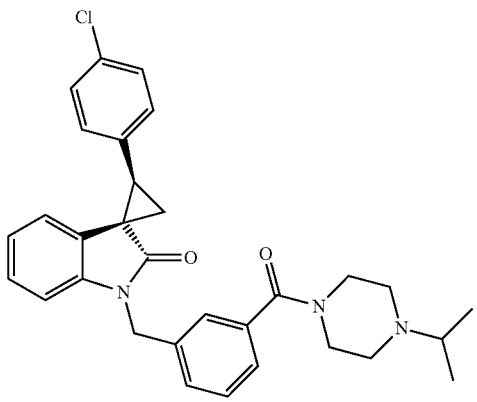

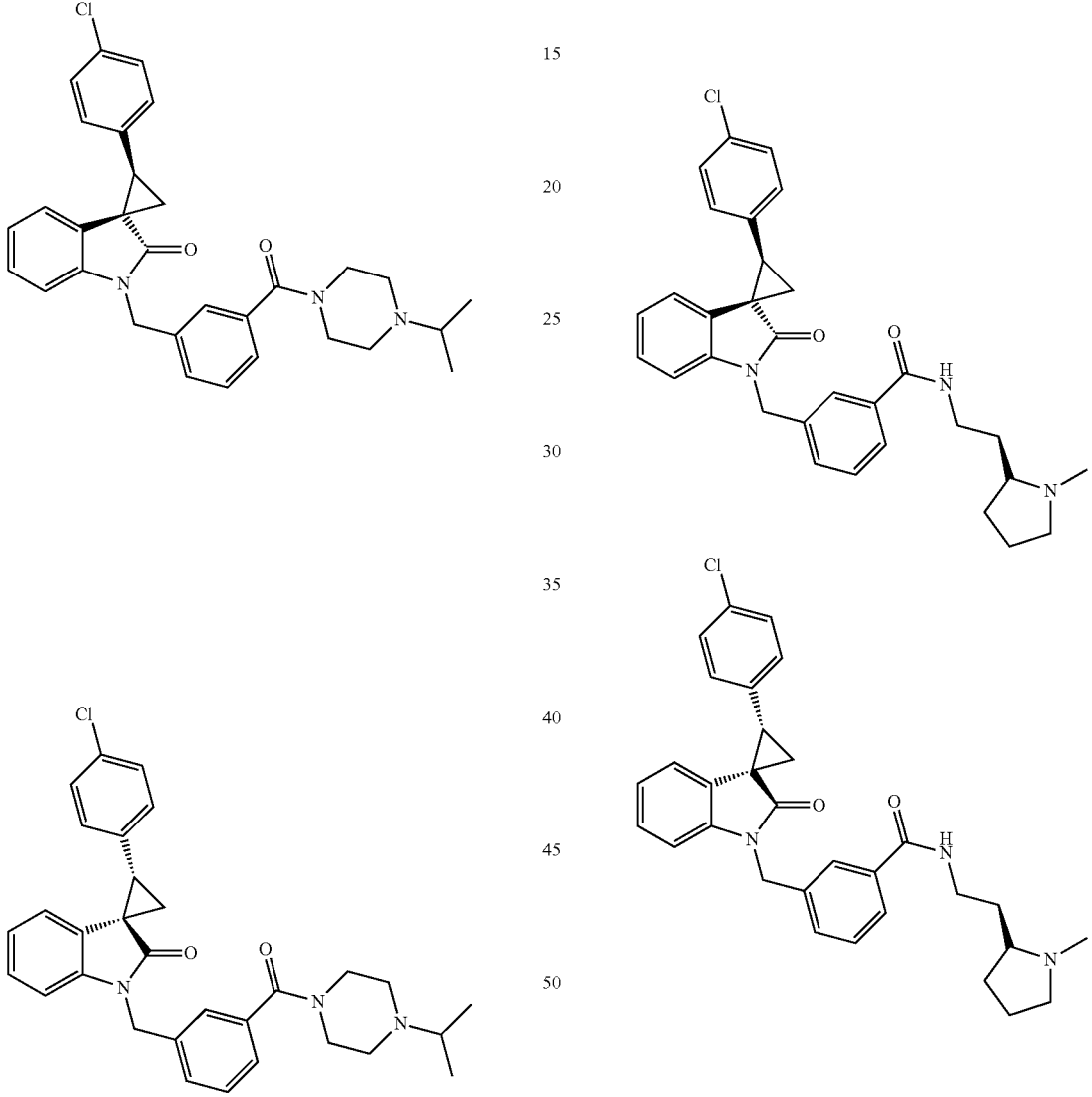

The title compound was prepared in analogy to Example 60 starting from 1-isopropylpiperazine, (3-bromomethyl)-benzoate (commercially available), (1R,2S) and (1S,2R)-3-((2-(4-chlorophenyl)-2'-oxospiro[cyclopropane-1,3'-indoline]-1'-yl)methyl)benzoic acid prepared as in Scheme 1. LC/MS m/e calcd. for $C_{31}H_{32}ClN_3O_2$: 513, observed (M+H)$^+$: 514.2 $^1$H NMR (400 MHz, CDCl$_3$) δppm 1.37 (d, J=6.32 Hz, 6 H) 2.04 (dd, J=7.71, 4.67 Hz, 1 H) 2.28 (dd, J=9.22, 4.67 Hz, 1 H) 2.86 (br. s., 2 H) 3.35 (t, J=8.46 Hz, 1 H) 3.61 (br. s., 6 H) 4.96 (d, J=15.92 Hz, 1H) 5.18 (d, J=16.17 Hz, 1 H) 6.02 (d, J=7.33 Hz, 1 H) 6.71-6.82 (m, 2 H) 7.06-7.19 (m, 3 H) 7.31 (s, 1 H) 7.33-7.39 (m, 1 H) 7.39-7.51 (m, 3 H).

Example 66

3-(((1S,2R)-2-(4-chlorophenyl)-2'-oxospiro[cyclopropane-1,3'-indoline]-1'-yl)methyl)-N-(2-((S)-1-methylpyrrolidin-2-yl)ethyl)benzamide and 3-(((1R,2S)-2-(4-chlorophenyl)-2'-oxospiro[cyclopropane-1,3'-indoline]-1'-yl)methyl)-N-(2-((S)-1-methylpyrrolidin-2-yl)ethyl)benzamide The title compound was prepared in analogy to Example 60 starting from (2S)-2-(3-aminopropyl)-N-methylpyrrolidine, (3-bromomethyl)-benzoate (commercially available), (1R, 2S) and (1S,2R)-3-((2-(4-chlorophenyl)-2'-oxospiro[cyclopropane-1,3'-indoline]-1'-yl)methyl)benzoic acid prepared as in Scheme 1. LC/MS m/e calcd. for $C_{31}H_{32}ClN_3O_2$: 513, observed (M+H)$^+$: 514.2 1H NMR (400 MHz, MeOD-d$_4$) δppm 1.76-1.94 (m, 2 H) 2.00-2.20 (m, 2 H) 2.24 (d, J=8.59 Hz, 2 H) 2.26-2.37 (m, 1 H) 2.42-2.58 (m, 1 H) 2.94 (s, 3 H) 3.10-3.22 (m, 1 H) 3.25-3.31 (m, 1 H) 3.35-3.43 (m, 1 H) 3.52 (t, J=6.69 Hz, 2 H) 3.63-3.75 (m, 1 H) 5.13 (s, 2 H) 6.09 (d, J=7.58 Hz, 1 H) 6.73 (t, J=7.58 Hz, 1 H) 6.91 (d, J=7.83 Hz, 1 H) 7.09 (t, J=7.71 Hz, 1 H) 7.21-7.28 (m, 2 H) 7.28-7.37 (m, 2 H) 7.45-7.52 (m, 1 H) 7.52-7.60 (m, 1 H) 7.76 (d, J=7.58 Hz, 1 H) 7.85 (s, 1 H).

Example 67

(1R,2S) and (1S,2R)-3-((2-(4-chlorophenyl)-2'-oxospiro[cyclopropane-1,3'-indoline]-1'-yl)methyl)-N-(3-methyl-1 H-pyrazol-5-yl)benzamide

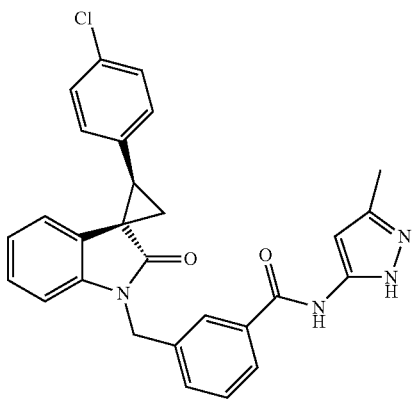

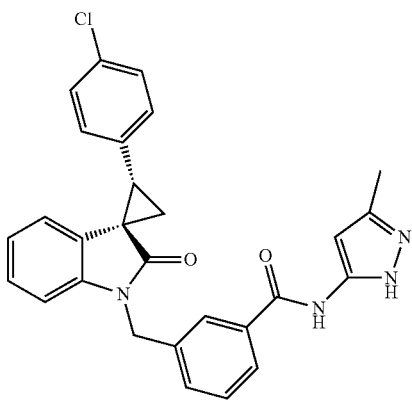

The title compound was prepared in analogy to Example 60 starting from 3-methyl-1 H-pyrazol-5-amine, (3-bromomethyl)-benzoate (commercially available), racemic (1R,2S) and (1S,2R)-3-((2-(4-chlorophenyl)-2'-oxospiro[cyclopropane-1,3'-indoline]-1'-yl)methyl)benzoic acid prepared as in Scheme 1. LC/MS m/e calcd. for $C_{28}H_{23}ClN_4O_2$: 482, observed (M+H)+: 483.2 1H NMR (400 MHz, MeOD-$d_4$) δ ppm 2.23 (d, J=8.59 Hz, 2 H) 2.55 (s, 3 H) 3.26-3.32 (m, 1 H) 5.08-5.23 (m, 2 H) 5.85 (d, J=1.01 Hz, 1 H) 6.08 (d, J=7.07 Hz, 1 H) 6.73 (t, J=7.58 Hz, 1 H) 6.94 (d, J=7.83 Hz, 1 H) 7.07-7.14 (m, 1 H) 7.19 (d, J=8.08 Hz, 2 H) 7.30 (d, J=8.59 Hz, 2 H) 7.48 (t, J=7.71 Hz, 1 H) 7.58 (d, J=8.34 Hz, 1 H) 7.80 (d, J=7.83 Hz, 1 H) 7.85 (s, 1 H).

Example 68

(1S,2R) and (1R,2S)-6-((2-(4-chlorophenyl)-2'-oxospiro[cyclopropane-1,3'-indoline]-1'-yl)methyl)picolinic acid

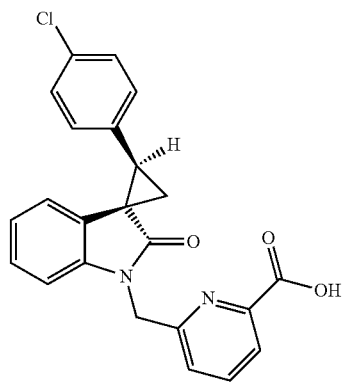

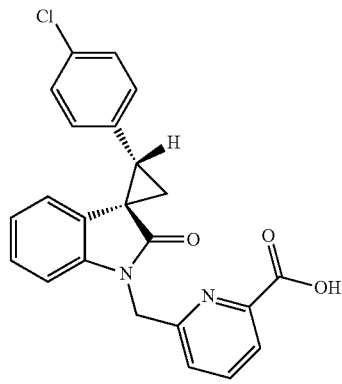

The title compound was prepared in analogy to Example 1 starting from 6-bromomethyl-pyridine-2-carboxylic acid methyl ester (commercially available), (1R,2S) and (1S,2R)-2-(4-chlorophenyl)spiro[cyclopropane-1,3'-indolin]-2'-one prepared as in Scheme 1. LC/MS m/e calcd. for $C_{23}H_{17}ClN_2O_3$: 404, observed (M+H)+: 405.2 1H NMR (400 MHz, DMSO-$d_6$) δppm 2.12 (dd, J=9.09, 4.80 Hz, 1 H) 2.39 (dd, J=8.08, 4.80 Hz, 1 H) 3.22 (t, J=8.59 Hz, 1 H) 5.14 (s, 2 H) 6.15 (d, J=7.33 Hz, 1 H) 6.73 (t, J=7.45 Hz, 1 H) 6.88 (d, J=7.58 Hz, 1 H) 7.00-7.10 (m, 1 H) 7.26 (d, J=1.01 Hz, 1 H) 7.38 (s, 4 H) 7.84-7.98 (m, 2 H).

Example 69

(1S,2R) and (1R,2S)-6-((2-(4-fluorophenyl)-2'-oxospiro[cyclopropane-1,3'-indoline]-1'-yl)methyl)picolinic acid

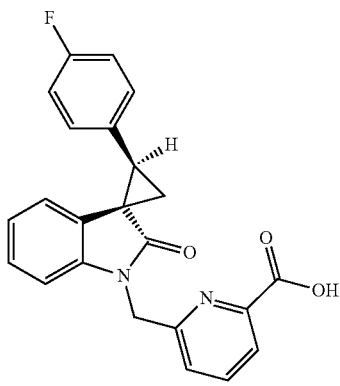

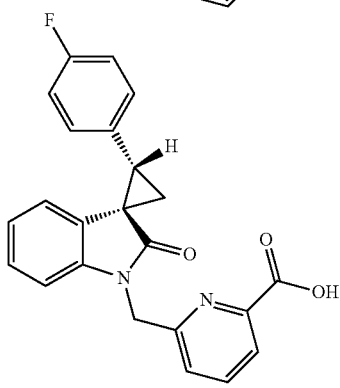

The title compound was prepared in analogy to Example 1 starting from 6-bromomethyl-pyridine-2-carboxylic acid methyl ester (commercially available) and (1R,2S) and (1S,2R)-2-(4-chlorophenyl)spiro[cyclopropane-1,3'-indolin]-2'-one prepared as in Scheme 1. LC/MS m/e calcd. for $C_{23}H_{17}FN_2O_3$: 388, observed (M+H)$^+$: 389.1 $^1$H NMR (400 MHz, DMSO-d$_6$) δppm 2.06-2.18 (m, 1 H) 2.32-2.39 (m, 1 H) 3.13-3.31 (m, 1 H) 5.12 (s, 2 H) 6.13 (d, 1 H) 6.68 (t, 1 H) 6.88 (d, 1 H) 6.98-7.08 (m, 1 H) 7.10-7.18 (m, 2 H) 7.23 (d, 1 H) 7.33-7.47 (m, 2 H) 7.79-7.93 (m, 2 H).

Example 70

(1S,2R) and (1R,2S)-2-(4-chlorophenyl)-1'-((tetrahydro-2H-pyran-4-yl)methyl)spiro[cyclopropane-1,3'-indolin]-2'-one

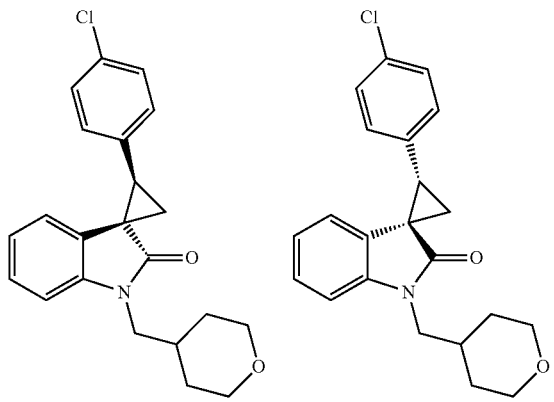

Racemic (1S,2R)-2-(4-chlorophenyl)spiro[cyclopropane-1,3'-indolin]-2'-one and (1R,2S)-2-(4-chlorophenyl)spiro[cyclopropane-1,3'-indolin]-2'-one (270 mg, 1.0 mmol, 1.0 equiv.) were added to a stirred solution of sodium hydride (60%, 60 mg, 1.5 mmol) in 5 mL of DMF under argon atmosphere at 0° C. After stirring for 1 hour, 4-bromomethyl-tetrahydropyran (215 mg, 1.2 mmol) was added. The reaction mixture was stirred for 14 hours at room temperature. The crude product was purified by HPLC to give the title compound as a white solid (258 mg, 70%). LC/MS m/e calcd. for $C_{22}H_{22}ClNO_2$: 367, observed (M+H)$^+$: 368.2 $^1$H NMR (400 MHz, MeOD-d$_4$) δppm 1.39-1.55 (m, 2 H) 1.65 (dd, J=13.14, 1.77 Hz, 2 H) 2.11-2.25 (m, 3 H) 3.22 (t, J=8.46 Hz, 1 H) 3.37-3.47 (m, 2 H) 3.79 (d, J=7.33 Hz, 2 H) 3.94-4.04 (m, 2 H) 6.09 (d, J=7.58 Hz, 1 H) 6.76 (t, J=7.58 Hz, 1 H) 7.11 (d, J=7.83 Hz, 1 H) 7.17-7.25 (m, 3 H) 7.33 (d, J=8.34 Hz, 2 H). MS calcd. For $C_{22}H_{22}ClNO_2$ 367, obsd. (ESI$^+$) [(M+H)$^+$] 368.

Example 71

(1S,2R) and (1R,2S)-2-(4-chlorophenyl)-1'-(2-(diethylamino)ethyl)spiro[cyclopropane-1,3'-indolin]-2'-one

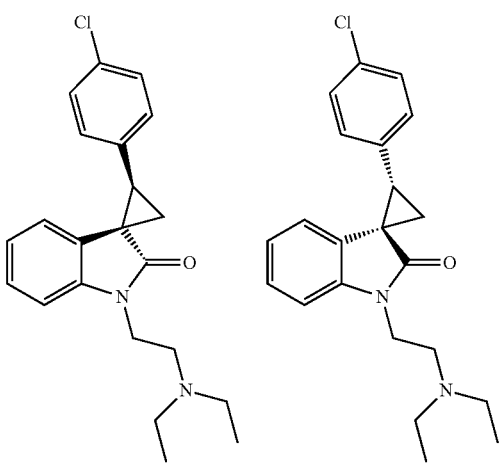

The title compound was prepared in analogy to Example 70 starting from 2-Chloro-N,N-diethylethaneamine hydrochloride (commercially available), (1S,2R) and (1R,2S)-2-(4-chlorophenyl)Spiro[cyclopropane-1,3'-indolin]-2'-one prepared as in Scheme 1. LC/MS m/e calcd. for $C_{22}H_{25}ClN_2O$: 368, observed (M+H)$^+$: 369.1 $^1$H NMR (400 MHz, MeOD-d$_4$) δppm 1.41 (t, J=7.20 Hz, 6 H) 2.21-2.31 (m, 2 H) 3.32 (t, J=8.59 Hz, 1 H) 3.39-3.55 (m, 4 H) 3.60 (t, J=6.44 Hz, 2 H) 4.23-4.42 (m, 2 H) 6.16 (d, J=7.58 Hz, 1 H) 6.85 (t, J=7.45 Hz, 1 H) 7.19 (d, J=7.83 Hz, 1 H) 7.24-7.32 (m, 3 H) 7.33-7.40 (m, 2 H).

Example 72

(1S,2R) and (1R,2S)-2-(4-chlorophenyl)-1'-(2-morpholino ethyl) spiro[cyclopropane-1,3'-indolin]-2'-one

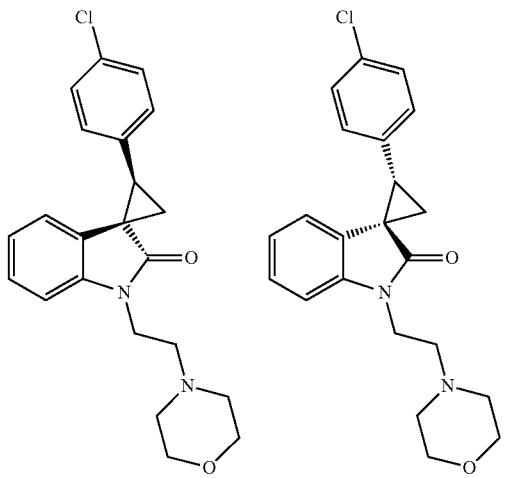

The title compound was prepared in analogy to Example 70 starting from 4-(2-chloroethyl)morpholine hydrochloride (commercially available), (1S,2R) and (1R,2S)-2-(4-chlorophenyl)spiro[cyclopropane-1,3'-indolin]-2'-one prepared as in Scheme 1. LC/MS m/e calcd. for $C_{22}H_{23}ClN_2O_2$: 382, observed (M+H)+: 383.1 $^1$H NMR (400 MHz, MeOD-$d_4$) δ ppm 2.21-2.29 (m, 2 H) 3.30 (t, J=8.72 Hz, 1 H) 3.54-3.69 (m, 2 H) 3.97 (br. s., 8 H) 4.21-4.32 (m, 1 H) 4.36-4.48 (m, 1 H) 6.15 (d, J=7.33 Hz, 1 H) 6.83 (t, J=7.20 Hz, 1 H) 7.14-7.21 (m, 1 H) 7.22-7.30 (m, 3 H) 7.31-7.39 (m, 2 H).

Example 73

(1S,2R) and (1R,2S)-2-(4-chlorophenyl)-1'-((1-(methylsulfonyl)piperidin-4-yl)methyl) Spiro[cyclopropane-1,3'-indolin]-2'-one

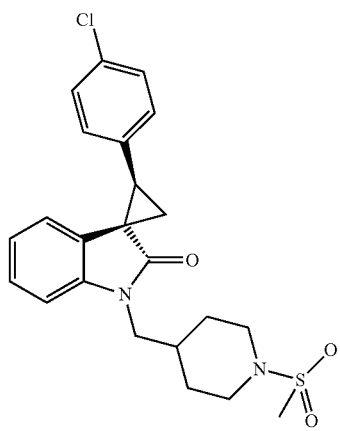

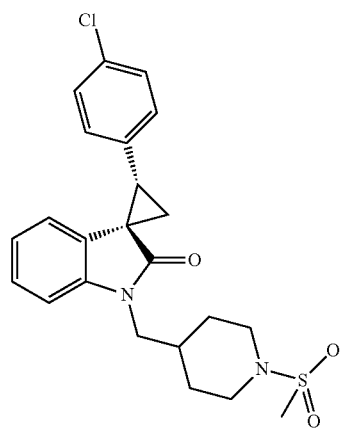

The title compound was prepared in analogy to Example 70 starting from 4-chloromethyl-1-methanesulfonyl-piperidine (commercially available), (1R,2S) and (1S,2R)-2-(4-chlorophenyl)spiro[cyclopropane-1,3'-indolin]-2'-one prepared as in Scheme 1. LC/MS m/e calcd. for $C_{23}H_{25}ClN_2O_3S$: 444, observed (M+H)+: 445.1 $^1$HNMR (400 MHz, DMSO-$d_6$) δ ppm 1.23-1.41 (m, 2 H) 1.66-1.78 (m, 2 H) 1.84-1.98 (m, 1 H) 2.02 (dd, J=9.09, 4.80 Hz, 1 H) 2.30 (dd, J=7.71, 4.67 Hz, 1 H) 2.67 (t, J=11.75 Hz, 2 H) 2.83 (s, 3 H) 3.11 (t, J=8.46 Hz, 1 H) 3.56 (d, J=12.13 Hz, 2 H) 3.71 (d, J=7.33 Hz, 2 H) 6.12 (d, J=7.33 Hz, 1 H) 6.66-6.80 (m, 1 H) 7.10-7.20 (m, 2 H) 7.25-7.34 (m, 2 H) 7.34-7.43 (m, 2 H).

Example 74

(1S,2R) and (1R,2S)-2-(4-chlorophenyl)-1'-(2-(4-isopropylpiperazin-1-yl)ethyl)spiro [cyclopropane-1,3'-indolin]-2'-one

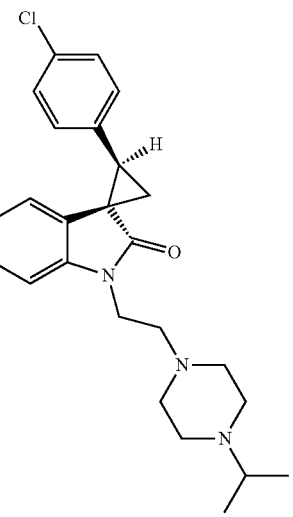

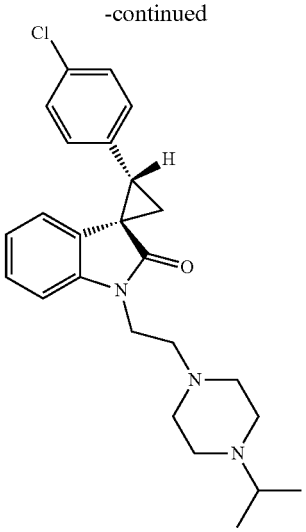

(1R,2S) and (1S,2R)-2-(4-chlorophenyl)-1'-(2,2-dimethoxyethyl)spiro[cyclopropane-1,3'-indolin]-2'-one

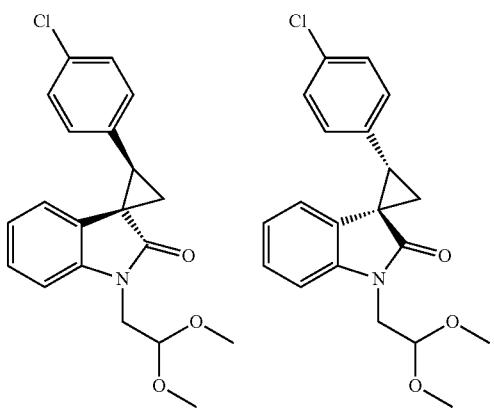

To a solution of (1R,2S) and (1S,2R)-2-(4-chlorophenyl) spiro[cyclopropane-1,3'-indolin]-2'-one (135 mg, 1 mmol) in DMF (1 mL) was added KHMDS (0.5 M in THF, 1.1 mL) was dropwise at room temperature. The mixture was stirred for half an hour before adding bromoacetaldehyde dimethyl acetal (95 mg, 0.55 mmol). The mixture was warmed to 50° C. and stirred at that temperature for 2 hours. The mixture was poured into water, extracted with ethyl acetate (3×15 mL), dried and concentrated under reduced pressure. Purification by flash column chromatography on silica gel, eluting with hexanes-EtOAc (6:1 and then 4:1) gave the desire product as colorless oil (268 mg, 75%). LC/MS m/e calcd. for $C_{20}H_{20}ClNO_3$: 3570, observed $(M+H)^+$: 358.7.

(1R,2S) and (1S,2R)-2-(2-(4-chlorophenyl)-2'-oxospiro[cyclopropane-1,3'-indoline]-1'-yl)acetaldehyde

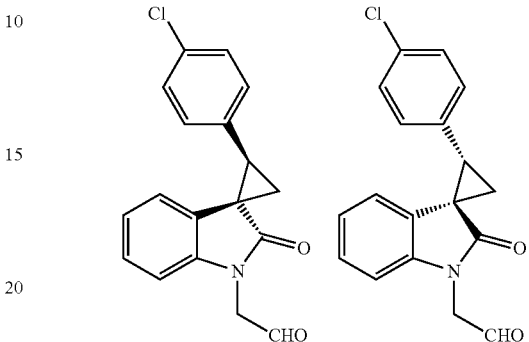

A suspension of (1R,2S) and (1S,2R)-2-(4-chlorophenyl)-1'-(2,2-dimethoxyethyl) spiro[cyclopropane-1,3'-indolin]-2'-one (1 g) in water (1 mL) was cooled to 0° C. and treated with a mixture of DCM and TFA (1:1, 6 mL) for 2 hours. The reaction mixture was poured into saturated aq. $NaHCO_3$ solution and extracted with DCM (3×6 mL). The combined organic layers were washed with brine and dried over $Na_2SO_4$. The solvent was evaporated under reduced pressure. The crude product was used for next step directly without any further purification. LC/MS m/e calcd. for $C_{18}H_{14}ClNO_2$: 311, observed $(M+H)^+$: 312.3.

(1S,2R) and (1R,2S)-2-(4-chlorophenyl)-1'-(2-(4-isopropylpiperazin-1-yl)ethyl)spiro [cyclopropane-1,3'-indolin]-2'-one

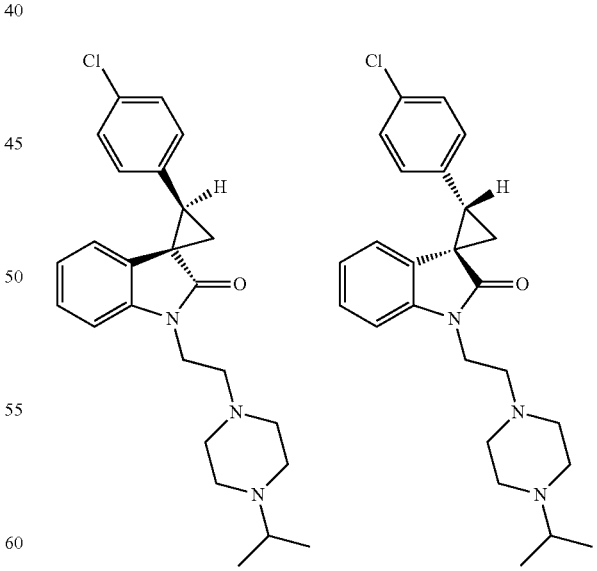

A mixture of (1R,2S) and (1S,2R)-2-(2-(4-chlorophenyl)-2'-oxospiro[cyclopropane-1,3'-indoline]-1'-yl)acetaldehyde (0.1 mmol), (1-Isopropyl)piperazine (0.15 mmol) and acetic acid (catalytic amount) in DCM (2 ml) was stirred for 20 minutes at room temperature. The mixture was cooled to 0° C.

and NaBH(OAc)$_3$ (2 mmol) was added carefully. The mixture was warmed to room temperature and stirred for 14 hours at room temperature. The mixture was concentrated under reduced pressure and dissolved in DMF. Purification by preparative HPLC gave the title product as colorless oil (35 mg). LC/MS m/e calcd. for C$_{25}$H$_{30}$ClN$_3$O: 423, observed (M+H)$^+$: 424.1 $^1$HNMR (400 MHz, MeOD-d$_4$) δppm 1.37 (d, J=6.57 Hz, 6 H) 2.18 (dd, J=8.46, 5.94 Hz, 2 H) 2.46-2.64 (m, 1H) 2.85 (d, J=3.54 Hz, 2 H) 3.22 (s, 2 H) 3.50 (d, J=6.57 Hz, 2 H) 3.90-4.27 (m, 2 H) 6.09 (d, J=7.58 Hz, 1H) 6.76 (s, 1 H) 7.10 (d, J=7.83 Hz, 1 H) 7.16-7.25 (m, 3 H) 7.33 (d, J=8.59 Hz, 2 H).

Example 75
(1S,2R) and (1R,2S)-2-(4-chlorophenyl)-1'-(2-(4-(2-(dimethylamino)ethyl)piperazin-1-yl)ethyl) Spiro [cyclopropane-1,3'-indolin]-2'-one

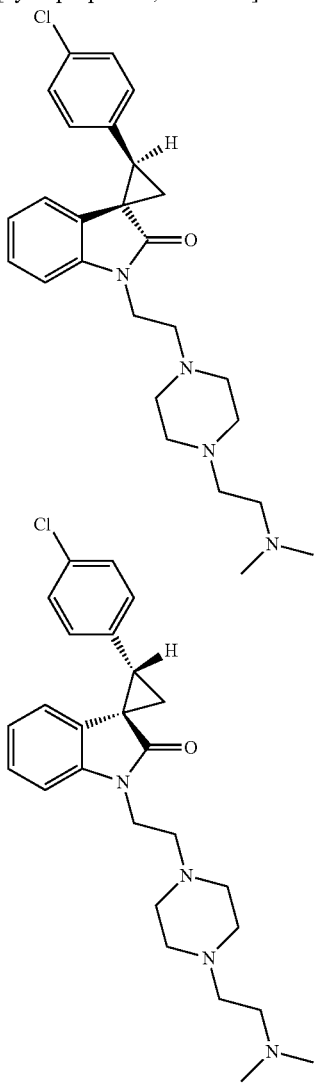

The title compound was prepared in analogy to Example 74 starting from 1-(2-Dimethylamino-ethyl)-piperazine, bromoacetaldehyde dimethyl acetal (commercially available), (1R,2S) and (1S,2R)-2-(4-chlorophenyl)spiro[cyclopropane-1,3'-indolin]-2'-one prepared as in Scheme 1. LC/MS m/e calcd. for C$_{26}$H$_{33}$ClN$_4$O: 452, observed (M+H)$^+$: 453.1 $^1$HNMR (400 MHz, MeOD-d$_4$) δppm 2.15-2.33 (m, 3 H) 2.86 (t, J=5.81 Hz, 3 H) 2.96 (s, 6 H) 3.27 (t, J=8.59 Hz, 3 H) 3.45-3.76 (m, 3 H) 4.32 (d, J=48.76 Hz, 3 H) 6.12 (d, J=7.58 Hz, 1 H) 6.81 (t, J=7.20 Hz, 1 H) 7.11-7.19 (m, 1 H) 7.20-7.28 (m, 3 H) 7.30-7.41 (m, 2 H).

Example 76
(1S,2R)-2-(4-chlorophenyl)-1'-(2-((S)-3-(dimethylamino)pyrrolidin-1-yl)ethyl)spiro[cyclopropane-1,3'-indolin]-2'-one and (1R,2S)-2-(4-chlorophenyl)-1'-(2-((S)-3-(dimethylamino)pyrrolidin-1-yl)ethyl)spiro [cyclopropane-1,3'-indolin]-2'-one

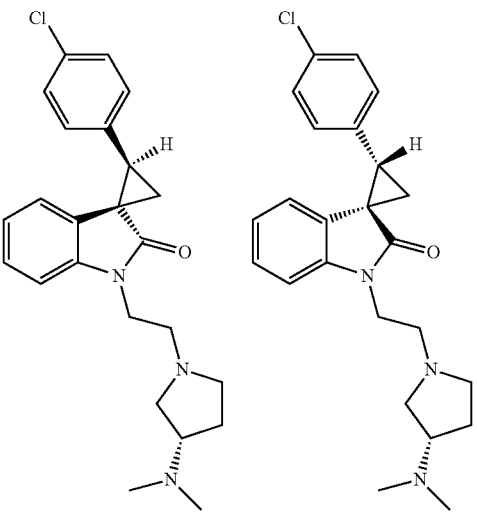

The title compound was prepared in analogy to Example 74 starting from (3S)-(−)-3-(dimethylamino)pyrrolidine, bromoacetaldehyde dimethyl acetal (commercially available), (1R,2S) and (1S,2R)-2-(4-chlorophenyl)spiro[cyclopropane-1,3'-indolin]-2'-one prepared as in Scheme 1. LC/MS m/e calcd. for C$_{24}$H$_{28}$ClN$_3$O: 409, observed (M+H)$^+$: 410.2 $^1$H NMR (400 MHz, MeOD-d$_4$) δppm 1.32 (s, 2 H) 2.09-2.40 (m, 5 H) 2.50-2.76 (m, 1 H) 2.96 (d, J=6.82 Hz, 6 H) 3.15-3.32 (m, 3 H) 3.43-3.55 (m, 1 H) 3.66 (br. s., 3 H) 3.75-3.93 (m, 1 H) 4.00-4.42 (m, 5 H) 6.09 (d, J=7.58 Hz, 1 H) 6.79 (t, J=7.58 Hz, 1 H) 7.13 (d, J=7.58 Hz, 1 H) 7.18-7.26 (m, 3 H) 7.28-7.40 (m, 2 H).

Example 77
(1S,2R)-2-(4-chlorophenyl)-1'-(2-((R)-3-(dimethylamino)pyrrolidin-1-yl)ethyl)spiro[cyclopropane-1,3'-indolin]-2'-one and (1R,2S)-2-(4-chlorophenyl)-1'-(2-((R)-3-(dimethylamino)pyrrolidin-1-yl)ethyl)spiro [cyclopropane-1,3'-indolin]-2'-one

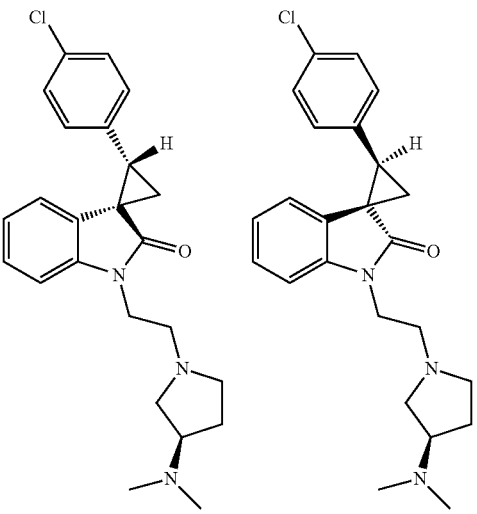

The title compound was prepared in analogy to Example 74 starting from (3R)-(+)-3-(dimethylamino)pyrrolidine, bromoacetaldehyde dimethyl acetal (commercially available), (1R,2S) and (1S,2R)-2-(4-chlorophenyl)spiro[cyclopropane-1,3'-indolin]-2'-one prepared as in Scheme 1. LC/MS m/e calcd. for $C_{29}H_{27}ClN_2O_2$: 470, observed (M+H)$^+$: 471.2 1H NMR (400 MHz, MeOD-d$_4$) δppm 1.32 (s, 1 H) 2.04-2.39 (m, 4 H) 2.47-2.69 (m, 1 H) 2.95 (d, J=6.82 Hz, 6 H) 3.23 (s, 3 H) 3.58 (br. s., 4 H) 3.72-3.93 (m, 1 H) 3.98-4.50 (m, 4 H) 6.09 (d, J=7.33 Hz, 1 H) 6.79 (t, J=7.58 Hz, 1 H) 7.13 (d, J=7.83 Hz, 1 H) 7.17-7.25 (m, 3 H) 7.28-7.39 (m, 2 H).

Example 78

(1R,2S) and (1S,2R)-2-(4-chlorophenyl)-1'-(pyridin-4-ylmethyl)spiro[cyclopropane-1,3'-indolin]-2'-one

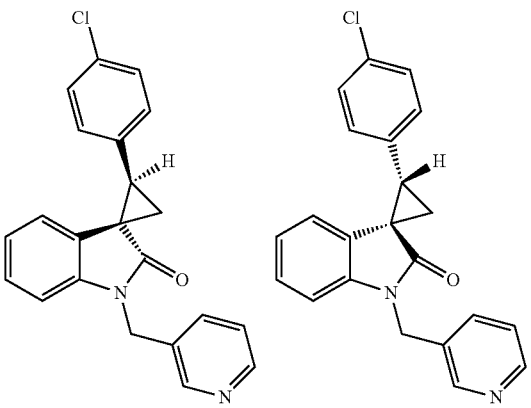

(1R,2S) and (1S,2R)-2-(4-chlorophenyl)spiro[cyclopropane-1,3'-indolin]-2'-one (135 mg, 0.5 mmol), 4-bromomethyl-pyridine (98 mg, 0.6 mmol) and Cs$_2$CO$_3$ (245 mg, 0.75 mmol) were dissolved in DMF (2 mL). The mixture was stirred at room temperature for 14 hours. The mixture was poured into water, extracted with ethyl acetate, dried and concentrated under reduced pressure. The residue was dissolved in 2 mL of DMF. Purification by preparative HPLC gave the title compound as little yellow solid (140 mg, 76%). LC/MS m/e calcd. for C$_{22}$H$_{17}$ClN$_2$O: 360, observed (M+H)$^+$: 361.2 $^1$HNMR (400 MHz, MeOD-d$_4$) δppm 2.22-2.37 (m, 2 H) 3.32-3.40 (m, 1 H) 5.39 (s, 2 H) 6.15 (d, J=7.58 Hz, 1 H) 6.74-6.85 (m, 1 H) 6.92 (d, J=7.83 Hz, 1 H) 7.10-7.19 (m, 1 H) 7.24-7.42 (m, 4 H) 7.93 (d, J=6.32 Hz, 2 H) 8.80 (d, J=6.06 Hz, 2 H). MS calcd. for C$_{22}$H$_{17}$ClN$_2$O 360, obsd. (ESI$^+$) [(M+H)$^+$] 361.1.

Example 79

(1S,2R) and (2R,1S)-2-(4-chlorophenyl)-1'-(pyridin-3-ylmethyl)spiro[cyclopropane-1,3'-indolin]-2'-one The title compound was prepared in analogy to Example 78 starting from 3-bromomethyl-pyridine (commercially available), (1R,2S) and (1S,2R)-2-(4-chlorophenyl)spiro[cyclopropane-1,3'-indolin]-2'-one prepared as in Scheme 1. LC/MS m/e calcd. for C$_{29}$H$_{27}$ClN$_2$O$_2$: 470, observed (M+H)$^+$: 471.2 $^1$HNMR (400 MHz, MeOD-d$_4$) δppm 2.25 (dd, J=8.59, 1.77 Hz, 2 H) 3.31 (br. s., 1 H) 5.28 (d, J=3.03 Hz, 2 H) 6.12 (d, J=7.58 Hz, 1 H) 6.71-6.85 (m, 1 H) 7.03 (d, J=8.08 Hz, 1 H) 7.12-7.19 (m, 1 H) 7.21-7.29 (m, 2 H) 7.30-7.39 (m, 2 H) 7.86-7.99 (m, 1 H) 8.40 (d, J=8.59 Hz, 1 H) 8.74 (d, J=5.31 Hz, 1 H) 8.84 (s, 1 H).

Example 80

(1S,2R) and (1R,2S)-2-(4-(2-(4-chlorophenyl)-2'-oxospiro[cyclopropane-1,3'-indoline]-1'-yl)-1H-imidazol-1-yl)acetic acid

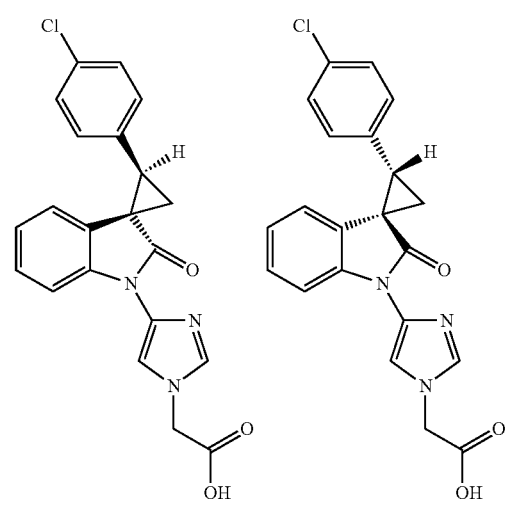

(1S,2R) and (1R,2S)-2-(4-chlorophenyl)-1'-(1-tri-tyl-1H-imidazol-4-yl)spiro[cyclopropane-1,3'-indolin]-2'-one

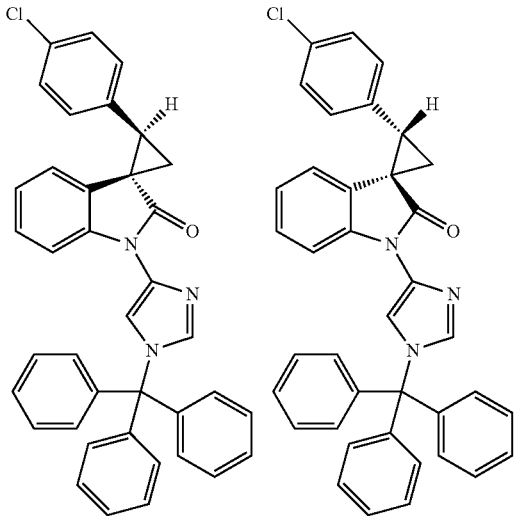

4-Iodo-1-trityl-1H-imidazole (210 mg, 0.48 mmol) was added to a suspension of racemic (1S,2R)-2-(4-chlorophenyl)spiro[cyclopropane-1,3'-indolin]-2'-one (107 mg, 0.4 mmol) in acetonitrile (2 mL) under a nitrogen atmosphere. A steady stream of nitrogen was bubbled through the suspension as it was heated to 40° C. over 15 minutes. Potassium carbonate (110 mg, 0.8 mmol), copper (I) iodide (12 mg, 15 mol %), and N,N-dimethylethylenediamine (0.12 mmol, 30 mol %) were added and the reaction mixture was heated to 80° C. and kept for 21 hours under nitrogen atmosphere. The mixture was cooled to room temperature, filtered and concentrated to give the title product. The residue was purified by flash column chromatography (gradient elution, 5-10% ethyl acetate in petroleum ether) to give racemic trans-2-(4-chlorophenyl)-1'-(1 H-imidazol-4-trityl)spiro[cyclopropane-1,3'-indolin]-2'-one (157 mg, 68%). LC/MS m/e calcd. for $C_{38}H_{28}ClN_3O$: 577, observed (M+H)$^+$: 578.2 MS calcd. for $C_{38}H_{28}ClN_3O$ 578, obsd. (ESI$^+$) [(M+H)$^+$] 579.3.

(1S,2R) and (1R,2S)-2-(4-chlorophenyl)-1'-(1H-imidazol-4-yl)spiro[cyclopropane-1,3'-indolin]-2'-one

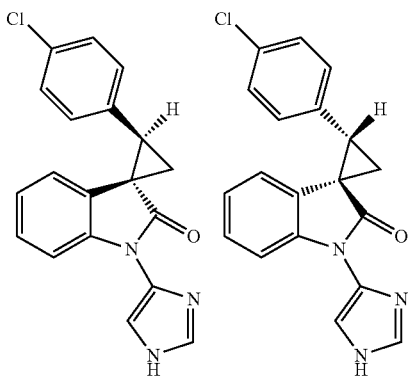

To a solution of racemic (1S,2R) and (1R,2S)-2-(4-chlorophenyl)-1'-(1-trityl-1H-imidazol-4-yl)spiro[cyclopropane-1,3'-indolin]-2'-one (115 mg, 0.2 mmol) in DCM (2 mL) and water (0.5 mL) was added TFA (0.1 mL) dropwise at 0° C. The mixture was stirred for 14 hours at room temperature. The mixture was poured into the sat. aqueous NaHCO$_3$ solution, extracted with DCM (3×10 mL), dried and concentrated to give the title product. The residue was dissolved in 2 mL of DMF. Purification by preparative HPLC gave the title compound as white powder (60 mg, 89%). LC/MS m/e calcd. for $C_{19}H_{14}ClN_3O$: 335, observed (M+H)$^+$: 336.1 $^1$H NMR (400 MHz, DMSO-d$_6$) δppm 2.13 (dd, J=9.09, 5.05 Hz, 1 H) 2.42 (dd, J=8.08, 4.80 Hz, 1 H) 3.23 (t, J=8.72 Hz, 1 H) 6.20 (d, J=7.58 Hz, 1 H) 6.81 (t, J=7.20 Hz, 1 H) 7.16 (t, J=7.83 Hz, 1 H) 7.30-7.45 (m, 5 H) 7.66 (s, 1 H) 8.27 (s, 1 H). MS calcd. for $C_{19}H_{14}ClN_3O$ 335, obsd. (ESI$^+$) [(M+H)$^+$] 336.3.

Synthesis of (1S,2R) and (1R,2S)-2-(4-(2-(4-chlorophenyl)-2'-oxospiro[cyclopropane-1,3'-indoline]-1'-yl)-1H-imidazol-1-yl)acetic acid

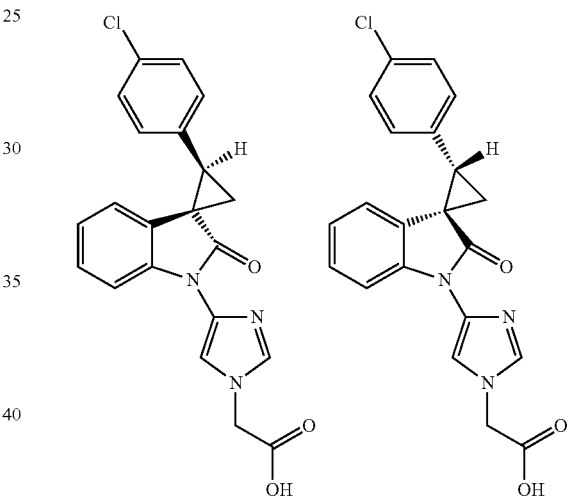

To a mixture of racemic (1S,2R) and (1S,2R)-2-(4-chlorophenyl)-1'-(1H-imidazol-4-yl)spiro[cyclopropane-1,3'-indolin]-2'-one (0.4 mmol, 134 mg), methyl-bromoacetate (61.2 mg, 0.4 mmol) and 5 mg of TEBA (0.008 mmol) in 2 mL of DCM was added 50% KOH (0.5 mL). The reaction mixture was stirred at room temperature for 14 hours. Then the mixture was concentrated under reduced pressure and acidified to pH~4. The residue was dissolved in 2 mL of DMF. Purification by preparative HPLC gave the title compound as a white powder (113 mg, 68%). LC/MS m/e calcd. for $C_{21}H_{16}ClN_3O_3$: 393, observed (M+H)$^+$: 394.2 $^1$H NMR (400 MHz, DMSO-d$_6$) δppm 2.05-2.16 (m, 1 H) 2.39 (dd, J=7.96, 4.93 Hz, 1 H) 3.20 (t, J=8.72 Hz, 1 H) 4.97 (s, 2 H) 6.18 (d, J=7.07 Hz, 1 H) 6.79 (t, J=7.20 Hz, 1 H) 7.06-7.22 (m, 1 H) 7.38 (s, 4 H) 7.54 (d, J=1.01 Hz, 1 H) 7.69 (d, J=7.83 Hz, 1 H) 7.74 (d, J=1.26 Hz, 1 H). MS calcd. for $C_{21}H_{16}ClN_3O_3$ 393, obsd. (ESI$^+$) [(M+H)$^+$] 394.3.

Example 81

(1S,2R) and (1R,2S)-1-(2-(2-(4-chlorophenyl)-2'-oxospiro[cyclopropane-1,3'-indoline]-1'-yl)ethyl)-1H-imidazole-4-carboxylic acid

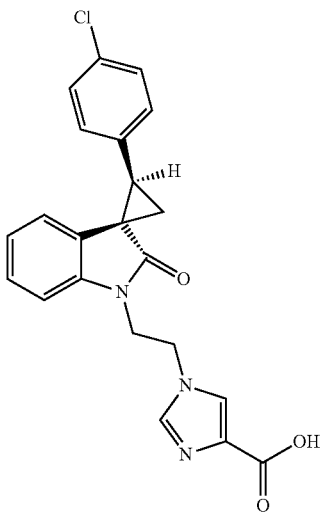

Synthesis of (1S,2R) and (1R,2S)-1'-(2-bromoethyl)-2-(4-chlorophenyl)spiro[cyclopropane-1,3'-indolin]-2'-one

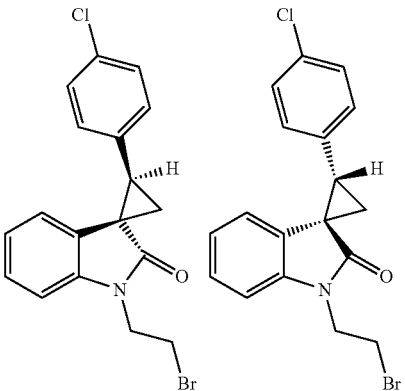

To a solution of (1R,2S) and (1S,2R)-2-(4-chlorophenyl)spiro[cyclopropane-1,3'-indolin]-2'-one (173 mg, 0.64 mmol) in DMF (2 mL) was added KHMDS (0.5 M, 1.4 mL) dropwise at room temperature. The mixture was stirred for half an hour before adding ethylene dibromide (300 mg, 1.6 mmol). The mixture was warmed to 50° C. and stirred at that temperature for 14 hours. The mixture was poured into water, extracted with ethyl acetate (3×15 mL), dried and concentrated under reduced pressure. The residue was purified by flash column chromatography (gradient elution, 5-10% ethyl acetate in petroleum ether) to give the title compound as white solid (98 mg, 41%). LC/MS m/e calcd. for $C_{18}H_{15}BrClNO$: 375, observed (M+H)$^+$: 376.

Synthesis of (1S,2R) and (1R,2S)-methyl-1-(2-(2-(4-chlorophenyl)-2'-oxospiro[cyclopropane-1,3'-indoline]-1'-yl)ethyl)-1H-imidazole-4-carboxylate

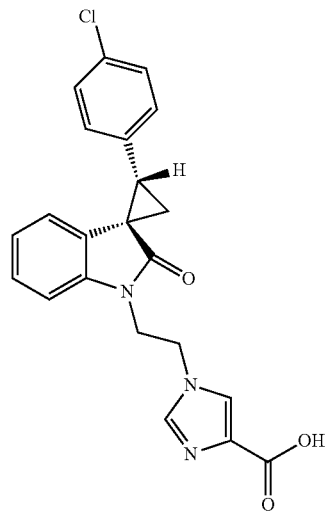

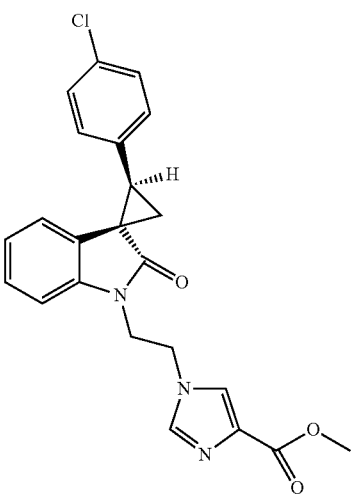

111

-continued

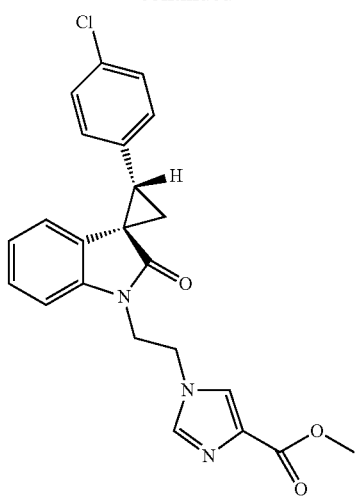

To a solution of methyl-imidazole-4-carboxylate (100 mg, 0.2 mmol) in 1 mL of anhydrous DMF was added NaH (60% disp.) (8.8 mg, 0.22 mmol) at room temperature. The reaction mixture was stirred for 1 hour at that temperature. To the mixture was added a solution of racemic (1R,2S) and (1S,2R)-1'-(2-bromoethyl)-2-(4-chlorophenyl)spiro[cyclopropane-1,3'-indolin]-2'-one (75.2 mg, 0.2 mmol) in 1 mL of DMF. The reaction was stirred at room temperature for 14 hours and then concentrated under reduced pressure. The residue was dissolved in EtOAc and washed with saturated aqueous NaHCO$_3$. The layers were separated and the aqueous layer was extracted with EtOAc. The organic layers were combined and washed with brine, dried over anhydrous Na$_2$SO$_4$, filtered and concentrated in vacuo to give the title compound as white solid (30 mg, 35%). LC/MS m/e calcd. for C$_{23}$H$_{20}$ClN$_3$O$_3$: 421, observed (M+H)$^+$: 422.3.

Synthesis of (1S,2R) and (1R,2S)-1-(2-(2-(4-chlorophenyl)-2'-oxospiro[cyclopropane-1,3'-indoline]-1'-yl)ethyl)-1H-imidazole-4-carboxylic acid

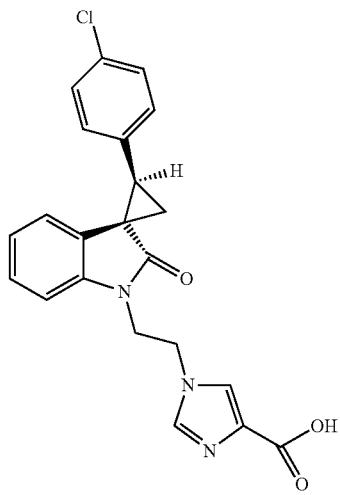

112

-continued

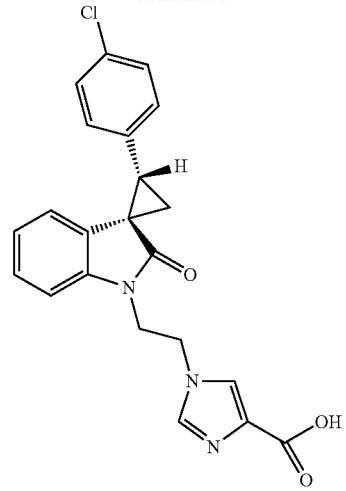

To a solution of methyl-1-(2-((1S,2R)-2-(4-chlorophenyl)-2'-oxospiro[cyclopropane-1,3'-indoline]-1'-yl)ethyl)-1H-imidazole-4-carboxylate and methyl-1-(2-((1R,2S)-2-(4-chlorophenyl)-2'-oxospiro[cyclopropane-1,3'-indoline]-1'-yl)ethyl)-1H-imidazole-4-carboxylate (0.07 mmol) in methanol (2 mL) and water (1 mL) was added LiOH.H$_2$O (18 mg, 0.4 mmol) in one portion. The mixture was stirred at room temperature for 3 hours until the starting material was consumed. The mixture was concentrated under reduced pressure and acidified to pH~3. The residue was dissolved in 2 mL of DMF. Purification by preparative HPLC gave the title compound as a white powder (26 mg, 88%). LC/MS m/e calcd. for C$_{22}$H$_{18}$ClN$_3$O$_3$: 407, observed (M+H)$^+$: 408.8 $^1$H NMR (400 MHz, MeOD) δppm 2.10 (dd, J=28.17, 8.46 Hz, 2 H) 3.10 (s, 1 H) 4.31 (s, 2 H) 4.86 (s, 2 H) 6.05 (d, J=7.33 Hz, 1 H) 6.75 (s, 1 H) 6.90-7.45 (m, 6 H) 7.86 (s, 1 H) 8.27 (s, 1 H).

Example 82

(1S,2S) and (1R,2R)-1-(2-(2-(4-chlorophenyl)-2'-oxospiro[cyclopropane-1,3'-indoline]-1'-yl)ethyl)-1H-imidazole-4-carboxylic acid

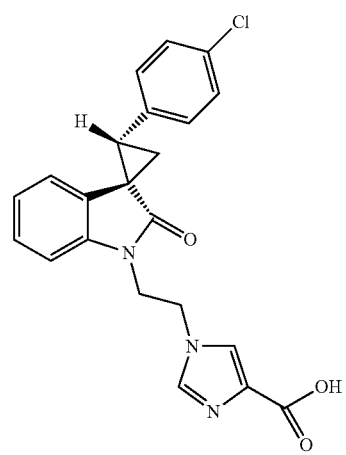

113
-continued

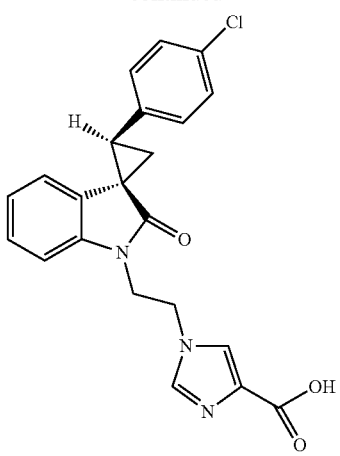

The title compound was prepared in analogy to Example 81 starting from methyl-imidazole-4-carboxylate, ethylene dibromide (commercially available), (1R,2S) and (1S,2R)-2-(4-chlorophenyl)spiro[cyclopropane-1,3'-indolin]-2'-one prepared as in Scheme 1. LC/MS m/e calcd. for $C_{22}H_{18}ClN_3O_3$: 407, observed (M+H)$^+$: 408.8 $^1$H NMR (400 MHz, MeOD-d$_4$) δppm 2.25 (dd, J=8.59, 1.77 Hz, 2 H) 3.31 (br. s., 1 H) 5.28 (d, J=3.03 Hz, 2 H) 6.12 (d, J=7.58 Hz, 1 H) 6.71-6.85 (m, 1 H) 7.03 (d, J=8.08 Hz, 1 H) 7.12-7.19 (m, 1 H) 7.21-7.29 (m, 2H) 7.30-7.39 (m, 2 H) 7.86-7.99 (m, 1 H) 8.40 (d, J=8.59 Hz, 1 H) 8.74 (d, J=5.31 Hz, 1 H) 8.84 (s, 1 H).

Example 83

(1S,2R) and (1R,2S)-3-(2-(4-chlorophenyl)-2'-oxospiro[cyclopropane-1,3'-indoline]-1'-yl)benzoic acid

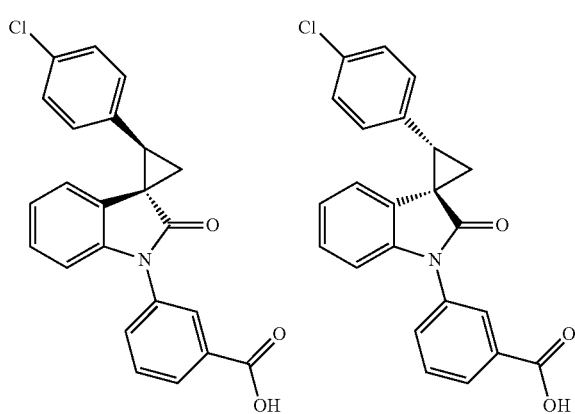 [SMILES: O=C(O)c1cccc(N2C(=O)[C@]3(C[C@@H]3c3ccc(Cl)cc3)c3ccccc32)c1 ; O=C(O)c1cccc(N2C(=O)[C@@]3(C[C@H]3c3ccc(Cl)cc3)c3ccccc32)c1]

114
Synthesis of (1S,2R) and (1R,2S)-methyl-3-(2-(4-chlorophenyl)-2'-oxospiro[cyclopropane-1,3'-indoline]-1'-yl)benzoate

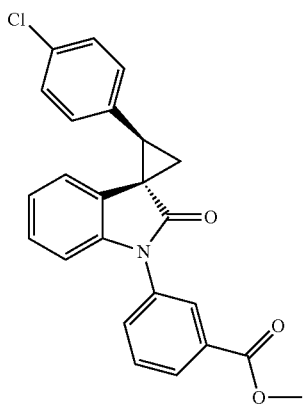

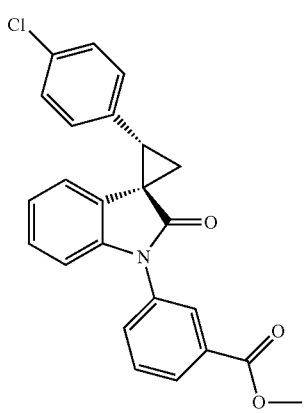

A Schlenk tube was charged with CuI (9.6 mg, 0.05 mmol, 5.0 mol %), racemic (1R,2S) and (1S,2R)-2-(4-chlorophenyl)spiro[cyclopropane-1,3'-indolin]-2'-one (270 mg, 1.0 mmol), and K$_2$CO$_3$ (276 mg, 2.0 mmol), evacuated, and backfilled with argon. N,N'-Dimethylethylenediamine (11 μL, 0.10 mmol, 10 mol %), ethyl 3-iodobenzoate (278.8 mg, 1.01 mmol), and acetonitrile (1.5 mL) were added under argon. The Schlenk tube was sealed with a Teflon valve and the reaction mixture was stirred at 80° C. for 23 hours. HPLC monitored the reaction finished. The solvent was removed under reduced pressure. The residue was purified by flash column chromatography column (gradient elution, 5-10% ethyl acetate in petroleum ether) to give the title compound as Synthesis of (1S,2R) and (1R,2S)-3-(2-(4-chlorophenyl)-2'-oxospiro[cyclopropane-1,3'-indoline]-1'-yl)benzoic acid

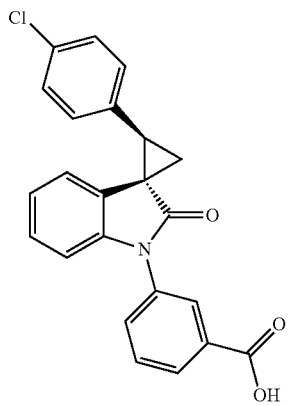

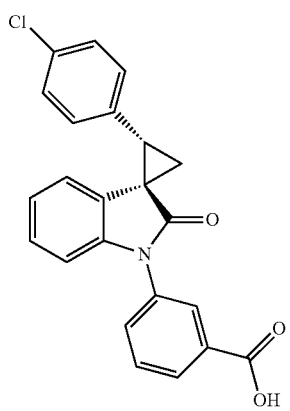

To a solution of methyl-3-((1S,2R)-2-(4-chlorophenyl)-2'-oxospiro[cyclopropane-1,3'-indoline]-1'-yl)benzoate and methyl-3-((1R,2S)-2-(4-chlorophenyl)-2'-oxospiro[cyclopropane-1,3'-indoline]-1'-yl)benzoate (50 mg) in 1 mL of methanol was added 0.1 mL of water, followed by lithium hydroxide (10 mg), The mixture was stirred for 14 hours at room temperature. HPLC monitored the reaction finished. The solvent was removed under reduced pressure. The residue was dissolved in 2 mL of DMF. Purification by preparative HPLC gave the title compound as a white powder. (11 mg) LC/MS m/e calcd. for $C_{23}H_{16}ClNO_3$ 389, observed (M+H)$^+$: 390.1. $^1$H NMR (400 MHz, DMSO-$d_6$) δppm 2.14 (dd, J=9.09, 5.05 Hz, 1 H) 2.41 (dd, J=8.08, 5.05 Hz, 1 H) 3.25 (t, J=8.59 Hz, 1 H) 6.19 (d, J=7.33 Hz, 1 H) 6.77-6.86 (m, 2 H) 7.12 (t, J=7.71 Hz, 1 H) 7.36-7.46 (m, 4 H) 7.72 (t, J=7.83 Hz, 1 H) 7.76-7.85 (m, 1 H) 8.01-8.09 (m, 2 H).

Example 84

(1S,2S) and (1R,2R)-3-(-2-(4-chlorophenyl)-2'-oxospiro[cyclopropane-1,3'-indoline]-1'-yl)benzoic acid

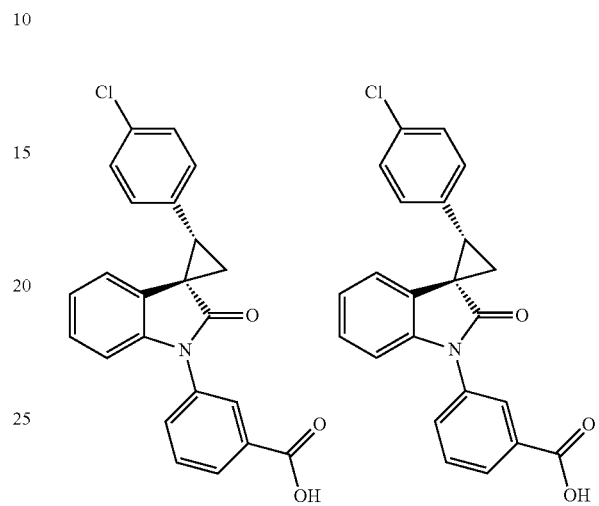

The title compound was prepared in analogy to Example 81 starting from methyl-ethyl-3-iodobenzoate (commercially available), (1R,2R) and (1S,2S)-2-(4-chlorophenyl)spiro [cyclopropane-1,3'-indolin]-2'-one prepared as in Scheme 1 LC/MS m/e calcd. for $C_{23}H_{16}ClNO_3$ 389, observed (M+H)$^+$: 390.1. $^1$H NMR (400 MHz, DMSO-$d_6$) δppm 2.31-2.42 (m, 2 H) 3.42 (t, J=8.72 Hz, 1 H) 6.88 (d, J=7.58 Hz, 1 H) 7.15 (t, J=7.20 Hz, 1 H) 7.22-7.28 (m, 1 H) 7.28-7.36 (m, 3 H) 7.36-7.41 (m, 2 H) 7.60-7.70 (m, 2 H) 7.86 (s, 1 H) 7.93-8.00 (m, 1 H) 13.24 (br. s, 1 H).

Example 85

(1S,2S) and (1R,2R)-2-(4-chlorophenyl)-1'-(3-(morpholine-4-carbonyl)phenyl)spiro [cyclopropane-1,3'-indolin]-2'-one

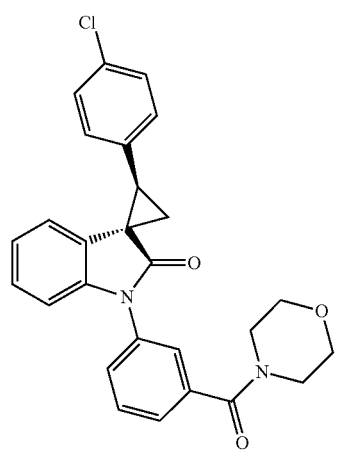

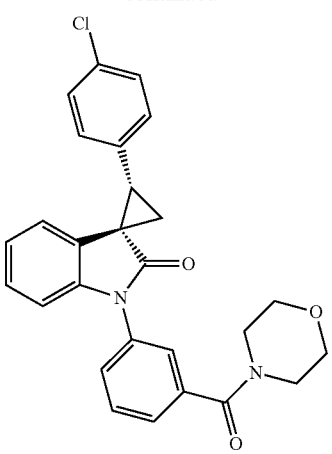
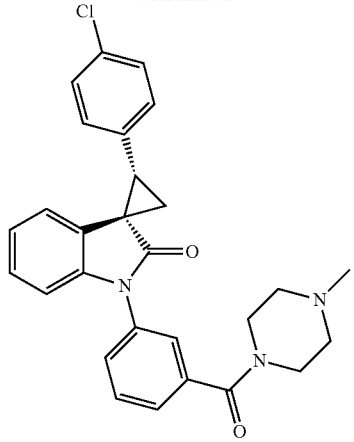

A mixture of (1S,2S) and (1R,2R)-3-(2-(4-chlorophenyl)-2'-oxospiro[cyclopropane-1,3'-indoline]-1'-yl)benzoic acid (117 mg, 0.3 mmol), O-(1H-benzotriazol-1-yl)-N,N,N',N'-tetramethyluronium tetrafluoroborate (TBTU)(145 mg, 0.45 mmol), N,N-Diisopropylethylamine (DIPEA) (154 µL, 0.9 mmol) and morpholine (79 µL, 0.9 mmol) in DMF (2 mL) was stirred at room temperature for 14 hours. Purification by preparative HPLC gave desired product as a white solid (83 mg, 60%). LC/MS m/e calcd. for $C_{27}H_{23}ClN_2O_3$: 458, observed (M+H)$^+$: 459.2 $^1$H NMR (400 MHz, MeOD-d$_4$) δ ppm 2.23-2.31 (m, 2 H) 3.28-3.32 (m, 1 H) 3.77 (br. s., 8 H) 6.16 (d, J=7.58 Hz, 1 H) 6.81 (t, J=7.58 Hz, 1 H) 6.93 (d, J=7.83 Hz, 1 H) 7.11-7.19 (m, 1 H) 7.26-7.33 (m, 2 H) 7.33-7.38 (m, 2 H) 7.56 (d, J=7.58 Hz, 1 H) 7.60-7.67 (m, 2 H) 7.68-7.76 (m, 1 H).

The title compound was prepared in analogy to Example 85 starting from 1-methylpiperazine, methyl-3-iodobenzoate (commercially available), (1R,2R) and (1S,2S)-2-(4-chlorophenyl)spiro[cyclopropane-1,3'-indolin]-2'-one prepared as in Scheme 1. LC/MS m/e calcd. for $C_{28}H_{26}ClN_3O_2$: 471, observed (M+H)$^+$: 472.2 $^1$H NMR (400 MHz, MeOD-d$_4$) δ ppm 2.22-2.35 (m, 2 H) 2.98 (s, 3 H) 3.35-3.39 (m, 1 H) 6.17 (d, J=7.58 Hz, 1 H) 6.83 (t, J=7.58 Hz, 1 H) 6.96 (d, J=8.08 Hz, 1 H) 7.13-7.21 (m, 1 H) 7.27-7.33 (m, 2 H) 7.34-7.40 (m, 2 H) 7.60-7.65 (m, 1 H) 7.68-7.80 (m, 3 H).

Example 86

(1S,2S) and (1R,2R)-2-(4-chlorophenyl)-1'-(3-(4-methylpiperazine-1-carbonyl)phenyl) Spiro[cyclopropane-1,3'-indolin]-2'-one Example 87

(1S,2S) and (1R,2R)-2-(4-chlorophenyl)-1'-(3-(4-(methylsulfonyl)piperazine-1-carbonyl)phenyl)spiro[cyclopropane-1,3'-indolin]-2'-one

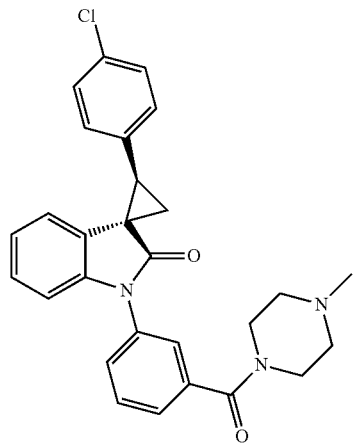
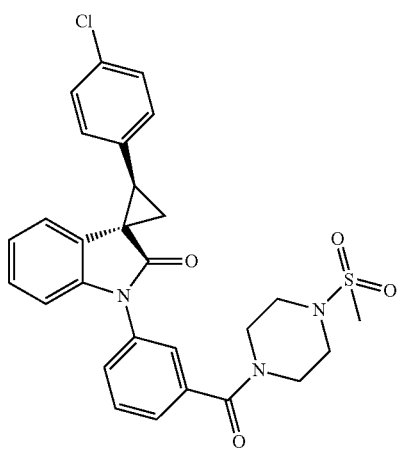

-continued

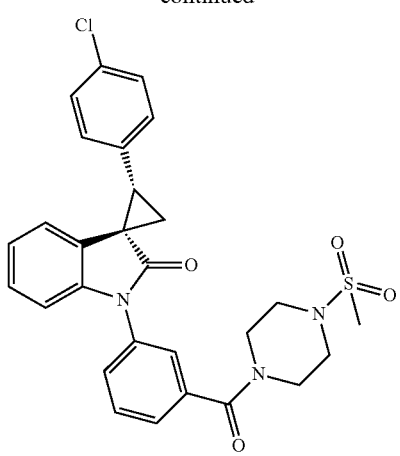

The title compound was prepared in analogy to Example 85 starting from 1-methanesulfonyl-piperazine, methyl-3-iodobenzoate (commercially available), (1R,2R) and (1S,2S)-2-(4-chlorophenyl)spiro[cyclopropane-1,3'-indolin]-2'-one prepared as in Scheme 1. LC/MS m/e calcd. for $C_{28}H_{26}ClN_3O_4S$: 535, observed (M+H)$^+$: 536.2 $^1$H NMR (400 MHz, MeOD-d$_4$) δppm 2.22-2.36 (m, 2 H) 2.90 (s, 3 H) 3.35-3.39 (m, 1 H) 3.58-4.01 (m, 8 H) 6.16 (d, J=7.58 Hz, 1 H) 6.82 (t, J=7.58 Hz, 1 H) 6.95 (d, J=7.58 Hz, 1 H) 7.16 (t, J=7.83 Hz, 1H) 7.27-7.40 (m, 4 H) 7.58 (d, J=7.33 Hz, 1 H) 7.62-7.79 (m, 3 H).

-continued

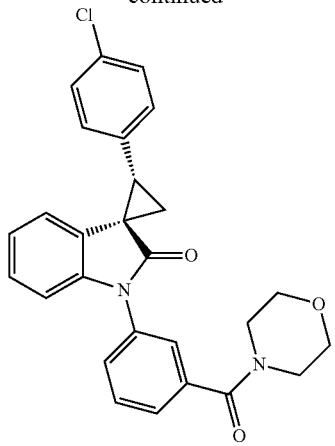

The title compound was prepared in analogy to Example 85 starting from morpholine, methyl-3-iodobenzoate (commercially available), (1R,2S) and (1S,2R)-2-(4-chlorophenyl) spiro[cyclopropane-1,3'-indolin]-2'-one prepared as in Scheme 1. LC/MS m/e calcd. for $C_{27}H_{23}ClN_2O_3$: 458, observed (M+H)$^+$: 459.1 $^1$H NMR (400 MHz, MeOD-d$_4$) δ ppm 2.34 (dd, J=8.97, 4.93 Hz, 1 H) 2.44 (dd, J=8.59, 5.05 Hz, 1 H) 3.35-3.39 (m, 1 H) 3.67 (br. s., 8 H) 6.96 (d, J=7.83 Hz, 1 H) 7.17-7.26 (m, 2 H) 7.26-7.36 (m, 5 H) 7.41 (s, 1 H) 7.46-7.52 (m, 2 H) 7.64 (t, J=7.83 Hz, 1 H).

Example 88

(1R,2S) and (1S,2R)-2-(4-chlorophenyl)-1'-(3-(morpholine-4-carbonyl)phenyl)spiro [cyclopropane-1,3'-indolin]-2'-one

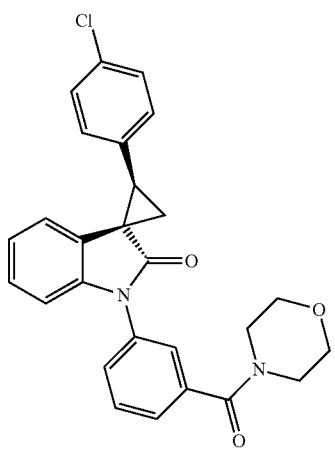

Example 89

(1S,2R) and (1R,2S)-2-(4-chlorophenyl)-1'-(3-(4-methylpiperazine-1-carbonyl)phenyl)spiro[cyclopropane-1,3'-indolin]-2'-one

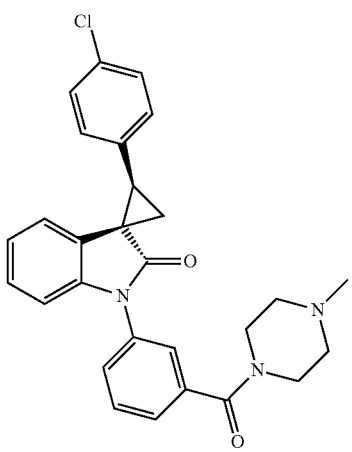

121

-continued

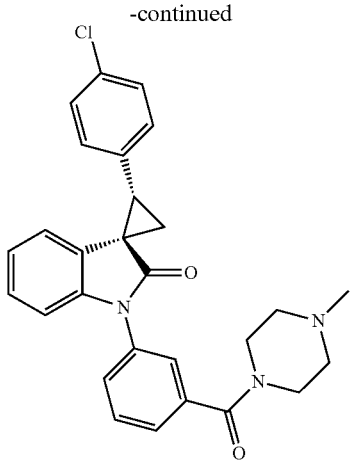

The title compound was prepared in analogy to Example 85 starting from 1-methylpiperazine, methyl-3-iodobenzoate (commercially available), (1R,2S) and (1S,2R)-2-(4-chlorophenyl)spiro[cyclopropane-1,3'-indolin]-2'-one prepared as in Scheme 1. LC/MS m/e calcd. for $C_{28}H_{26}ClN_3O_2$: 471, observed (M+H)$^+$: 472.2 $^1$H NMR (400 MHz, MeOD-d$_4$) δ ppm 2.34 (dd, J=9.09, 5.05 Hz, 1 H) 2.43 (dd, J=8.59, 5.05 Hz, 1 H) 2.93 (s, 3 H) 3.17 (br. s., 4 H) 3.40 (t, J=8.84 Hz, 1 H) 3.62 (br. s., 4 H) 6.97 (d, J=7.83 Hz, 1 H) 7.16-7.25 (m, 2 H) 7.26-7.38 (m, 5 H) 7.49 (s, 1 H) 7.55 (t, J=7.71 Hz, 2 H) 7.67 (t, J=7.83 Hz, 1 H).

Example 90

(1R,2S) and (1S,2R)-2-(4-chlorophenyl)-1'-(3-(4-(methylsulfonyl)piperazine-1-carbonyl)phenyl)spiro[cyclopropane-1,3'-indolin]-2'-one

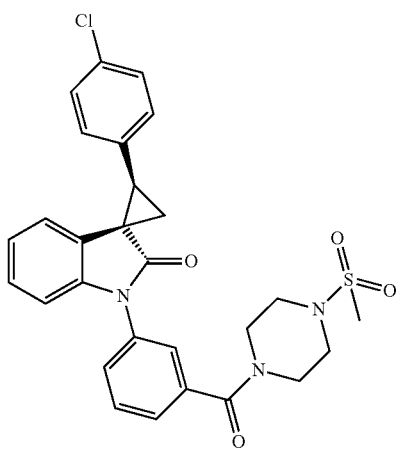

122

-continued

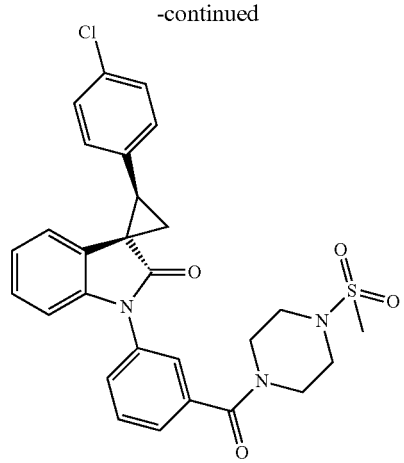

The title compound was prepared in analogy to Example 85 starting from 1-Methanesulfonyl-piperazine, methyl-3-iodobenzoate (commercially available), (1S,2R) and (1R,2S)-2-(4-chlorophenyl)spiro[cyclopropane-1,3'-indolin]-2'-one prepared as in Scheme 1. LC/MS m/e calcd. for $C_{28}H_{26}ClN_3O_4S$: 535, observed (M+H)$^+$: 536.2 $^1$H NMR (400 MHz, MeOD-d$_4$) ppm 2.32 (dd, J=8.97, 4.93 Hz, 1 H) 2.43 (dd, J=8.72, 4.93 Hz, 1 H) 2.86 (s, 3 H) 3.20 (br. s., 4 H) 3.38 (t, J=8.84 Hz, 1 H) 3.71 (br. s., 4 H) 6.96 (d, J=7.83 Hz, 1 H) 7.14-7.24 (m, 2 H) 7.24-7.36 (m, 5 H) 7.46 (s, 1 H) 7.47-7.53 (m, 2 H) 7.64 (t, J=7.83 Hz, 1 H).

Example 91

(1R,2R) and (1S,2S)-3-(2-(4-chlorophenyl)-2'-oxospiro[cyclopropane-1,3'-indoline]-1'-yl)-N-(methylsulfonyl)benzamide

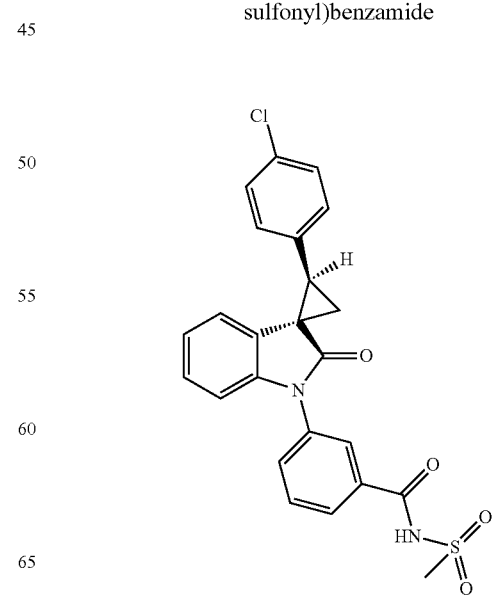

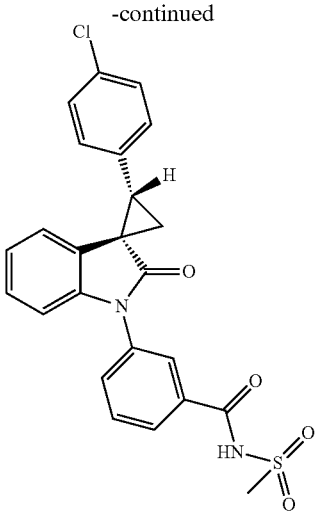

The title compound was prepared in analogy to Example 85 starting from methanesulfonamide, methyl-3-iodobenzoate (commercially available), (1R,2R) and (1S,2S)-2-(4-chlorophenyl)spiro[cyclopropane-1,3'-indolin]-2'-one prepared as in Scheme 1. LC/MS m/e calcd. for $C_{24}H_{19}ClN_2O_4S$: 466, observed (M+H)$^+$: 467.2 $^1$H NMR (400 MHz, DMSO-$d_6$) δ ppm 2.31-2.41 (m, 2 H) 3.37 (s, 3 H) 3.43 (t, J=8.72 Hz, 1 H) 6.90 (d, J=7.83 Hz, 1 H) 7.16 (t, J=7.33 Hz, 1 H) 7.25 (dd, J=7.83, 1.01 Hz, 1 H) 7.27-7.35 (m, 3 H) 7.35-7.43 (m, 2H) 7.62-7.70 (m, 2 H) 7.94-7.99 (m, 2 H) 12.24 (br. s., 1 H).

Example 92

(1S,2S) and (1R,2R)-3-(2-(4-chlorophenyl)-2'-oxospiro[cyclopropane-1,3'-indoline]-1'-yl)-5-(2-oxooxazolidin-3-yl)benzoic acid

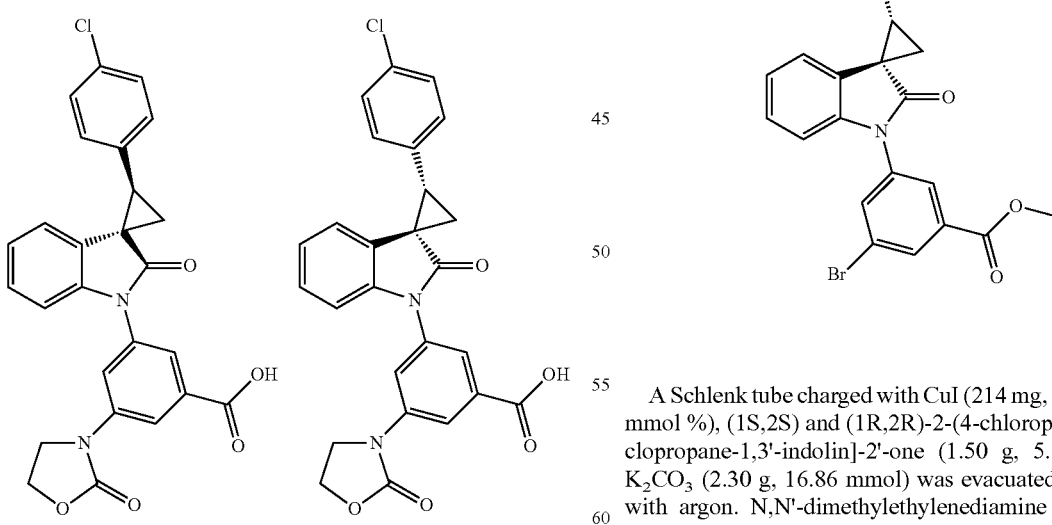

Synthesis of 3-bromo-5-iodo-benzoic acid methylester

To a suspension of 3-bromo-5-iodo-benzoic acid (6.5 g, 20 mmol) in 25 mL of methanol was added SOCl$_2$ (1.14 mL, 40 mmol) dropwise at 0° C. The mixture was then warmed to room temperature and stirred at room temperature for 2 days. The precipitates formed were collected by filtration to afford the desired product as white solid 5.12 g (75%). LC/MS m/e calcd. for $C_8H_6BrIO_2$: 341, observed (M+H)$^+$: 342.2.

Synthesis of (1S,2S) and (1R,2R)-methyl-3-bromo-5-(2-(4-chlorophenyl)-2'-oxospiro[cyclopropane-1,3'-indoline]-1'-yl)benzoate

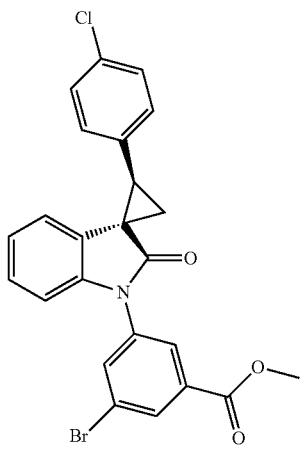

A Schlenk tube charged with CuI (214 mg, 1.124 mmol, 20 mmol %), (1S,2S) and (1R,2R)-2-(4-chlorophenyl)spiro[cyclopropane-1,3'-indolin]-2'-one (1.50 g, 5.62 mmol) and K$_2$CO$_3$ (2.30 g, 16.86 mmol) was evacuated and backfilled with argon. N,N'-dimethylethylenediamine (242 μL, 2.25 mmol, 40 mol %), 3-Bromo-5-iodo-benzoic acid methyl ester (2.30 g, 6.75 mmol, 1.2 equiv.) and acetonitrile (5 mL) were added under argon. The Schlenk tube was sealed with a Teflon valve and the reaction mixture was stirred at 90° C. for 3 hours. HPLC monitor the reaction finished. The solvent was removed under reduced pressure. The residue was purified by flash column chromatography (gradient elution, 5-15% ethyl acetate in petroleum ether) to give the title compound as white powder (1.3 g, 48%). LC/MS m/e calcd. for $C_{24}H_{17}BrClNO_3$: 482, observed (M+H)$^+$: 483.

Synthesis of racemic methyl-(1R,2R) and (1S,2S)-3-(2-(4-chlorophenyl)-2'-oxospiro[cyclopropane-1,3'-indoline]-1'-yl)-5-(2-oxooxazolidin-3-yl)benzoate

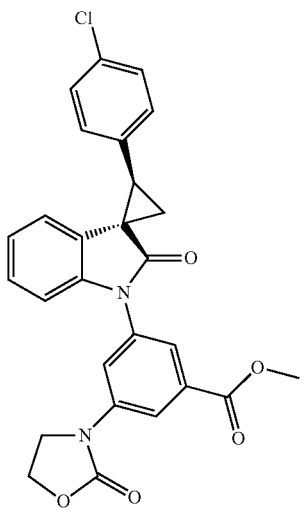

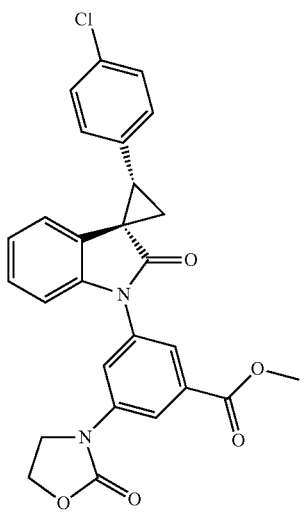

A mixture of (1S,2S) and (1R,2R)-3-bromo-5-(2-(4-chlorophenyl)-2'-oxospiro [cyclopropane-1,3'-indoline]-1'-yl) benzoate (120 mg, 0.25 mmol), oxazolidin-2-one (27 mg, 0.3 mmol), CuI (10 mg, 20 mmol %), Dimethylamino-acetic acid (11 mg, 40 mmol %) and $K_2CO_3$ (68 mg, 0.5 mmol) in DMSO (5.0 mL) was stirred at 150° C. under microwave irradiation for 1.5 hours. The precipitate was filtered off and the filtrate was concentrated to give the crude desired product (43 mg, 35%) which was used for the next step without further purification.

Synthesis of (1S,2S) and (1R,2R)-3-(2-(4-chlorophenyl)-2'-oxospiro[cyclopropane-1,3'-indoline]-1'-yl)-5-(2-oxooxazolidin-3-yl)benzoic acid

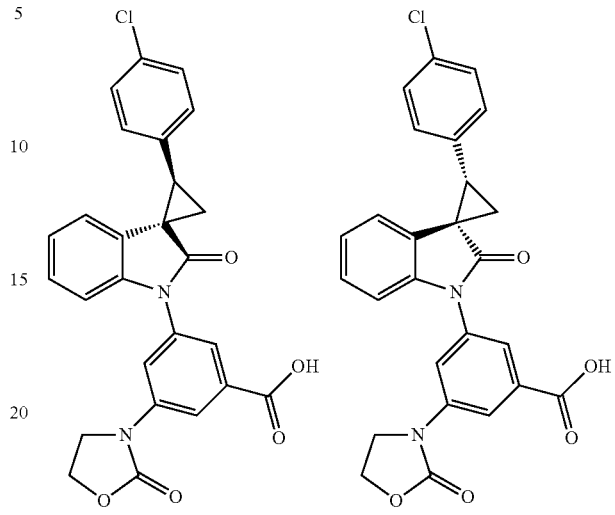

To a solution of (1S,2S) and (1R,2R)-3-(2-(4-chlorophenyl)-2'-oxospiro[cyclopropane-1,3'-indoline]-1'-yl)-5-(2-oxooxazolidin-3-yl)benzoate (43 mg, 0.088 mmol) in MeOH (2 mL) and $H_2O$ (0.2 mL) was added lithium hydroxide (18 mg, 0.44 mmol). The reaction mixture was stirred at room temperature until TLC indicated no further reaction. The methanol was removed under reduced pressure. After quenching with concentrated HCl (3.0 N), the mixture was extracted with ethyl acetate for three times. The organic layers were dried over anhydrous $Na_2SO_4$ and concentrated to give the crude product. Purification by preparative HPLC gave desired product as white solid (29 mg, 70%). LC/MS m/e calcd. for $C_{26}H_{19}ClN_2O_5$: 474, observed (M+H)$^+$: 475.1 $^1$H NMR (400 MHz, MeOD-d$_4$) δppm 2.22-2.33 (m, 2 H) 3.35-3.39 (m, 1 H) 4.22 (t, J=8.08 Hz, 2H) 4.56 (t, J=7.96 Hz, 2 H) 6.15 (d, J=7.07 Hz, 1 H) 6.81 (t, J=7.20 Hz, 1 H) 6.96 (d, J=7.83 Hz, 1 H) 7.15 (t, J=7.33 Hz, 1 H) 7.33 (q, J=8.51 Hz, 4 H) 7.91 (s, 1 H) 8.11 (t, J=2.02 Hz, 1 H) 8.26 (s, 1 H).

Example 93

(1S,2S) and (1R,2R)-3-(2-(4-chlorophenyl)-2'-oxospiro[cyclopropane-1,3'-indoline]-1'-yl)-5-(methylsulfonyl)benzoic acid

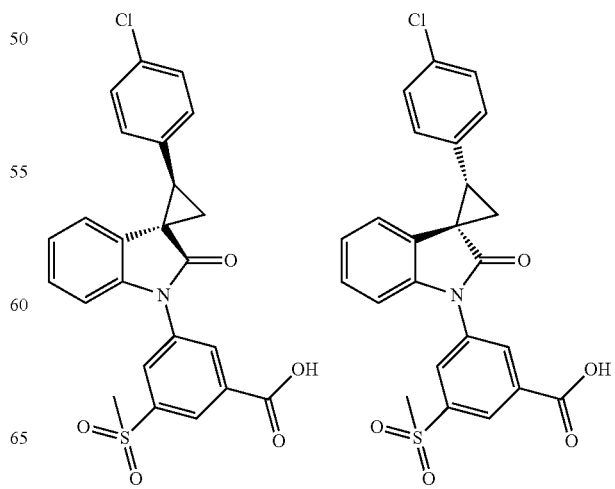

The title compound was prepared in analogy to Example 92 starting from methanesulfinic acid sodium salt, 3-bromo-5-iodo-benzoic acid (commercially available), (1R,2R) and (1S,2S)-2-(4-chlorophenyl)spiro[cyclopropane-1,3'-indolin]-2'-one prepared as in Scheme 1. LC/MS m/e calcd. for $C_{24}H_{18}ClNO_5S$: 467, observed (M+H)$^+$: 468.1 $^1$H NMR (400 MHz, MeOD-d$_4$) δppm 2.27-2.36 (m, 2 H) 3.28 (s, 3 H) 3.38 (t, J=8.59 Hz, 1 H) 6.18 (d, J=7.58 Hz, 1 H) 6.85 (t, J=7.20 Hz, 1 H) 7.00 (d, J=7.83 Hz, 1 H) 7.14-7.23 (m, 1 H) 7.28-7.40 (m, 4 H) 8.38 (t, J=1.89 Hz, 1 H) 8.49 (s, 1 H) 8.62 (s, 1 H).

Example 94

(1S,2S) and (1R,2R)-3-(2-(4-chlorophenyl)-2'-oxospiro[cyclopropane-1,3'-indoline]-1'-yl)-5-(2-oxopyrrolidin-1-yl)benzoic acid

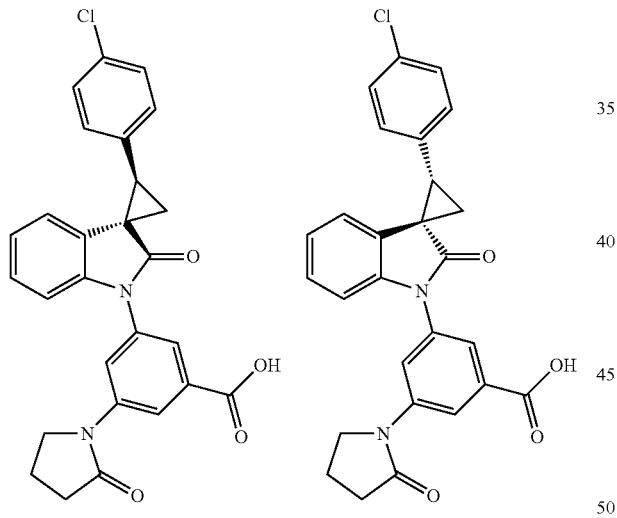

The title compound was prepared in analogy to Example 92 starting from 2-pyrrolidone, 3-bromo-5-iodo-benzoic acid (commercially available), (1R,2R) and (1S,2S)-2-(4-chlorophenyl)spiro[cyclopropane-1,3'-indolin]-2'-one prepared as in Scheme 1. LC/MS m/e calcd. for $C_{27}H_{21}ClN_2O_4$: 472, observed (M+H)$^+$: 4731.2 $^1$HNMR (400 MHz, MeOD-d$_4$) δ ppm 2.18-2.35 (m, 4 H) 2.67 (t, J=8.08 Hz, 2 H) 3.35-3.39 (m, 1 H) 4.05 (t, J=7.07 Hz, 2 H) 6.16 (d, J=7.07 Hz, 1 H) 6.82 (t, J=7.45 Hz, 1 H) 6.97 (d, J=7.33 Hz, 1 H) 7.12-7.20 (m, 1H) 7.34 (q, J=8.67 Hz, 4 H) 7.95 (s, 1 H) 8.20 (t, J=1.89 Hz, 1 H) 8.33 (s, 1 H).

Example 95

(1R,2R) and (1S,2S)-3-(2-(4-chlorophenyl)-5'-fluoro-2-isopropyl-2'-oxospiro[cyclopropane-1,3'-indoline]-1'-yl)-5-(2-oxooxazolidin-3-yl)benzoic acid

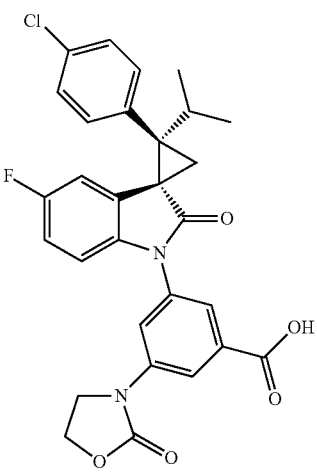

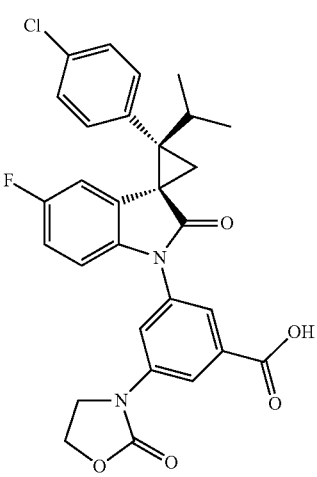

Synthesis of (1S,2S) and (1R,2R)-methyl-3-bromo-5-(2-(4-chlorophenyl)-5'-fluoro-2-isopropyl-2'-oxospiro[cyclopropane-1,3'-indoline]-1'-yl)benzoate

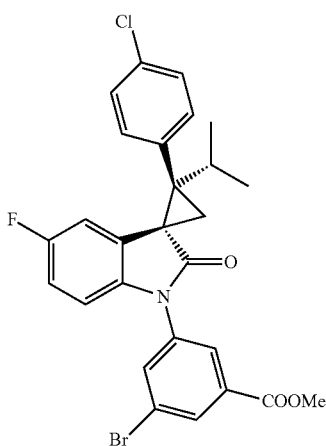

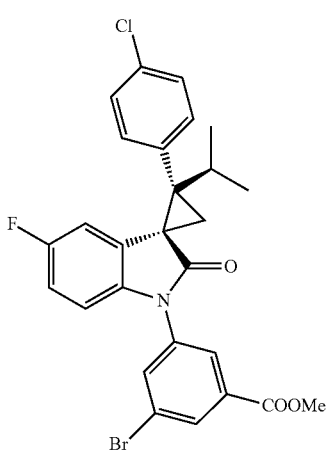

(1R,2R) and (1S,2S)-2-(4-chlorophenyl)-5'-fluoro-2-isopropylspiro[cyclopropane-1,3'-indolin]-2'-one prepared according to Scheme 2 (0.33 g, 1 mmol), and the 3-bromo-5-iodo-benzoic acid methyl ester (0.409 g, 1.2 mmol), CuI (20 mg), K₂CO₃ (0.276 g, 2 mmol) were placed in a Schlenk tube under argon atmosphere and dissolved in dry acetonitrile. The N,N'-dimethyl-1,2-ethanediamine (21 μL) was added into the mixture. The mixture was stirred at 80° C. for 14 hours. The solvent was removed in vacuo and the residue was purified by flash column chromatography to give the title compound as white powder (0.444 g, 82%). LC/MS m/e calcd. for $C_{27}H_{22}BrClFNO_3$: 541, observed (M+H)⁺: 542.

Synthesis of (1R,2R) and (1S,2S)-methyl-3-(2-(4-chlorophenyl)-5'-fluoro-2-isopropyl-2'-oxospiro[cyclopropane-1,3'-indoline]-1'-yl)-5-(2-oxooxazolidin-3-yl)benzoate

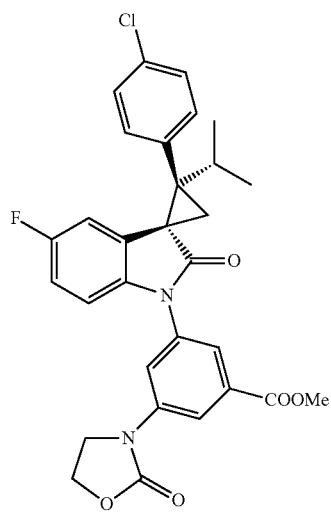

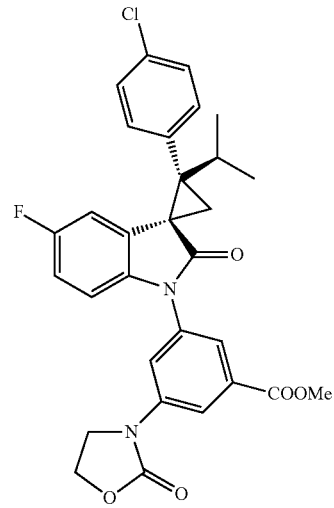

3-bromo-5-(((1S,2S)-2-(4-chlorophenyl)-5'-fluoro-2-isopropyl-2'-oxospiro[cyclopropane-1,3'-indoline]-1'-yl)benzoate, 3-bromo-5-(((1R,2R)-2-(4-chlorophenyl)-5'-fluoro-2-isopropyl-2'-oxospiro[cyclopropane-1,3'-indoline]-1'-yl) benzoate (0.545 g, 1 mmol), 2-oxazolidone (0.105 g, 1.2 mmol), CuI (20 mg), and K₂CO₃ (0.276 g, 2 mmol) were placed in a Schlenk tube under Argon atmosphere and dissolved in dry acetonitrile. The N,N'-dimethyl-1,2-ethanediamine (21 μL, 20% equiv) was added into the mixture. The mixture was stirred at 80° C. for 14 hours. The solvent was removed in vacuo and the residue was purified by flash column chromatography to give the title compound as white powder (0.40 g, 73%). LC/MS m/e calcd. for $C_{30}H_{26}ClFN_2O_5$: 548, observed (M+H)+: 549.5

Synthesis of (1R,2R) and (1S,2S)-3-(2-(4-chlorophenyl)-5'-fluoro-2-isopropyl-2'-oxospiro[cyclopropane-1,3'-indoline]-1'-yl)-5-(2-oxooxazolidin-3-yl)benzoic acid

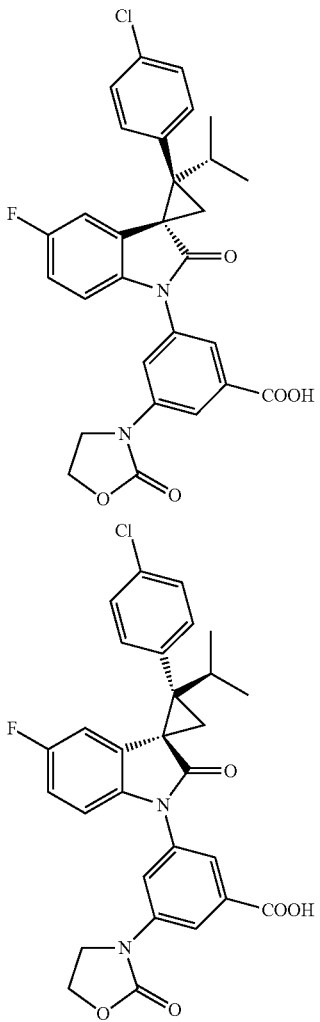

To a solution of (1R,2R) and (1S,2S)-3-bromo-5-(2-(4-chlorophenyl)-5'-fluoro-2-isopropyl-2'-oxospiro[cyclopropane-1,3'-indoline]-1'-yl)benzoate (27.4 mg) in methanol (2 mL) and water (1 mL) was added LiOH.H$_2$O (18 mg, 0.4 mmol) in one portion. The mixture was stirred at room temperature for 3 hours until the starting material was consumed. The mixture was concentrated under reduced pressure and acidified to pH~3. The precipitates was collected by filtration and dissolved in 2 mL of DMF. Purification by preparative HPLC gave the title compound as white solid (15 mg). LC/MS m/e calcd. for $C_{29}H_{24}ClFN_2O_5$ 534, observed (M+H)+: 545.7. $^1$H NMR (400 MHz, MeOD-d$_4$) δppm 0.89 (dd, J=20.34, 6.69 Hz, 6 H) 2.21-2.28 (m, 2 H) 2.89-3.01 (m, 1H) 4.22 (t, J=8.08 Hz, 2 H) 4.55 (t, J=8.08 Hz, 2 H) 5.28 (dd, J=8.84, 2.27 Hz, 1 H) 6.65 (dd, J=8.34, 1.77 Hz, 1 H) 6.80-6.89 (m, 2 H) 7.19 (dd, J=8.34, 2.02 Hz, 1 H) 7.45-7.54 (m, 2 H) 7.86 (s, 1 H) 8.09 (s, 1 H) 8.22 (s, 1 H).

Example 96

(1R,2S) and (1S,2R)-3-(2-(4-chlorophenyl)-5'-fluoro-2-isopropyl-2'-oxospiro[cyclopropane-1,3'-indoline]-1'-yl)-5-(2-oxooxazolidin-3-yl)benzoic acid

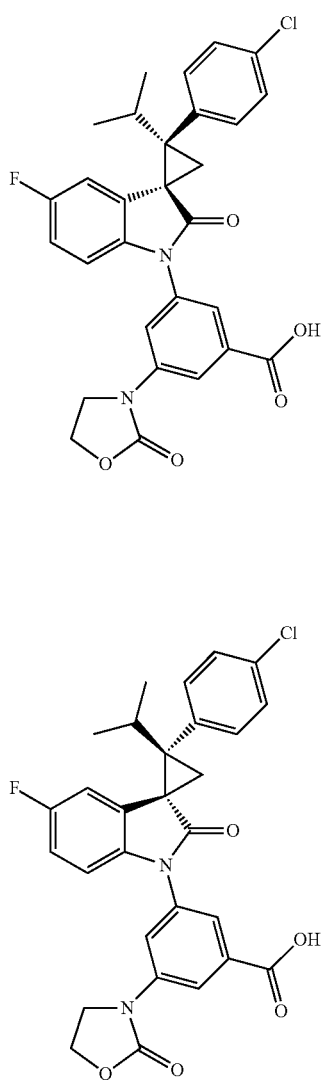

The title compound was prepared in analogy to Example 95 starting from 2-oxazolidone (commercially available), bromo-5-iodo-benzoic acid methyl ester prepared in Example 92, (1S,2R) and (1R,2S)-2-(4-chlorophenyl)-5'-fluoro-2-isopropylspiro[cyclopropane-1,3'-indolin]-2'-one prepared as in Scheme 2. LC/MS m/e calcd. for $C_{29}H_{24}ClFN_2O_5$: 534, observed (M+H)+: 535.1 $^1$H NMR (400 MHz, DMSO-d$_6$) δppm 0.55-0.61 (m, 3 H) 0.87 (s, 3 H) 2.11-2.18 (m, 1 H) 2.28-2.39 (m, 2 H) 4.07-4.19 (m, 2 H) 4.42-4.52 (m, 2 H) 6.84-6.98 (m, 1 H) 7.07-7.15 (m, 1 H) 7.23

(d, J=8.34 Hz, 1 H) 7.32-7.42 (m, 1 H) 7.52 (d, J=9.35 Hz, 1 H) 7.64 (br. s., 1 H) 7.79 (br. s., 1 H) 8.11 (br. s., 1 H).

Example 97

(1R,2R) and (1S,2S)-3-(2-(4-chlorophenyl)-2-isopropyl-2'-oxospiro[cyclopropane-1,3'-indoline]-1'-yl)-5-(2-oxooxazolidin-3-yl)benzoic acid

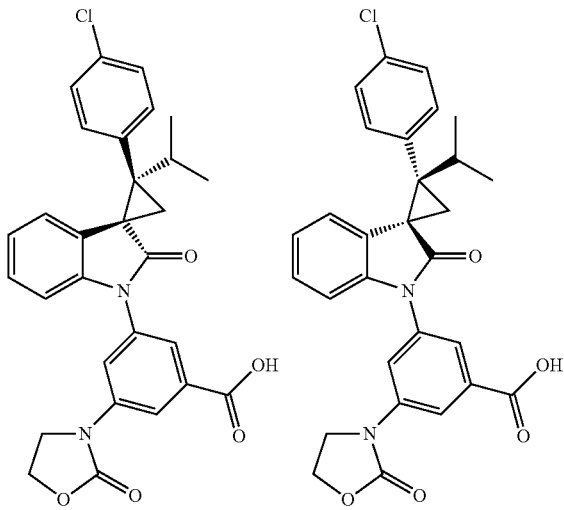

The title compound was prepared in analogy to Example 95 starting from 2-oxazolidone (commercially available), bromo-5-iodo-benzoic acid methyl ester prepared as in Example 92, (1R,2R) and (1S,2S)-2-(4-chlorophenyl)-2-isopropylspiro[cyclopropane-1,3'-indolin]-2'-one prepared as in Scheme 2. LC/MS m/e calcd. for $C_{29}H_{25}ClN_2O_5$: 516, observed (M+H)$^+$: 516.1 $^1$H NMR (400 MHz, DMSO-d$_6$) δ ppm 0.77 (d, 3 H) 0.85 (d, 3 H) 2.10-2.16 (m, 1 H) 2.18-2.25 (m, 1H) 2.81-2.97 (m, 1 H) 4.17 (t, 2 H) 4.50 (t, 2 H) 5.49 (d, 1 H) 6.64 (d, 1 H) 6.71 (t, 1 H) 6.86 (d, 1 H) 7.10 (t, 1 H) 7.22 (d, 1 H) 7.45-7.62 (m, 2 H) 7.77 (s, 1 H) 7.98 (s, 1 H) 8.20 (s, 1 H).

Example 98

(1S,2S) and (1R,2R)-3-(2-(4-cyanophenyl)-2-isopropyl-2'-oxospiro[cyclopropane-1,3'-indoline]-1'-yl)-5-(2-oxooxazolidin-3-yl)benzoic acid

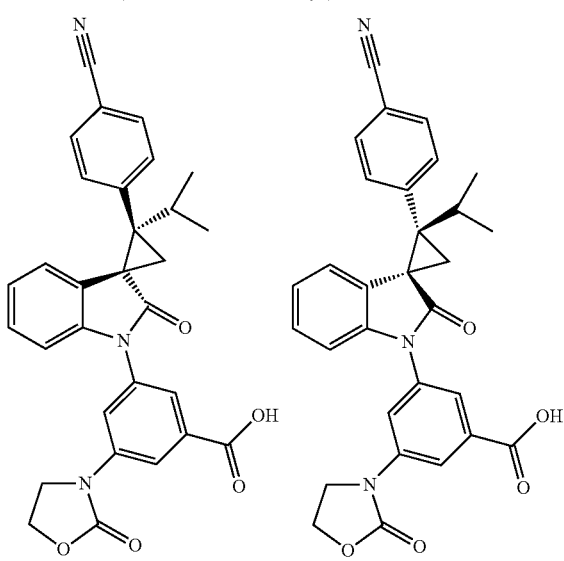

The title compound was prepared in analogy to Example 95 starting from 2-oxazolidone (commercially available), bromo-5-iodo-benzoic acid methyl ester prepared as in example 92, (1R,2R) and (1S,2S)-4-(2-isopropyl-2'-oxospiro[cyclopropane-1,3'-indoline]-2-yl)benzonitrile prepared as in Scheme 2. LC/MS m/e calcd. for $C_{30}H_{25}IN_3O_5$: 507, observed (M+H)$^+$: 508.2 $^1$H NMR (400 MHz, DMSO-d$_6$) δ ppm 0.78 (d, 3 H) 0.86 (d, 3 H) 2.14-2.21 (m, 1 H) 2.23-2.33 (m, 1H) 2.85-3.02 (m, 1 H) 4.10-4.24 (m, 2 H) 4.50 (t, 2 H) 5.43 (d, 1 H) 6.68 (t, 1 H) 6.79-6.89 (m, 2 H) 7.11 (t, 1 H) 7.61 (d, 2 H) 7.70 (d, 2 H) 7.80 (s, 1 H) 7.94-8.02 (m, 2 H) 8.22 (s, 1 H) 13.45 (s, 1 H).

Example 99

(1S,2S) and (1R,2R)-3-(2-(4-chlorophenyl)-2'-oxospiro[cyclopropane-1,3'-indoline]-1'-yl)-5-(2-oxoimidazolidin-1-yl)benzoic acid

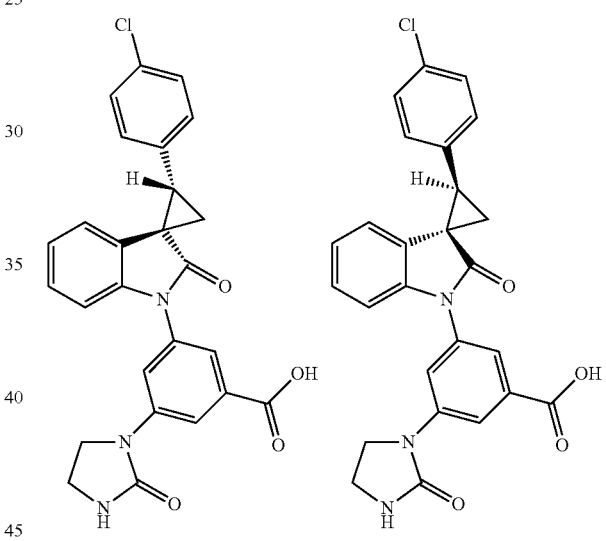

The title compound was prepared in analogy to Example 92 starting from ethyleneurea (commercially available), bromo-5-iodo-benzoic acid methyl ester prepared as in Example 92, (1R,2R) and (1S,2S)-2-(4-chlorophenyl)spiro[cyclopropane-1,3'-indolin]-2'-one prepared as in Scheme 1. LC/MS m/e calcd. for $C_{26}H_{20}ClN_3O_4$: 473, observed (M+H)$^+$: 474.2 $^1$H NMR (400 MHz, DMSO-d$_6$) δppm 2.14 (dd, J=9.22, 4.93 Hz, 1 H) 2.41 (dd, J=7.96, 4.67 Hz, 1 H) 3.22-3.28 (m, 1 H) 3.43-3.49 (m, 1 H) 3.92-3.98 (m, 1 H) 6.19 (d, J=7.58 Hz, 1 H) 6.80 (t, J=7.71 Hz, 1 H) 6.85 (d, J=7.83 Hz, 1 H) 7.12 (t, J=8.34 Hz, 1 H) 7.22 (s, 1 H) 7.42 (q, J=8.59 Hz, 3 H) 7.64 (s, 1 H) 7.99 (t, J=2.02 Hz, 1 H) 8.13 (s, 1 H).

Example 100

(R) and (S)-3-((5'-fluoro-2,2-dimethyl-2'-oxospiro[cyclopropane-1,3'-indoline]-1'-yl)methyl)benzoic acid

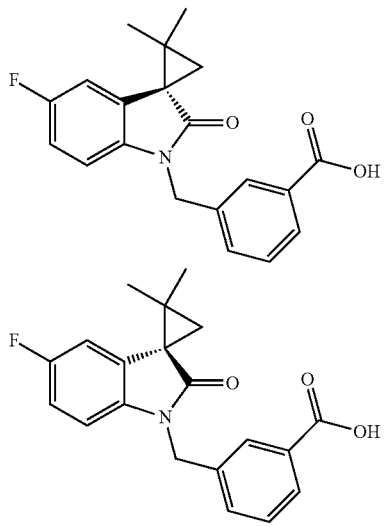

Synthesis of 5-fluoro-3-(propan-2-ylidene)indolin-2-one

A mixture of 5-fluoro-1,3-dihydro-indol-2-one (2.84 g, 20 mmol), acetone (2.2 mL, 30 mmol) and piperidine (0.8 mL, 8 mmol) in methanol (100 mL) was heated to reflux for 16 hours. Then the reaction mixture was allowed to cool to room temperature. The solid was collected by filtration, washed with methanol (20 mL) and dried in vacuo to afford 5-fluoro-3-isopropylidene-1,3-dihydro-indol-2-one (2.6 g, 68%) as powder.

Synthesis of (R) and (S)-5'-fluoro-2,2-dimethylspiro[cyclopropane-1,3'-indolin]-2'-one A solution of NaH (60%) (0.6 g, 15 mmol) and trimethylsulfoxonium iodide (3.3 g, 15 mmol) in dimethyl sulfoxide (30 mL) was stirred for 30 minutes at 25° C. Then a solution of 5-fluoro-3-isopropylidene-1,3-dihydro-indol-2-one (2.6 g, 13.6 mmol) in dry tetrahydrofuran (30 mL) was added dropwise over 20 minutes. After being stirred for 1 hour at 25° C. and 1 hour at 50° C., the reaction solution was poured into ice-cold water and extracted with ether (3×100 mL), washed with water, dried over anhydrous sodium sulfate, filtered and concentrated in vacuo. The residue was recrystallized from ether to afford the title compound as white solid (2.39 g, 85%).

Synthesis of methyl-(R) and (S)-3-((5'-fluoro-2,2-dimethyl-2'-oxospiro[cyclopropane-1,3'-indoline]-1'-yl)methyl)benzoate 3-Bromomethyl-benzoic acid methyl ester (610 mg, 2.68 mmol) was added to a suspension of cesium carbonate (1.2 g, 3.66 mmol) and (R) and (S)-5'-fluoro-2,2-dimethylspiro[cyclopropane-1,3'-indolin]-2'-one (500 mg, 2.44 mmol) in DMF (10 mL). The reaction mixture was stirred for 1 hour at 25° C. Then extracted with ethyl acetate (3×25 mL), washed with brine, dried over anhydrous sodium sulfate, filtered and concentrated in vacuo to afford the title compound as white powder (850 mg, 98%).

Synthesis of 3-((5'-fluoro-2,2-dimethyl-2'-oxospiro[cyclopropane-1,3'-indoline]-1'-yl)methyl)benzoic acid A mixture of (R) and (S)-3-((5'-fluoro-2,2-dimethyl-2'-oxospiro[cyclopropane-1,3'-indoline]-1'-yl)methyl)benzoate (850 mg, 2.4 mmol) in tetrahydrofuran (10 mL) and 30% sodium hydroxide in water (5 mL) was stirred at 25° C. for 16 hours. The mixture was neutralized with a 2 N aqueous hydrochloric acid solution, diluted with ethyl acetate (50 mL), washed with water, dried over anhydrous sodium sulfate and then concentrated in vacuo. Purification by waters automated flash system (column: Xterra 30 mm×100 mm, sample manager 2767, pump 2525, detector: ZQ mass and UV 2487, solvent system: acetonitrile and 0.1% trifluoro-acetic acid in water) afforded the title compound as white solid (410 mg, 50%): LC/MS m/e calcd. for $C_{20}H_{15}FNO_3$ (M+H)$^+$: 340.37, observed: 340.2; LC/MS m/e calcd. for $C_{20}H_{18}FNO_3$: 339, observed (M+H)$^+$: 340.1 $^1$H NMR (400 MHz, DMSO-d$_6$) δ ppm 1.37 (s, 3 H) 1.48 (s, 3 H) 1.76 (d, J=4.29 Hz, 1 H) 1.88 (d, J=4.29 Hz, 1 H) 5.04 (dd, 2 H) 6.91-7.08 (m, 2 H) 7.17 (dd, J=9.35, 2.53 Hz, 1 H) 7.44-7.57 (m, 2 H) 7.80-7.93 (m, 2H) 12.99 (s, 1 H).

Example 101

(R) and (S)-3-(5'-fluoro-2,2-dimethyl-2'-oxospiro[cyclopropane-1,3'-indoline]-1'-yl)-5-(2-oxooxazolidin-3-yl)benzoic acid

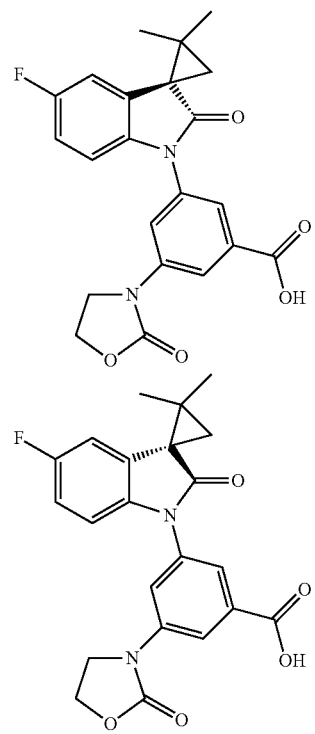

Synthesis of methyl-3-bromo-5-(2-oxooxazolidin-3-yl)benzoate

A suspension of 3-bromo-5-iodo-benzoic acid methyl ester (682 mg, 2 mmol), oxazolidin-2-one (191 mg, 2.2 mmol), CuI (76 mg, 0.4 mmol), potassium carbonate (545 mg, 4 mmol) and N,N'-dimethyl-ethane-1,2-diamine (86 uL, 0.8 mmol) in acetonitrile (15 mL) was stirred for 16 hours at 90° C. The precipitate was filtered off and washed with ethyl acetate. The filtrate was concentrated in vacuo to afford 3-bromo-5-(2-oxo-oxazolidin-3-yl)-benzoic acid methyl ester (480 mg, 80%) which was used for next step without further purification.

Synthesis of (R) and (S)-methyl-3-(5'-fluoro-2,2-dimethyl-2'-oxospiro[cyclopropane-1,3'-indoline]-1'-yl)-5-(2-oxooxazolidin-3-yl)benzoate

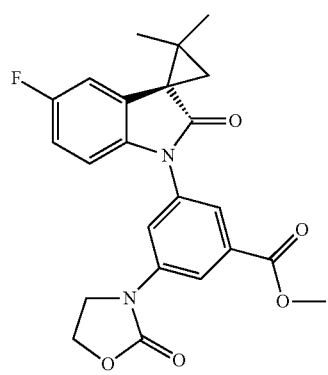

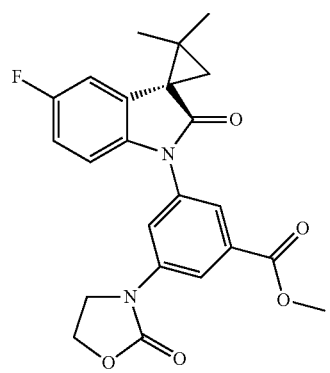

A suspension of (R) and (S)-5'-fluoro-2,2-dimethylspiro[cyclopropane-1,3'-indolin]-2'-one (2 mmol) (prepared as in Example 100), methyl-3-bromo-5-(2-oxooxazolidin-3-yl)benzoate (682 mg, 2 mmol), CuI (76 mg, 0.4 mmol), potassium carbonate (545 mg, 4 mmol) and N,N'-dimethyl-ethane-1,2-diamine (86 uL, 0.8 mmol) in acetonitrile (15 mL) was stirred for 16 hours at 90° C. The precipitate was filtered off and washed with ethyl acetate. The filtrate was concentrated in vacuo to afford the title compound as white powder (480 mg, 80%) which was used for the next step without further purification.

Synthesis of (R) and (S)-3-(5'-fluoro-2,2-dimethyl-2'-oxospiro[cyclopropane-1,3'-indoline]-1'-yl)-5-(2-oxooxazolidin-3-yl)benzoic acid

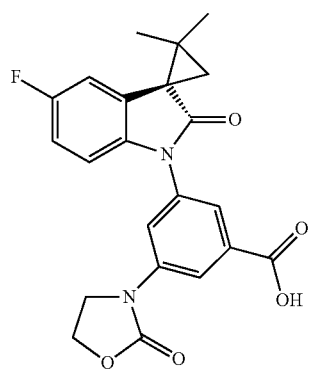

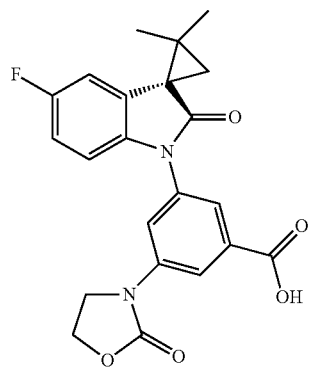

A mixture of (R) and (S)-methyl-3-(5'-fluoro-2,2-dimethyl-2'-oxospiro[cyclopropane-1,3'-indoline]-1'-yl)-5-(2-oxooxazolidin-3-yl)benzoate (850 mg, 2.4 mmol) in tetrahydrofuran (10 mL) and 30% sodium hydroxide in water (5 mL) was stirred at 25° C. for 16 hours. The mixture was neutralized with a 2N aqueous hydrochloric acid solution, diluted with ethyl acetate (50 mL), washed with water, dried over anhydrous sodium sulfate and then concentrated in vacuo. Purification by waters automated flash system (column: Xterra 30 mm×100 mm, sample manager 2767, pump 2525, detector: ZQ mass and UV 2487, solvent system: acetonitrile and 0.1% trifluoro-acetic acid in water) afforded the title compound (410 mg, 50%) as a white solid: LC/MS m/e calcd. for $C_{20}H_{18}FNO_3$: 340, observed (M+H)+: 340.; $^1$H NMR (400 MHz, MeOD) δppm 1.50 (s, 3 H) 1.57 (s, 3 H) 1.86 (d, J=4.29 Hz, 1 H) 1.93 (d, J=4.55 Hz, 1 H) 4.22 (t, J=7.96 Hz, 2 H) 4.56 (t, J=7.96 Hz, 2 H) 6.86-6.94 (m, 1 H) 6.94-7.02 (m, 1 H) 7.06 (d, J=8.59 Hz, 1 H) 7.84 (s, 1 H) 8.03 (br. s., 1 H) 8.25 (br. s., 1 H).

Example 102

(R) and (S)-3-[(2-oxo-2'',3'',5'',6''-tetrahydrodispiro[indole-3,1'-cyclopropane-2',4''-pyran]-1(2 H)-yl)methyl]benzoic acid

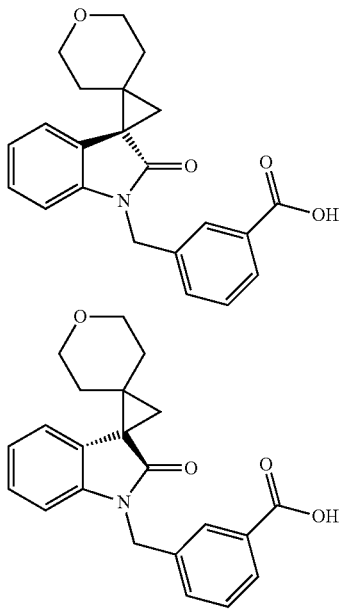

The title compound was prepared in analogy to Example 100 starting from methyl-(3-bromomethyl)-benzoate, 4-methylene-tetrahydro-pyran and isatin (commercially available) according to Scheme 2. LC/MS m/e calcd. for $C_{22}H_{21}NO_4$: 363, observed (M+H)$^+$: 364.2 $^1$H NMR (400 MHz, DMSO-d$_6$) δppm 1.66-1.76 (m, 1 H) 1.76-1.81 (m, 1 H) 1.88-2.04 (m, 3 H) 2.09-2.16 (m, 1 H) 3.21-3.29 (m, 1 H) 3.42-3.46 (m, 1 H) 3.54-3.66 (m, 2 H) 4.99 (d, 1 H) 5.12 (d, 1 H) 6.95-7.04 (m, 2 H) 7.19 (t, 2 H) 7.48 (t, J=7.58 Hz, 1 H) 7.57 (d, 1 H) 7.84 (d, J=7.83 Hz, 1 H) 7.87 (s, 1H) 12.98 (d, J=2.27 Hz, 1 H).

Example 103

(R) and (S)-3-(2-oxo-1,3-oxazolidin-3-yl)-5-(2-oxo-2'',3'',5'',6''-tetrahydrodispiro[indole-3,1'-cyclopropane-2',4''-pyran]-1(2H)-yl)benzoic acid

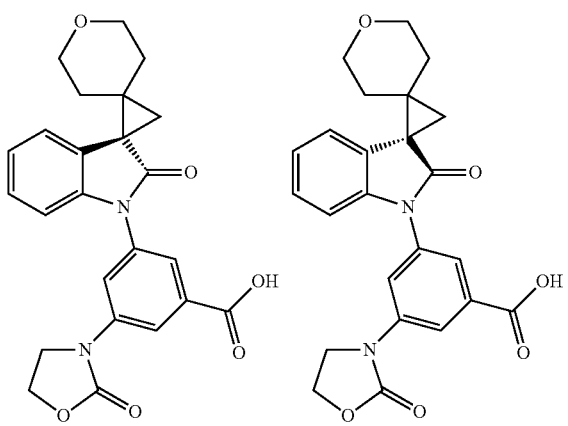

The title compound was prepared in analogy to Example 101 starting from methyl-3-bromo-5-(2-oxooxazolidin-3-yl)benzoate prepared as in Example 101, 4-methylene-tetrahydro-pyran, isatin (commercially available) according to Scheme 2. LC/MS m/e calcd. for $C_{24}H_{22}N_2O_6$: 434, observed (M+H)$^+$: 434.2 $^1$H NMR (400 MHz, DMSO-d$_6$) δppm 1.72-1.80 (m, 1 H) 1.83 (d, J=4.29 Hz, 1 H) 1.91-2.01 (m, 3 H) 2.06-2.16 (m, 1 H) 3.36-3.44 (m, 1 H) 3.50-3.56 (m, 1 H) 3.58-3.65 (m, 2 H) 4.13-4.21 (m, 2 H) 4.48 (t, J=7.96 Hz, 2 H) 6.90 (d, J=8.08 Hz, 1 H) 7.07 (t, 1 H) 7.23 (t, 1 H) 7.29 (d, J=7.58 Hz, 1 H) 7.71 (s, 1H) 7.92 (s, 1 H) 8.19 (s, 1 H) 13.40 (s, 1 H).

Example 104

(1S,2S) and (1R,2R)-2-chloro-5-((2-(4-fluorophenyl)-2'-oxospiro[cyclopropane-1,3'-indoline]-1'-yl)methyl)benzoic acid

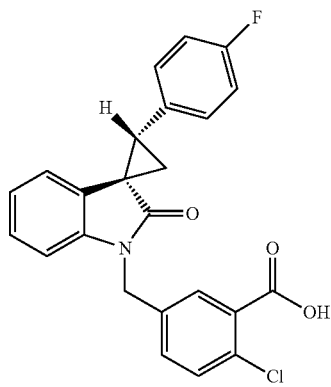

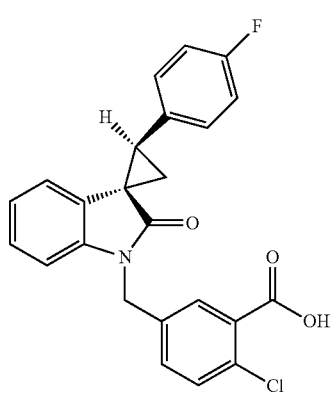

The title compound was prepared in analogy to Example 1 starting from methyl-2-chloro-(3-bromomethyl)-benzoate (commercially available), (1S,2S) and (1R,2R)-2-(4-chlorophenyl)spiro[cyclopropane-1,3'-indolin]-2'-one prepared as in Scheme 1. LC/MS m/e calcd. for $C_{24}H_{17}ClFNO_3$: 421, observed (M+H)$^+$: 422.2 1H NMR (400 MHz, DMSO-d$_6$) δ ppm 2.22-2.29 (m, 1 H) 2.32 (dd, J=8.34, 4.80 Hz, 1 H) 3.29-3.32 (m, 1 H) 4.81-4.98 (m, 2 H) 6.96-7.00 (m, 1 H) 7.02-7.14 (m, 3 H) 7.17-7.23 (m, 2 H) 7.32 (dd, J=8.46, 5.68

Hz, 2 H) 7.37 (dd, J=8.34, 2.27 Hz, 1 H) 7.50 (d, J=8.34 Hz, 1 H) 7.56 (d, J=2.02 Hz, 1 H) 13.46 (br.s., 1 H).

Example 105

(1R,2S) and (1S,2R)-4-((2'-oxo-2-(pyridin-3-yl)spiro[cyclopropane-1,3'-indoline]-1'-yl)methyl)benzoic acid

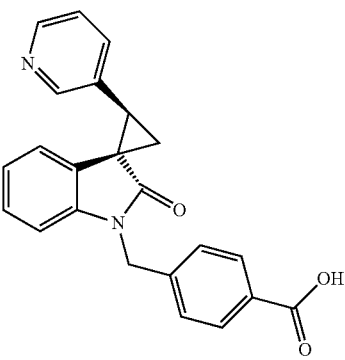

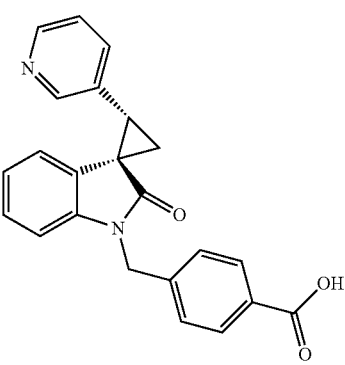

The title compound was prepared in analogy to Example 1 starting from 4-bromomethyl-benzoic acid methyl ester (commercially available), (1R,2S) and (1S,2R)-2-(pyridin-3-yl)spiro[cyclopropane-1,3'-indolin]-2'-one prepared as in Scheme 1. LC/MS m/e calcd. for $C_{23}H_{18}ClN_2O_3$: 370, observed (M+H)$^+$: 371.2 $^1$H NMR (400 MHz, DMSO-d$_6$) δ ppm 2.14-2.23 (m, 1 H) 3.30 (t, 1 H) 5.10 (s, 2 H) 6.14 (d, 1 H) 6.70 (t, 1 H) 6.93 (d, 1 H) 7.10 (t, 1 H) 7.45 (d, 2 H) 7.57-7.65 (m, 1 H) 7.93 (d, 2 H) 8.06 (d, 1 H) 8.61 (d, 1H) 8.71 (s, 1 H).

Example 106

(1S,2R) and (1R,2S)-4-((2-(4-cyanophenyl)-2'-oxospiro[cyclopropane-1,3'-indoline]-1'-yl)methyl)benzoic acid

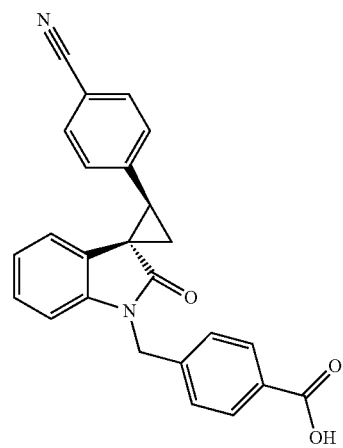

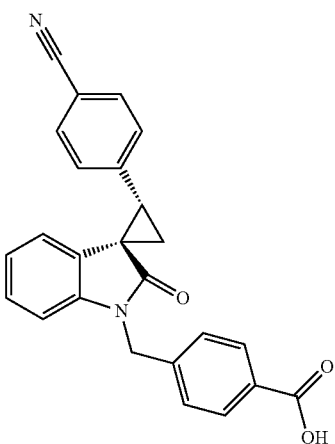

The title compound was prepared in analogy to Example 1 starting from 4-bromomethyl-benzoic acid methyl ester (commercially available), (1R,2S) and (1S,2R)-4-(2'-oxospiro[cyclopropane-1,3'-indoline]-2-yl)benzonitrile prepared as in Scheme 1. LC/MS m/e calcd. for $C_{25}H_{18}ClN_2O_3$: 394, observed (M+H)$^+$: 395.2 $^1$H NMR (400 MHz, DMSO-d$_6$) δppm 2.11-2.20 (m, 1 H) 2.43-2.50 (m, 1 H) 5.10 (s, 2 H)

6.16 (d, 1 H) 6.70 (t, 1 H) 6.92 (d, 1 H) 7.08 (t, 1 H) 7.43 (d, 2 H) 7.55 (d, 2 H) 7.80 (d, 2 H) 7.93 (d, 2 H).

Example 107

(1R,2S) and (1R,2S)-4-((2-(4-fluorophenyl)-2'-oxospiro[cyclopropane-1,3'-indoline]-1'-yl)methyl)benzoic acid

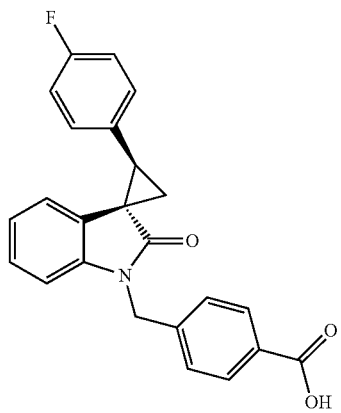

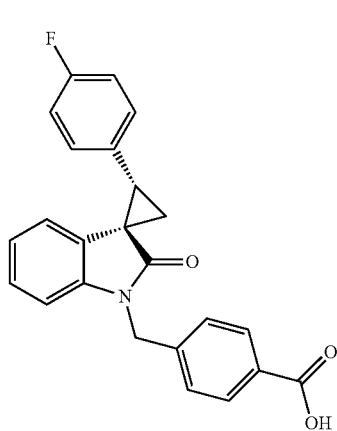

The title compound was prepared in analogy to Example 1 starting from 4-bromomethyl-benzoic acid methyl ester (commercially available), (1R,2S) and (1S,2R)-2-(4-fluorophenyl)spiro[cyclopropane-1,3'-indolin]-2'-one prepared as in Scheme 1. LC/MS m/e calcd. for $C_{24}H_{18}FNO_3$: 387, observed (M+H)+: 388.1 $^1$H NMR (400 MHz, DMSO-$d_6$) δ ppm 2.05-2.14 (m, 1 H) 2.30-2.40 (m, 1 H) 3.21 (t, 2 H) 5.09

(s, 2 H) 6.10 (d, 1 H) 6.70 (t, 1 H) 6.92 (d, 1 H) 7.07 (t, 1 H) 7.11-7.20 (m, 2 H) 7.31-7.38 (m, 2 H) 7.44 (d, 2 H) 7.93 (d, 2 H).

Example 108

(1S,2R) and (1R,2S)-2-chloro-5-((2-(4-chlorophenyl)-5'-fluoro-2'-oxospiro[cyclopropane-1,3'-indoline]-1'-yl)methyl)benzoic acid

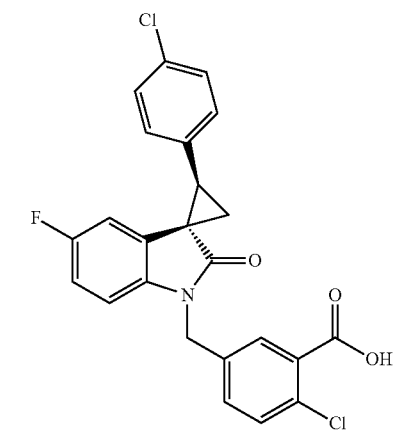

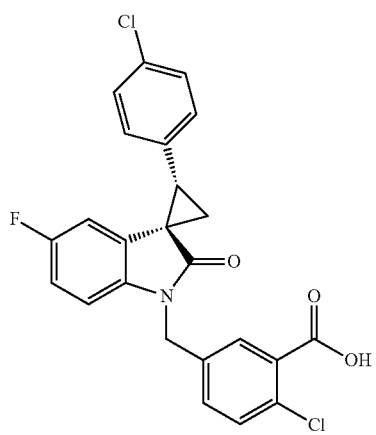

The title compound was prepared in analogy to Example 1 starting from methyl-2-chloro-(3-bromomethyl)-benzoate (commercially available), (1R,2S) and (1S,2R)-2-(4-chlorophenyl)-5'-fluorospiro[cyclopropane-1,3'-indolin]-2'-one prepared as in Scheme 1. LC/MS m/e calcd. for $C_{24}H_{16}Cl_2FNO_3$: 455, observed (M+H)+: 456.2 $^1$HNMR (400 MHz, DMSO-$d_6$) ppm 2.15 (dd, J=9.09, 4.80 Hz, 1 H) 2.46-2.50 (m, 1 H) 3.25 (t, J=8.59 Hz, 1 H) 5.05 (s, 2 H) 6.00

(dd, J=8.97, 1.89 Hz, 1 H) 6.91-6.98 (m, 2 H) 7.33-7.42 (m, 4 H) 7.44-7.49 (m, 1 H) 7.52-7.57 (m, 1 H) 7.73 (d, J=2.02 Hz, 1 H) 13.47 (br. s., 1 H).

Example 109

(1R,2S) and (1S,2R)-3-((2-(3-chloro-4-fluorophenyl)-2'-oxospiro[cyclopropane-1,3'-indoline]-1'-yl)methyl)benzoic acid

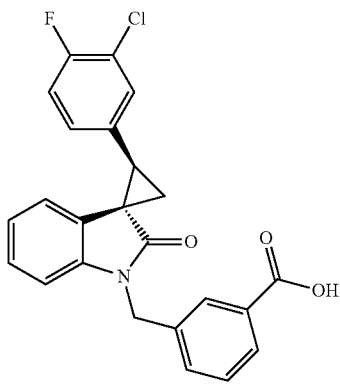

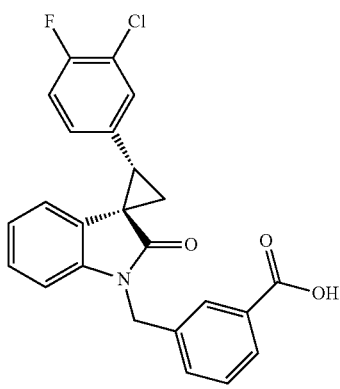

The title compound was prepared in analogy to Example 1 starting from 3-bromomethyl-benzoic acid methyl ester (commercially available), (1R,2S) and (1S,2R)-2-(3-chloro-4-fluorophenyl)spiro[cyclopropane-1,3'-indolin]-2'-one prepared as in Scheme 1. LC/MS m/e calcd. for $C_{24}H_{17}ClFNO_3$: 421, observed (M+H)+: 422.2 $^1$H NMR (400 MHz, DMSO-$d_6$) δppm 2.04-2.15 (m, 1 H) 2.40-2.49 (m, 1 H) 3.21 (t, 1 H) 5.09 (s, 2 H) 6.18 (d, 1 H) 6.75 (t, 1 H) 6.96 (d, 1 H) 7.06-7.14 (m, 1 H) 7.29-7.39 (m, 2 H) 7.46-7.53 (m, 1 H) 7.56-7.65 (m, 2 H) 7.82-7.93 (m, 2 H) 13.03 (s, 1 H).

Example 110

(1R,2S) and (1S,2R)-3-((2-(4-chlorophenyl)-2'-oxospiro[cyclopropane-1,3'-indoline]-1'-yl)methyl)-N-methylbenzamide

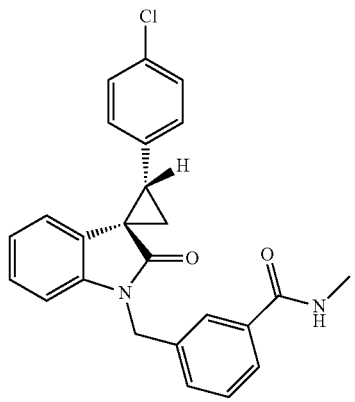

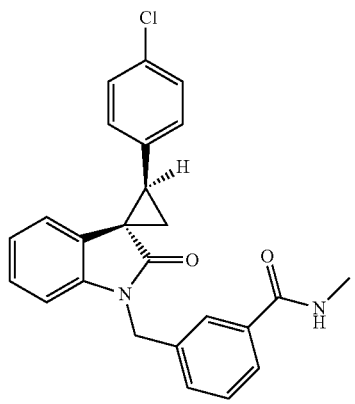

The title compound was prepared in analogy to Example 60 starting from 3-bromomethyl-benzoic acid methyl ester (commercially available), (1R,2S) and (1S,2R)-2-(4-chlorophenyl)spiro[cyclopropane-1,3'-indolin]-2'-one prepared as in Scheme 1. LC/MS m/e calcd. for $C_{25}H_{21}ClN_2O_2$: 416, observed (M+H)+: 417.1 $^1$H NMR (400 MHz, MeOH-$d_4$) δ ppm 2.24 (d, J=8.84 Hz, 2 H) 2.93 (s, 3 H) 3.27-3.39 (m, 1 H) 5.13 (s, 2 H) 6.09 (d, J=7.58 Hz, 1 H) 6.73 (t, J=7.71 Hz, 1 H) 6.91 (d, J=7.83 Hz, 1 H) 7.03-7.13 (m, 1 H) 7.21-7.28 (m, 2 H) 7.29-7.38 (m, 2 H) 7.41-7.50 (m, 1 H) 7.50-7.56 (m, 1 H) 7.72

(d, J=7.58 Hz, 1 H) 7.82 (s, 1 H). MS calcd. For C$_{25}$H$_{21}$N$_2$O$_2$ 381, obsd. (ESI$^+$) [(M+H)$^+$] 382.

Example 111

(1S,2R) and (1R,2S)-3-((2-(4-chlorophenyl)-2'-oxospiro[cyclopropane-1,3'-indoline]-1'-yl)methyl)-N,N-dimethylbenzamide

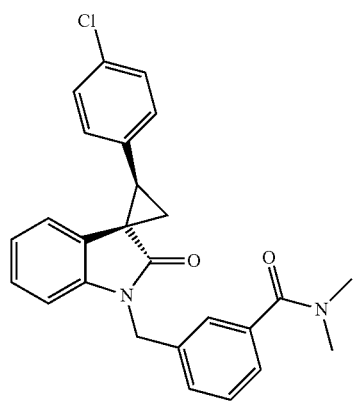

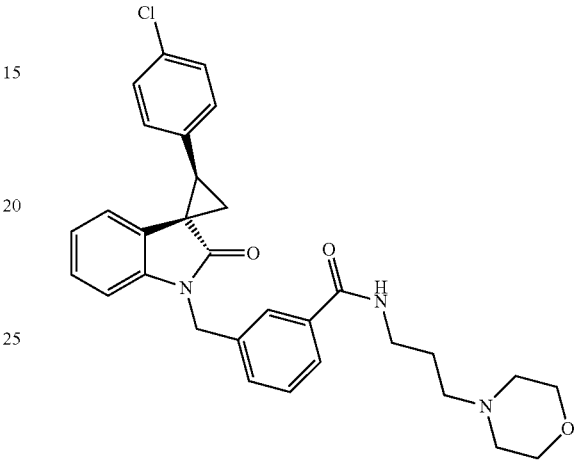

The title compound was prepared in analogy to Example 60 starting from 3-bromomethyl-benzoic acid methyl ester, dimethylamine, methylamine (commercially available), (1R,2S) and (1S,2R)-2-(4-chlorophenyl)spiro[cyclopropane-1,3'-indolin]-2'-one prepared as in Scheme 1. LC/MS m/e calcd. for C$_{29}$H$_{27}$ClN$_2$O$_2$: 470, observed (M+H)$^+$: 471.2 $^1$H NMR (400 MHz, MeOD-d$_4$) δppm 2.15-2.24 (m, 2 H) 2.90 (s, 3 H) 3.06 (s, 3 H) 3.21-3.35 (m, 1 H) 5.09 (s, 2 H) 6.05 (d, J=7.58 Hz, 1 H) 6.69 (t, J=7.58 Hz, 1 H) 6.89 (d, J=8.08 Hz, 1 H) 7.01-7.10 (m, 1 H) 7.19 (d, J=8.59 Hz, 2 H) 7.25-7.38 (m, 4 H) 7.40-7.49 (m, 2 H).

Example 112

(1R,2S) and (1S,2R)-3-((2-(4-chlorophenyl)-2'-oxospiro[cyclopropane-1,3'-indoline]-1'-yl)methyl)-N-(3-morpholinopropyl)benzamide

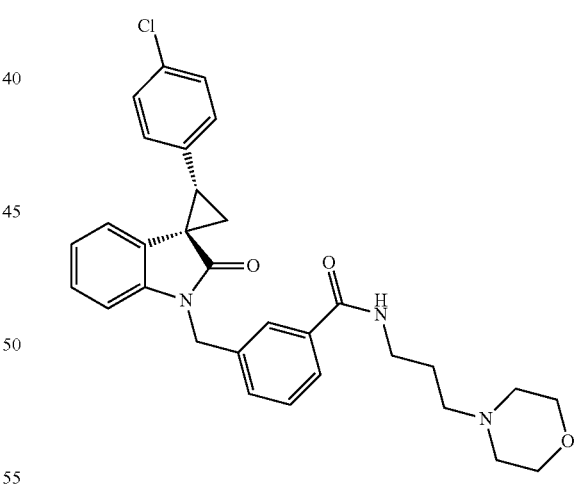

The title compound was prepared in analogy to Example 60 starting from form 3 3-morpholinopropan-1-amine, 3-bromomethyl-benzoic acid methyl ester (commercially available), (1R,2S) and (1S,2R)-2-(4-chlorophenyl)spiro[cyclopropane-1,3'-indolin]-2'-one prepared as in Scheme 1. LC/MS m/e calcd. for C$_{31}$H$_{32}$ClN$_3$O$_3$: 529, observed (M+H)$^+$: 530.2 $^1$H NMR (400 MHz, MeOD-d$_4$) δppm 2.02-2.15 (m, 2 H) 2.24 (d, J=8.59 Hz, 2 H) 3.15 (br. s., 2 H) 3.23 (d, J=8.08 Hz, 2 H) 3.25-3.31 (m, 1 H) 3.47-3.57 (m, 4 H) 3.79 (t, J=12.38 Hz, 2 H) 4.06 (br. s., 2 H) 5.14 (s, 2 H) 6.09 (d, J=7.33 Hz, 1 H) 6.73 (t, J=7.58 Hz, 1 H) 6.91 (d, J=8.08 Hz, 1 H) 7.09 (t, J=7.71 Hz, 1 H) 7.20-7.28 (m, 2 H) 7.28-7.37 (m, 2 H) 7.49 (t, J=7.71 Hz, 1 H) 7.53-7.61 (m, 1 H) 7.78 (d, J=8.08 Hz, 1 H) 7.87 (s, 1 H).

Example 113

(1R,2S) and (1S,2R)-2-(4-chlorophenyl)-1'-(3-(4-(2-(dimethylamino)ethyl)piperazine-1-carbonyl)benzyl)spiro[cyclopropane-1,3'-indolin]-2'-one

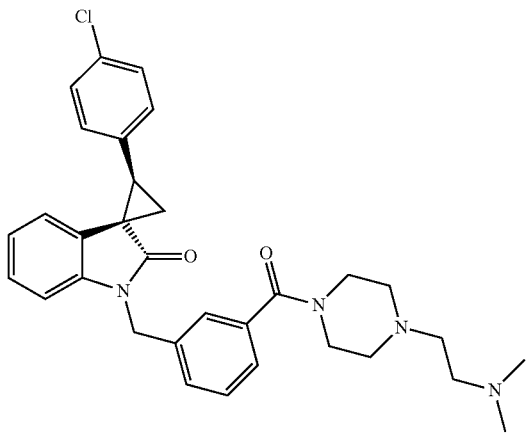

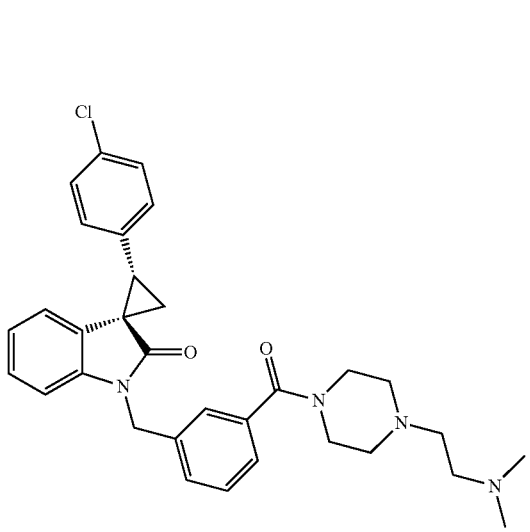

The title compound was prepared in analogy to Example 60 starting from N,N-dimethyl-2-(piperazin-1-yl)ethanamine, 3-bromomethyl-benzoic acid methyl ester (commercially available), (1R,2S) and (1S,2R)-2-(4-chlorophenyl)spiro[cyclopropane-1,3'-indolin]-2'-one prepared as in Scheme 1. LC/MS m/e calcd. for $C_{32}H_{35}ClN_4O_2$: 542, observed (M+H)$^+$: 543.1 $^1$H NMR (400 MHz, CDCl$_3$) δppm 2.04 (dd, J=7.96, 4.67 Hz, 1 H) 2.28 (dd, J=8.97, 4.67 Hz, 1H) 2.93 (s, 6 H) 3.18 (br. s., 4 H) 3.34 (t, J=8.59 Hz, 1 H) 3.62 (br. s., 4 H) 3.87 (br. s., 4 H) 4.95 (d, J=15.92 Hz, 1 H) 5.16 (d, J=15.92 Hz, 1 H) 6.02 (d, J=7.58 Hz, 2 H) 6.70-6.84 (m, 2 H) 7.06-7.19 (m, 3 H) 7.31 (s, 1H) 7.35 (d, J=5.31 Hz, 1 H) 7.43 (d, J=6.06 Hz, 3 H).

Example 114

(1R,2S) and (1S,2R)-3-((2-(4-chlorophenyl)-2'-oxospiro[cyclopropane-1,3'-indoline]-1'-yl)methyl)-N-(2-morpholinoethyl)benzamide

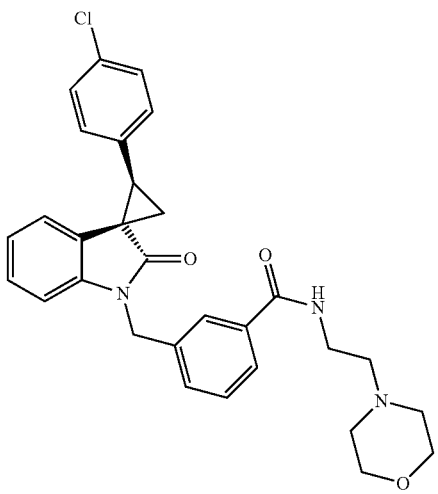

The title compound was prepared in analogy to Example 60 starting from 2-morpholinoethanamine, 3-bromomethyl-benzoic acid methyl ester (commercially available), (1R,2S) and (1S,2R)-2-(4-chlorophenyl)spiro[cyclopropane-1,3'-indolin]-2'-one prepared as in Scheme 1. LC/MS m/e calcd. for $C_{30}H_{30}ClN_3O_3$: 515, observed (M+H)$^+$: 516.2 $^1$H NMR (400 MHz, MeOD-d$_4$) δppm 2.24 (d, J=8.59 Hz, 2 H) 3.20 (br. s., 2 H) 3.29 (s, 1 H) 3.42 (t, J=5.81 Hz, 2 H) 3.69 (br. s., 4 H) 3.80 (t, J=5.81 Hz, 2 H) 4.08 (br. s., 2 H) 5.14 (d, J=1.52 Hz, 2 H) 6.09 (d, J=7.33 Hz, 1 H) 6.73 (t, J=7.58 Hz, 1 H) 6.91 (d, J=8.08 Hz, 1 H) 7.04-7.13 (m, 1 H) 7.22-7.28 (m, 2 H)

7.29-7.36 (m, 2 H) 7.50 (t, J=7.71 Hz, 1 H) 7.55-7.62 (m, 1 H) 7.80 (d, J=7.58 Hz, 1 H) 7.90 (s, 1 H).

Example 115

(1R,2S) and (1S,2R)-2-(4-chlorophenyl)-1'-(3-(4-(methylsulfonyl)piperazine-1-carbonyl)benzyl)spiro[cyclopropane-1,3'-indolin]-2'-one

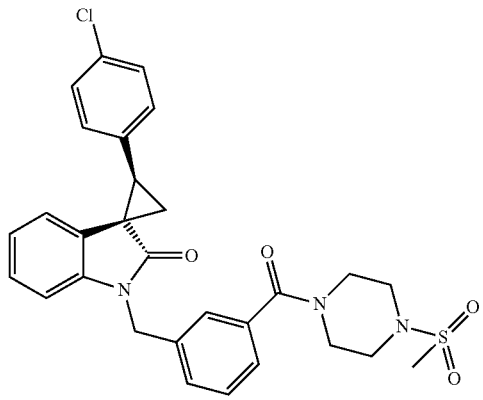

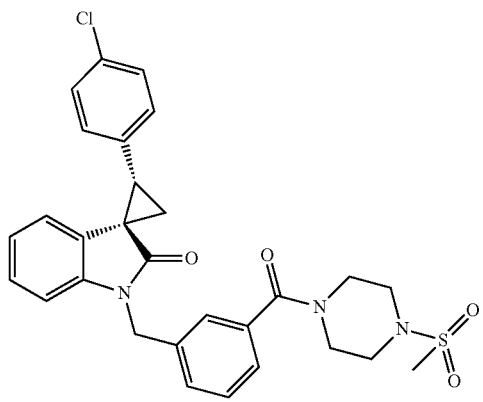

The title compound was prepared in analogy to Example 60 starting from 1-(methylsulfonyl)piperazine, 3-bromomethyl-benzoic acid methyl ester (commercially available), (1R,2S) and (1S,2R)-2-(4-chlorophenyl)spiro[cyclopropane-1,3'-indolin]-2'-one prepared as in Scheme 1. LC/MS m/e calcd. for $C_{29}H_{28}ClN_3O_4S$: 549, observed (M+H)$^+$: 550.2 $^1$H NMR (400 MHz, MeOD-d$_4$) δppm 8.19-8.05 (m, 2 H) 7.49 (s, 3 H) 7.25 (br. s., 4 H) 7.09-7.05 (m, 1H) 6.88 (br. s., 2 H) 6.50 (br. s., 2 H) 5.29-5.12 (m, 2 H) 4.23 (d, J=7.58 Hz, 1 H) 3.64-3.56 (m, 1H) 3.41 (d, J=7.58 Hz, 1 H) 3.29-3.19 (m, 1 H) 3.11 (d, J=8.08 Hz, 2 H) 3.07-2.99 (m, 2 H) 2.98-2.91 (m, 2 H) 2.88-2.75 (m, 2 H).

Example 116

(1S,2R) and (1R,2S)-3-((2-(4-chlorophenyl)-2'-oxospiro[cyclopropane-1,3'-indoline]-1'-yl)methyl)-N-(3-cyclopropyl-1H-pyrazol-5-yl)benzamide

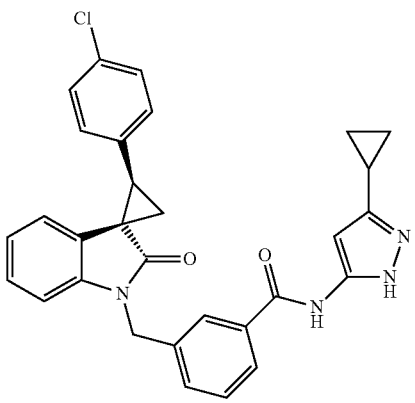

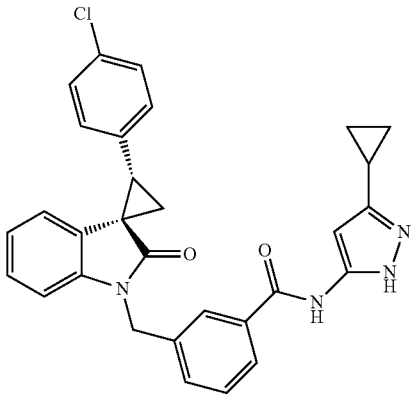

The title compound was prepared in analogy to Example 60 starting from 3-cyclopropyl-1H-pyrazol-5-amine, 3-bromomethyl-benzoic acid methyl ester (commercially available), (1R,2S) and (1S,2R)-2-(4-chlorophenyl)spiro[cyclopropane-1,3'-indolin]-2'-one prepared as in Scheme 1. LC/MS m/e calcd. for $C_{30}H_{25}ClN_4O_2$: 508, observed (M+H)$^+$: 509.2 $^1$H NMR (400 MHz, MeOD-d$_4$) δppm 0.66-0.77 (m, 2 H) 1.02 (dd, J=8.34, 1.77 Hz, 2 H) 2.24 (d, J=8.59 Hz, 2H) 2.47-2.57 (m, 1 H) 3.26-3.32 (m, 1 H) 5.07-5.25 (m, 2 H) 5.65 (s, 1 H) 6.09 (d, J=7.58 Hz, 1 H) 6.73 (t, J=7.58 Hz, 1 H) 6.96 (d, J=7.83 Hz, 1 H) 7.07-7.14 (m, 1 H) 7.20 (d, J=8.34 Hz, 2 H) 7.31 (d, J=8.34 Hz, 2H) 7.49 (t, J=7.83 Hz, 1 H) 7.55-7.63 (m, 1 H) 7.80 (d, J=7.83 Hz, 1 H) 7.83 (s, 1 H).

Example 117

(1S,2R) and (1R,2S)-3-((2-(4-chlorophenyl)-2'-oxospiro[cyclopropane-1,3'-indoline]-1'-yl)methyl)-N-(5-cyclopropyl-1H-pyrazol-3-yl)benzamide

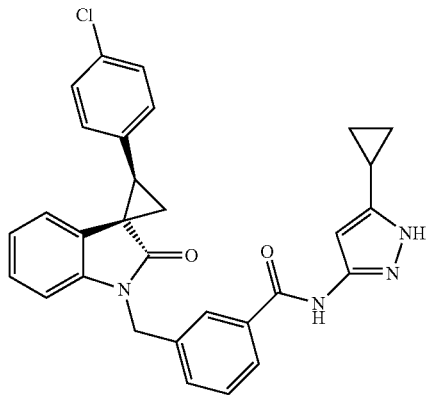

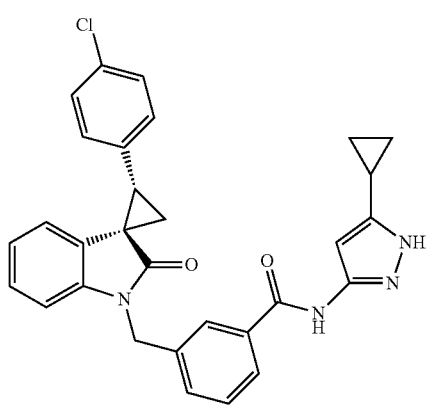

The title compound was prepared in analogy to Example 60 starting from 5-cyclopropyl-1H-pyrazol-3-amine, 3-bromomethyl-benzoic acid methyl ester, (commercially available), (1R,2S) and (1S,2R)-2-(4-chlorophenyl)spiro[cyclopropane-1,3'-indolin]-2'-one prepared as in Scheme 1. LC/MS m/e calcd. for $C_{30}H_{25}ClN_4O_2$: 508, observed (M+H)$^+$: 509.2 $^1$H NMR (400 MHz, MeOD-d$_4$) δppm 0.54-0.77 (m, 2 H) 0.79-0.95 (m, 2 H) 1.62-1.77 (m, 1 H) 2.05 (s, 1H) 2.18-2.30 (m, 2 H) 3.23-3.31 (m, 1 H) 5.07-5.26 (m, 2 H) 6.09 (d, J=6.82 Hz, 1 H) 6.72 (t, J=7.58 Hz, 1H) 6.95 (d, J=7.83 Hz, 1H) 7.05-7.14 (m, 1 H) 7.14-7.20 (m, 2 H) 7.30 (d, J=8.34 Hz, 2 H) 7.51 (t, J=7.71 Hz, 1 H) 7.62 (d, J=7.83 Hz, 1 H) 7.89 (d, J=7.83 Hz, 1 H) 7.94 (s, 1 H).

Example 118

(1R,2S) and (1S,2R)-6-((2-(4-cyanophenyl)-2'-oxospiro[cyclopropane-1,3'-indoline]-1'-yl)methyl)-N-(cyclopropylsulfonyl)picolinamide

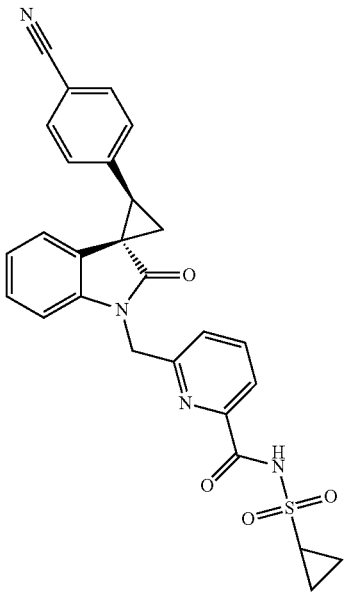

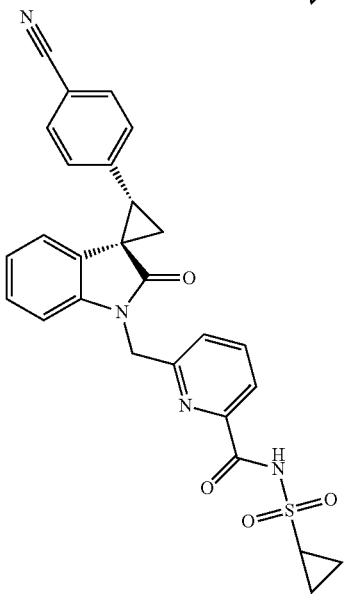

The title compound was prepared in analogy to Example 60 starting from methyl-6-(bromomethyl)picolinate, cyclopropanesulfonamide and (1R,2S) and (1S,2R)-4-(2'-oxospiro[cyclopropane-1,3'-indoline]-2-yl)benzonitrile prepared as in Scheme 1. LC/MS m/e calcd. for $C_{27}H_{22}N_4O_4S$: 498, observed (M+H)$^+$: 499.2 $^1$HNMR (400 MHz, DMSO-d$_6$) δ ppm 1.02-1.15 (m, 2 H) 1.14-1.24 (m, 2 H) 2.08-2.20 (m, 1 H) 2.43-2.48 (m, 1 H) 2.99-3.15 (m, 1 H) 3.27-3.34 (m, 1 H) 5.19

(s, 2 H) 6.14 (d, 1 H) 6.72 (t, 1 H) 6.99 (d, 1H) 7.09 (t, 1 H) 7.47 (d, 1 H) 7.59 (d, 2 H) 7.79 (d, 2 H) 7.92-8.06 (m, 2 H).

Example 119

(1S,2R) and (1R,2S)-4-((2-(4-cyanophenyl)-2'-oxospiro[cyclopropane-1,3'-indoline]-1'-yl)methyl)-N-(cyclopropylsulfonyl)benzamide

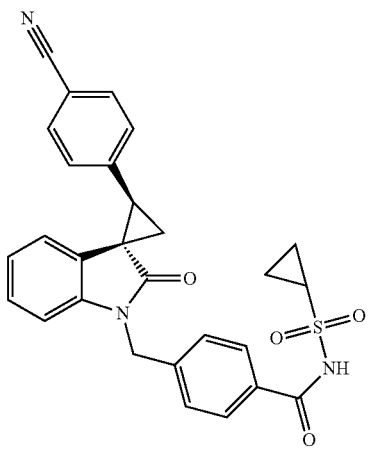

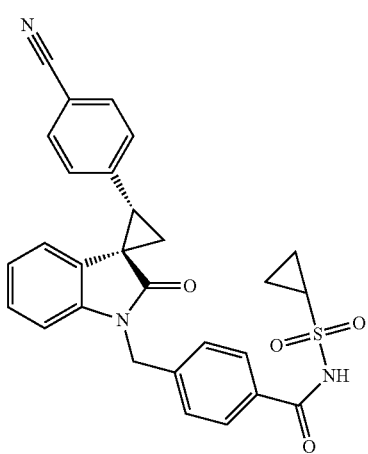

The title compound was prepared in analogy to Example 60 starting from 4-bromomethyl-benzoic acid methyl ester, cyclopropanesulfonamide (commercially available), (1R,2S) and (1S,2R)-4-(2'-oxospiro[cyclopropane-1,3'-indoline]-2-yl)benzonitrile prepared as in Scheme 1. LC/MS m/e calcd. for $C_{28}H_{23}ClN_3O_4S$: 497, observed (M+H)$^+$: 498.2, $^1$H NMR (400 MHz, DMSO-d$_6$) δppm 0.69-0.79 (m, 2 H) 0.83-0.92 (m, 2 H) 2.11-2.18 (m, 1 H) 2.44-2.49 (m, 1 H) 2.91-3.00 (m, 1 H) 3.12-3.20 (m, 1 H) 3.27-3.32 (m, 1 H) 5.04 (s, 2 H) 6.15 (d, 1 H) 6.68 (t, 1 H) 6.91 (d, 1 H) 7.02-7.09 (m, 2 H) 7.28-7.37 (m, 2 H) 7.50-7.59 (m, 2 H) 7.77-7.82 (m, 2H) 7.87-7.94 (m, 2 H).

Example 120

(1R,2S) and (1S,2R)-3-((2-(4-chlorophenyl)-2'-oxospiro[cyclopropane-1,3'-indoline]-1'-yl)methyl)-N-(methylsulfonyl)benzamide

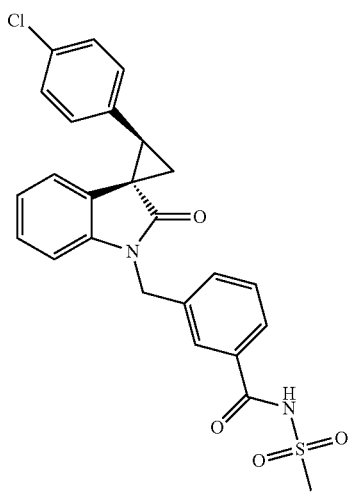

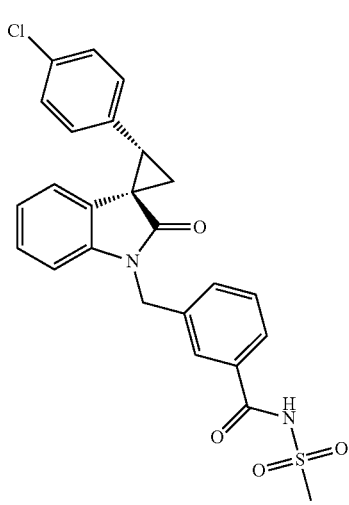

The title compound was prepared in analogy to Example 60 starting from 3-bromomethyl-benzoic acid methyl ester, methylsulfonamide (commercially available), (1R,2S) and 1S, 2R)-2-(4-chlorophenyl)spiro[cyclopropane-1,3'-indolin]-2'-one prepared as in Scheme 1. LC/MS m/e calcd. for $C_{25}H_{21}ClN_2O_4S$: 480, observed (M+H)$^+$: 481.2 $^1$H NMR (400 MHz, DMSO-d$_6$) δppm 2.08-2.18 (m, 1 H) 2.35-2.42 (m, 1 H) 2.92 (s, 3 H) 3.13-3.25 (m, 2 H) 4.95-5.13 (m, 2 H)

6.15 (d, 1 H) 6.70 (t, 1 H) 6.87 (d, 1 H) 7.02-7.10 (m, 2 H) 7.30-7.44 (m, 6H) 7.81-7.89 (m, 2 H).

Example 121

(1R,2S) and (1S,2R)-3-((2-(4-fluorophenyl)-2'-oxospiro[cyclopropane-1,3'-indoline]-1'-yl)methyl)-N-(methylsulfonyl)benzamide

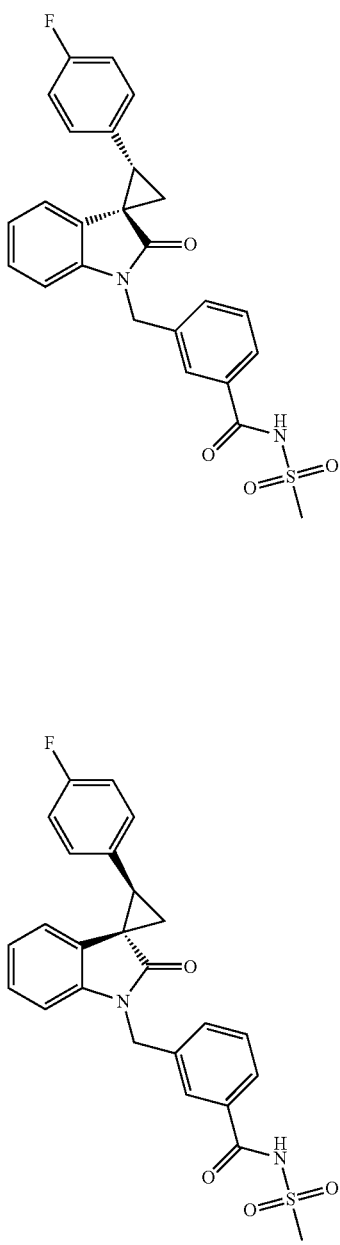

6.71 (t, 1 H) 6.89-6.97 (m, 1 H) 7.03-7.09 (m, 1 H) 7.11-7.18 (m, 2H) 7.31-7.41 (m, 2 H) 7.48-7.55 (m, 1 H) 7.56-7.63 (m, 1 H) 7.82-7.93 (m, 2 H).

Example 122

(1S,2R) and (1R,2S)—N-(cyclopropylsulfonyl)-3-((2-(4-fluorophenyl)-2'-oxospiro [cyclopropane-1,3'-indoline]-1'-yl)methyl)benzamide

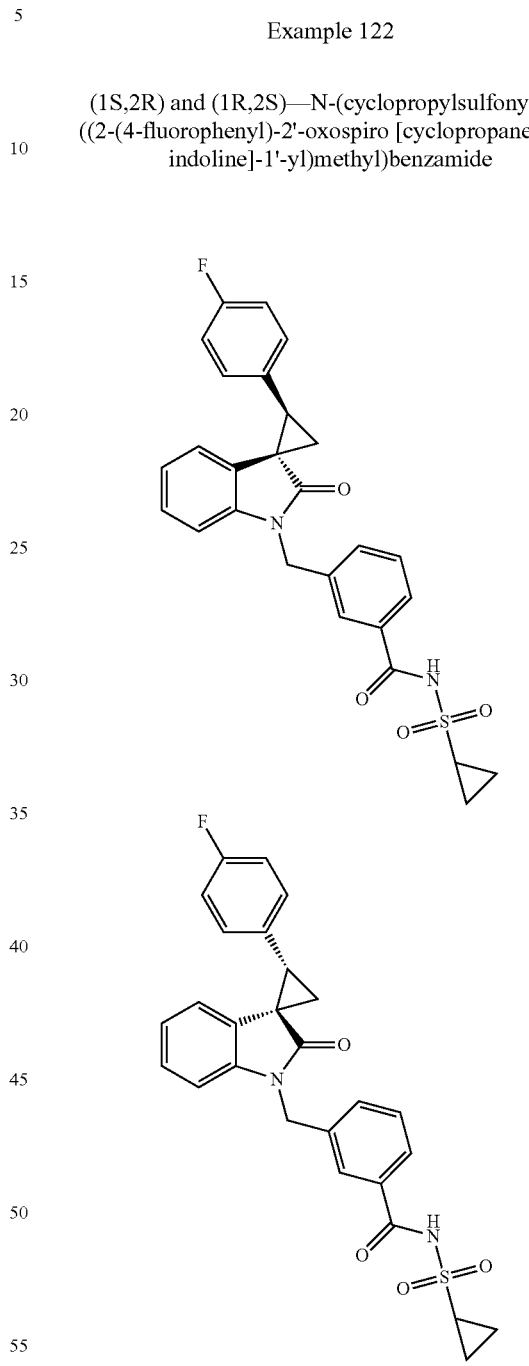

The title compound was prepared in analogy to Example 60 starting from 3-bromomethyl-benzoic acid methyl ester, methylsulfonamide (commercially available), (1R,2S) and (1S,2R)-2-(4-fluorophenyl)spiro[cyclopropane-1,3'-indolin]-2'-one prepared as in Scheme 1. LC/MS m/e calcd. for $C_{25}H_{21}FN_2O_4S$: 470, observed (M+H)$^+$: 471.2 $^1$HNMR (400 MHz, DMSO-d$_6$) δppm 2.10-2.18 (m, 1 H) 2.33-2.42 (m, 1 H) 3.18-3.27 (m, 1 H) 3.38 (s, 3 H) 5.10 (s, 2 H) 6.12 (d, 1 H)

The title compound was prepared in analogy to Example 60 starting from 3-bromomethyl-benzoic acid methyl ester, cyclopropanesulfonamide (commercially available), (1R,2S) and (1S,2R)-2-(4-fluorophenyl)spiro[cyclopropane-1,3'-indolin]-2'-one prepared as in Scheme 1. LC/MS m/e calcd. for $C_{27}H_{23}FN_2O_4S$: 490, observed (M+H)$^+$: 491.2 $^1$HNMR (400 MHz, DMSO-d$_6$) δppm 0.84-0.94 (m, 2 H) 0.94-1.04 (m, 2 H) 2.08-2.18 (m, 1 H) 2.32-2.40 (m, 1 H) 2.98-3.09 (m, 1 H)

3.21 (t, 1 H) 5.06 (s, 2 H) 6.09 (d, 1 H) 6.68 (t, 1 H) 6.89 (d, 1 H) 7.00-7.18 (m, 4 H) 7.33-7.50 (m, 4 H) 7.80-7.92 (m, 2 H).

Example 123

(1S,2R) and (1R,2S)—N-(cyclopropylsulfonyl)-4-((2-(4-fluorophenyl)-2'-oxospiro [cyclopropane-1,3'-indoline]-1'-yl)methyl)benzamide

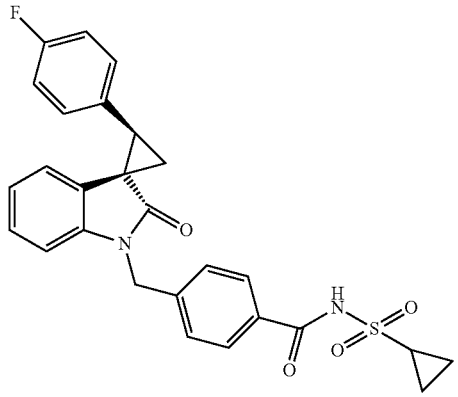

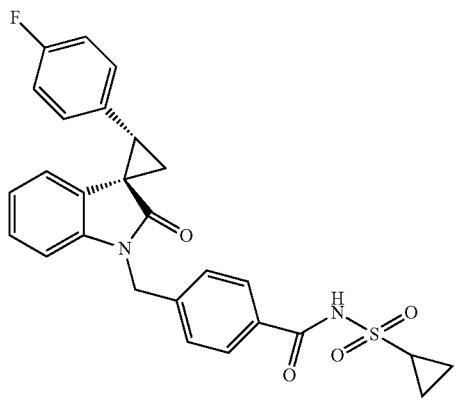

The title compound was prepared in analogy to Example 60 starting from 4-bromomethyl-benzoic acid methyl ester, cyclopropanesulfonamide (commercially available), (1R,2S) and (1S,2R)-2-(4-fluorophenyl)spiro[cyclopropane-1,3'-indolin]-2'-one prepared as in Scheme 1. LC/MS m/e calcd. for $C_{27}H_{23}FN_2O_4S$: 490, observed (M+H)$^+$: 491.2 $^1$H NMR (400 MHz, DMSO-d$_6$) δppm 0.70-0.81 (m, 2 H) 0.84-0.91 (m, 2 H) 2.06-2.17 (m, 1 H) 2.31-2.40 (m, 1 H) 2.91-3.02 (m, 1 H)

3.14-3.24 (m, 2 H) 5.04 (s, 2 H) 6.09 (d, 1 H) 6.68 (t, 1 H) 6.89 (d, 1 H) 7.05 (t, 2 H) 7.11-7.19 (m, 3 H) 7.89 (d, 2 H).

Example 124

(1S,2R) and (1R,2S)-2-(4-chlorophenyl)-1'-(piperidin-4-ylmethyl) Spiro[cyclopropane-1,3'-indolin]-2'-one

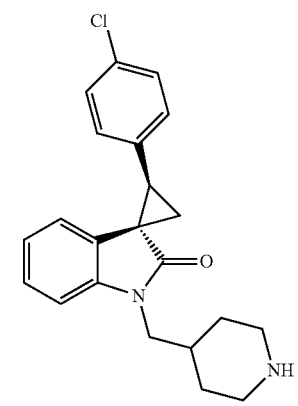

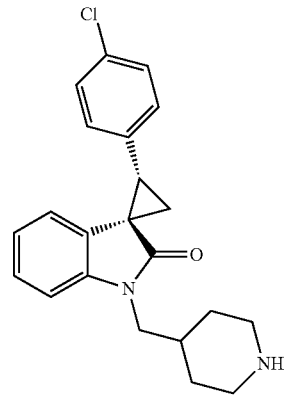

The title compound was prepared in analogy to Example 70 starting from 4-(chloromethyl)piperidine (commercially available), (1R,2S) and (1S,2R)-2-(4-chlorophenyl)spiro[cyclopropane-1,3'-indolin]-2'-one prepared as in Scheme 1. LC/MS m/e calcd. for $C_{22}H_{23}ClN_2O$: 366, observed (M+H)$^+$: 367.2 $^1$HNMR (400 MHz, MeOD-d$_4$) δppm 1.51-1.67 (m, 2 H) 1.96 (br. s., 2 H) 2.12-2.21 (m, 2 H) 2.21-2.35 (m, 1 H) 2.93-3.07 (m, 2 H) 3.22 (t, J=8.59 Hz, 1 H) 3.38-3.50 (m, 2 H)

3.84 (d, J=7.33 Hz, 2 H) 6.09 (d, J=7.58 Hz, 1 H) 6.77 (t, J=7.58 Hz, 1 H) 7.11 (d, J=7.83 Hz, 1 H) 7.16-7.26 (m, 3 H) 7.29-7.35 (m, 2 H).

Example 125

(1S,2R) and (1R,2S)-2-(4-chlorophenyl)-1'-(2-(piperidin-1-yl)ethyl)spiro[cyclopropane-1,3'-indolin]-2'-one

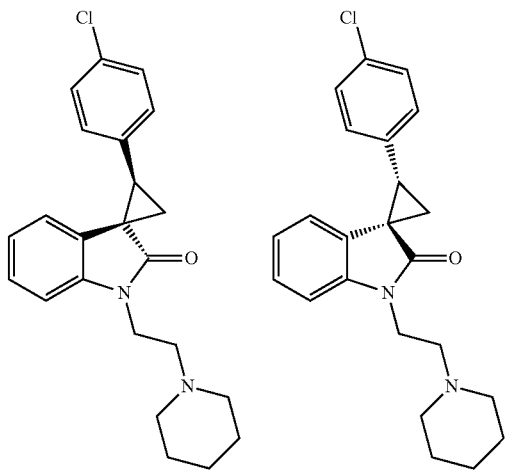

The title compound was prepared in analogy to Example 70 starting from with 1-(2-chloroethyl)piperidine (commercially available), (1R,2S) and (1S,2R)-2-(4-chlorophenyl) spiro[cyclopropane-1,3'-indolin]-2'-one prepared as in Scheme 1. LC/MS m/e calcd. for $C_{23}H_{25}ClN_2O$: 380, observed (M+H)$^+$: 371.2 $^1$HNMR (400 MHz, MeOD-d$_4$) δ ppm 1.62 (br. s., 1 H) 1.89 (br. s., 3 H) 2.05 (br. s., 2 H) 2.21-2.30 (m, 2 H) 3.09 (br. s., 2 H) 3.30 (t, J=8.59 Hz, 1 H) 3.48-3.62 (m, 2 H) 3.76 (br. s., 1 H) 3.93 (br. s., 1 H) 4.22-4.32 (m, 1 H) 4.34-4.46 (m, 1 H) 6.15 (d, J=7.58 Hz, 1 H) 6.84 (t, J=7.58 Hz, 1 H) 7.15-7.21 (m, 1 H) 7.23-7.31 (m, 3 H) 7.33-7.40 (m, 2 H).

Example 126

(1S,2R) and (1R,2S)-2-(4-chlorophenyl)-1'-(2-(3-morpholinopropylamino)ethyl) spiro[cyclopropane-1,3'-indolin]-2'-one

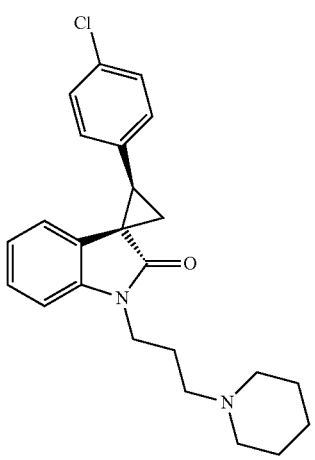

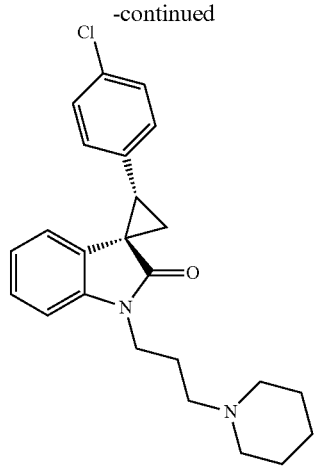

The title compound was prepared in analogy to Example 70 starting from 1-(3-chloropropyl)piperidine (commercially available), (1R,2S) and (1S,2R)-2-(4-chlorophenyl)spiro[cyclopropane-1,3'-indolin]-2'-one prepared as in Scheme 1. LC/MS m/e calcd. for $C_{24}H_{27}ClN_2O$: 394, observed (M+H)$^+$: 395.2 $^1$HNMR (400 MHz, MeOD-d$_4$) δppm 1.46-1.62 (m, 1 H) 1.69-1.91 (m, 3 H) 1.98 (d, J=14.91 Hz, 2H) 2.15-2.27 (m, 4 H) 2.97 (t, J=12.76 Hz, 2 H) 3.17-3.29 (m, 3 H) 3.57 (d, J=12.13 Hz, 2 H) 3.92-4.07 (m, 2 H) 6.11 (d, J=7.58 Hz, 1 H) 6.79 (t, J=7.58 Hz, 1 H) 7.12 (d, J=7.83 Hz, 1 H) 7.18-7.26 (m, 3 H) 7.28-7.37 (m, 2 H).

Example 127

(1S,2R) and (1R,2S)-2-(4-chlorophenyl)-1'-(2-(3-morpholinopropylamino)ethyl) spiro[cyclopropane-1,3'-indolin]-2'-one

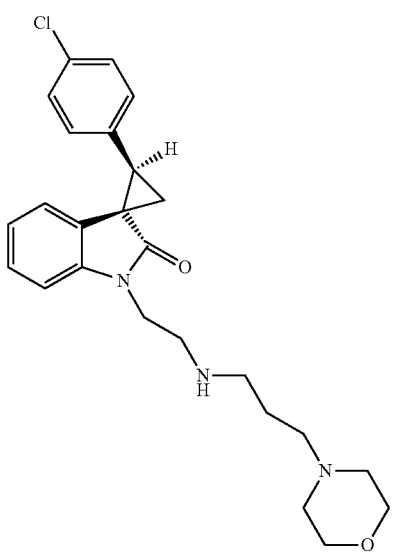

163

-continued

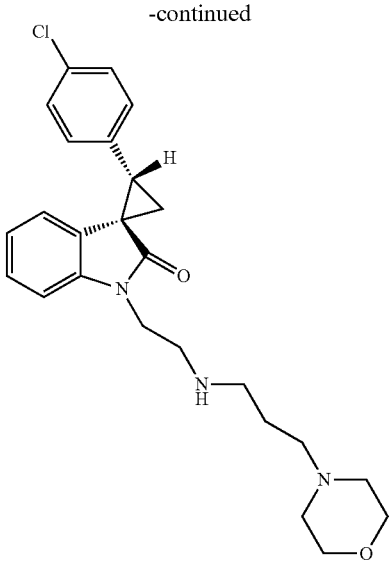

The title compound was prepared in analogy to Example 81 starting from dibromo ethylene, 3-morpholinopropan-1-amine (commercially available), (1R,2S) and (1S,2R)-2-(4-chlorophenyl)spiro[cyclopropane-1,3'-indolin]-2'-one prepared as in Scheme 1. LC/MS m/e calcd. for $C_{25}H_{30}ClN_3O_2$: 439, observed (M+H)$^+$: 440.1 $^1$HNMR (400 MHz, MeOD-d$_4$) δppm 2.07-2.32 (m, 6 H) 3.26 (s, 8 H) 3.47 (t, J=5.94 Hz, 3 H) 4.24 (d, J=28.55 Hz, 3 H) 6.12 (d, J=7.07 Hz, 1 H) 6.81 (t, J=7.07 Hz, 1 H) 7.14 (d, J=7.58 Hz, 1 H) 7.19-7.29 (m, 3H) 7.30-7.39 (m, 2 H).

Example 128

(1S,2R) and (1R,2S)-2-(4-chlorophenyl)-1'-(2-(2-morpholinoethylamino)ethyl) spiro[cyclopropane-1,3'-indolin]-2'-one

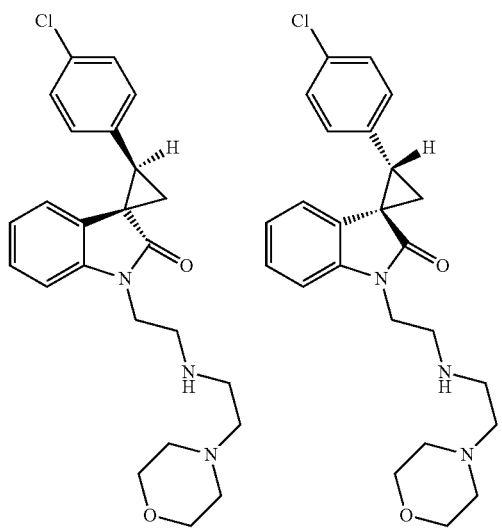

The title compound was prepared in analogy to Example 81 starting from dibromo ethylene, 2-morpholinoethanamine (commercially available), (1R,2S) and (1S,2R)-2-(4-chlorophenyl)spiro[cyclopropane-1,3'-indolin]-2'-one prepared as in Scheme 1. LC/MS m/e calcd. for $C_{24}H_{28}ClN_3O_2$: 425, observed (M+H)$^+$: 426.2 $^1$HNMR (400 MHz, MeOD-d$_4$) δ ppm 2.09-2.34 (m, 3 H) 3.02 (br. s., 4 H) 3.17 (t, J=6.19 Hz, 2 H) 3.27 (t, J=8.72 Hz, 1 H) 3.44-3.61 (m, 4 H) 3.87 (t, J=4.67 Hz, 4 H) 4.12-4.45 (m, 2 H) 6.11 (d, J=7.83 Hz, 1 H) 6.80 (t, J=7.58 Hz, 1 H) 7.10-7.18 (m, 1 H) 7.20-7.27 (m, 3 H) 7.29-7.40 (m, 2 H).

Example 129

(1S,2R) and (1R,2S)-2-(4-chlorophenyl)-1'-(2-(4-(pyridin-4-yl)piperazin-1-yl)ethyl) spiro[cyclopropane-1,3'-indolin]-2'-one

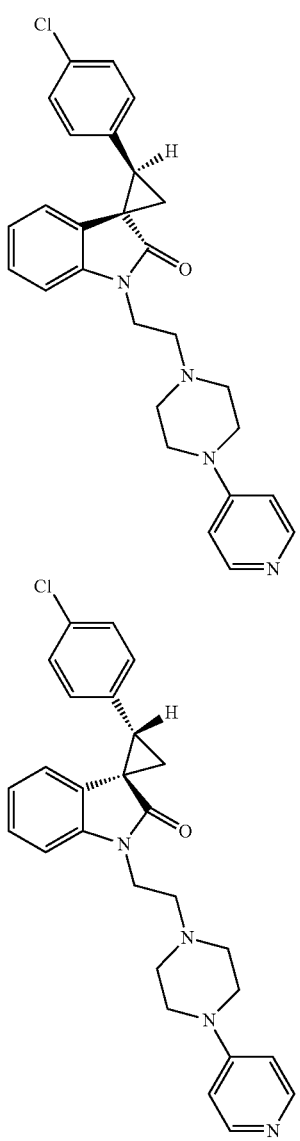

The title compound was prepared in analogy to Example 81 starting from dibromo ethylene, 1-(pyridin-4-yl)piperazine (commercially available), (1R,2S) and (1S,2R)-2-(4-chlorophenyl)spiro[cyclopropane-1,3'-indolin]-2'-one prepared as in Scheme 1. LC/MS m/e calcd. for $C_{27}H_{27}ClN_4O$: 458, observed (M+H)$^+$: 459.2 $^1$HNMR (400 MHz, MeOD-d$_4$) δ ppm 1.32 (s, 2 H) 2.02-2.40 (m, 3 H) 3.26 (s, 1 H) 3.47 (d, J=9.09 Hz, 8 H) 4.02 (br. s., 4 H) 4.25 (s, 2 H) 6.11 (d, J=7.33 Hz, 1 H) 6.80 (s, 1 H) 7.12-7.18 (m, 1 H) 7.19-7.27 (m, 3 H) 7.32 (t, J=8.97 Hz, 4 H) 8.27 (d, J=7.83 Hz, 2 H).

Example 130

(1S,2R) and (1R,2S)-2-(4-chlorophenyl)-1'-(2-(2-(2,6-dimethylmorpholino) ethylamino) ethyl) Spiro [cyclopropane-1,3'-indolin]-2'-one

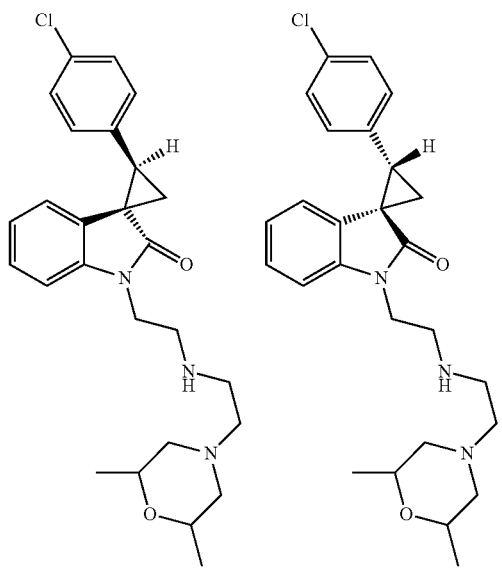

The title compound was prepared in analogy to Example 81 starting from 2-(2,6-dimethylmorpholino)ethanamine, dibromo ethylene (commercially available), (1R,2S) and (1S,2R)-2-(4-chlorophenyl)spiro[cyclopropane-1,3'-indolin]-2'-one prepared as in Scheme 1. LC/MS m/e calcd. for $C_{26}H_{32}ClN_3O_2$: 453, observed (M+H)$^+$: 454.1 $^1$HNMR (400 MHz, MeOD-$d_4$) δppm 1.22 (dd, J=6.32, 2.27 Hz, 2 H) 1.26-1.37 (m, 6 H) 2.15-2.32 (m, 3 H) 2.43-2.67 (m, 1 H) 2.88 (br. s., 3 H) 3.26 (d, J=8.59 Hz, 2 H) 3.40-3.62 (m, 4 H) 3.70-3.96 (m, 1 H) 4.13 (br. s., 4 H) 6.05-6.21 (m, 1 H) 6.81 (t, J=7.58 Hz, 1 H) 7.06-7.18 (m, 1 H) 7.24 (d, J=8.34 Hz, 3 H) 7.29-7.38 (m, 2 H).

Example 131

(1S,2R) and (1R,2S)-2-(4-chlorophenyl)-1'-(1H-imidazol-4-yl)spiro[cyclopropane-1,3'-indolin]-2'-one

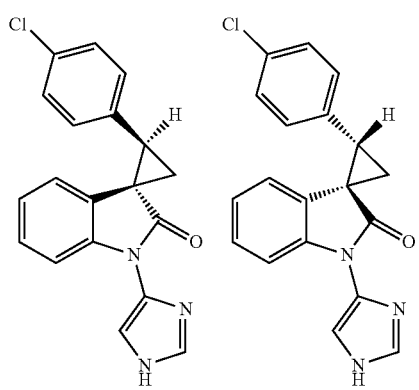

Synthesis of (1S,2R) and (1R,2S)-2-(4-chlorophenyl)-1'-(1-trityl-1H-imidazol-4-yl)spiro [cyclopropane-1,3'-indolin]-2'-one

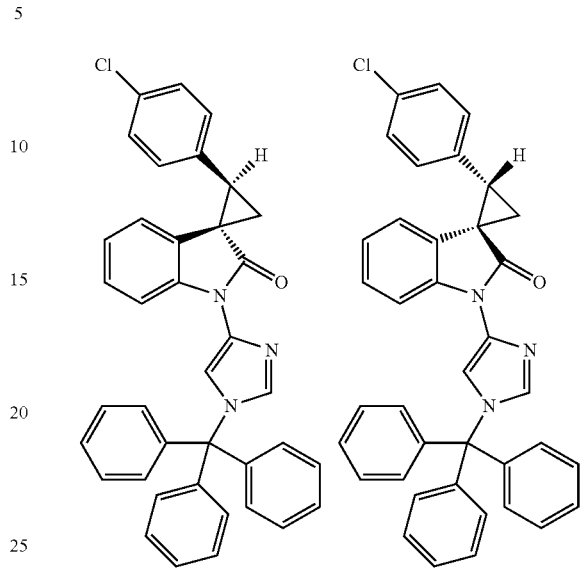

4-iodo-1-trityl-1H-imidazole (210 mg, 0.48 mmol) was added to a suspension of (1R,2S) and (1S,2R)-2-(4-chlorophenyl)spiro[cyclopropane-1,3'-indolin]-2'-one (107 mg, 0.4 mmol) in acetonitrile (2 mL) under a nitrogen atmosphere. A steady stream of nitrogen was bubbled through the suspension as it was heated to 40° C. over 15 minutes. Potassium carbonate (110 mg, 0.8 mmol), copper (I) iodide (12 mg, 15 mol %), and N,N-dimethylethylenediamine (0.12 mmol, 30 mol %) were added and the reaction mixture was heated to 80° C. for 21 hours under nitrogen atmosphere. The mixture was cooled to room temperature, filtrated, and concentrated to give the title product. The residue was purified by flash column chromatography (gradient elution, 5-10% ethyl acetate in petroleum ether) to give racemic trans-2-(4-chlorophenyl)-1'-(1H-imidazol-4-trityl) spiro[cyclopropane-1,3'-indolin]-2'-one (157 mg, 68%). LC/MS m/e calcd. for $C_{38}H_{28}ClN_3O$: 577, observed (M+H)$^+$: 578.3.

Synthesis of (1S,2R) and (1R,2S)-2-(4-chlorophenyl)-1'-(1H-imidazol-4-yl)spiro [cyclopropane-1,3'-indolin]-2'-one

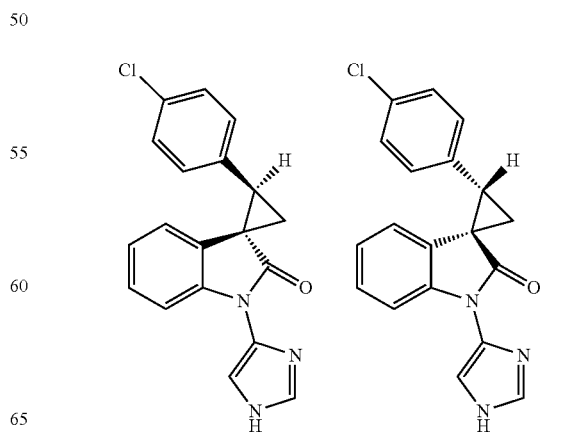

(1S,2R) and (1R,2S)-2-(4-chlorophenyl)-1'-(1-trityl-1H-imidazol-4-yl)spiro [cyclopropane-1,3'-indolin]-2'-one (115 mg, 0.2 mmol) was dissolved in DCM (2 mL) and water (0.5 mL). TFA (0.1 mL) was added dropwise at 0° C. The mixture was stirred for 14 hours at room temperature. The mixture was poured into the sat. NaHCO$_3$, extracted with DCM (3×10 mL), dried and concentrated to give the title product. The residue was dissolved in 2 mL of DMF. Purification by preparative HPLC to give the title compound as white powder (60 mg, 89%). $^1$H NMR (400 MHz, DMSO-d$_6$) δppm 2.13 (dd, J=9.09, 5.05 Hz, 1 H) 2.42 (dd, J=8.08, 4.80 Hz, 1 H) 3.23 (t, J=8.72 Hz, 1 H) 6.20 (d, J=7.58 Hz, 1 H) 6.81 (t, J=7.20 Hz, 1 H) 7.16 (t, J=7.83 Hz, 1 H) 7.30-7.45 (m, 5H) 7.66 (s, 1 H) 8.27 (s, 1 H). LC/MS m/e calcd. for C$_{19}$H$_{14}$ClN$_3$O 335, observed (M+H)$^+$: 336.3.

Example 132

(1S,2R) and (1R,2S)-3-(2-(4-chlorophenyl)-2'-oxospiro[cyclopropane-1,3'-indoline]-1'-yl)-N-(methylsulfonyl)benzamide

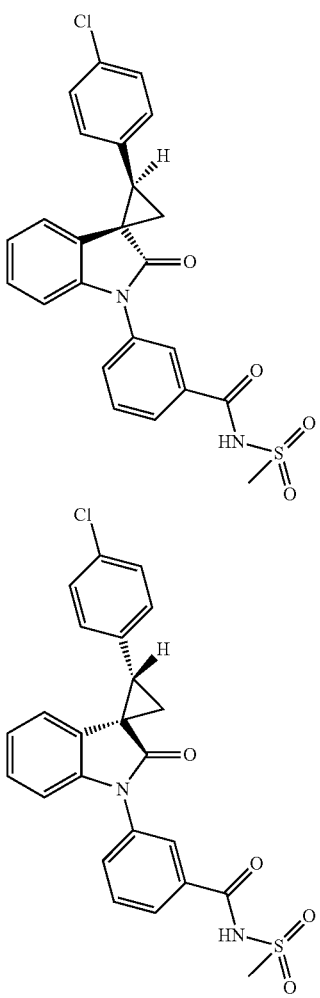

The title compound was prepared in analogy to Example 85 starting from methylsulfonamide, methyl-3-iodobenzoate (commercially available), (1R,2S) and (1S,2R)-2-(4-chlorophenyl)spiro[cyclopropane-1,3'-indolin]-2'-one prepared as in Scheme 1. LC/MS m/e calcd. for C$_{24}$H$_{19}$ClN$_2$O$_4$S: 466, observed (M+H)$^+$: 467.2 $^1$H NMR (400 MHz, DMSO-d$_6$) δppm 2.15 (dd, J=9.09, 4.80 Hz, 1 H) 2.44 (dd, J=8.08, 4.80 Hz, 1 H) 3.25 (t, J=8.59 Hz, 1 H) 3.41 (s, 3 H) 6.21 (d, J=7.58 Hz, 1 H) 6.79-6.88 (m, 2 H) 7.10-7.17 (m, 1 H) 7.37-7.45 (m, 4 H) 7.75 (t, J=7.83 Hz, 1 H) 7.80-7.85 (m, 1 H) 8.04 (d, J=7.83 Hz, 1 H) 8.11-8.16 (m, 1 H) 12.29 (br. s., 1 H).

Example 133

(1S,2S) and (1R,2R)-3-(2-(4-chlorophenyl)-2-methyl-2'-oxospiro[cyclopropane-1,3'-indoline]-1'-yl)-5-(2-oxooxazolidin-3-yl)benzoic acid

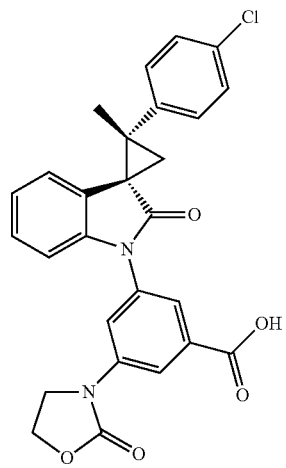

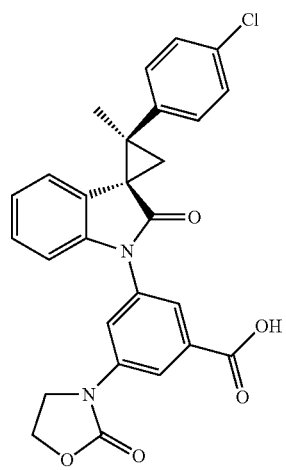

The title compound was prepared in analogy to Example 95 starting from oxazolidin-2-one (commercially available), 3-bromo-5-iodobenzoic acid methylester prepared in Example 92, (1R,2R) and (1S,2S)-2-(4-chlorophenyl)-2-methylspiro[cyclopropane-1,3'-indolin]-2'-one prepared as in Scheme 2. LC/MS m/e calcd. for C$_{27}$H$_{21}$ClN$_2$O$_5$: 488, observed (M+H)$^+$: 489.1 $^1$H NMR (400 MHz, DMSO-d$_6$) δ ppm 1.66 (s, 3 H) 2.18 (d, J=4.80 Hz, 1 H) 2.38 (d, J=5.05 Hz, 1 H) 4.12 (t, J=8.08 Hz, 2 H) 4.47 (t, J=7.96 Hz, 2 H) 6.95 (d, J=8.08 Hz, 1 H) 7.15 (t, J=7.45 Hz, 1 H) 7.25-7.34 (m, 5 H) 7.45 (d, J=7.33 Hz, 1 H) 7.59-7.62 (m, 1 H) 7.85 (t, J=2.02 Hz, 1 H) 8.12 (s, 1 H).

6.78-6.91 (m, 2 H) 7.11 (t, 1 H) 7.61 (d, 1 H) 7.69 (d, 1 H) 7.79 (s, 1 H) 7.92-8.03 (m, 2 H) 8.21 (s, 1 H) 13.44 (s, 1 H).

Example 134

(1S,2S) and (1R,2R)-3-(2-(4-chlorophenyl)-2-isopropyl-2'-oxospiro[cyclopropane-1,3'-indoline]-1'-yl)-5-(2-oxooxazolidin-3-yl)benzoic acid

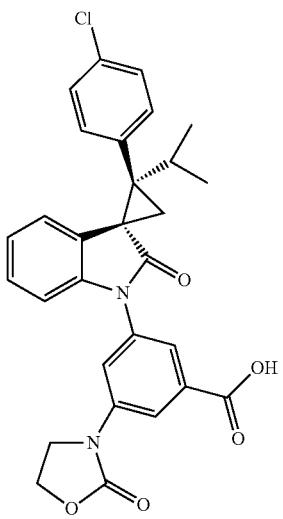

Example 135

(1S,2S) and (1R,2R)-3-(2-(4-chlorophenyl)-2-isopropyl-2'-oxospiro[cyclopropane-1,3'-indoline]-1'-yl)-5-(2-oxooxazolidin-3-yl)benzoic acid

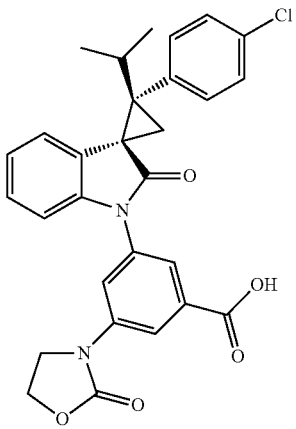

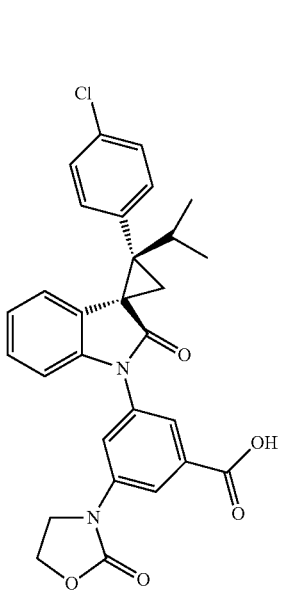

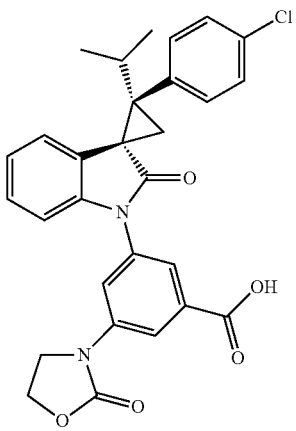

The title compound was prepared in analogy to Example 95 starting from oxazolidin-2-one, 3-bromo-5-iodobenzoic methylester (prepared as in Example 92), (1R,2R) and (1S,2S)-2-(4-chlorophenyl)-2-isopropylspiro[cyclopropane-1,3'-indolin]-2'-one prepared as in Scheme 2. LC/MS m/e calcd. for $C_{29}H_{25}ClN_2O_5$: 516, observed (M+H)$^+$: 517.2 $^1$H NMR (400 MHz, DMSO-d$_6$) δppm 0.77 (d, 3 H) 0.89 (d, 3 H) 2.16 (d, 1 H) 2.28 (d, 1 H) 2.95-3.02 (m, 1 H) 4.17-4.25 (m, 2 H) 4.40-4.58 (m, 2 H) 5.43 (d, 1 H) 6.65-6.76 (m, 1 H)

The title compound was prepared in analogy to Example 95 starting from oxazolidin-2-one (commercially available), 3-bromo-5-iodobenzoic methylester (prepared as in Example 92), (1S,2S) and (1R,2R)-2-(4-chlorophenyl)-2-isopropyl-spiro[cyclopropane-1,3'-indolin]-2'-one prepared as in Scheme 2. LC/MS m/e calcd. for $C_{29}H_{25}ClN_2O_5$: 516, observed (M+H)$^+$: 517.2 $^1$H NMR (400 MHz, DMSO-d$_6$) δ ppm 0.77 (d, 3 H) 0.89 (d, 3 H) 2.16 (d, 1 H) 2.28 (d, 1 H) 2.85-3.02 (m, 1 H) 4.07-4.25 (m, 2 H) 4.41-4.59 (m, 2 H) 5.43

(d, 1 H) 6.62-6.75 (m, 1 H) 6.78-6.91 (m, 2 H) 7.11 (t, 1 H) 7.61 (d, 1 H) 7.69 (d, 1 H) 7.79 (s, 1 H) 7.92-8.03 (m, 2 H) 8.21 (s, 1 H) 13.44 (s, 1 H).

Example 136

(R) and (S)-methyl-3-(2,2-dimethyl-2'-oxospiro[cyclopropane-1,3'-indoline]-1'-yl)-5-(2-oxooxazolidin-3-yl)benzoate

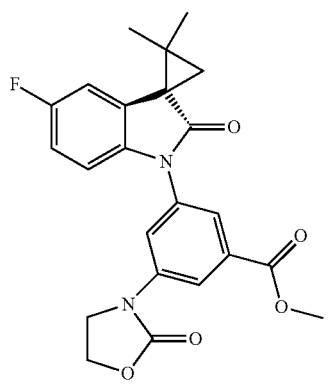

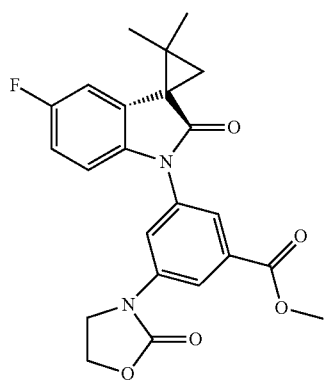

A suspension of (R) and (S)-5'-fluoro-2,2-dimethylspiro[cyclopropane-1,3'-indolin]-2'-one (2 mmol) (prepared as in Example 100), methyl 3-bromo-5-(2-oxooxazolidin-3-yl)benzoate (682 mg, 2 mmol) (prepared as in Example 100), CuI (76 mg, 0.4 mmol), potassium carbonate (545 mg, 4 mmol) and N,N'-dimethyl-ethane-1,2-diamine (86 uL, 0.8 mmol) in acetonitrile (15 mL) was stirred for 16 hours at 90° C. The precipitate was filtered off and washed with ethyl acetate. The filtrate was concentrated in vacuo to afford the title compound as white powder (480 mg, 80%). LC/MS m/e calcd. for $C_{23}H_{21}FN_2O_5$: 424, observed (M+H)$^+$: 425.2 $^1$H NMR (400 MHz, DMSO-d$_6$) δppm 1.42 (s, 3 H) 1.48 (s, 3 H) 1.79 (d, J=4.29 Hz, 1 H) 1.95 (d, J=4.55 Hz, 1 H) 3.90 (s, 3 H) 4.17 (t, 2 H) 4.48 (t, J=7.96 Hz, 2 H) 6.87 (dd, J=8.72, 4.42 Hz, 1 H) 7.04 (t, J=9.09 Hz, 1 H) 7.27 (dd, J=8.84, 2.53 Hz, 1 H) 7.73 (s, 1 H) 7.91 (s, 1 H) 8.24 (s, 1 H).

Example 137

(R) and (S)-3-(5'-fluoro-2,2-dimethyl-2'-oxospiro[cyclopropane-1,3'-indoline]-1'-yl)-5-(2-hydroxyethylamino)benzoic acid

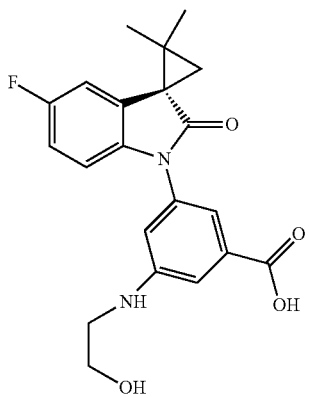

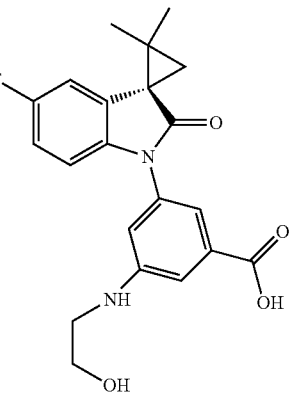

The title compound was prepared in analogy to Example 95 starting from 2-aminoethanol (commercially available), methyl-3-bromo-5-iodobenzoate prepared as in Example 92, (R) and (S)-5'-fluoro-2,2-dimethylspiro[cyclopropane-1,3'-indolin]-2'-one prepared as in Scheme 2. LC/MS m/e calcd. for $C_{21}H_{21}FN_2O_4$: 384, observed (M+H)$^+$: 385.1 $^1$H NMR (400 MHz, MeOD-d$_4$) δppm 1.48 (s, 3 H) 1.56 (s, 3 H) 1.83 (d, J=4.55 Hz, 1 H) 1.90 (d, J=4.55 Hz, 1 H) 3.30-3.37 (m, 2

H) 3.76 (t, J=5.68 Hz, 2 H) 6.84 (dd, J=8.59, 4.55 Hz, 1 H) 6.91-6.99 (m, 2 H) 7.03 (dd, J=8.84, 2.27 Hz, 1 H) 7.33 (s, 1 H) 7.47 (s, 1 H).

Example 138

(R) and (S)-methyl-3-(2-oxo-1,3-oxazolidin-3-yl)-5-(2-oxo-2",3",5",6"-tetrahydrodispiro[indole-3,1'-cyclopropane-2',4"-pyran]-1(2 H)-yl)benzoate

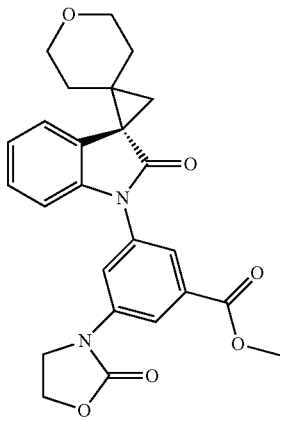

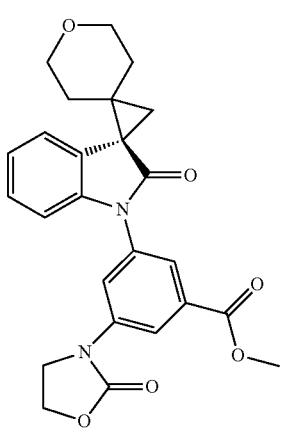

The title compound was prepared in analogy to Example 101 starting from methyl-3-bromo-5-(2-oxooxazolidin-3-yl)benzoate prepared as in Example 101, 4-methylenetetrahydro-2H-pyran, isatin (commercially available) according to Scheme 2. LC/MS m/e calcd. for $C_{25}H_{24}ClN_2O_6$: 448, observed (M+H)$^+$: 449.21 $^1$HNMR (400 MHz, DMSO-d$_6$) δ ppm 1.72-1.81 (m, 1 H) 1.83 (d, J=4.55 Hz, 1 H) 1.92-1.99 (m, 3 H) 2.07-2.15 (m, 1 H) 3.38-3.47 (m, 1 H) 3.51-3.57 (m, 1 H) 3.57-3.66 (m, 2 H) 3.90 (s, 3 H) 4.16 (t, J=7.83 Hz, 2 H) 4.49 (t, J=7.83 Hz, 2 H) 6.90 (d, J=7.83 Hz, 1 H) 7.08 (t, J=7.58 Hz, 1 H) 7.23 (t, J=7.71 Hz, 1 H) 7.29 (d, J=7.58 Hz, 1 H) 7.74 (s, 1 H) 7.93 (s, 1 H) 8.24 (s, 1 H).

Example 139

(1S,2R) and (1R,2S)-1'-(3-fluorobenzyl)-2-(4-fluorophenyl)-2'-oxospiro[cyclopropane-1,3'-indoline]-5'-carboxylic acid

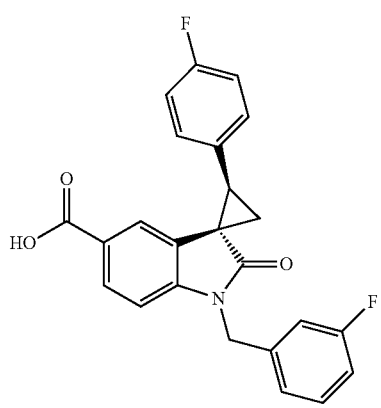

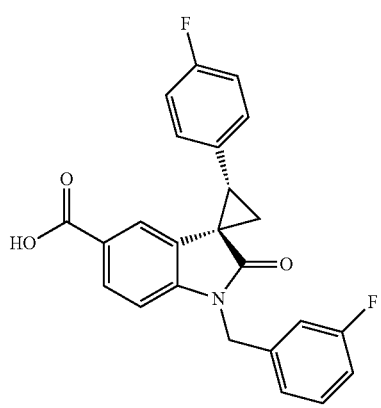

Synthesis of (Z)-methyl-3-(4-fluorobenzylidene)-2-oxoindoline-5-carboxylate

To a solution of methyl-2-oxindole-5-carboxylate (4.764 g) in EtOH (100 mL) was added 4-fluoro-benzaldehyde (4.72 mL) in one portion, followed by piperidine (790 μL). The mixture was refluxed for 3 hours and the yellow precipitate was collected by filtration. The yellow product was used for the next step without further purification.

Synthesis of (1S,2R) and (1R,2S)-methyl-2-(4-fluorophenyl)-2'-oxospiro[cyclopropane-1,3'-indoline]-5'-carboxylate

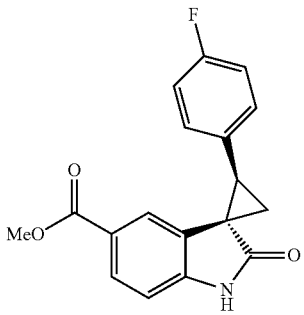

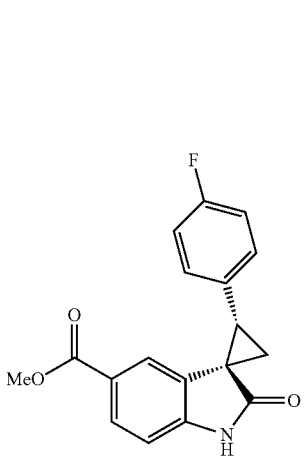

A solution of dimethylsulfoxoniummethylide was prepared under argon from a 60% NaH mineral oil dispersion (88 mg, 2.2 mmol), trimethylsulfoxoniumiodide (2.2 mmol) and DMSO (10 mL). After 20 min, a solution of (Z)-methyl-3-(4-fluorobenzylidene)-2-oxoindoline-5-carboxylate (594 mg, 2 mmol) in THF (5 mL) was added dropwise over 20 minutes. After being stirred for 1 hour at room temperature and another 1 hour at 50° C., the solution was poured into ice-cold water (20 mL) and extracted with ether (3×20 mL). The combined ethereal extracts were washed with brine, dried, and evaporated to an oil, which was separated by flash column chromatography (gradient elution, 15-25% ethyl acetate in petro-leum ether) to give the title product as white solid (317 mg, 51% yield). LC/MS m/e calcd. for $C_{18}H_{14}FNO_3$: 311, observed (M+H)+: 312.6.

Synthesis of (1R,2S) and (1S,2R)-2-(4-fluorophenyl)-2'-oxospiro[cyclopropane-1,3'-indoline]-5'-carboxylic acid

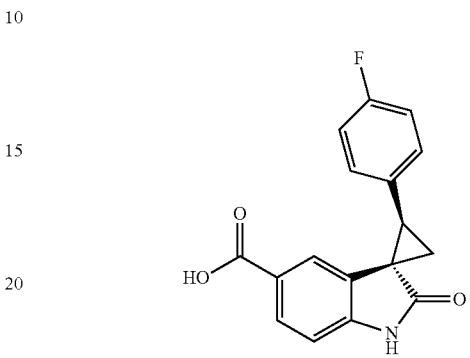

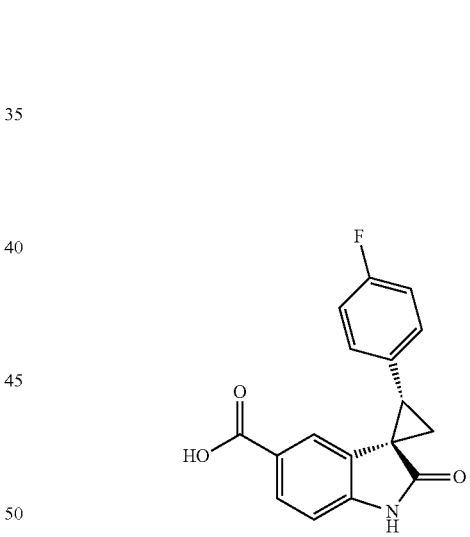

To a solution of (1S,2R) and (1R,2S)-methyl-2-(4-fluorophenyl)-2'-oxospiro [cyclopropane-1,3'-indoline]-5'-carboxylate (80 mg) in methanol (1 mL); water (0.1 mL) was added lithium hydroxide (10 mg) at room temperature. The mixture was stirred for 14 hours at room temperature. HPLC monitored the reaction finished. The solvent was removed under reduced pressure. The residue was dissolved in 2 mL of DMF. Purification by preparative HPLC gave the title compound as white solid (30 mg). LC/MS m/e calcd. for $C_{17}H_{12}FNO_3$ 297, observed (M−H)+: 296. ¹HNMR (400 MHz, DMSO-d$_6$) δppm 1.99 (dd, J=9.09, 4.80 Hz, 1 H) 2.35 (dd, J=8.08, 4.80 Hz, 1 H), 3.11 (t, J=8.46 Hz, 1 H) 6.65 (d, J=1.52 Hz, 1 H) 6.94 (d, J=8.08 Hz, 1 H) 7.14 (t, J=8.84 Hz, 2 H) 7.34 (dd, J=8.34, 5.56 Hz, 2 H) 7.72 (dd, J=8.08, 1.52 Hz, 1 H) 10.97 (s, 1 H) 12.36 (br. s., 1 H).

Synthesis of (1R,2S) and (1S,2R)-methyl-1'-(3-fluorobenzyl)-2-(4-fluorophenyl)-2'-oxospiro[cyclopropane-1,3'-indoline]-5'-carboxylate

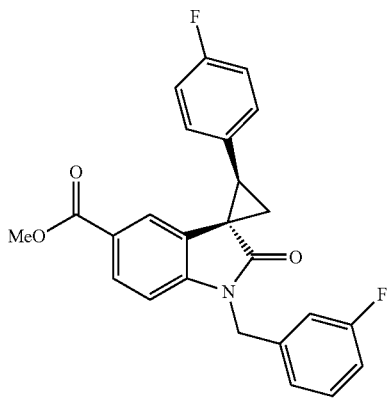

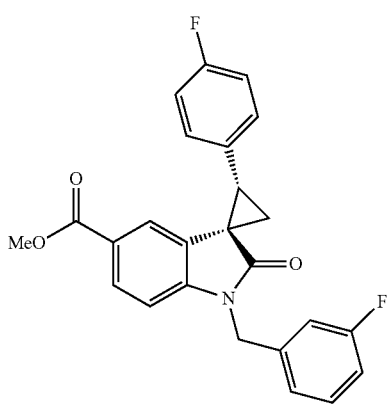

(1S,2R) and (1R,2S)-methyl-2-(4-fluorophenyl)-2'-oxospiro[cyclopropane-1,3'-indoline]-5'-carboxylate (500 mg, 1.61 mmol), 1-bromomethyl-2-fluoro-benzene (456 mg, 2.14 mmol) and Cs$_2$CO$_3$ (785 mg, 4.2 mmol) were mixed in anhydrous DMF and stirred at room temperature for 8 hours. HPLC monitored the reaction finished. The solvent was removed under reduced pressure. The residue was purified by flash column chromatography (gradient elution, 15-25% ethyl acetate in petroleum ether) to give title compound as white solid (405 mg, 60%). LC/MS m/e calcd. for C$_{25}$H$_{19}$F$_2$NO$_3$ 420, observed (M+H)$^+$: 420.5.

Synthesis of (1R,2S) and (1S,2R)-1'-(3-fluorobenzyl)-2-(4-fluorophenyl)-2'-oxospiro[cyclopropane-1,3'-indoline]-5'-carboxylic acid

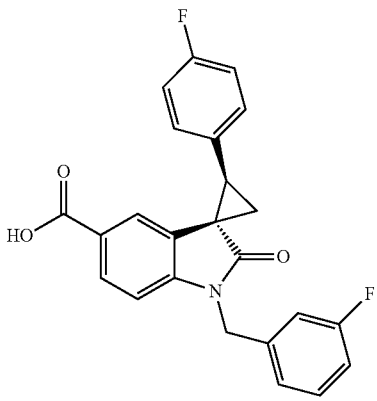

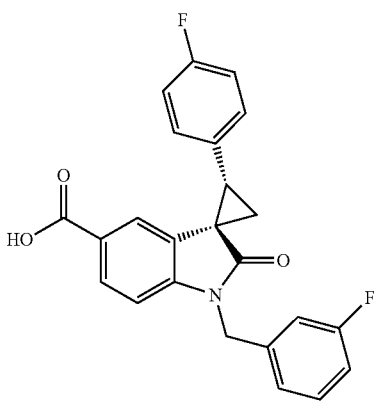

To a solution of (1R,2S) and (1S,2R)-methyl-1'-(3-fluorobenzyl)-2-(4-fluorophenyl)-2'-oxospiro[cyclopropane-1,3'-indoline]-5'-carboxylate (50 mg) in methanol (5 mL), THF (5 mL) and water (1 mL) was added lithium hydroxide (50 mg) at room temperature. The mixture was heated to 60° C. and stirred at 60° C. for 3 hours. HPLC monitored the reaction finished. The solvent was removed under reduced pressure. Purification by preparative HPLC gave the title compound as white powder (10 mg). LC/MS m/e calcd. for C$_{24}$H$_{17}$F$_2$lNO$_3$: 405, observed (M+H)$^+$: 406.2 $^1$H NMR (400 MHz, MeOD) δ ppm 7.83 (dd, J=8.34, 1.52 Hz, 1 H) 7.24-7.38 (m, 5 H) 7.15 (d, J=2.02 Hz, 1 H) 7.18 (d, J=7.83 Hz, 2 H) 7.06 (t, J=8.72

Hz, 2 H) 6.99 (d, J=8.08 Hz, 1 H) 6.75 (d, J=1.52 Hz, 1 H) 5.17 (s, 2 H) 2.24-2.35 (m, 2 H); MS calcd. $C_{24}H_{17}F_2NO_3$ 406, obsd. (ESI$^+$) [(M+H)$^+$] 406.4.

Example 140

(1R,2R) and (1S,2S)-1'-(2-fluorobenzyl)-2-(4-fluorophenyl)-2'-oxospiro[cyclopropane-1,3'-indoline]-5'-carboxylic acid

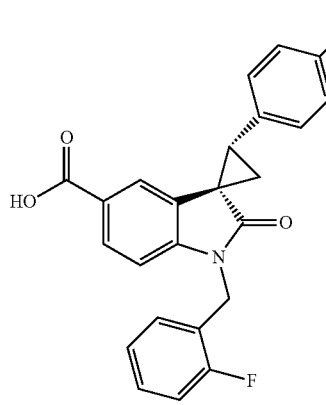

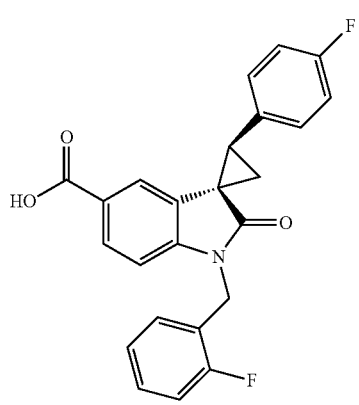

The title compound was prepared in analogy to Example 139 starting from methyl-2-oxoindoline-5-carboxylate, 1-(bromomethyl)-3-fluorobenzene, 4-fluorobenzaldehyde (commercially available). LC/MS m/e calcd. for $C_{24}H_{17}F_{21}NO_3$: 405, observed (M+H)$^+$: 406.2 $^1$HNMR (400 MHz, MeOD) δppm 7.96 (dd, J=8.34, 1.52 Hz, 1 H) 7.80 (d, J=1.52 Hz, 1 H) 7.32 (dd, J=8.46, 5.43 Hz, 3 H) 7.08-7.15 (m, 3 H) 7.02 (t, J=8.97 Hz, 3 H) 5.01 (d, J=16.93 Hz, 2 H) 4.93-5.09 (m, 1 H) 2.45 (dd, J=8.59, 5.05 Hz, 1 H) 2.36 (dd, J=9.09, 4.80 Hz, 1 H).

Example 141

(1R,2R) and (1S,2S)-2-(4-fluorophenyl)-2'-oxospiro[cyclopropane-1,3'-indoline]-5'-carboxylic acid

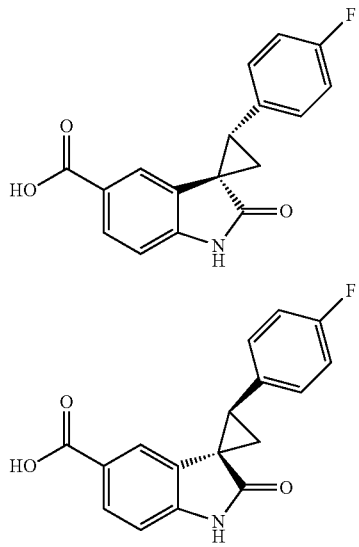

The title compound was prepared in analogy to Example 139 starting from methyl-2-oxoindoline-5-carboxylate, 4-fluorobenzaldehyde (commercially available) LC/MS m/e calcd. for $C_{17}H_{12}FNO_3$: 297, observed (M+H)$^+$: 298.2 $^1$HNMR (400 MHz, DMSO-d$_6$) δppm 2.19-2.31 (m, 2 H) 3.31 (s, 1 H) 6.95 (d, J=8.08 Hz, 1 H) 7.08 (t, J=8.84 Hz, 2 H) 7.33 (dd, J=8.59, 5.56 Hz, 2 H) 7.69 (d, J=1.52 Hz, 1 H) 7.83 (dd, J=8.21, 1.64 Hz, 1 H) 10.72 (s, 1 H).

Example 142

(1R,2S) and (1S,2R)-2-(4-cyanophenyl)-2'-oxospiro[cyclopropane-1,3'-indoline]-5'-carboxylic acid

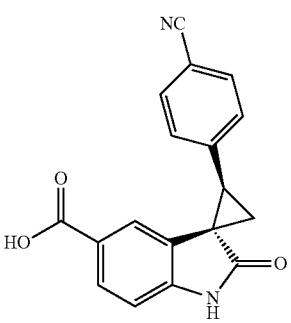

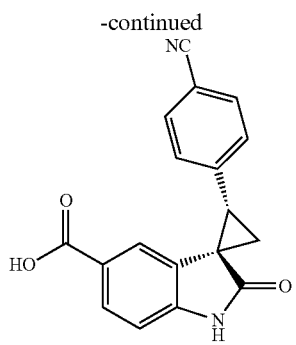

The title compound was prepared in analogy to Example 139 starting from methyl-2-oxoindoline-5-carboxylate, 4-formylbenzonitrile (commercially available). LC/MS m/e calcd. for $C_{18}H_{12}N_2O_3$: 304, observed $(M+H)^+$: 305.2 $^1$HNMR (400 MHz, DMSO-$d_6$) δppm 2.02 (dd, J=8.84, 5.05 Hz, 1 H) 2.49 (s, 1 H) 3.19 (t, J=8.59 Hz, 1H) 6.67 (d, J=1.26 Hz, 1 H) 6.94 (d, J=8.08 Hz, 1 H) 7.55 (d, =8.08 Hz, 2 H) 7.72 (dd, J=8.21, 0.64 Hz, 1H) 7.79 (d, J=8.34 Hz, 2 H) 11.01 (br. s., 1 H) 12.40 (br. s., 1 H).

Example 143

(1R,2R) and (1S,2S)-2-(4-cyanophenyl)-2'-oxospiro [cyclopropane-1,3'-indoline]-5'-carboxylic acid

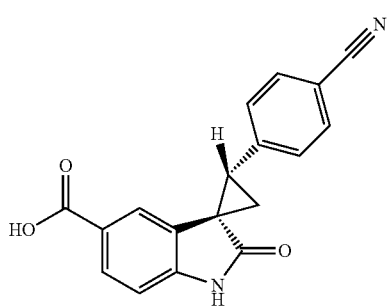

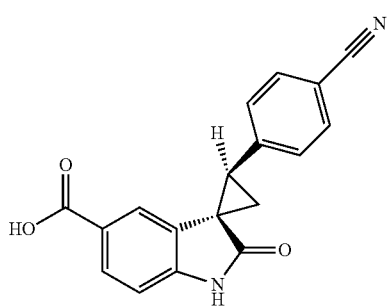

The title compound was prepared in analogy to Example 139 starting from methyl-2-oxoindoline-5-carboxylate, 4-formylbenzonitrile) LC/MS m/e calcd. for $C_{18}H_{12}N_2O_3$: 304, observed $(M+H)^+$: 305.2 $^1$HNMR (400 MHz, DMSO-$d_6$) δppm 2.29-2.37 (m, 2 H) 3.45 (t, J=8.72 Hz, 1 H) 6.96 (d, J=8.08 Hz, 1H) 7.52 (d, J=8.34 Hz, 2 H) 7.73 (dd, J=4.93, 3.41 Hz, 3 H) 7.85 (dd, J=8.21, 1.64 Hz, 1 H) 10.77 (br. s., 1H).

Example 144

(1S,2R) and (1R,2S)-2-(4-fluorophenyl)-2'-oxospiro [cyclopropane-1,3'-indoline]-5'-carboxylic acid

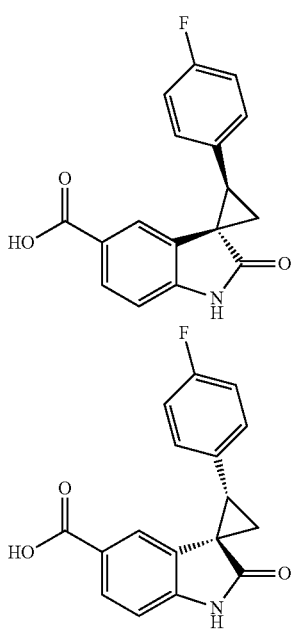

To a solution (1R,2S) and (1S,2R)-methyl-2-(4-fluorophenyl)-2'-oxospiro[cyclopropane-1,3'-indoline]-5'-carboxylate (80 mg) (prepared as in Example 139) in methanol (1 mL) and water (0.1 mL) was added lithium hydroxide (10 mg) at room temperature. The mixture was stirred for 14 hours at room temperature. HPLC monitored the reaction finished. The solvent was removed under reduced pressure. Purification by preparative HPLC gave the title compound as white solid (30 mg). LC/MS m/e calcd. for $C_{17}H_{12}FNO_3$: 297, observed $(M+H)^+$: 298.2 LC/MS m/e calcd for $C_{17}H_{12}FNO_3$297.08, observed $(M-H)^+$: 296.1; $^1$HNMR (400 MHz, DMSO-$d_6$) δ ppm 1.99 (dd, J=9.09, 4.80 Hz, 1 H) 2.35 (dd, J=8.08, 4.80 Hz, 1 H), 3.11 (t, J=8.46 Hz, 1 H) 6.65 (d, J=1.52 Hz, 1 H) 6.94 (d, J=8.08 Hz, 1 H) 7.14 (t, J=8.84 Hz, 2 H) 7.34 (dd, J=8.34, 5.56 Hz, 2 H) 7.72 (dd, J=8.08, 1.52 Hz, 1 H) 10.97 (s, 1 H) 12.36 (br. s., 1 H).

Example 145

Evaluation of AMPK Modulator by Analysis of AMPK and ACC Phosphorylation

This method evaluates endogenous expression and phosphorylation of AMP-activated protein kinase (AMPK) and acetyl CoA carboxylase (ACC) in L6 cell line using Western blot analysis. It is used to determine the potency and efficacy of small molecular AMPK modulators.

L6 cells (ATCC) are cultured and maintained at DMEM (high glucose, Gibco, BRL) with 10% fetal bovine serum (FBS, Hyclone). In an assay, cells are plated at $3 \times 10^6$ per plate in 10 ml on a 10 cm dish and they reach subconfluent of 70-80% within 24 hrs. The cells are serum starved overnight prior to be treated with an AMPK modulator. The compound concentration typically ranges from 0 to 100 μM and treat the cells for 1-4 hrs. Once the incubation is completed, the medium is aspirated and the cell layer is gently rinsed with 2 ml of ice-cold PBS. 500 μl of lysis buffer containing 150 mM NaCl, 5 mM EDTA, 2 mM EGTA, 25 mM NaF, 2 mM $Na_3VO_4$, 1 mg/ml of Pefabloc, 1% Triton X-100, and a Roche Complete Protease Inhibitor Tablet is added and incubated on ice for 10 min. The cell lysate is harvested and subsequently centrifuged at 12,000 rpm for 10 min at 4° C. The supernatant is saved and its protein concentration is determined using Quick Start Bradford protein quantification kit (Bio-Rad). 40 μg is loaded for 7.5% SDS-PAGE analysis and subsequently blotted to PVDF membrane following a standard procedure. The membrane is treated with a blocking buffer (5% nonfat milk) for 1 h at room temperature in agitation. The levels of phospho-AMPK and phospho-ACC are determined using phospho-AMPKα(Thr172)(40 H9) rabbit mAb (Cell Signaling) and phospho-acetyl CoA carboxylase (Ser79) antibody (Cell Signaling) as primary antibodies by incubating the blot at 4° C. overnight. The blots are stripped and re-probed using acetyl CoA carboxylase (C83B10) rabbit mAb (Cell signaling), AMPKα(23A3) rabbit mAb (Cell Signaling), and β-actin antibody (Cell Signaling) to determine the whole protein level of ACC, AMPK and β-actin, respectively. Each protein band in a blot is visualized via ECL Plus Western blotting detection kit (Amersham) and quantified by the scan analysis. The $EC_{50}$ value, defined as an activator concentration that produces half of the maximal protein phosphorylation level, and Emax, defined as the maximal phosphorylation at the infinite activator concentration, are determined semi-quantitatively and recorded.

All the compounds of formula (I) are active in the foregoing AMPK and ACC phosphorylation assay.

Example 146

Scintillation Proximity Assay

Preparation of Enzymes

Recombinant human AMPK α1β1γ1, α2β1γ1 or AMPK a subunit truncations α1 (1-335), α1 (1-394) and α2(1-394) were constructed, expressed and purified as described previously (Pang, T., Zhang, Z. S., Gu, M., Qiu, B. Y., Yu, L. F., Cao, P. R., Shao, W., Su, M. B., Li, J. Y., Nan, F. J., and Li, J. (2008) or purchased from Invitrogen (San Diego, Calif., U.S.A.). Rat liver AMPK heterotrimer enzyme was obtained from Upstate (Billerica, Mass., U.S.A.).

Scintillation Proximity Assay

Before the Scintillation Proximity Assay (SPA) assay, 200 nM recombinant AMPK proteins (α1β1γ1, α2β1γ1, α1(1-335), α1(1-394) or α2(1-394)) were fully phosphorylated as described previously (Pang et al., 2008). SPA reactions were performed in 96-well plates at a final volume of 50 μl containing 20 mM Tris-HCl pH 7.5, 5 mM $MgCl_2$, 1 mM DTT, 2 μM biotin-SAMS, 2 μM ATP, 0.2 μCi/well [γ-$^{33}$P]ATP, and various amount of activator. Reactions were initiated by the addition of 50 nM recombinant AMPK proteins to the reaction solutions and incubated at 30° C. for 2 hr. After that, reactions were terminated by the addition of 40 μl stop solution containing 80 μg streptavidin-coated SPA beads per well, 50 mM EDTA, 0.1% Triton X-100 in PBS, pH 7.5 and incubated for 1 hr. Finally, a 160 μl suspension solution containing 2.4 M CsCl, 50 mM EDTA, and 0.1% Triton X-100 in PBS (pH 7.5) was added to the reaction solution to suspend SPA beads completely. SPA signals were determined with a Wallac MicroBeta plate counter (PerkinElmer) 30 min later for calculation of the amount of product formed. The amount of products formed in 2 hr was plotted against activator concentrations to determine the effective concentration of the activator ($EC_{50}$) required for 50% of maximal enzyme activity.

Compounds as described above have $EC_{50}$ values between 0.5 uM and 50 uM. Preferred compounds have $EC_{50}$ values between 0.5 uM and 10 uM. Particularly preferred compounds have $EC_{50}$ values between 0.5 uM and 1 uM. These results have been obtained by using the foregoing Scintillation Proximity Assay (uM means microMolar).

The $EC_{50}$ values obtained for particular compounds of formula (I) are listed in the table below.

| Examples | $EC_{50}$ (uM) |
|---|---|
| Example 1 | 2.57 |
| Example 2 | 0.96 |
| Example 3 | 2.98 |
| Example 4 | 2.2 |
| Example 5 | 5.3 |
| Example 6 | 7.1 |
| Example 7 | 10.85 |
| Example 8 | 2.77 |
| Example 9 | 1.19 |
| Example 10 | 2.02 |
| Example 11 | 2.04 |
| Example 12 | 2.36 |
| Example 13 | 3.23 |
| Example 14 | 2.03 |
| Example 15 | 2.48 |
| Example 16 | 2.72 |
| Example 17 | 1.63 |
| Example 18 | 1.66 |
| Example 19 | 1.42 |
| Example 20 | 0.90 |
| Example 21 | 2.03 |
| Example 22 | 11.16 |
| Example 23 | 1.66 |
| Example 24 | 5.75 |
| Example 26 | 1.79 |
| Example 60 | 3.5 |
| Example 61 | 8.67 |
| Example 62 | 6.57 |
| Example 63 | 1.54 |
| Example 64 | 1.6 |
| Example 65 | 1.71 |
| Example 66 | 1.07 |
| Example 67 | 2.29 |
| Example 68 | 2.8 |
| Example 70 | 1.54 |
| Example 71 | 3.2 |
| Example 72 | 4.1 |
| Example 73 | 1.65 |
| Example 74 | 8.8 |
| Example 75 | 5.91 |
| Example 76 | 1.09 |
| Example 77 | 2.17 |
| Example 78 | 4.2 |
| Example 79 | 2.6 |
| Example 80 | 1.25 |
| Example 81 | 2.22 |
| Example 82 | 4.03 |
| Example 83 | 2.59 |
| Example 84 | 2.98 |
| Example 85 | 0.95 |
| Example 86 | 1.73 |
| Example 87 | 6.73 |
| Example 88 | 2.56 |
| Example 89 | 1.40 |
| Example 90 | 1.47 |
| Example 91 | 1.55 |
| Example 92 | 0.87 |
| Example 93 | 0.91 |
| Example 94 | 1.50 |
| Example 110 | 1.37 |

-continued

| Examples | EC$_{50}$ (uM) |
|---|---|
| Example 111 | 1.29 |
| Example 112 | 1.27 |
| Example 113 | 1.84 |
| Example 114 | 6.48 |
| Example 115 | 5.14 |
| Example 116 | 4.33 |
| Example 117 | 0.99 |
| Example 124 | 5.4 |
| Example 125 | 1.75 |
| Example 126 | 1.7 |
| Example 127 | 4.5 |
| Example 128 | 2.04 |
| Example 129 | 1.68 |
| Example 130 | 1.10 |
| Example 131 | 3.27 |
| Example 132 | 1.55 |

Example A

A compound of formula (I) can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula (I) can be used in a manner known per se as the active ingredient for the production of capsules of the following composition:

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

The invention claimed is:

1. A compound of formula (I)

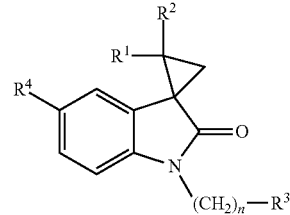

wherein
one of $R^1$ and $R^2$ is selected from hydrogen and alkyl and the other is selected from the group consisting of: halophenyl, alkylsulfonylphenyl, cyanophenyl and trifluoromethylphenyl;
$R^3$ is selected from the group consisting of: pyridinyl, piperidinyl, carboxypyridinyl, tetrahydropyranyl, alkylamino, morpholinyl, morpholinylalkylamino, alkylmorpholinylalkylamino, alkylsulfonylpiperidinyl, alkylpiperazinyl, alkylaminoalkylpiperazinyl, pyridinylpiperazinyl, alkylaminopyrrolidinyl, 1H-imidazolyl, carboxyalkyl-1H-imidazolyl, carboxy-1H-imidazolyl, cycloalkylsulfonylaminocarbonylpyridinyl and substituted phenyl, wherein substituted phenyl is phenyl substituted with one or two substituents independently selected from the group consisting of: alkyl, halogen, hydroxyalkylamino, carboxy, alkylsulfonyl, alkylaminocarbonyl, alkylsulfonylaminocarbonyl, piperidinylcarbonyl, piperazinylcarbonyl, morpholinylcarbonyl, pyridinylpiperazinylcarbonyl, alkylpiperazinylcarbonyl, alkylsulfonylpiperazinylcarbonyl, alkylpyrrolidinylalkylaminocarbonyl, alkyl-1H-pyrazolylaminocarbonyl, oxo-oxazolidinyl, oxo-pyrrolidinyl, oxo-imidazolidinyl, morpholinylalkylaminocarbonyl, alkylaminoalkylpiperazinylcarbonyl, cycloalkyl-1H-pyrazolylaminocarbonyl and cycloalkylsulfonylaminocarbonyl;
$R^4$ is selected from the group consisting of: hydrogen, halogen, carboxy, cyano, trifluoromethyl and alkylsulfonyl; and
n is 0, 1, 2 or 3;
or a pharmaceutically acceptable salt or ester thereof.

2. A compound according to claim 1, wherein one of $R^1$ and $R^2$ is selected from hydrogen and isopropyl and the other is selected from the group consisting of: fluorophenyl, chlorophenyl, cyanophenyl, methylsulfonylphenyl and trifluoromethylphenyl.

3. A compound according to claim 1 wherein $R^3$ is selected from the group consisting of: pyridinyl, carboxypyridinyl, tetrahydropyranyl, dialkylamino, morpholinyl, alkylsulfonylpiperidinyl, alkylpiperazinyl, dialkylaminoalkylpiperazinyl, dialkylaminopyrrolidinyl, carboxyalkyl-1H-imidazolyl, carboxy-1H-imidazolyl or substituted phenyl, wherein substituted phenyl is phenyl substituted with one or two substituents independently selected from alkyl, halogen, carboxy, alkylsulfonyl, alkylaminocarbonyl, alkylsulfonylaminocarbonyl, piperidinylcarbonyl, piperazinylcarbonyl, morpholinylcarbonyl, pyridinylpiperazinylcarbonyl, alkylpiperazinylcarbonyl, alkylsulfonylpiperazinylcarbonyl, alkylpyrrolidinylalkylaminocarbonyl, alkyl-1H-pyrazolylaminocarbonyl, oxo-oxazolidinyl, oxo-pyrrolidinyl and oxo-imidazolidinyl.

4. A compound according to claim 1, wherein $R^3$ is selected from the group consisting of: carboxypyridinyl, carboxyalkyl-1H-imidazolyl, carboxyphenyl and phenyl substituted with carboxy and oxo-oxazolidinyl.

5. A compound according to claim 1, wherein $R^4$ is selected from the group consisting of: hydrogen, halogen and carboxy.

6. A compound according to claim 1, wherein $R^4$ is selected from the group consisting of: hydrogen, fluoro, chloro and carboxy.

7. A compound according to claim 1, wherein n is 0 or 1.

8. A pharmaceutical composition comprising a compound according to claim 1 and a therapeutically inert carrier.

9. A compound according to claim 1 selected from the group consisting of:
- (1R,2S)-3-((2-(4-chlorophenyl)-2'-oxospiro[cyclopropane-1,3'-indoline]-1'-yl)methyl)benzoic acid;
- (1S,2R)-3-((2-(4-chlorophenyl)-2'-oxospiro[cyclopropane-1,3'-indoline]-1'-yl)methyl)benzoic acid;
- (1R,2R)-3-((2-(4-chlorophenyl)-2'-oxospiro[cyclopropane-1,3'-indoline]-1'-yl)methyl)benzoic acid;
- (1S,2S)-3-((2-(4-chlorophenyl)-2'-oxospiro[cyclopropane-1,3'-indoline]-1'-yl)methyl)benzoic acid;
- (1S,2R)-3-((2-(3-chlorophenyl)-2'-oxospiro[cyclopropane-1,3'-indoline]-1'-yl)methyl)benzoic acid;
- (1R,2S)-3-((2-(3-chlorophenyl)-2'-oxospiro[cyclopropane-1,3'-indoline]-1'-yl)methyl)benzoic acid;
- (1S,2R)-2-chloro-5-((2-(4-chlorophenyl)-2'-oxospiro[cyclopropane-1,3'-indoline]-1'-yl)methyl)benzoic acid;
- (1R,2S)-2-chloro-5-((2-(4-chlorophenyl)-2'-oxospiro[cyclopropane-1,3'-indoline]-1'-yl)methyl)benzoic acid;
- (1S,2R)-((5'-chloro-2-(4-chlorophenyl)-2'-oxospiro[cyclopropane-1,3'-indoline]-1'-yl)methyl)benzoic acid;
- (1R,2S)-((5'-chloro-2-(4-chlorophenyl)-2'-oxospiro[cyclopropane-1,3'-indoline]-1'-yl)methyl)benzoic acid;
- (1R,2R)-3-((5'-chloro-2-(4-chlorophenyl)-2'-oxospiro[cyclopropane-1,3'-indoline]-1'-yl)methyl)benzoic acid;
- (1S,2S)-3-((5'-chloro-2-(4-chlorophenyl)-2'-oxospiro[cyclopropane-1,3'-indoline]-1'-yl)methyl)benzoic acid;
- (1R,2R)-3-((5'-bromo-2-(4-chlorophenyl)-2'-oxospiro[cyclopropane-1,3'-indoline]-1'-yl)methyl)benzoic acid;
- (1S,2S)-3-((5'-bromo-2-(4-chlorophenyl)-2'-oxospiro[cyclopropane-1,3'-indoline]-1'-yl)methyl)benzoic acid;
- (1S,2R)-3-((5'-bromo-2-(4-chlorophenyl)-2'-oxospiro[cyclopropane-1,3'-indoline]-1'-yl)methyl)benzoic acid; and
- (1R,2S)-3-((5'-bromo-2-(4-chlorophenyl)-2'-oxospiro[cyclopropane-1,3'-indoline]-1'-yl)methyl)benzoic acid.

10. A compound according to claim 1 selected from the group consisting of:
- (1S,2R)-2-chloro-5-((2-(4-chlorophenyl)-2'-oxospiro[cyclopropane-1,3'-indoline]-1'-yl)methyl)benzoic acid;
- (1R,2S)-2-chloro-5-((2-(4-chlorophenyl)-2'-oxospiro[cyclopropane-1,3'-indoline]-1'-yl)methyl)benzoic acid;
- (1S,2R)-((5'-chloro-2-(4-chlorophenyl)-2'-oxospiro[cyclopropane-1,3'-indoline]-1'-yl)methyl)benzoic acid;
- (1R,2S)-((5'-chloro-2-(4-chlorophenyl)-2'-oxospiro[cyclopropane-1,3'-indoline]-1'-yl)methyl)benzoic acid;
- (1R,2R)-3-((5'-chloro-2-(4-chlorophenyl)-2'-oxospiro[cyclopropane-1,3'-indoline]-1'-yl)methyl)benzoic acid;
- (1S,2S)-3-((5'-chloro-2-(4-chlorophenyl)-2'-oxospiro[cyclopropane-1,3'-indoline]-1'-yl)methyl)benzoic acid;
- (1R,2R)-3-((5'-bromo-2-(4-chlorophenyl)-2'-oxospiro[cyclopropane-1,3'-indoline]-1'-yl)methyl)benzoic acid;
- (1S,2S)-3-((5'-bromo-2-(4-chlorophenyl)-2'-oxospiro[cyclopropane-1,3'-indoline]-1'-yl)methyl)benzoic acid;
- (1S,2R)-3-((5'-bromo-2-(4-chlorophenyl)-2'-oxospiro[cyclopropane-1,3'-indoline]-1'-yl)methyl)benzoic acid;
- (1R,2S)-3-((5'-bromo-2-(4-chlorophenyl)-2'-oxospiro[cyclopropane-1,3'-indoline]-1'-yl)methyl)benzoic acid;
- (1S,2R)-3-((2-(4-chlorophenyl)-5'-fluoro-2'-oxospiro[cyclopropane-1,3'-indoline]-1'-yl)methyl)benzoic acid;
- (1R,2S)-3-((2-(4-chlorophenyl)-5'-fluoro-2'-oxospiro[cyclopropane-1,3'-indoline]-1'-yl)methyl)benzoic acid;
- (1S,2S)-3-((2-(4-chlorophenyl)-5'-fluoro-2'-oxospiro[cyclopropane-1,3'-indoline]-1'-yl)methyl)benzoic acid;
- (1R,2R)-3-((2-(4-chlorophenyl)-5'-fluoro-2'-oxospiro[cyclopropane-1,3'-indoline]-1'-yl)methyl)benzoic acid;
- (1S,2S)-3-((2-(4-chlorophenyl)-2-isopropyl-2'-oxospiro[cyclopropane-1,3'-indoline]-1'-yl)methyl)benzoic acid; and
- (1R,2R)-3-((2-(4-chlorophenyl)-2-isopropyl-2'-oxospiro[cyclopropane-1,3'-indoline]-1'-yl)methyl)benzoic acid.

11. A compound according to claim 1 selected from the group consisting of:
- (+)-3-((2-(4-chlorophenyl)-2-isopropyl-2'-oxospiro[(trans)-cyclopropane-1,3'-indoline]-1'-yl)methyl)benzoic acid;
- (−)-3-((2-(4-chlorophenyl)-2-isopropyl-2'-oxospiro[(trans)-cyclopropane-1,3'-indoline]-1'-yl)methyl)benzoic acid;
- (1S,2S)-3-((2-(4-chlorophenyl)-2-isopropyl-2'-oxospiro[cyclopropane-1,3'-indoline]-1'-yl)methyl)benzoic acid;
- (1R,2R)-3-((2-(4-chlorophenyl)-2-isopropyl-2'-oxospiro[cyclopropane-1,3'-indoline]-1'-yl)methyl)benzoic acid;
- (+)-3-((2-(4-chlorophenyl)-5'-fluoro-2-isopropyl-2'-oxospiro[(trans)-cyclopropane-1,3'-indoline]-1'-yl)methyl)benzoic acid;
- (−)-3-((2-(4-chlorophenyl)-5'-fluoro-2-isopropyl-2'-oxospiro[(trans)-cyclopropane-1,3'-indoline]-1'-yl)methyl)benzoic acid;
- (1S,2S)-3-((2-(4-chlorophenyl)-5'-fluoro-2-isopropyl-2'-oxospiro[cyclopropane-1,3'-indoline]-1'-yl)methyl)benzoic acid;
- (1R,2R)-3-((2-(4-chlorophenyl)-5'-fluoro-2-isopropyl-2'-oxospiro[cyclopropane-1,3'-indoline]-1'-yl)methyl)benzoic acid;
- (1S,2S)-3-((2-(3-chlorophenyl)-2-isopropyl-2'-oxospiro[cyclopropane-1,3'-indoline]-1'-yl)methyl)benzoic acid;
- (1R,2R)-3-((2-(3-chlorophenyl)-2-isopropyl-2'-oxospiro[cyclopropane-1,3'-indoline]-1'-yl)methyl)benzoic acid;
- (+)-3-((2-(4-chlorophenyl)-2-isopropyl-2'-oxospiro[(trans)-cyclopropane-1,3'-indoline]-1'-yl)methyl)benzoic acid;
- (−)-3-((2-(4-chlorophenyl)-2-isopropyl-2'-oxospiro[(trans)-cyclopropane-1,3'-indoline]-1'-yl)methyl)benzoic acid;
- (1R,2S)-3-((2-(4-chlorophenyl)-2-methyl-2'-oxospiro[cyclopropane-1,3'-indoline]-1'-yl)methyl)benzoic acid;
- (1S,2R)-3-((2-(4-chlorophenyl)-2-methyl-2'-oxospiro[cyclopropane-1,3'-indoline]-1'-yl)methyl)benzoic acid;
- (+)-3-((2-(4-chlorophenyl)-2-methyl-2'-oxospiro[(trans)-cyclopropane-1,3'-indoline]-1'-yl)methyl)benzoic acid; and
- (−)-3-((2-(4-chlorophenyl)-2-methyl-2'-oxospiro[(trans)-cyclopropane-1,3'-indoline]-1'-yl)methyl)benzoic acid.

12. A compound according to claim 1 selected from the group consisting of:
- (1R,2R)-3-((2-(4-chlorophenyl)-2-methyl-2'-oxospiro[cyclopropane-1,3'-indoline]-1'-yl)methyl)benzoic acid;
- (1S,2S)-3-((2-(4-chlorophenyl)-2-methyl-2'-oxospiro[cyclopropane-1,3'-indoline]-1'-yl)methyl)benzoic acid;
- (+)-3-((2-(4-chlorophenyl)-2-methyl-2'-oxospiro[(cis)-cyclopropane-1,3'-indoline]-1'-yl)methyl)benzoic acid;
- (−)-3-((2-(4-chlorophenyl)-2-methyl-2'-oxospiro[(cis)-cyclopropane-1,3'-indoline]-1'-yl)methyl)benzoic acid;
- (1R,2S)-3-((2-(4-chlorophenyl)-5'-fluoro-2-methyl-2'-oxospiro[cyclopropane-1,3'-indoline]-1'-yl)methyl)benzoic acid;
- (1S,2R)-3-((2-(4-chlorophenyl)-5'-fluoro-2-methyl-2'-oxospiro[cyclopropane-1,3'-indoline]-1'-yl)methyl)benzoic acid;
- (−)-3-((2-(4-chlorophenyl)-5'-fluoro-2-methyl-2'-oxospiro[(trans)-cyclopropane-1,3'-indoline]-1'-yl)methyl)benzoic acid;
- (+)-3-((2-(4-chlorophenyl)-5'-fluoro-2-methyl-2'-oxospiro[(trans)-cyclopropane-1,3'-indoline]-1'-yl)methyl)benzoic acid;
- (1S,2R)-2-(4-chlorophenyl)-1'-(3-(piperidine-1-carbonyl)benzyl)spiro[cyclopropane-1,3'-indolin]-2'-one;
- (1R,2S)-2-(4-chlorophenyl)-1'-(3-(piperidine-1-carbonyl)benzyl)spiro[cyclopropane-1,3'-indolin]-2'-one;
- (1R,2S)-3-((2-(4-chlorophenyl)-2'-oxospiro[cyclopropane-1,3'-indoline]-1'-yl)methyl)-N-isopropylbenzamide;
- (1S,2R)-3-((2-(4-chlorophenyl)-2'-oxospiro[cyclopropane-1,3'-indoline]-1'-yl)methyl)-N-isopropylbenzamide;
- (1S,2R)-2-(4-chlorophenyl)-1'-(3-(piperazine-1-carbonyl)benzyl)spiro[cyclopropane-1,3'-indolin]-2'-one;
- (1R,2S)-2-(4-chlorophenyl)-1'-(3-(piperazine-1-carbonyl)benzyl)spiro[cyclopropane-1,3'-indolin]-2'-one;
- (1R,2S)-2-(4-chlorophenyl)-1'-(3-(morpholine-4-carbonyl)benzyl)spiro[cyclopropane-1,3'-indolin]-2'-one; and
- (1S,2R)-2-(4-chlorophenyl)-1'-(3-(morpholine-4-carbonyl)benzyl)spiro[cyclopropane-1,3'-indolin]-2'-one.

13. A compound according to claim 1 selected from the group consisting of:
- (1R,2S)-2-(4-chlorophenyl)-1'-(3-(4-(pyridin-4-yl)piperazine-1-carbonyl)benzyl)spiro[cyclopropane-1,3'-indolin]-2'-one;
- (1S,2R)-2-(4-chlorophenyl)-1'-(3-(4-(pyridin-4-yl)piperazine-1-carbonyl)benzyl)spiro[cyclopropane-1,3'-indolin]-2'-one;
- (1S,2R)-2-(4-chlorophenyl)-1'-(3-(4-isopropylpiperazine-1-carbonyl)benzyl)spiro[cyclopropane-1,3'-indolin]-2'-one;
- (1R,2S)-2-(4-chlorophenyl)-1'-(3-(4-isopropylpiperazine-1-carbonyl)benzyl)spiro[cyclopropane-1,3'-indolin]-2'-one;
- 3-(((1S,2R)-2-(4-chlorophenyl)-2'-oxospiro[cyclopropane-1,3'-indoline]-1'-yl)methyl)-N-(2-((S)-1-methylpyrrolidin-2-yl)ethyl)benzamide
- 3-(((1R,2S)-2-(4-chlorophenyl)-2'-oxospiro[cyclopropane-1,3'-indoline]-1'-yl)methyl)-N-(2-((S)-1-methylpyrrolidin-2-yl)ethyl)benzamide;
- (1R,2S)-3-((2-(4-chlorophenyl)-2'-oxospiro[cyclopropane-1,3'-indoline]-1'-yl)methyl)-N-(3-methyl-1H-pyrazol-5-yl)benzamide;
- (1S,2R)-3-((2-(4-chlorophenyl)-2'-oxospiro[cyclopropane-1,3'-indoline]-1'-yl)methyl)-N-(3-methyl-1H-pyrazol-5-yl)benzamide;
- (1S,2R)-6-((2-(4-chlorophenyl)-2'-oxospiro[cyclopropane-1,3'-indoline]-1'-yl)methyl)picolinic acid;
- (1R,2S)-6-((2-(4-chlorophenyl)-2'-oxospiro[cyclopropane-1,3'-indoline]-1'-yl)methyl)picolinic acid;
- (1S,2R)-2-(4-chlorophenyl)-1'-((tetrahydro-2H-pyran-4-yl)methyl)spiro[cyclopropane-1,3'-indolin]-2'-one;
- (1R,2S)-2-(4-chlorophenyl)-1'-((tetrahydro-2H-pyran-4-yl)methyl)spiro[cyclopropane-1,3'-indolin]-2'-one;
- (1S,2R)-2-(4-chlorophenyl)-1'-(2-(diethylamino)ethyl)spiro[cyclopropane-1,3'-indolin]-2'-one;
- (1R,2S)-2-(4-chlorophenyl)-1'-(2-(diethylamino)ethyl)spiro[cyclopropane-1,3'-indolin]-2'-one;
- (1S,2R)-2-(4-chlorophenyl)-1'-(2-morpholinoethyl)spiro[cyclopropane-1,3'-indolin]-2'-one; and
- (1R,2S)-2-(4-chlorophenyl)-1'-(2-morpholinoethyl)spiro[cyclopropane-1,3'-indolin]-2'-one.

14. A compound according to claim 1 selected from the group consisting of:
- (1S,2R)-2-(4-chlorophenyl)-1'-((1-(methylsulfonyl)piperidin-4-yl)methyl)spiro[cyclopropane-1,3'-indolin]-2'-one;
- (1R,2S)-2-(4-chlorophenyl)-1'-((1-(methylsulfonyl)piperidin-4-yl)methyl)spiro[cyclopropane-1,3'-indolin]-2'-one;
- (1S,2R)-2-(4-chlorophenyl)-1'-(2-(4-isopropylpiperazin-1-yl)ethyl)spiro[cyclopropane-1,3'-indolin]-2'-one;
- (1R,2S)-2-(4-chlorophenyl)-1'-(2-(4-isopropylpiperazin-1-yl)ethyl)spiro[cyclopropane-1,3'-indolin]-2'-one;
- (1S,2R)-2-(4-chlorophenyl)-1'-(2-(4-(2-(dimethylamino)ethyl)piperazin-1-yl)ethyl)spiro[cyclopropane-1,3'-indolin]-2'-one;
- (1R,2S)-2-(4-chlorophenyl)-1'-(2-(4-(2-(dimethylamino)ethyl)piperazin-1-yl)ethyl)spiro[cyclopropane-1,3'-indolin]-2'-one;
- (1S,2R)-2-(4-chlorophenyl)-1'-(2-((S)-3-(dimethylamino)pyrrolidin-1-yl) ethyl)spiro[cyclopropane-1,3'-indolin]-2'-one;
- (1R,2S)-2-(4-chlorophenyl)-1'-(2-((S)-3-(dimethylamino)pyrrolidin-1-yl) ethyl)spiro[cyclopropane-1,3'-indolin]-2'-one;
- (1S,2R)-2-(4-chlorophenyl)-1'-(2-((R)-3-(dimethylamino)pyrrolidin-1-yl) ethyl)spiro[cyclopropane-1,3'-indolin]-2'-one;
- (1R,2S)-2-(4-chlorophenyl)-1'-(2-((R)-3-(dimethylamino)pyrrolidin-1-yl) ethyl)spiro[cyclopropane-1,3'-indolin]-2'-one;
- (1R,2S)-2-(4-chlorophenyl)-1'-(pyridin-4-ylmethyl)spiro[cyclopropane-1,3'-indolin]-2'-one;
- (1S,2R)-2-(4-chlorophenyl)-1'-(pyridin-4-ylmethyl)spiro[cyclopropane-1,3'-indolin]-2'-one;
- (1S,2R)-2-(4-chlorophenyl)-1'-(pyridin-3-ylmethyl)spiro[cyclopropane-1,3'-indolin]-2'-one;
- (2R,1S)-2-(4-chlorophenyl)-1'-(pyridin-3-ylmethyl)spiro[cyclopropane-1,3'-indolin]-2'-one;
- (1S,2R)-2-(4-(2-(4-chlorophenyl)-2'-oxospiro[cyclopropane-1,3'-indoline]-1'-yl)-1H-imidazol-1-yl)acetic acid; and
- (1R,2S)-2-(4-(2-(4-chlorophenyl)-2'-oxospiro[cyclopropane-1,3'-indoline]-1'-yl)-1H-imidazol-1-yl)acetic acid.

15. A compound according to claim 1 selected from the group consisting of:
- (1S,2R)-1-(2-(2-(4-chlorophenyl)-2'-oxospiro[cyclopropane-1,3'-indoline]-1'-yl) ethyl)-1H-imidazole-4-carboxylic acid;
- (1R,2S)-1-(2-(2-(4-chlorophenyl)-2'-oxospiro[cyclopropane-1,3'-indoline]-1'-yl) ethyl)-1H-imidazole-4-carboxylic acid;
- (1S,2S)-1-(2-(2-(4-chlorophenyl)-2'-oxospiro[cyclopropane-1,3'-indoline]-1'-yl) ethyl)-1H-imidazole-4-carboxylic acid;
- (1R,2R)-1-(2-(2-(4-chlorophenyl)-2'-oxospiro[cyclopropane-1,3'-indoline]-1'-yl) ethyl)-1H-imidazole-4-carboxylic acid;
- (1S,2R)-3-(2-(4-chlorophenyl)-2'-oxospiro[cyclopropane-1,3'-indoline]-1'-yl)benzoic acid;
- (1R,2S)-3-(2-(4-chlorophenyl)-2'-oxospiro[cyclopropane-1,3'-indoline]-1'-yl)benzoic acid;
- (1S,2S)-3-(2-(4-chlorophenyl)-2'-oxospiro[cyclopropane-1,3'-indoline]-1'-yl)benzoic acid;
- (1R,2R)-3-(-2-(4-chlorophenyl)-2'-oxospiro[cyclopropane-1,3'-indoline]-1'-yl)benzoic acid;
- (1S,2S)-2-(4-chlorophenyl)-1'-(3-(morpholine-4-carbonyl)phenyl)spiro[cyclopropane-1,3'-indolin]-2'-one;
- (1R,2R)-2-(4-chlorophenyl)-1'-(3-(morpholine-4-carbonyl)phenyl)spiro[cyclopropane-1,3'-indolin]-2'-one;
- (1S,2S)-2-(4-chlorophenyl)-1'-(3-(4-methylpiperazine-1-carbonyl)phenyl)spiro[cyclopropane-1,3'-indolin]-2'-one;
- (1R,2R)-2-(4-chlorophenyl)-1'-(3-(4-methylpiperazine-1-carbonyl)phenyl)spiro[cyclopropane-1,3'-indolin]-2'-one;
- (1S,2S)-2-(4-chlorophenyl)-1'-(3-(4-(methylsulfonyl)piperazine-1-carbonyl)phenyl)spiro[cyclopropane-1,3'-indolin]-2'-one;
- (1R,2R)-2-(4-chlorophenyl)-1'-(3-(4-(methylsulfonyl)piperazine-1-carbonyl)phenyl)spiro[cyclopropane-1,3'-indolin]-2'-one;
- (1R,2S)-2-(4-chlorophenyl)-1'-(3-(morpholine-4-carbonyl)phenyl)spiro[cyclopropane-1,3'-indolin]-2'-one; and
- (1S,2R)-2-(4-chlorophenyl)-1'-(3-(morpholine-4-carbonyl)phenyl)spiro[cyclopropane-1,3'-indolin]-2'-one.

16. A compound according to claim 1 selected from the group consisting of:
- (1S,2R)-2-(4-chlorophenyl)-1'-(3-(4-methylpiperazine-1-carbonyl)phenyl)spiro[cyclopropane-1,3'-indolin]-2'-one;
- (1R,2S)-2-(4-chlorophenyl)-1'-(3-(4-methylpiperazine-1-carbonyl)phenyl)spiro[cyclopropane-1,3'-indolin]-2'-one;
- (1R,2S)-2-(4-chlorophenyl)-1'-(3-(4-(methylsulfonyl)piperazine-1-carbonyl)phenyl)spiro[cyclopropane-1,3'-indolin]-2'-one;
- (1S,2R)-2-(4-chlorophenyl)-1'-(3-(4-(methylsulfonyl)piperazine-1-carbonyl) phenyl)spiro[cyclopropane-1,3'-indolin]-2'-one;
- (1R,2R)-3-(2-(4-chlorophenyl)-2'-oxospiro[cyclopropane-1,3'-indoline]-1'-yl)-N-(methylsulfonyl)benzamide;
- (1S,2S)-3-(2-(4-chlorophenyl)-2'-oxospiro[cyclopropane-1,3'-indoline]-1'-yl)-N-(methylsulfonyl)benzamide;
- (1S,2S)-3-(2-(4-chlorophenyl)-2'-oxospiro[cyclopropane-1,3'-indoline]-1'-yl)-5-(2-oxooxazolidin-3-yl)benzoic acid;
- (1R,2R)-3-(2-(4-chlorophenyl)-2'-oxospiro[cyclopropane-1,3'-indoline]-1'-yl)-5-(2-oxooxazolidin-3-yl)benzoic acid;
- (1S,2S)-3-(2-(4-chlorophenyl)-2'-oxospiro[cyclopropane-1,3'-indoline]-1'-yl)-5-(methylsulfonyl)benzoic acid;
- (1R,2R)-3-(2-(4-chlorophenyl)-2'-oxospiro[cyclopropane-1,3'-indoline]-1'-yl)-5-(methylsulfonyl)benzoic acid;
- (1S,2S)-3-(2-(4-chlorophenyl)-2'-oxospiro[cyclopropane-1,3'-indoline]-1'-yl)-5-(2-oxopyrrolidin-1-yl)benzoic acid;
- (1R,2R)-3-(2-(4-chlorophenyl)-2'-oxospiro[cyclopropane-1,3'-indoline]-1'-yl)-5-(2-oxopyrrolidin-1-yl)benzoic acid;
- (1R,2R)-3-(2-(4-chlorophenyl)-5'-fluoro-2-isopropyl-2'-oxospiro[cyclopropane-1,3'-indoline]-1'-yl)-5-(2-oxooxazolidin-3-yl)benzoic acid;
- (1S,2S)-3-(2-(4-chlorophenyl)-5'-fluoro-2-isopropyl-2'-oxospiro[cyclopropane-1,3'-indoline]-1'-yl)-5-(2-oxooxazolidin-3-yl)benzoic acid;
- (1R,2S)-3-(2-(4-chlorophenyl)-5'-fluoro-2-isopropyl-2'-oxospiro[cyclopropane-1,3'-indoline]-1'-yl)-5-(2-oxooxazolidin-3-yl)benzoic acid; and
- (1S,2R)-3-(2-(4-chlorophenyl)-5'-fluoro-2-isopropyl-2'-oxospiro[cyclopropane-1,3'-indoline]-1'-yl)-5-(2-oxooxazolidin-3-yl)benzoic acid.

17. A compound according to claim 1 selected from the group consisting of:
- (1R,2R)-3-(2-(4-chlorophenyl)-2-isopropyl-2'-oxospiro[cyclopropane-1,3'-indoline]-1'-yl)-5-(2-oxooxazolidin-3-yl)benzoic acid;
- (1S,2S)-3-(2-(4-chlorophenyl)-2-isopropyl-2'-oxospiro[cyclopropane-1,3'-indoline]-1'-yl)-5-(2-oxooxazolidin-3-yl)benzoic acid;
- (1S,2S)-3-(2-(4-chlorophenyl)-2'-oxospiro[cyclopropane-1,3'-indoline]-1'-yl)-5-(2-oxoimidazolidin-1-yl)benzoic acid;
- (1R,2R)-3-(2-(4-chlorophenyl)-2'-oxospiro[cyclopropane-1,3'-indoline]-1'-yl)-5-(2-oxoimidazolidin-1-yl)benzoic acid;
- (1S,2R)-2-chloro-5-((2-(4-chlorophenyl)-5'-fluoro-2'-oxospiro[cyclopropane-1,3'-indoline]-1'-yl)methyl)benzoic acid;
- (1R,2S)-2-chloro-5-((2-(4-chlorophenyl)-5'-fluoro-2'-oxospiro[cyclopropane-1,3'-indoline]-1'-yl)methyl)benzoic acid;
- (1R,2S)-3-((2-(3-chloro-4-fluorophenyl)-2'-oxospiro[cyclopropane-1,3'-indoline]-1'-yl)methyl)benzoic acid;
- (1S,2R)-3-((2-(3-chloro-4-fluorophenyl)-2'-oxospiro[cyclopropane-1,3'-indoline]-1'-yl)methyl)benzoic acid;
- (1R,2S)-3-((2-(4-chlorophenyl)-2'-oxospiro[cyclopropane-1,3'-indoline]-1'-yl)methyl)-N-methylbenzamide;
- (1S,2R)-3-((2-(4-chlorophenyl)-2'-oxospiro[cyclopropane-1,3'-indoline]-1'-yl)methyl)-N-methylbenzamide;
- (1S,2R)-3-((2-(4-chlorophenyl)-2'-oxospiro[cyclopropane-1,3'-indoline]-1'-yl)methyl)-N,N-dimethylbenzamide;
- (1R,2S)-3-((2-(4-chlorophenyl)-2'-oxospiro[cyclopropane-1,3'-indoline]-1'-yl)methyl)-N,N-dimethylbenzamide;
- (1R,2S)-3-((2-(4-chlorophenyl)-2'-oxospiro[cyclopropane-1,3'-indoline]-1'-yl)methyl)-N-(3-morpholinopropyl)benzamide;
- (1S,2R)-3-((2-(4-chlorophenyl)-2'-oxospiro[cyclopropane-1,3'-indoline]-1'-yl)methyl)-N-(3-morpholinopropyl)benzamide;

(1R,2S)-2-(4-chlorophenyl)-1'-(3-(4-(2-(dimethylamino)ethyl)piperazine-1-carbonyl)benzyl)spiro[cyclopropane-1,3'-indolin]-2'-one; and (1S,2R)-2-(4-chlorophenyl)-1'-(3-(4-(2-(dimethylamino)ethyl)piperazine-1-carbonyl)benzyl)spiro[cyclopropane-1,3'-indolin]-2'-one.

18. A compound according to claim 1 selected from the group consisting of:
- (1R,2S)-3-((2-(4-chlorophenyl)-2'-oxospiro[cyclopropane-1,3'-indoline]-1'-yl)methyl)-N-(2-morpholinoethyl)benzamide;
- (1S,2R)-3-((2-(4-chlorophenyl)-2'-oxospiro[cyclopropane-1,3'-indoline]-1'-yl)methyl)-N-(2-morpholinoethyl)benzamide;
- (1R,2S)-2-(4-chlorophenyl)-1'-(3-(4-(methylsulfonyl)piperazine-1-carbonyl)benzyl)spiro[cyclopropane-1,3'-indolin]-2'-one;
- (1S,2R)-2-(4-chlorophenyl)-1'-(3-(4-(methylsulfonyl)piperazine-1-carbonyl)benzyl)spiro[cyclopropane-1,3'-indolin]-2'-one;
- (1S,2R)-3-((2-(4-chlorophenyl)-2'-oxospiro[cyclopropane-1,3'-indoline]-1'-yl)methyl)-N-(3-cyclopropyl-1H-pyrazol-5-yl)benzamide;
- (1R,2S)-3-((2-(4-chlorophenyl)-2'-oxospiro[cyclopropane-1,3'-indoline]-1'-yl)methyl)-N-(3-cyclopropyl-1H-pyrazol-5-yl)benzamide;
- (1R,2S)-3-((2-(4-chlorophenyl)-2'-oxospiro[cyclopropane-1,3'-indoline]-1'-yl)methyl)-N-(5-cyclopropyl-1H-pyrazol-3-yl)benzamide;
- (1R,2S)-3-((2-(4-chlorophenyl)-2'-oxospiro[cyclopropane-1,3'-indoline]-1'-yl)methyl)-N-(5-cyclopropyl-1H-pyrazol-3-yl)benzamide;
- (1R,2S)-3-((2-(4-chlorophenyl)-2'-oxospiro[cyclopropane-1,3'-indoline]-1'-yl)methyl)-N-(methylsulfonyl)benzamide;
- (1S,2R)-3-((2-(4-chlorophenyl)-2'-oxospiro[cyclopropane-1,3'-indoline]-1'-yl)methyl)-N-(methylsulfonyl)benzamide;
- (1S,2R)-2-(4-chlorophenyl)-1'-(piperidin-4-ylmethyl)spiro[cyclopropane-1,3'-indolin]-2'-one;
- (1R,2S)-2-(4-chlorophenyl)-1'-(piperidin-4-ylmethyl)spiro[cyclopropane-1,3'-indolin]-2'-one;
- (1S,2R)-2-(4-chlorophenyl)-1'-(2-(piperidin-1-yl)ethyl)spiro[cyclopropane-1,3'-indolin]-2'-one;
- (1R,2S)-2-(4-chlorophenyl)-1'-(2-(piperidin-1-yl)ethyl)spiro[cyclopropane-1,3'-indolin]-2'-one;
- (1S,2R)-2-(4-chlorophenyl)-1'-(2-(3-morpholinopropylamino)ethyl)spiro[cyclopropane-1,3'-indolin]-2'-one;
- (1R,2S)-2-(4-chlorophenyl)-1'-(2-(3-morpholinopropylamino)ethyl)spiro[cyclopropane-1,3'-indolin]-2'-one;
- (1S,2R)-2-(4-chlorophenyl)-1'-(2-(3-morpholinopropylamino)ethyl)spiro[cyclopropane-1,3'-indolin]-2'-one; and
- (1R,2S)-2-(4-chlorophenyl)-1'-(2-(3-morpholinopropylamino)ethyl)spiro[cyclopropane-1,3'-indolin]-2'-one.

19. A compound according to claim 1 selected from the group consisting of:
- (1S,2R)-2-(4-chlorophenyl)-1'-(2-(2-morpholinoethylamino)ethyl)spiro[cyclopropane-1,3'-indolin]-2'-one;
- (1R,2S)-2-(4-chlorophenyl)-1'-(2-(2-morpholinoethylamino)ethyl)spiro[cyclopropane-1,3'-indolin]-2'-one;
- (1S,2R)-2-(4-chlorophenyl)-1'-(2-(4-(pyridin-4-yl)piperazin-1-yl)ethyl)spiro[cyclopropane-1,3'-indolin]-2'-one;
- (1R,2S)-2-(4-chlorophenyl)-1'-(2-(4-(pyridin-4-yl)piperazin-1-yl)ethyl)spiro[cyclopropane-1,3'-indolin]-2'-one;
- (1S,2R)-2-(4-chlorophenyl)-1'-(2-(2-(2,6-dimethylmorpholino)ethylamino)ethyl)spiro[cyclopropane-1,3'-indolin]-2'-one;
- (1R,2S)-2-(4-chlorophenyl)-1'-(2-(2-(2,6-dimethylmorpholino)ethylamino)ethyl)spiro[cyclopropane-1,3'-indolin]-2'-one;
- (1S,2R)-2-(4-chlorophenyl)-1'-(1H-imidazol-4-yl)spiro[cyclopropane-1,3'-indolin]-2'-one;
- (1R,2S)-2-(4-chlorophenyl)-1'-(1H-imidazol-4-yl)spiro[cyclopropane-1,3'-indolin]-2'-one;
- (1S,2R)-3-(2-(4-chlorophenyl)-2'-oxospiro[cyclopropane-1,3'-indoline]-1'-yl)-N-(methylsulfonyl)benzamide;
- (1R,2S)-3-(2-(4-chlorophenyl)-2'-oxospiro[cyclopropane-1,3'-indoline]-1'-yl)-N-(methylsulfonyl)benzamide;
- (1S,2S)-3-(2-(4-chlorophenyl)-2-methyl-2'-oxospiro[cyclopropane-1,3'-indoline]-1'-yl)-5-(2-oxooxazolidin-3-yl)benzoic acid;
- (1R,2R)-3-(2-(4-chlorophenyl)-2-methyl-2'-oxospiro[cyclopropane-1,3'-indoline]-1'-yl)-5-(2-oxooxazolidin-3-yl)benzoic acid;
- (1S,2S)-3-(2-(4-chlorophenyl)-2-isopropyl-2'-oxospiro[cyclopropane-1,3'-indoline]-1'-yl)-5-(2-oxooxazolidin-3-yl)benzoic acid;
- (1R,2R)-3-(2-(4-chlorophenyl)-2-isopropyl-2'-oxospiro[cyclopropane-1,3'-indoline]-1'-yl)-5-(2-oxooxazolidin-3-yl)benzoic acid;
- (1S,2S)-3-(2-(4-chlorophenyl)-2-isopropyl-2'-oxospiro[cyclopropane-1,3'-indoline]-1'-yl)-5-(2-oxooxazolidin-3-yl)benzoic acid; and
- (1R,2R)-3-(2-(4-chlorophenyl)-2-isopropyl-2'-oxospiro[cyclopropane-1,3'-indoline]-1'-yl)-5-(2-oxooxazolidin-3-yl)benzoic acid.

20. A compound according to claim 1 selected from the group consisting of: (1S,2R)-3-((2-(2-fluorophenyl)-2'-oxospiro[cyclopropane-1,3'-indoline]-1'-yl)methyl)benzoic acid;
- (1R,2S)-3-((2-(2-fluorophenyl)-2'-oxospiro[cyclopropane-1,3'-indoline]-1'-yl)methyl)benzoic acid;
- (1S,2S)-3-((2-(2-fluorophenyl)-2'-oxospiro[cyclopropane-1,3'-indoline]-1'-yl)methyl)benzoic acid;
- (1R,2R)-3-((2-(2-fluorophenyl)-2'-oxospiro[cyclopropane-1,3'-indoline]-1'-yl)methyl)benzoic acid;
- (1S,2R)-3-((2-(3-fluorophenyl)-2'-oxospiro[cyclopropane-1,3'-indoline]-1'-yl)methyl)benzoic acid;
- (1R,2S)-3-((2-(3-fluorophenyl)-2'-oxospiro[cyclopropane-1,3'-indoline]-1'-yl)methyl)benzoic acid;
- (1S,2S)-3-((2-(3-fluorophenyl)-2'-oxospiro[cyclopropane-1,3'-indoline]-1'-yl)methyl)benzoic acid;
- (1R,2R)-3-((2-(3-fluorophenyl)-2'-oxospiro[cyclopropane-1,3'-indoline]-1'-yl)methyl)benzoic acid;
- (1S,2R)-3-((-2-(4-fluorophenyl)-2'-oxospiro[cyclopropane-1,3'-indoline]-1'-yl)methyl)benzoic acid;
- (1R,2S)-3-((-2-(4-fluorophenyl)-2'-oxospiro[cyclopropane-1,3'-indoline]-1'-yl)methyl)benzoic acid;
- (1S,2S)-3-((-2-(4-fluorophenyl)-2'-oxospiro[cyclopropane-1,3'-indoline]-1'-yl)methyl)benzoic acid;
- (1R,2R)-3-((-2-(4-fluorophenyl)-2'-oxospiro[cyclopropane-1,3'-indoline]-1'-yl)methyl)benzoic acid;
- (1S,2S)-3-((5'-fluoro-2-(4-fluorophenyl)-2-isopropyl-2'-oxospiro[cyclopropane-1,3'-indoline]-1'-yl)methyl)benzoic acid;
- (1R,2R)-3-((5'-fluoro-2-(4-fluorophenyl)-2-isopropyl-2'-oxospiro[cyclopropane-1,3'-indoline]-1'-yl)methyl)benzoic acid;

(1S,2S)-3-((2-(3-fluorophenyl)-2-isopropyl-2'-oxospiro [cyclopropane-1,3'-indoline]-1'-yl)methyl)benzoic acid;

(1R,2R)-3-((2-(3-fluorophenyl)-2-isopropyl-2'-oxospiro [cyclopropane-1,3'-indoline]-1'-yl)methyl)benzoic acid;

(1S,2S)-3-((2-(4-fluorophenyl)-2-isopropyl-2'-oxospiro [cyclopropane-1,3'-indoline]-1'-yl)methyl)benzoic acid; and (1R,2R)-3-((2-(4-fluorophenyl)-2-isopropyl-2'-oxospiro [cyclopropane-1,3'-indoline]-1'-yl)methyl)benzoic acid.

21. A compound according to claim 1 selected from the group consisting of:
- (1S,2R)-6-((2-(4-fluorophenyl)-2'-oxospiro[cyclopropane-1,3'-indoline]-1'-yl)methyl)picolinic acid;
- (1R,2S)-6-((2-(4-fluorophenyl)-2'-oxospiro[cyclopropane-1,3'-indoline]-1'-yl)methyl)picolinic acid;
- (1S,2S)-2-chloro-5-((2-(4-fluorophenyl)-2'-oxospiro[cyclopropane-1,3'-indoline]-1'-yl)methyl)benzoic acid;
- (1R,2R)-2-chloro-5-((2-(4-fluorophenyl)-2'-oxospiro[cyclopropane-1,3'-indoline]-1'-yl)methyl)benzoic acid;
- (1R,2S)-4-((2-(4-fluorophenyl)-2'-oxospiro[cyclopropane-1,3'-indoline]-1'-yl)methyl)benzoic acid;
- (1R,2S)-4-((2-(4-fluorophenyl)-2'-oxospiro[cyclopropane-1,3'-indoline]-1'-yl)methyl)benzoic acid;
- (1R,2S)-3-((2-(4-fluorophenyl)-2'-oxospiro[cyclopropane-1,3'-indoline]-1'-yl)methyl)-N-(methylsulfonyl) benzamide;
- (1S,2R)-3-((2-(4-fluorophenyl)-2'-oxospiro[cyclopropane-1,3'-indoline]-1'-yl)methyl)-N-(methylsulfonyl) benzamide;
- (1S,2R)-1'-(3-fluorobenzyl)-2-(4-fluorophenyl)-2'-oxospiro[cyclopropane-1,3'-indoline]-5'-carboxylic acid;
- (1R,2S)-1'-(3-fluorobenzyl)-2-(4-fluorophenyl)-2'-oxospiro[cyclopropane-1,3'-indoline]-5'-carboxylic acid;
- (1R,2R)-1'-(2-fluorobenzyl)-2-(4-fluorophenyl)-2'-oxospiro[cyclopropane-1,3'-indoline]-5'-carboxylic acid; and
- (1S,2S)-1'-(2-fluorobenzyl)-2-(4-fluorophenyl)-2'-oxospiro[cyclopropane-1,3'-indoline]-5'-carboxylic acid.

22. A compound according to claim 1 selected from the group consisting of: (1R,2R)-((2-(4-(methylsulfonyl)phenyl)-2'-oxospiro[cyclopropane-1,3'-indoline]-1'-yl)methyl) benzoic acid;
- (1S,2S)-((2-(4-(methylsulfonyl)phenyl)-2'-oxospiro[cyclopropane-1,3'-indoline]-1'-yl)methyl)benzoic acid;
- (1S,2R)-3-((2-(4-(methylsulfonyl)phenyl)-2'-oxospiro [cyclopropane-1,3'-indoline]-1'-yl)methyl)benzoic acid; and
- (1R,2S)-3-((2-(4-(methylsulfonyl)phenyl)-2'-oxospiro [cyclopropane-1,3'-indoline]-1'-yl)methyl)benzoic acid.

23. A compound according to claim 1 selected from the group consisting of:
- (1S,2R)-3-((2-(4-cyanophenyl)-2'-oxospiro[cyclopropane-1,3'-indoline]-1'-yl)methyl)benzoic acid;
- (1R,2S)-3-((2-(4-cyanophenyl)-2'-oxospiro[cyclopropane-1,3'-indoline]-1'-yl)methyl)benzoic acid;
- (1S,2S)-3-((2-(4-cyanophenyl)-2'-oxospiro[cyclopropane-1,3'-indoline]-1'-yl)methyl)benzoic acid;
- (1R,2R)-3-((2-(4-cyanophenyl)-2'-oxospiro[cyclopropane-1,3'-indoline]-1'-yl)methyl)benzoic acid;
- (1S,2S)-3-((2-(4-cyanophenyl)-2-methyl-2'-oxospiro[cyclopropane-1,3'-indoline]-1'-yl)methyl)benzoic acid;
- (1R,2R)-3-((2-(4-cyanophenyl)-2-methyl-2'-oxospiro[cyclopropane-1,3'-indoline]-1'-yl)methyl)benzoic acid;
- (1S,2R)-3-((2-(4-cyanophenyl)-2-methyl-2'-oxospiro[cyclopropane-1,3'-indoline]-1'-yl)methyl)benzoic acid;
- (1R,2S)-3-((2-(4-cyanophenyl)-2-methyl-2'-oxospiro[cyclopropane-1,3'-indoline]-1'-yl)methyl)benzoic acid;
- (1R,2S)-3-((2-(4-cyanophenyl)-5'-fluoro-2-methyl-2'-oxospiro[cyclopropane-1,3'-indoline]-1'-yl)methyl)benzoic acid;
- (1S,2R)-3-((2-(4-cyanophenyl)-5'-fluoro-2-methyl-2'-oxospiro[cyclopropane-1,3'-indoline]-1'-yl)methyl)benzoic acid;
- (−)-3-((2-(4-cyanophenyl)-5'-fluoro-2-methyl-2'-oxospiro[(trans)-cyclopropane-1,3'-indoline]-1'-yl)methyl)benzoic acid;
- (+)-3-((2-(4-cyanophenyl)-5'-fluoro-2-methyl-2'-oxospiro[(trans)-cyclopropane-1,3'-indoline]-1'-yl)methyl)benzoic acid;
- (1S,2S)-3-((2-(4-cyanophenyl)-2-isopropyl-2'-oxospiro [cyclopropane-1,3'-indoline]-1'-yl)methyl)benzoic acid;
- (1R,2R)-3-((2-(4-cyanophenyl)-2-isopropyl-2'-oxospiro [cyclopropane-1,3'-indoline]-1'-yl)methyl)benzoic acid;
- (−)-3-((2-(4-cyanophenyl)-2-isopropyl-2'-oxospiro [(trans)-cyclopropane-1,3'-indoline]-1'-yl)methyl)benzoic acid; and
- (+)-3-((2-(4-cyanophenyl)-2-isopropyl-2'-oxospiro [(trans)-cyclopropane-1,3'-indoline]-1'-yl)methyl)benzoic acid.

24. A compound according to claim 1 selected from the group consisting of:
- (1R,2R)-3-((2-(4-cyanophenyl)-5'-fluoro-2-methyl-2'-oxospiro[cyclopropane-1,3'-indoline]-1'-yl)methyl)benzoic acid;
- (1S,2S)-3-((2-(4-cyanophenyl)-5'-fluoro-2-methyl-2'-oxospiro[cyclopropane-1,3'-indoline]-1'-yl)methyl)benzoic acid;
- (−)-3-((2-(4-cyanophenyl)-5'-fluoro-2-methyl-2'-oxospiro[(cis)-cyclopropane-1,3'-indoline]-1'-yl)methyl) benzoic acid;
- (+)-3-((2-(4-cyanophenyl)-5'-fluoro-2-methyl-2'-oxospiro[(cis)-cyclopropane-1,3'-indoline]-1'-yl)methyl) benzoic acid;
- (1S,2S)-3-(2-(4-cyanophenyl)-2-isopropyl-2'-oxospiro [cyclopropane-1,3'-indoline]-1'-yl)-5-(2-oxooxazolidin-3-yl)benzoic acid;
- (1R,2R)-3-(2-(4-cyanophenyl)-2-isopropyl-2'-oxospiro [cyclopropane-1,3'-indoline]-1'-yl)-5-(2-oxooxazolidin-3-yl)benzoic acid;
- (1S, 2R)-4-((2-(4-cyanophenyl)-2'-oxospiro[cyclopropane-1,3'-indoline]-1'-yl)methyl)benzoic acid;
- (1R,2S)-4-((2-(4-cyanophenyl)-2'-oxospiro[cyclopropane-1,3'-indoline]-1'-yl)methyl)benzoic acid;
- (1R,2S)-6-((2-(4-cyanophenyl)-2'-oxospiro[cyclopropane-1,3'-indoline]-1'-yl)methyl)-N-(cyclopropylsulfonyl)picolinamide;
- (1S,2R)-6-((2-(4-cyanophenyl)-2'-oxospiro[cyclopropane-1,3'-indoline]-1'-yl)methyl)-N-(cyclopropylsulfonyl)picolinamide;
- (1S,2R)-4-((2-(4-cyanophenyl)-2'-oxospiro[cyclopropane-1,3'-indoline]-1'-yl)methyl)-N-(cyclopropylsulfonyl)benzamide; and
- (1R,2S)-4-((2-(4-cyanophenyl)-2'-oxospiro[cyclopropane-1,3'-indoline]-1'-yl)methyl)-N-(cyclopropylsulfonyl)benzamide.

25. A compound according to claim 1 selected from the group consisting of: (1S,2S)-3-((2'-oxo-2-(2-(trifluoromethyl)phenyl)-spiro[cyclopropane-1,3'-indoline]-1'-yl)methyl)benzoic acid; and
(1R,2R)-3-((2'-oxo-2-(2-(trifluoromethyl)phenyl)-spiro[cyclopropane-1,3'-indoline]-1'-yl)methyl)benzoic acid.

26. A compound according to claim 1 selected from the group consisting of:
(1S,2R)-3-((2'-oxo-2-(pyridin-3-yl)spiro[cyclopropane-1,3'-indoline]-1'-yl)methyl)benzoic acid;
(1R,2S)-3-((2'-oxo-2-(pyridin-3-yl)spiro[cyclopropane-1,3'-indoline]-1'-yl)methyl)benzoic acid;
(1R,2S)-4-((2'-oxo-2-(pyridin-3-yl)spiro[cyclopropane-1,3'-indoline]-1'-yl)methyl)benzoic acid; and
(1S,2R)-4-((2'-oxo-2-(pyridin-3-yl)spiro[cyclopropane-1,3'-indoline]-1'-yl)methyl)benzoic acid.

27. A compound according to claim 1 selected from the group consisting of:
(1S,2R)-N-(cyclopropylsulfonyl)-3-((2-(4-fluorophenyl)-2'-oxospiro[cyclopropane-1,3'-indoline]-1'-yl)methyl)benzamide;
(1R,2S)-N-(cyclopropylsulfonyl)-3-((2-(4-fluorophenyl)-2'-oxospiro[cyclopropane-1,3'-indoline]-1'-yl)methyl)benzamide;
(1S,2R)-N-(cyclopropylsulfonyl)-4-((2-(4-fluorophenyl)-2'-oxospiro[cyclopropane-1,3'-indoline]-1'-yl)methyl)benzamide; and
(1R,2S)-N-(cyclopropylsulfonyl)-4-((2-(4-fluorophenyl)-2'-oxospiro[cyclopropane-1,3'-indoline]-1'-yl)methyl)benzamide.

28. A compound according to claim 1 selected from the group consisting of:
(2S,1R)-3-((2-(4-chlorophenyl)-2'-oxospiro[cyclopropane-1,3'-indoline]-1'-yl)methyl)benzoic acid;
(1S,2R)-3-((2-(4-chlorophenyl)-2'-oxospiro[cyclopropane-1,3'-indoline]-1'-yl)methyl)benzoic acid;
(1S,2R)-3-((2-(3-chlorophenyl)-2'-oxospiro[cyclopropane-1,3'-indoline]-1'-yl)methyl)benzoic acid;
(1R,2S)-3-((2-(3-chlorophenyl)-2'-oxospiro[cyclopropane-1,3'-indoline]-1'-yl)methyl)benzoic acid;
(1S,2R)-((5'-chloro-2-(4-chlorophenyl)-2'-oxospiro[cyclopropane-1,3'-indoline]-1'-yl)methyl)benzoic acid;
(1R,2S)-((5'-chloro-2-(4-chlorophenyl)-2'-oxospiro[cyclopropane-1,3'-indoline]-1'-yl)methyl)benzoic acid;
(1S,2S)-3-((2-(4-chlorophenyl)-5'-fluoro-2'-oxospiro[cyclopropane-1,3'-indoline]-1'-yl)methyl)benzoic acid;
(1R,2R)-3-((2-(4-chlorophenyl)-5'-fluoro-2'-oxospiro[cyclopropane-1,3'-indoline]-1'-yl)methyl)benzoic acid;
(+)-3-((2-(4-chlorophenyl)-2-isopropyl-2'-oxospiro[(trans)-cyclopropane-1,3'-indoline]-1'-yl)methyl)benzoic acid;
(−)-3-((2-(4-chlorophenyl)-2-isopropyl-2'-oxospiro[(trans)-cyclopropane-1,3'-indoline]-1'-yl)methyl)benzoic acid;
(1S,2S)-3-((2-(4-chlorophenyl)-2-isopropyl-2'-oxospiro[cyclopropane-1,3'-indoline]-1'-yl)methyl)benzoic acid;
(1R,2R)-3-((2-(4-chlorophenyl)-2-isopropyl-2'-oxospiro[cyclopropane-1,3'-indoline]-1'-yl)methyl)benzoic acid;
(1S,2R)-6-((2-(4-chlorophenyl)-2'-oxospiro[cyclopropane-1,3'-indoline]-1'-yl)methyl)picolinic acid;
(1R,2S)-6-((2-(4-chlorophenyl)-2'-oxospiro[cyclopropane-1,3'-indoline]-1'-yl)methyl)picolinic acid; and
(1S,2R)-6-((2-(4-fluorophenyl)-2'-oxospiro[cyclopropane-1,3'-indoline]-1'-yl)methyl)picolinic acid.

29. A compound according to claim 1 selected from the group consisting of:
(1S,2R)-2-(4-(2-(4-chlorophenyl)-2'-oxospiro[cyclopropane-1,3'-indoline]-1'-yl)-1H-imidazol-1-yl)acetic acid;
(1R,2S)-2-(4-(2-(4-chlorophenyl)-2'-oxospiro[cyclopropane-1,3'-indoline]-1'-yl)-1H-imidazol-1-yl)acetic acid;
(1S,2R)-3-(2-(4-chlorophenyl)-2'-oxospiro[cyclopropane-1,3'-indoline]-1'-yl)benzoic acid;
(1R,2S)-3-(2-(4-chlorophenyl)-2'-oxospiro[cyclopropane-1,3'-indoline]-1'-yl)benzoic acid;
(1S,2S)-3-(2-(4-chlorophenyl)-2'-oxospiro[cyclopropane-1,3'-indoline]-1'-yl)benzoic acid;
(1R,2R)-3-(-2-(4-chlorophenyl)-2'-oxospiro[cyclopropane-1,3'-indoline]-1'-yl)benzoic acid;
(1S,2S)-3-(2-(4-chlorophenyl)-2'-oxospiro[cyclopropane-1,3'-indoline]-1'-yl)-5-(2-oxooxazolidin-3-yl)benzoic acid;
(1R,2R)-3-(2-(4-chlorophenyl)-2'-oxospiro[cyclopropane-1,3'-indoline]-1'-yl)-5-(2-oxooxazolidin-3-yl)benzoic acid;
(1S,2R)-2-chloro-5-((2-(4-chlorophenyl)-5'-fluoro-2'-oxospiro[cyclopropane-1,3'-indoline]-1'-yl)methyl)benzoic acid;
(1R,2S)-2-chloro-5-((2-(4-chlorophenyl)-5'-fluoro-2'-oxospiro[cyclopropane-1,3'-indoline]-1'-yl)methyl)benzoic acid;
(1R,2S)-3-((2-(4-chlorophenyl)-2'-oxospiro[cyclopropane-1,3'-indoline]-1'-yl)methyl)-N-(methylsulfonyl)benzamide; and
(1S,2R)-3-((2-(4-chlorophenyl)-2'-oxospiro[cyclopropane-1,3'-indoline]-1'-yl)methyl)-N-(methylsulfonyl)benzamide.

30. A compound according to claim 1 selected from the group consisting of:
(1S,2R)-3-((2-(4-cyanophenyl)-2'-oxospiro[cyclopropane-1,3'-indoline]-1'-yl)methyl)benzoic acid;
(1R,2S)-3-((2-(4-cyanophenyl)-2'-oxospiro[cyclopropane-1,3'-indoline]-1'-yl)methyl)benzoic acid;
(1S,2R)-4-((2-(4-cyanophenyl)-2'-oxospiro[cyclopropane-1,3'-indoline]-1'-yl)methyl)benzoic acid;
(1R,2S)-4-((2-(4-cyanophenyl)-2'-oxospiro[cyclopropane-1,3'-indoline]-1'-yl)methyl)benzoic acid;
(1R,2S)-6-((2-(4-cyanophenyl)-2'-oxospiro[cyclopropane-1,3'-indoline]-1'-yl)methyl)-N-(cyclopropylsulfonyl)picolinamide;
(1S,2R)-6-((2-(4-cyanophenyl)-2'-oxospiro[cyclopropane-1,3'-indoline]-1'-yl)methyl)-N-(cyclopropylsulfonyl)picolinamide;
(1S,2R)-4-((2-(4-cyanophenyl)-2'-oxospiro[cyclopropane-1,3'-indoline]-1'-yl)methyl)-N-(cyclopropylsulfonyl)benzamide;
(1R,2S)-4-((2-(4-cyanophenyl)-2'-oxospiro[cyclopropane-1,3'-indoline]-1'-yl)methyl)-N-(cyclopropylsulfonyl)benzamide;
(1R,2S)-2-(4-cyanophenyl)-2'-oxospiro[cyclopropane-1,3'-indoline]-5'-carboxylic acid;
(1S,2R)-2-(4-cyanophenyl)-2'-oxospiro[cyclopropane-1,3'-indoline]-5'-carboxylic acid; and
(1R,2R) and (1S,2S)-2-(4-cyanophenyl)-2'-oxospiro[cyclopropane-1,3'-indoline]-5'-carboxylic acid.

31. A compound according to claim 1 selected from the group consisting of:
(1S,2R)-3-((2-(4-(methylsulfonyl)phenyl)-2'-oxospiro[cyclopropane-1,3'-indoline]-1'-yl)methyl)benzoic acid; and (1R,2S)-3-((2-(4-(methylsulfonyl)phenyl)-2'-oxospiro[cyclopropane-1,3'-indoline]-1'-yl)methyl)benzoic acid.

32. A compound according to claim 1 selected from the group consisting of:
- (1S,2R)-3-((2-(2-fluorophenyl)-2'-oxospiro[cyclopropane-1,3'-indoline]-1'-yl)methyl)benzoic acid;
- (1R,2S)-3-((2-(2-fluorophenyl)-2'-oxospiro[cyclopropane-1,3'-indoline]-1'-yl)methyl)benzoic acid;
- (1S,2S)-3-((2-(2-fluorophenyl)-2'-oxospiro[cyclopropane-1,3'-indoline]-1'-yl)methyl)benzoic acid;
- (1R,2R)-3-((2-(2-fluorophenyl)-2'-oxospiro[cyclopropane-1,3'-indoline]-1'-yl)methyl)benzoic acid;
- (1S,2R)-3-((2-(3-fluorophenyl)-2'-oxospiro[cyclopropane-1,3'-indoline]-1'-yl)methyl)benzoic acid;
- (1R,2S)-3-((2-(3-fluorophenyl)-2'-oxospiro[cyclopropane-1,3'-indoline]-1'-yl)methyl)benzoic acid;
- (1R,2S)-6-((2-(4-fluorophenyl)-2'-oxospiro[cyclopropane-1,3'-indoline]-1'-yl)methyl)picolinic acid;
- (1S,2S)-2-chloro-5-((2-(4-fluorophenyl)-2'-oxospiro[cyclopropane-1,3'-indoline]-1'-yl)methyl)benzoic acid;
- (1R,2R)-2-chloro-5-((2-(4-fluorophenyl)-2'-oxospiro[cyclopropane-1,3'-indoline]-1'-yl)methyl)benzoic acid;
- (1R,2S)-4-((2-(4-fluorophenyl)-2'-oxospiro[cyclopropane-1,3'-indoline]-1'-yl)methyl)benzoic acid;
- (1R,2S)-4-((2-(4-fluorophenyl)-2'-oxospiro[cyclopropane-1,3'-indoline]-1'-yl)methyl)benzoic acid;
- (1R,2S)-3-((2-(3-chloro-4-fluorophenyl)-2'-oxospiro[cyclopropane-1,3'-indoline]-1'-yl)methyl)benzoic acid;
- (1S,2R)-3-((2-(3-chloro-4-fluorophenyl)-2'-oxospiro[cyclopropane-1,3'-indoline]-1'-yl)methyl)benzoic acid;
- (1R,2S)-3-((2-(4-fluorophenyl)-2'-oxospiro[cyclopropane-1,3'-indoline]-1'-yl)methyl)-N-(methylsulfonyl)benzamide; and
- (1S,2R)-3-((2-(4-fluorophenyl)-2'-oxospiro[cyclopropane-1,3'-indoline]-1'-yl)methyl)-N-(methylsulfonyl)benzamide.

33. A compound according to claim 1 selected from the group consisting of:
- (1S,2R)-N-(cyclopropylsulfonyl)-3-((2-(4-fluorophenyl)-2'-oxospiro[cyclopropane-1,3'-indoline]-1'-yl)methyl)benzamide;
- (1R,2S)-N-(cyclopropylsulfonyl)-3-((2-(4-fluorophenyl)-2'-oxospiro[cyclopropane-1,3'-indoline]-1'-yl)methyl)benzamide;
- (1S,2R)-N-(cyclopropylsulfonyl)-4-((2-(4-fluorophenyl)-2'-oxospiro[cyclopropane-1,3'-indoline]-1'-yl)methyl)benzamide;
- (1R,2S)-N-(cyclopropylsulfonyl)-4-((2-(4-fluorophenyl)-2'-oxospiro[cyclopropane-1,3'-indoline]-1'-yl)methyl)benzamide;
- (1S,2R)-1'-(3-fluorobenzyl)-2-(4-fluorophenyl)-2'-oxospiro[cyclopropane-1,3'-indoline]-5'-carboxylic acid;
- (1R,2S)-1'-(3-fluorobenzyl)-2-(4-fluorophenyl)-2'-oxospiro[cyclopropane-1,3'-indoline]-5'-carboxylic acid;
- (1R,2R)-1'-(2-fluorobenzyl)-2-(4-fluorophenyl)-2'-oxospiro[cyclopropane-1,3'-indoline]-5'-carboxylic acid;
- (1S,2S)-1'-(2-fluorobenzyl)-2-(4-fluorophenyl)-2'-oxospiro[cyclopropane-1,3'-indoline]-5'-carboxylic acid;
- (1R,2R)-2-(4-fluorophenyl)-2'-oxospiro[cyclopropane-1,3'-indoline]-5'-carboxylic acid; and
- (1S,2S)-2-(4-fluorophenyl)-2'-oxospiro[cyclopropane-1,3'-indoline]-5'-carboxylic acid.

34. A compound according to claim 1 selected from the group consisting of:
- (1S,2S)-3-((2'-oxo-2-(2-(trifluoromethyl)phenyl)-spiro[cyclopropane-1,3'-indoline]-1'-yl)methyl)benzoic acid; and
- (1R,2R)-3-((2'-oxo-2-(2-(trifluoromethyl)phenyl)-spiro[cyclopropane-1,3'-indoline]-1'-yl)methyl)benzoic acid.

35. A compound according to claim 1 selected from the group consisting of:
- (1S,2R)-3-((2'-oxo-2-(pyridin-3-yl)spiro[cyclopropane-1,3'-indoline]-1'-yl)methyl)benzoic acid;
- (1R,2S)-3-((2'-oxo-2-(pyridin-3-yl)spiro[cyclopropane-1,3'-indoline]-1'-yl)methyl)benzoic acid;
- (1R,2S)-4-((2'-oxo-2-(pyridin-3-yl)spiro[cyclopropane-1,3'-indoline]-1'-yl)methyl)benzoic acid; and
- (1S,2R)-4-((2'-oxo-2-(pyridin-3-yl)spiro[cyclopropane-1,3'-indoline]-1'-yl)methyl)benzoic acid.

* * * * *